(12) United States Patent
Baley et al.

(10) Patent No.: US 10,440,907 B2
(45) Date of Patent: Oct. 15, 2019

(54) MAIZE PLANTS WITH IMPROVED DISEASE RESISTANCE

(71) Applicant: Monsanto Technology LLC, St. Louis, MO (US)

(72) Inventors: George J. Baley, St. Louis, MO (US); Juan Cruz, Tlaquepaque (MX); Hongwu Jia, Grover, MO (US); Yule Pan, Chesterfield, MO (US); Hao Zhou, Coralville, IA (US)

(73) Assignee: Monsanto Technology LLC, St. Louis, MO (US)

( * ) Notice: Subject to any disclaimer, the term of this patent is extended or adjusted under 35 U.S.C. 154(b) by 1208 days.

(21) Appl. No.: 14/333,293

(22) Filed: Jul. 16, 2014

(65) Prior Publication Data

US 2015/0026839 A1 Jan. 22, 2015

Related U.S. Application Data

(60) Provisional application No. 61/847,153, filed on Jul. 17, 2013.

(51) Int. Cl.
*A01H 5/10* (2018.01)
*A01H 1/04* (2006.01)
*C12Q 1/6895* (2018.01)

(52) U.S. Cl.
CPC ............... *A01H 1/04* (2013.01); *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 7,173,171 | B1 | 2/2007 | Boerboom |
| 7,237,973 | B1 * | 7/2007 | Lou ............ A45D 40/264 132/218 |
| 7,709,709 | B1 | 5/2010 | Page et al. |
| 7,875,775 | B2 | 1/2011 | Cook |
| 8,471,127 | B2 | 6/2013 | Roucolle |

OTHER PUBLICATIONS

Lee et al., "Expanding the genetic map of maize with the intermated B73 x Mo17 (IBM) population," *Plant Mol Biol.* 48(5-6):453-61, 2002.
Selitrennikoff et al., "Antifungal proteins," *Appl Environ Microb* 67(7):2883-2894, 2001.
Waniska et al., "Antifungal proteins and other mechanisms in the control of sorghum stalk rot and grain mold," *J Agric Food Chem* 49:4732-4742, 2001.
Wong et al., "Proteins with antifungal properties and other medicinal applications from plants and mushrooms," *Appl Microb Biotechnol* 87:1221-1235, 2010.

* cited by examiner

*Primary Examiner* — Bratislav Stankovic
(74) *Attorney, Agent, or Firm* — Dentons US LLP; Matthew Madsen

(57) ABSTRACT

The present invention is in the field of plant breeding and disease resistance. More specifically, the invention includes a method for breeding corn plants containing one or more markers that are associated with resistance to fungi. The invention further includes germplasm and the use of germplasm containing at least one marker associated with resistance to *Fusarium* stalk rot (FSR) infection for introgression into elite germplasm in a breeding program, thus producing novel FSR resistant germplasm.

8 Claims, No Drawings

Specification includes a Sequence Listing.

MAIZE PLANTS WITH IMPROVED DISEASE RESISTANCE

CROSS REFERENCE TO RELATED APPLICATIONS

This application claims the benefit of U.S. Provisional Application No. 61/847,153, filed Jul. 17, 2013, incorporated herein by reference in its entirety.

INCORPORATION OF SEQUENCE LISTING

A sequence listing containing the file named "MONS364US_ST25.txt" which is 51,332 bytes (measured in MS-Windows®) and created on Jun. 25, 2014 comprises 165 nucleotide sequences, and is incorporated herein by reference in its entirety.

FIELD OF THE INVENTION

The present invention relates to the field of plant breeding and more specifically to methods and compositions for producing corn plants exhibiting improved disease resistance.

BACKGROUND

Stalk rot infection reduces the efficiency of carbohydrate transport from the stalk up to the ears during grainfill, which reduces crop yield. A corn plant will die altogether if infection advances to the point that the pith pulls away from the outer rind of the stalk, which can eventually result in a stalk consisting of little more than a hollow tube that is no longer able transport water and nutrients to the rest of the plant. Furthermore, a stalk weakened by infection is more likely to collapse at one or more points along its length (lodging), which typically results in a plant that yields no harvestable grain. Stalk rots typically reduce yields up to 5% in almost any field where corn is cultivated. In years with particularly bad infection rates, yield losses reach 10-20%, and in some locations when infection is particularly acute, 100% yield loss can occur.

One of the most common forms of stalk rot is *Fusarium* stalk rot, caused by several species of fungi, including *Fusarium verticilliodes* e J. Sheld. (sexual stage: *G. moniliformis* Sawada) Ito in Ito & Kimura, formerly *Fusarium moniliforme*, telemorph *Gibberella fujikoroi, F. proliferatum* (T. Matsushima) *Nirenberg* (sexual stage: *G. proliferatum*), and *F. subglutinans* (sexual stage: *G. subglutinans*). FSR infection is characterized by rotting roots, crown, and lower internodes that begins shortly after pollination and progresses as the plant matures. Eventually the pith will disintegrate resulting in weak, spongy stalks that are prone to lodging.

Due to the lack of fungicides and or other chemical controls for FSR, growers are faced with limited options for managing the disease. Since the most effective approach is to select hybrids that are intrinsically resistant, what is needed are methods of identifying genetic sources of FSR resistance and more effective methods of introgressing those genetic elements into commercial lines to provide new hybrids with improved genetic resistance to FSR infection.

SUMMARY OF THE INVENTION

Identifying and selecting plants that exhibit resistance to *Fusarium* stalk rot (FSR) using marker-assisted selection (MAS) provides an effective and efficient method of improving the survivability of corn to FSR infection. This invention provides marker loci and quantitative trait loci (QTL) chromosome intervals that demonstrate significant co-segregation with FSR resistance. These markers, or additional loci linked to these markers, can be used in MAS breeding programs to produce plants with improved FSR resistance.

Marker loci and quantitative trait loci (QTL) chromosome intervals that demonstrate significant co-segregation with FSR resistance are provided. These markers, or additional loci linked to these markers, can be used in MAS breeding programs to produce plants with improved FSR resistance.

The FSR-3.01 and FSR-8.01 loci correspond to QTL discovered on chromosome 3 and chromosome 8, respectively, of the corn genome. These loci contain genotypes closely linked to FSR resistance. Embodiments of this invention include methods of detecting genotypes within and/or linked to FSR-3.01 or FSR-8.01 to create disease resistant corn lines. Provided herein are examples of markers that are useful for detecting the presence or absence of disease resistance alleles linked to FSR-3.01 or FSR-8.01 as part of a MAS breeding program to produce plants with improved resistance to FSR infection.

Embodiments of this invention include identifying one or more corn plants with FSR resistance, improved resistance, or susceptibility to FSR infection by using a marker within the FSR-3.01 or FSR-8.01 chromosome intervals, or a marker closely linked to FSR-3.01 or FSR-8.01. As used herein, "closely linked" means that the marker or locus is within about 20 cM, preferably within about 15 cM, more preferably within about 10 cM, even more preferably within about 5 cM, even more preferably within about 1 cM, even more preferably about 0.5 cM, and even more preferably less than 0.5 cM of the identified FSR locus.

The location in the maize genome of FSR-3.01 and FSR-8.01, and chromosome intervals and sub-intervals containing markers closely linked to FSR-3.01 and FSR-8.01, are referenced herein to a public maize genome map (IBM2 2008 Neighbors). Genomic markers such as psk2 and gpm753d can be used to define the flanks of the FSR-3.01 chromosome interval, which includes markers closely linked to the FSR-3.01. Genomic markers such as umc1790 and mHbrBC384-Mo17 can be used to define the flanks of the FSR-8.01 chromosome interval, which includes markers closely linked to FSR-8.01. Other genomic markers may be used to define chromosome sub-intervals linked to FSR-3.01 or FSR-8.01.

Embodiments of this invention include methods of creating a population of corn plants with enhanced FSR resistance by providing a first population of corn plants, detecting the presence of a genetic marker that is genetically linked to FSR-3.01 by 20 cM or less in the first population, selecting one or more corn plants containing said marker from the first population of corn plants, and producing a population of offspring from at lease one of said selected corn plants. In other embodiments, the genetic marker detected is genetically linked to FSR-3.01 by less than 15 cM, 10 cM, 5 cM, 1 cM, or 0.5 cM of FSR-3.01.

In another embodiment of this invention, a population of corn plants with enhanced FSR resistance is created by providing a first population of corn plants, detecting the presence of a genetic marker within the FSR3.01 chromosome interval, selecting one or more corn plants containing said marker from the first population of corn plants, and producing a population of offspring from at lease one of said selected corn plants. The FSR-3.01 chromosome interval includes any marker flanked by psk2 and gpm753d, including psk2 and gpm753d. Sub-intervals of the FSR-3.01 chromosome interval are also useful for this invention, and include any interval wherein one or both boarders of the sub-interval are between psk2 and gpm753d, including psk2 and gpm753d. In one embodiment, an FSR-3.01 sub-interval is flanked by, and includes, TIDP3078 and umc60. In another embodiment, an FSR-3.01 sub-interval is flanked by, and includes, SEQ ID NO: 1 and SEQ ID NO: 5. In another embodiment, an FSR-3.01 sub-interval is flanked by, and includes, TIDP6282 and SEQ ID NO: 4. In another embodiment, an FSR-3.01 sub-interval is flanked by, and includes, SEQ ID NO: 90 and SEQ ID NO: 2. All manner of chromosome interval lengths between, and including, psk2 and gpm753d can be used in conjunction with this invention.

In another embodiment of this invention, a population of corn plants with enhanced FSR resistance is created by providing a first population of corn plants, detecting the presence of a genetic marker that is selected from the group consisting of SEQ ID NOs: 1-5 and SEQ ID NOs: 86-101 in the first population, selecting one or more corn plants containing said marker from the first population of corn plants, and producing a population of offspring from at lease one of said selected corn plants.

Other embodiments of this invention include creating a population of corn plants with enhanced FSR resistance, wherein a portion of the FSR is caused by *Fusarium moniliforme*, by providing a first population of corn plants, detecting the presence of a genetic marker that is genetically linked to FSR-3.01 by 20 cM or less in the first population, selecting one or more corn plants containing said marker from the first population of corn plants, and producing a population of offspring from at lease one of said selected corn plants.

Embodiments of this invention also include methods of creating a population of corn plants with enhanced FSR resistance by providing a first population of corn plants, detecting the presence of a genetic marker that is genetically linked to FSR-8.01 by 20 cM or less in the first population, selecting one or more corn plants containing said marker from the first population of corn plants, and producing a population of offspring from at lease one of said selected corn plants. In other embodiments, the genetic marker detected is genetically linked to FSR-8.01 by less than 15 cM, 10 cM, 5 cM, 1 cM, or 0.5 cM of FSR-8.01.

In another embodiment of this invention, a population of corn plants with enhanced FSR resistance is created by providing a first population of corn plants, detecting the presence of a genetic marker within the FSR-3.01 chromosome interval, selecting one or more corn plants containing said marker from the first population of corn plants, and producing a population of offspring from at lease one of said selected corn plants. The FSR-8.01 chromosome interval includes the FSR-8.01 locus and any marker flanked by umc1790 and mHbrBC384-Mo17, including umc1790 and mHbrBC384-Mo17. Sub-intervals of the FSR-8.01 chromosome interval are also useful, and include any interval wherein one or both boarders of the sub-interval are between umc1790 and mHbrBC384-Mo17, including umc1790 or mHbrBC384-Mo17. In one embodiment, an FSR-3.01 sub-interval is flanked by, and includes, TIDP3728 and TIDP5537. In another embodiment, an FSR-8.01 sub-interval is flanked by, and includes, csu329 and IDP6942. All manner of chromosome interval lengths between, and including, umc1790 and mHbrBC384-Mo17 can be used in conjunction with this invention.

In another embodiment of this invention, a population of corn plants with enhanced FSR resistance is created by providing a first population of corn plants, detecting the presence of a genetic marker that is selected from the group consisting of SEQ ID NOs: 6-17 in the first population, selecting one or more corn plants containing said marker from the first population of corn plants, and producing a population of offspring from at lease one of said selected corn plants.

Other embodiments of this invention include creating a population of corn plants with enhanced FSR resistance, wherein a portion of the FSR is caused by *Fusarium moniliforme*, by providing a first population of corn plants, detecting the presence of a genetic marker that is genetically linked to FSR-3.01 by 20 cM or less in the first population, selecting one or more corn plants containing said marker from the first population of corn plants, and producing a population of offspring from at lease one of said selected corn plants.

In one aspect, the present invention provides a method of obtaining a corn plant with enhanced *Fusarium* stalk rot resistance comprising: a) providing a population of corn plants; b) detecting in said plants the presence of a *Fusarium* stalk rot resistance allele at a polymorphic locus genetically linked to a chromosomal segment flanked by marker loci AY110352 and TIDP5096 or marker loci TIDP3099 and IDP4363; and c) selecting from said population at least a first plant comprising said allele and enhanced *Fusarium* stalk rot resistance compared to a plant lacking said allele. In some embodiments, said segment is flanked by marker loci TIDP3078 and umc60 or marker loci TIDP3728 and TIDP5537. In further embodiments, said segment is flanked by marker loci SEQ ID NO: 1 and SEQ ID NO: 5 or marker loci csu329 and IDP6942. In yet further embodiments, said segment is flanked by marker loci SEQ ID NO: 90 and SEQ ID NO: 2 or marker loci SEQ ID NO: 6 and SEQ ID NO: 17. In other embodiments, said polymorphic locus comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17; SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, and SEQ ID NO: 101. In some embodiments, said method further comprises selecting from said population at least two plants, thereby forming a population of corn plants comprising said allele and enhanced *Fusarium* stalk rot resistance compared to a plant lacking said allele. In certain embodiments, said *Fusarium* stalk rot resistance allele was introgressed into said population of corn plants from a starting plant or population of corn plants containing said allele. In other embodiments, said method further comprises producing a progeny plant with *Fusarium* stalk rot resistance from said first plant. In some embodiments, producing the progeny plant comprises marker-assisted selection for *Fusarium* stalk rot resistance. In further embodiments, said progeny plant is an F2-F6 progeny plant. In yet further embodiments, producing said progeny plant comprises backcrossing.

In another aspect, the invention provides a method of producing a corn plant with enhanced *Fusarium* stalk rot resistance comprising: a) crossing a first corn plant comprising a *Fusarium* stalk rot resistance allele with a second corn plant of a different genotype to produce one or more progeny plants; and b) selecting a progeny plant based on the presence of said allele at a polymorphic locus genetically linked to a chromosomal segment flanked by marker loci AY110352 and TIDP5096 or marker loci TIDP3099 and IDP4363; and wherein said allele confers enhanced resistance to Fusarium stalk rot compared to a plant lacking said allele. In some embodiments, said segment is flanked by marker loci TIDP3078 and umc60 or marker loci TIDP3728 and TIDP5537. In other embodiments, said segment is flanked by marker loci SEQ ID NO: 1 and SEQ ID NO: 5 or marker loci csu329 and IDP6942. In yet other embodiments, said segment is flanked by marker loci SEQ ID NO: 90 and SEQ ID NO: 2 or marker loci SEQ ID NO: 6 and SEQ ID NO: 17. In some embodiments, said polymorphic locus comprises a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17; SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, and SEQ ID NO: 101. In certain embodiments, said progeny plant is an F2-F6 progeny plant. In other embodiments, producing said progeny plant comprises backcrossing. In some embodiments, backcrossing comprises from 2-7 generations of backcrosses. In further embodiments, backcrossing comprises marker-assisted selection in at least two generations. In yet further embodiments, backcrossing comprises marker-assisted selection in all generations. In some embodiments, said first corn plant is an inbred or a hybrid. In other embodiments, said second corn plant is an agronomically elite corn plant. In further embodiments, said agronomically elite corn plant is an inbred or a hybrid.

DETAILED DESCRIPTION OF THE INVENTION

I. Chromosome Intervals

The term "chromosome interval" designates a contiguous linear span of genomic DNA that resides in planta on a single chromosome. The term also designates any and all genomic intervals defined by any of the markers set forth in this invention. The genetic elements located on a single chromosome interval are physically linked and the size of a chromosome interval is not particularly limited. In some aspects, the genetic elements located within a single chromosome interval are genetically linked, typically with a genetic recombination distance of, for example, less than or equal to 20 cM, or alternatively, less than or equal to 10 cM. That is, two genetic elements within a single chromosome interval undergo meiotic recombination at a frequency of less than or equal to 20% or 10%, respectively.

The boundaries of a chromosome interval can be defined by genetic recombination distance or by markers. In one embodiment, the boundaries of a chromosome interval comprise markers. In another embodiment, the boundaries of a chromosome interval comprise markers that will be linked to the gene controlling the trait of interest, i.e., any marker that lies within a given interval, including the terminal markers that defining the boundaries of the interval, and that can be used as a marker for the presents or absence of disease resistance. In one embodiment, the intervals described herein encompass marker clusters that co-segregate with disease resistance. The clustering of markers occurs in relatively small domains on the chromosomes, indicating the presence of a genetic locus controlling the trait of interest in those chromosome regions. The interval encompasses markers that map within the interval as well as the markers that define the terminal.

An interval described by the terminal markers that define the endpoints of the interval will include the terminal markers and any marker localizing within that chromosome domain, whether those markers are currently known or unknown. Although it is anticipated that one skilled in the art may describe additional polymorphic sites at marker loci in and around the markers identified herein, any marker within the chromosome intervals described herein that are associated with disease resistance fall within the scope of this claimed invention.

"Quantitative trait loci" or a "quantitative trait locus" (QTL) is a genetic domain that effects a phenotype that can be described in quantitative terms and can be assigned a "phenotypic value" which corresponds to a quantitative value for the phenotypic trait. A QTL can act through a single gene mechanism or by a polygenic mechanism. In some aspects, the invention provides QTL chromosome intervals, where a QTL (or multiple QTLs) that segregates with disease resistance is contained in those intervals. In one embodiment of this invention, the boundaries of chromosome intervals are drawn to encompass markers that will be linked to one or more QTL. In other words, the chromosome interval is drawn such that any marker that lies within that interval (including the terminal markers that define the boundaries of the interval) is genetically linked to the QTL. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

FSR-3.01 and FSR-8.01 Chromosome Intervals

In one embodiment, the present invention provides a plant comprising a nucleic acid molecule selected from the group consisting of SEQ ID NO: 1-17 and 86-87, fragments thereof, and complements of both. In another embodiment, the present invention also provides a plant comprising the alleles of the FSR-3.01 or FSR-8.01 chromosome intervals, or fragments and complements thereof, as well as any plant comprising any combination of one or more disease resistance loci linked to at least one marker selected from the group consisting of SEQ ID NOs: 1-17. Such alleles may be homozygous or heterozygous.

The locations in the maize genome of FSR-3.01 and the chromosome intervals comprising markers closely linked to it are disclosed in Table 1a. The locations in the maize genome of FSR-8.01 and the chromosome intervals comprising markers closely linked to it are disclosed in Table 1b. Genetic map loci are represented in cM, with position zero being the first (most distal) marker known at the beginning of the chromosome on both Monsanto's internal consensus genetic map and the Neighbors 2008 maize genomic map, which is freely available to the public from the Maize GDB website and commonly used by those skilled in the art. Also disclosed in Table 1a are the physical locations of loci as they are reported on the B73 RefGen_v2 sequence public assembly by the Arizona Genomics Institute, available on the internet.

TABLE 1a

Genetic and physical map positions of markers and chromosome intervals associated with FSR-3.01.

| | Relative Genetic Map Position† | | Physical Map Position†† | | |
|---|---|---|---|---|---|
| | MON | IBM2 | | | |
| Marker/Locus | Map cM | Map lcM | Contig | Chr Start | Chr End |
| AY110352 | 92.1 | 315.4 | AC210054.3 | 137,393,153 | 137,393,815 |
| umc2600 | 92.7 | 318.6 | * | * | * |
| psk2 | 92.9 | 319.2 | * | * | * |
| TIDP3705 | 93.9 | 322.7 | AC211202.4 | 146,523,093 | 146,525,347 |
| TIDP3078 | 97.3 | 336.8 | AC207629.3 | 151,704,461 | 151,708,725 |
| umc1307 | 98.2 | 339.6 | * | * | * |
| SEQ ID NO. 86 | 100.8 | 348.1 | * | * | * |
| IDP1974 | 102.1 | 349.8 | AC197365.3 | 158,226,570 | 158,227,199 |
| SEQ ID NO. 1 | 102.2 | 352.2 | * | * | * |
| SEQ ID NO. 87 | 102.49 | * | * | * | * |
| cdo109 | 103.0 | 352.0 | * | * | * |
| umc2265 | 103.9 | 354.0 | * | * | * |
| SEQ ID NO. 88 | 103.95 | * | * | * | * |
| TIDP5176 | 104.0 | 354.1 | AC209769.3 | 157,199,237 | 157,200,546 |
| SEQ ID NO. 89 | 104.2 | 358.1 | * | * | * |
| SEQ ID NO. 90 | 105 | 360.5 | * | * | * |
| SEQ ID NO. 91 | 106.19 | * | * | * | * |
| SEQ ID NO. 92 | 106.22 | * | * | * | * |
| SEQ ID NO. 93 | 107.14 | * | * | * | * |
| TIDP6282 | 107.8 | 367.6 | * | 160,569,420 | 160,571,111 |
| mHbrBC105-Mo17 | 108.1 | 368.4 | * | * | * |
| SEQ ID NO. 94 | 108.5 | 368.3 | * | * | * |
| SEQ ID NO. 95 | 108.7 | * | * | * | * |
| SEQ ID NO. 96 | 108.8 | 369.4 | * | * | * |
| SEQ ID NO. 97 | 109.01 | * | * | * | * |
| SEQ ID NO. 98 | 109.3 | 371.4 | * | * | * |
| SEQ ID NO. 99 | 110.3 | 378.4 | * | * | * |
| TIDP6314 | 110.9 | 381.8 | AC197369.3 | 162,296,473 | 162,297,710 |
| SEQ ID NO. 2 | 110.9 | 382.6 | * | * | * |
| umc1400 | 111.3 | 384.1 | * | * | * |
| AY111296 | 111.4 | 384.9 | AC196009.2 | 166,450,397 | 166,451,768 |
| phm2885 | 111.7 | 386.4 | * | * | * |
| SEQ ID NO. 3 | 111.8 | 388.9 | * | * | * |
| SEQ ID NO. 100 | 111.8 | 388.9 | * | * | * |
| SEQ ID NO. 101 | 112.2 | 390.8 | * | * | * |
| bnl5.37b | 112.2 | 390.8 | AC210716.4 | 168,366,251 | 168,368,471 |
| ig1 | 112.6 | 392.0 | * | * | * |
| FSR-3.01 | 112.9 | 392.8 | * | * | * |
| IDP7722 | 113.2 | 393.6 | AC209753.3 | 169,614,610 | 169,617,490 |
| IDP4102 | 114.0 | 396.0 | | 170,056,595 | 170,062,921 |
| IDP5975 | 117.3 | 405.2 | AC215304.3 | 172,136,757 | 172,138,424 |
| pza02402 | 117.7 | 407.1 | * | * | * |
| SEQ ID NO. 4 | 118.0 | 408.4 | * | * | * |
| agrr184b | 118.2 | 409.5 | * | * | * |
| IDP73 | 118.3 | 409.8 | AC207759.3 | 173,015,455 | 173,016,795 |
| IDP854 | 122.8 | 426.2 | AC218092.3 | 177,251,217 | 177,253,603 |
| SEQ ID NO. 5 | 122.8 | 426.3 | * | * | * |
| mHbrBG120-B73 | 123.1 | 427.7 | * | * | * |
| IDP9062 | 123.4 | 429.4 | AC191121.3 | 177,993,852 | 177,999,020 |
| TIDP3062 | 127.7 | 451.0 | AC209080.3 | 179,515,709 | 179,517,154 |
| umc1951 | 129.7 | 452.7 | * | * | * |
| umc60 | 128.0 | 452.7 | AC209784.3 | 181,079,164 | 181,079,889 |
| gpm298 | 132.8 | 464.9 | * | * | * |
| gpm753d | 133.1 | 465.9 | * | * | * |
| TIDP5096 | 133.9 | 468.2 | SV208660.3 | 183,383,223 | 183,384,638 |

†cM = centiMorgans, lcM = map units of the IBM2 2008 Neighbors Genetic Map.
††Arizona Genomics Institute B73 RefGen_v2 sequence.
*Exact coordinates not known. Coordinates can be estimated based on nearest flanking loci with known coordinates.

TABLE 1b

Genetic and physical map positions of markers and chromosome intervals associated with FSR-8.01

| | Relative Genetic Map Position† | | Physical Map Position†† | | |
|---|---|---|---|---|---|
| | MON | IBM2 | | | |
| Marker/Locus | Map cM | Map IcM | Contig | Chr Start | Chr End |
| TIDP3099 | 50.3 | 145.24 | AC211474.3 | 16,743,915 | 16,746,003 |
| umc1790 | 50.6 | 146.24 | * | * | * |
| pco120121b | 51.5 | 148.68 | * | * | * |
| umc1974 | 52.8 | 153.3 | AC187868.3 | 16,951,357 | 16,952,136 |
| TIDP3728 | 55.6 | 161.57 | AC211862.4 | 18,445,056 | 18,450,115 |
| pza02454 | 56.2 | 163.2 | * | * | * |
| csu329 | 60.9 | 175.9 | AC187096.5 | 20,836,155 | 20,836,957 |
| TIDP5282 | 61 | 176.22 | AC194455.3 | 21,845,185 | 21,846,346 |
| si605038f07 | 65.9 | 197.39 | * | * | * |
| mmp158b | 66 | 197.9 | * | * | * |
| umc1157 | 67.9 | 206 | AC203336.3 | 70,970,790 | 70,971,548 |
| umc1802 | 68.7 | 208.6 | * | * | * |
| SEQ ID NO: 6 | 69 | 233.6 | * | * | * |
| AY110113 | 69 | 209.5 | * | * | * |
| IDP4740 | 69.2 | 210.4 | AC203025.3 | 37,639,446 | 37,641,719 |
| mHbrMC218-Mo17 | 69.8 | 211.95 | * | * | * |
| TIDP2981 | 70.1 | 212.6 | AC233874.3 | 39,208,198 | 39,209,848 |
| umc1377 | 70.2 | 212.78 | * | * | * |
| FSR8.01 | 71 | 214.9 | * | * | * |
| TIDP3186 | 71.2 | 215.18 | AC200279.3 | 74,529,969 | 74,532,587 |
| IDP8100 | 71.3 | 215.4 | AC186573.3 | 72,875,502 | 72,876,977 |
| umc2354 | 71.7 | 216.2 | * | * | * |
| SEQ ID NO: 7 | 71.9 | 216.7 | * | * | * |
| bnl10.39 | 72 | 217.1 | * | * | * |
| phm11114 | 72.3 | 220.6 | * | * | * |
| SEQ ID NO: 8 | 72.7 | 223 | * | * | * |
| cdo202e(mcf) | 73 | 224.8 | * | * | * |
| umc1415 | 73.9 | 228.6 | AC198494.3 | 90,090,088 | 90,090,703 |
| SEQ ID NO: 9 | 74.2 | 236 | * | * | * |
| SEQ ID NO: 10 | 74.8 | 236.2 | * | * | * |
| umc2075 | 74.9 | 244.9 | AC187095.4 | 95,022,313 | 95,023,319 |
| umc1615 | 75.1 | 246.2 | * | * | * |
| SEQ ID NO: 11 | 75.3 | 240.4 | * | * | * |
| gpm842 | 75.3 | 247.8 | * | * | * |
| IDP7861 | 75.3 | 248 | AC195139.3 | 91,198,710 | 91,204,796 |
| TIDP2787 | 75.9 | 251.6 | AC206644.4 | 93,196,687 | 93,197,665 |
| SEQ ID NO: 12 | 77 | 254.7 | * | * | * |
| umc1302 | 77.1 | 260.4 | * | * | * |
| TIDP5619 | 77.8 | 265.2 | AC194944.3 | 98,401,907 | 98,403,980 |
| SEQ ID NO: 13 | 78.3 | 265.6 | * | * | * |
| SEQ ID NO: 14 | 78.3 | 265.6 | * | * | * |
| AY109740 | 78.3 | 268.6 | * | * | * |
| IDP179 | 79.3 | 275.2 | AC199187.3 | 100,957,496 | 100,958,829 |
| pza03135 | 79.4 | 275.7 | * | * | * |
| SEQ ID NO: 15 | 79.5 | 275.7 | * | * | * |
| bnlg119 | 79.7 | 277.8 | * | * | * |
| umc1735 | 80 | 279.9 | AC226575.4 | 101,349,090 | 101,349,799 |
| IDP6942 | 81 | 283.1 | AC204384.3 | 101,408,509 | 101,410,224 |
| SEQ ID NO: 16 | 81.1 | 283.3 | * | * | * |
| umc1457 | 81.5 | 284.6 | AC234152.3 | 102,138,514 | 102,138,808 |
| SEQ ID NO: 17 | 81.7 | 285.3 | * | * | * |
| agrc478 | 82.7 | 287.4 | * | * | * |
| TIDP5537 | 83.6 | 289.5 | AC234152.3 | 102,168,566 | 102,170,132 |
| IDP294 | 90.9 | 315.7 | AC197600.3 | 117,896,373 | 117,896,994 |
| mHbrBC384-Mo17 | 91.2 | 316.69 | * | * | * |
| IDP4363 | 91.7 | 318.05 | AC197705.4 | 118,075,051 | 118,077,149 |

†cM = centiMorgans, IcM = map units of the IBM2 2008 Neighbors Genetic Map.
††Arizona Genomics Institute B73 RefGen_v2 sequence.
* Exact coordinates not known. Coordinates can be estimated based on nearest flanking loci with known coordinates.

In Table 1, "IcM" refers to the map units of the IBM2 2008 Neighbors Genetic Map, which was generated with an intermated recombinant inbred population (syn 4) that resulted in approximately a four-fold increase in the number of meiosies as compared to the typical recombination experiment that is used to generate centiMorgan (cM) distances (Lee et al., 2002, *Plant Mol Biol* 48:453 and the Maize Genetics and Genomics Database). "cM" refers to the classical definition of a centimorgan (Haldane 1919 *J Genet* 8:299-309) wherein one cM is equal to a 1% chance that a trait at one genetic locus will be separated from a trait at another locus due to crossing over in a single meiosis (meaning the traits cosegregate 99% of the time), and this definition is used herein to delineate map locations pertaining to this invention.

For example, the FSR-3.01 chromosome interval contains SEQ ID NOs: 1-5 and SEQ ID Nos. 86-101, and is flanked by the markers AY110352 and TIDP5096, which are separated by approximately 40 cM on the internally-derived genetic map. This chromosome interval encompasses a marker cluster that co-segregates with FSR resistance in the populations studied at a p-value≤0.05. The FSR-3.01 interval provided herein comprises markers AY110352, umc2600, psk2, TIDP3705, TIDP3078, umc1307, IDP1974, SEQ ID NO: 1, cdo109, umc2265, TIDP5176, TIDP6282, mHbrBC105-Mo17, TIDP6314, SEQ ID NO: 2, umc1400, AY111296, phm2885, SEQ ID NO: 3, bnl5.37b, ig1, FSR-3.01, IDP7722, IDP4102, IDP5975, pza02402, SEQ ID NO: 4, agrr184b, IDP73, IDP854, SEQ ID NO: 5, mHbrBG120-B73, IDP9062, TIDP3062, umc1951, umc60, gpm298, gpm753d, and TIDP5096. An example of a subinterval of the FSR-3.01 interval is that which is flanked by SEQ ID NO: 1 and SEQ ID NO: 5, separated by approximately 20.6 cM on the internally-derived genetic map, that define a chromosome interval encompassing a cluster of markers that co-segregate with FSR resistance in the populations studied at a p-level≤0.05. In some embodiments, the marker co-segregating with FSR resistance is selected from the group consisting of: SEQ ID NO: 1, SEQ ID NO: 2, SEQ ID NO: 3, SEQ ID NO: 4, and SEQ ID NO: 5. A further example of a subinterval of the FSR-3.01 interval is that which is flanked by SEQ ID NO: 86 and SEQ ID NO: 101 encompassing a cluster of markers that co-segregate with FSR resistance. In some embodiments, the marker co-segregating with FSR resistance is selected from the group consisting of: SEQ ID NO: 86, SEQ ID NO: 1, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 2, SEQ ID NO: 100, and SEQ ID NO: 101.

Similarly, the FSR-8.01 chromosome interval contains SEQ ID NOs: 6-17 and is flanked by the markers TIDP3099 and IDP4363, which are separated by approximately 40 cM on the internally-derived genetic map. This chromosome interval encompasses a marker cluster that co-segregates with FSR resistance in the populations studied at a p-value≤0.05. The FSR-8.01 interval provided herein comprises markers TIDP3099, umc1790, pco120121b, umc1974, TIDP3728, pza02454, csu329, TIDP5282, si605038f07, mmp158b, umc1157, umc1802, SEQ ID NO: 6, AY110113, IDP4740, mHbrMC218-Mo17, TIDP2981, umc1377, FSR8.01, TIDP3186, IDP8100, umc2354, SEQ ID NO: 7, bnl10.39, phm11114, SEQ ID NO: 8, cdo202e (mcf), umc1415, SEQ ID NO: 9, SEQ ID NO: 10, umc2075, umc1615, SEQ ID NO: 11, gpm842, IDP7861, TIDP2787, SEQ ID NO: 12, umc1302, TIDP5619, SEQ ID NO: 13, SEQ ID NO: 14, AY109740, IDP179, pza03135, SEQ ID NO: 15, bnlg119, umc1735, IDP6942, SEQ ID NO: 16, umc1457, SEQ ID NO: 17, agrc478, TIDP5537, IDP294, mHbrBC384-Mo17, and IDP4363. An example of a subinterval of the FSR-8.01 interval is that which is flanked by SEQ ID NO: 6 and SEQ ID NO: 17, separated by approximately 12.7 cM on the internally-derived genetic map, that define a chromosome interval encompassing a cluster of markers that co-segregate with FSR resistance in the populations studied at a p-level≤0.05. In some embodiments, the marker co-segregating with FSR resistance is selected from the group consisting of: SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

Thus, one skilled in the art can use this invention to improve the efficiency of breeding for improved disease resistance in maize by associating disease resistance phenotypes with genotypes at previously unknown disease resistance loci in the maize genome. Disclosed herein are chromosome intervals that comprise alleles responsible for phenotypic differences between disease resistant and disease susceptible corn lines. Each chromosome interval is characterized by the genomic regions including and flanked by and including the markers psk2 and gpm753d on chromosome 3 or umc1790 and mHbrBC384-Mo17 on chromosome 8, and comprise markers within or closely linked to (within 20 cM of) FSR-3.01 or FSR-8.01, respectively. This invention also comprises other intervals whose boarders fall between, and including, those of psk2 and gpm753d or umc1790 and mHbrBC384-Mo17, or any interval closely linked to those intervals.

Examples of markers useful for this purpose comprise the SNP markers listed in Tables 1a or 1b, or any marker that maps within the chromosome intervals described herein (including the termini of the intervals), or any marker linked to those markers. Such markers can be assayed simultaneously or sequentially in a single sample or population of samples.

Accordingly, the markers and methods of the present invention can be utilized to guide MAS or breeding maize varieties with the desired complement (set) of allelic forms of chromosome intervals associated with superior agronomic performance (resistance, along with any other available markers for yield, disease resistance, etc.). Any of the disclosed marker alleles can be introduced into a corn line via introgression, by traditional breeding (or introduced via transformation, or both) to yield a corn plant with superior agronomic performance. The number of alleles associated with resistance that can be introduced or be present in a corn plant of the present invention ranges from one to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein could be useful and within the scope of this invention.

Similarly, by identifying plants lacking the desired marker locus, susceptible or less resistant plants can be identified, and, e.g., eliminated from subsequent crosses. Similarly, these marker loci can be introgressed into any desired genomic background, germplasm, plant, line, variety, etc., as part of an overall MAS breeding program designed to enhance yield. The invention also provides chromosome QTL intervals that find equal use in MAS to select plants that demonstrate disease resistance or improved tolerance. Similarly, the QTL intervals can also be used to counter-select plants that are susceptible or have reduced resistance to disease.

The present invention also extends to a method of making a progeny corn plant and these progeny corn plants, per se. The method comprises crossing a first parent corn plant with a second corn plant and growing the female corn plant under plant growth conditions to yield corn plant progeny. Methods of crossing and growing corn plants are well within the ability of those of ordinary skill in the art. Such corn plant progeny can be assayed for alleles associated with resistance and, thereby, the desired progeny selected. Such progeny plants or seed can be sold commercially for corn production, used for food, processed to obtain a desired constituent of the corn, or further utilized in subsequent rounds of breeding. At least one of the first or second corn plants is a corn plant of the present invention in that it comprises at least one of the allelic forms of the markers of the present invention, such that the progeny are capable of inheriting the allele.

Often, a method of the present invention is applied to at least one related corn plant such as from progenitor or descendant lines in the subject corn plants' pedigree such that inheritance of the desired resistance allele can be traced. The number of generations separating the corn plants being subject to the methods of the present invention will generally be from 1 to 20, commonly 1 to 5, and typically 1, 2, or 3 generations of separation, and quite often a direct descendant or parent of the corn plant will be subject to the method (i.e., one generation of separation).

Thus, with this invention, one skilled in the art can detect the presence or absence of disease resistance genotypes in the genomes of corn plants as part of a marker assisted selection program. In one embodiment, a breeder ascertains the genotype at one or more markers for a disease resistant parent, which contains a disease resistance allele, and the genotype at one or more markers for a susceptible parent, which lacks the resistance allele. For example, the markers of the present invention can be used in MAS in crosses involving elite×exotic corn lines by subjecting the segregating progeny to MAS to maintain disease resistance alleles, or alleles associated with yield under disease conditions. A breeder can then reliably track the inheritance of the resistance alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the disease resistant parent can be reliably predicted to express the resistant phenotype; progeny that share genotypes with the disease susceptible parent can be reliably predicted to express the susceptible phenotype. Thus, the laborious and inefficient process of manually phenotyping the progeny for disease resistance is avoided.

By providing the positions in the maize genome of the intervals and the disease resistance associated markers within, this invention also allows one skilled in the art to identify other markers within the intervals disclosed herein or linked to the chromosome intervals disclosed herein.

Closely linked markers flanking the locus of interest that have alleles in linkage disequilibrium with a resistance allele at that locus may be effectively used to select for progeny plants with enhanced resistance to disease conditions. Thus, the markers described herein, such as those listed in Tables 1a or 1b, as well as other markers genetically or physically mapped to the same chromosome interval, may be used to select for maize plants with enhanced resistance to disease conditions. Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. In an introgression program, this allows for selection of the gene or locus genotype at the more proximal polymorphic markers and selection for the recurrent parent genotype at the more distal polymorphic markers.

The choice of markers actually used to practice this invention is not particularly limited and can be any marker that maps within the FSR-3.01 or FSR-8.01 chromosome intervals described herein, any marker closely linked (within 10 cM) to a marker in the FSR-3.01 or FSR-8.01 chromosome intervals, or any marker selected from SEQ ID NO: 1-17 and 86-87, or the markers listed in Tables 1a or 1b. Furthermore, since there are many different types of marker detection assays known in the art, it is not intended that the type of marker detection assay (e.g. RAPDs, RFLPs, SNPs, AFLPs, etc.) used to practice this invention be limited in any way.

II. Molecular Genetic Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., disease resistance). As used herein, a QTL marker has a minimum of one favorable allele, although it is possible that the marker might have two or more favorable alleles found in the population. Any favorable allele of that marker can be used advantageously for the identification and construction of disease resistant plant lines. Optionally, one, two, three or more favorable allele(s) of different markers are identified in, or introgressed into a plant, and can be selected for or against during MAS. Desirably, plants or germplasm are identified that have at least one such favorable allele that positively correlates with disease resistance or improved disease resistance. Alternatively, a marker allele that co-segregates with disease susceptibility also finds use with the invention, since that allele can be used to identify and counter select disease susceptible plants. Such an allele can be used for exclusionary purposes during breeding to identify alleles that negatively correlate with resistance, to eliminate susceptible plants or germplasm from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of anyone particular marker) on the basis of polynucleotide length and/or sequence. A large number of corn molecular markers are known in the art, and are published or available from various sources, such as the MaizeGDB internet resource. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one resistance marker, or alternatively, favorable alleles from more than one resistance marker are introgressed into a desired germplasm. One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are known in the art. Identification and use of such favorable alleles is within the scope of this invention. Furthermore still, identification of favorable marker alleles in plant populations other than the populations used or described herein is within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more property of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

While the exemplary markers provided in the figures and tables herein are either SNP markers, any of the aforementioned marker types can be employed in the context of the invention to identify chromosome intervals encompassing genetic element that contribute to superior agronomic performance (e.g., disease resistance or improved disease tolerance).

Probes and Primers

In general, synthetic methods for making oligonucleotides, including probes, primers, molecular beacons, PNAs, LNAs (locked nucleic acids), etc., are known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon.

It is not intended that the nucleic acid probes of the invention be limited to any particular size.

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

III. Linkage Analysis and QTL

Linkage Analysis

"Linkage", or "genetic linkage," is used to describe the degree with which one marker locus is "associated with" another marker locus or some other locus (for example, a resistance locus). For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus can be associated with (linked to) a trait, e.g., a marker locus can be associated with resistance or improved tolerance to a plant pathogen when the marker locus is in linkage disequilibrium (LD) with the resistance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 20, 19, 18, 17, 16, 15, 14, 13, 12, 11, 10, 9, 8, 7, 6, 5, 4, 3, 2, 1, 0.75, 0.5 or 0.25 cM or less from each other.

Classical linkage analysis can be thought of as a statistical description of the relative frequencies of co segregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate. This can be expressed as a percentage of cosegregation (recombination frequency) or, also commonly, in centiMorgans (cM).

Linkage analysis is used to determine which polymorphic marker allele demonstrates a statistical likelihood of co-segregation with the resistance phenotype (thus, a "resistance marker allele"). Following identification of a marker allele for co-segregation with the resistance phenotype, it is possible to use this marker for rapid, accurate screening of plant lines for the resistance allele without the need to grow the plants through their life cycle and await phenotypic evaluations, and furthermore, permits genetic selection for the particular resistance allele even when the molecular identity of the actual resistance QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

Quantitative Trait Loci

An allele of a QTL can comprise multiple genes or other genetic factors even within a contiguous genomic region or linkage group, such as a haplotype. As used herein, an allele of a disease resistance locus can encompass more than one gene or nucleotide sequence where each individual gene or nucleotide sequence is also capable of exhibiting allelic variation and where each gene or nucleotide sequence is also capable of eliciting a phenotypic effect on the quantitative trait in question. In an aspect of the present invention the allele of a QTL comprises one or more genes or nucleic acid sequences that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular disease locus or for a particular polymorphic marker.

The principles of QTL analysis and statistical methods for calculating linkage between markers and useful QTL, or between any loci in a genome are well known in the art. Exemplary methods include penalized regression analysis, ridge regression, single point marker analysis, complex pedigree analysis, Bayesian MCMC, identity-by-descent analysis, interval mapping, composite interval mapping, and Haseman-Elston regression. QTL analyses are often performed with the help of a computer and specialized software available from a variety of public and commercial sources known to those of skill in the art.

IV. Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM). In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through Marker assisted selection (MAS), a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with the disease resistance phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

V. Marker Assisted Selection, Plant Breeding, and Genomic Introgression

Marker Assisted Selection

"Introgression" refers to the transmission of a desired allele of a genetic locus from one genetic background to another by. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that are resistant, exhibit improved resistance or are susceptible to FSR infection by identifying plants having a specified allele that is linked to FSR-3.01 or FSR-8.01.

In general, MAS uses polymorphic markers that have been identified as having a significant likelihood of co-segregation with a resistance trait. Such markers are presumed to map near a gene or genes that give the plant its resistance phenotype, and are considered indicators for the desired trait, and are termed QTL markers. Plants are tested for the presence or absence of a desired allele in the QTL marker.

Identification of plants or germplasm that include a marker locus or marker loci linked to a resistance trait or traits provides a basis for performing marker assisted selection. Plants that comprise favorable markers or favorable alleles are selected for, while plants that comprise markers or alleles that are negatively correlated with resistance can be selected against. Desired markers and/or alleles can be introgressed into plants having a desired (e.g., elite or exotic) genetic background to produce an introgressed resistant plant or germplasm. In some aspects, it is contemplated that a plurality of resistance markers are sequentially or simultaneous selected and/or introgressed. The combinations of resistance markers that are selected for in a single plant is not limited, and can include any combination of markers disclosed herein or any marker linked to the markers disclosed herein, or any markers located within the QTL intervals defined herein.

In some embodiments, the allele that is detected is a favorable allele that positively correlates with disease resistance or improved disease tolerance. In the case where more than one marker is selected, an allele is selected for each of the markers; thus, two or more alleles are selected. In some embodiments, it can be the case that a marker locus will have more than one advantageous allele, and in that case, either allele can be selected. It will be appreciated that the ability to identify QTL marker loci alleles that correlate with resistance, improved tolerance, or susceptibility of a corn plant to disease conditions provides a method for selecting plants that have favorable marker loci as well. That is, any plant that is identified as comprising a desired marker locus (e.g., a marker allele that positively correlates with resistance) can be selected for, while plants that lack the locus, or that have a locus that negatively correlates with resistance, can be selected against.

In some embodiments, a disease resistant first corn plant or germplasm (the donor) can be crossed with a second corn plant or germplasm (the recipient, e.g., an elite or exotic corn, depending on characteristics that are desired in the progeny) to create an introgressed corn plant or germplasm as part of a breeding program designed to improve disease resistance of the recipient corn plant or germplasm. In some aspects, the recipient plant can also contain one or more disease resistant loci, which can be qualitative or quantitative trait loci. In another aspect, the recipient plant can contain a transgene.

In some embodiments, the recipient corn plant or germplasm will typically display reduced resistance to disease conditions as compared to the first corn plant or germplasm, while the introgressed corn plant or germplasm will display an increased resistance to disease conditions as compared to the second plant or germplasm. An introgressed corn plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one or multiple traits, e.g., multiple loci involved in resistance, or multiple loci each involved in resistance or tolerance to different diseases, the efficiency of MAS compared to phenotypic screening becomes even greater, because all of the loci can be evaluated in the lab together from a single sample of DNA.

Marker Assisted Backcrossing

One application of MAS is to use the resistance or improved tolerance markers to increase the efficiency of an introgression effort aimed at introducing a resistance QTL into a desired (typically high yielding) background. If the nucleic acids from a plant are positive for a desired genetic marker allele, the plant can be self fertilized to create a true breeding line with the same genotype, or it can be crossed with a plant with the same marker or with other characteristics to create a sexually crossed hybrid generation.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable resistance marker loci) into an otherwise desirable genetic background from the recurrent parent (e.g., an otherwise high yielding line). The more cycles of back crossing that are done, the greater the genetic contribution of the recurrent parent to the resulting introgressed variety. This is often necessary, because resistant plants may be otherwise undesirable, e.g., due to low yield, low fecundity, or the like. In contrast, strains which are the result of intensive breeding programs may have excellent yield, fecundity or the like, merely being deficient in one desired trait such as resistance to FSR infection.

Moreover, in another aspect, while maintaining the introduced markers associated with resistance, the genetic contribution of the plant providing disease resistance can be reduced by back-crossing or other suitable approaches. In one aspect, the nuclear genetic material derived from the donor material in the plant can be less than or about 50%, less than or about 25%, less than or about 13%, less than or about 5%, 3%, 2% or 1%, but that the recipient remains resistant to disease.

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

VI. Transgenic Plants

Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the present disclosure, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant.

Regulatory elements such as promoters, leaders, enhancers, introns, and transcription termination regions (or 3' UTRs) can play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron. In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Regulatory elements may be characterized by their gene expression pattern, e.g., positive and/or negative effects, such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the disclosure.

In specific embodiments, chimeric DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

Exemplary promoters for expression of a nucleic acid sequence include plant promoters such as the CaMV 35S promoter, or others such as CaMV 19S, nos, Adh, sucrose synthase, α-tubulin, actin, cab, PEPCase or those promoters associated with the R gene complex. Tissue-specific promoters such as leaf specific promoters, or tissue selective promoters (e.g., promoters that direct greater expression in leaf primordia than in other tissues), and tissue-specific enhancers are also contemplated to be useful, as are inducible promoters such as ABA- and turgor-inducible promoters. Any suitable promoters known in the art may be used to express defensin or defensin-like coding sequences in a plant. In an embodiment, the CaMV35S promoter may be used to express defensin or defensin-like coding sequences in a plant. In yet another embodiment, a disease or pathogen inducible promoter can be used to express defensin or defensin like proteins. Examples of disease or pathogen inducible promoters can be found in Kooshki et al. Plant Science 165 (2003) 213-219, Koschmann et al. Plant Physiology 160 (2012) 178-191, Rushton et al. The Plant Cell, 14 (2002) 749-762, and Kirsch et al. The Plant Journal (2001) 26 217-227.

The DNA sequence between the transcription initiation site and the start of the coding sequence, i.e., the untranslated leader sequence, can also influence gene expression. As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. One may thus wish to employ a particular leader sequence with a transformation construct of the present disclosure. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of defensin or defensin-like coding sequences.

It is envisioned that defensin or defensin-like coding sequences may be introduced under the control of novel promoters, enhancers, etc., or homologous or tissue-specific or tissue-selective, or pathogen or disease promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure.

Transformation constructs prepared in accordance with the present disclosure may further include a 3' end DNA sequence that acts as a signal to terminate transcription and allow for the polyadenylation of the mRNA produced by coding sequences operably linked to a promoter. As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR. In one embodiment, the native terminator of a defensin or defensin-like coding sequence may be used. Alternatively, a heterologous 3' end may enhance the expression of sense or antisense defensin or defensin-like coding sequences.

Sequences that are joined to the coding sequence of an expressed gene, which are removed post-translationally from the initial translation product and which facilitate the transport of the protein into or through intracellular or extracellular membranes, are termed transit or targeting peptide (usually into vacuoles, vesicles, plastids and other intracellular organelles) and signal peptide or sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein.

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the present disclosure.

Selectable marker transgenes may also be used with the present disclosure. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the present disclosure are known in the art and include, but are not limited to, transcribable DNA molecules encoding ß-glucuronidase (GUS), green fluorescent protein (GFP), proteins that confer antibiotic resistance, and proteins that confer herbicide tolerance.

VII. Plant Cell Transformation Methods

Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. U.S. Pat. No. 6,384,301 (soybean), U.S. Pat. No. 7,026,528 (wheat) and U.S. Pat. No. 6,329,571 (rice), and US Patent Application Publication Nos. US 2004/0087030 A1 (cotton), and US 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance or pest resistance or enhanced water use efficiency, to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application using a selective agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and U.S. Pat. No. 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

VIII. Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits, such as resistance to *Fusarium* stalk rot in maize.

IX. General Terms and Definitions

Systems, including automated systems for selecting plants that comprise a marker of interest and/or for correlating presence of the marker with resistance are also a feature of the invention. These systems can include probes relevant to marker locus detection, detectors for detecting labels on the probes, appropriate fluid handling elements and temperature controllers that mix probes and templates and/or amplify templates and systems instructions that correlate label detection to the presence of a particular marker locus or allele.

In an aspect, this invention could be used on any plant. In another aspect, the plant is selected from the genus *Zea*. In another aspect, the plant is selected from the species *Zea mays*. In a further aspect, the plant is selected from the subspecies *Zea mays* L. ssp. *mays*. In an additional aspect, the plant is selected from the group *Zea mays* L. subsp. *mays* Indentata, otherwise known as dent corn. In another aspect, the plant is selected from the group *Zea mays* L. subsp. *mays* Indurata, otherwise known as flint corn. In an aspect, the plant is selected from the group *Zea mays* L. subsp. *mays* Saccharata, otherwise known as sweet corn. In another aspect, the plant is selected from the group *Zea mays* L. subsp. *mays* Amylacea, otherwise known as flour corn. In a further aspect, the plant is selected from the group *Zea mays* L. subsp. *mays* Everta, otherwise known as pop corn. *Zea* plants include hybrids, inbreds, partial inbreds, or members of defined or undefined populations.

In a preferred aspect, the present invention provides a plant to be assayed for resistance or susceptibility to disease by any method to determine whether a plant is resistant, susceptible, or whether it exhibits some degree of resistance or susceptibility. Populations of plants can be similarly characterized in this manner, or further characterized as segregating for the trait of disease resistance.

It is further understood that a plant of the present invention may exhibit the characteristics of any relative maturity group. In an aspect, the maturity group is selected from the group consisting of early maturing varieties, mid season maturing varieties, and full season varieties.

The present invention also provides for parts of the plants of the present invention. Plant parts, without limitation, include seed, endosperm, ovule and pollen. In a particularly preferred aspect of the present invention, the plant part is a seed.

In another aspect, the corn seed can be subjected to various treatments. For example, the seeds can be treated to improve germination by priming the seeds or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

In another aspect, the corn plant can show a comparative resistance compared to a non-resistant control corn plant. In this aspect, a control corn plant will preferably be genetically similar except for the disease resistance allele or alleles in question. Such plants can be grown under similar conditions with equivalent or near equivalent exposure to the pathogen.

Various patent and non-patent publications are cited herein, the disclosures of each of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

Descriptions of commonly used breeding terms and methods for crossing and producing hybrids that are used to describe present invention can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), *Center for Agricultural Publishing and Documentation*, 1979; Fehr, In: Soybeans: Improvement, Production and Uses, 2nd Edition, Monograph., 16:249, 1987; Fehr, "Principles of variety development," *Theory and Technique*, (Vol. 1) and *Crop Species Soybean* (Vol. 2), Iowa State Univ., Macmillan Pub. Co., NY, 360-376, 1987).

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in Alberts et al., Molecular Biology of The Cell, $5^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes Icorn, Oxford University Press New York, 2007. The nomenclature for DNA bases as set forth at 37 CFR § 1.822 is used.

Definitions

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

"Allele" generally refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self fertilization (selfing).

"Elite line" means any line that has resulted from breeding and selection for superior agronomic performance. Numerous elite lines are available and known to those of skill in the art of corn breeding. An "elite population" is an assortment of elite individuals or lines that can be used to represent the state of the art in terms of agronomically superior genotypes of a given crop species, such as corn. Similarly, an "elite germplasm" or elite strain of germplasm is an agronomically superior germplasm, typically derived from and/or capable of giving rise to a plant with superior agronomic performance, such as an existing or newly developed elite line of corn. In contrast, an "exotic line" or "exotic germplasm" is a line or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

"Linkage disequilibrium" or "LD" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

"Locus" a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker Assisted Selection" (MAS) is a process by which phenotypes are selected based on marker genotypes.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Percent identity" or "% identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc.,), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a resistance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different corn line) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant lines, or plant families under disease conditions, and furthermore, will also recognize the phenotypic gradations of "resistant."

"Resistance locus" means a locus that contributes resistance, tolerance, or susceptibility to *Fusarium* stalk rot.

"Resistance allele" means the nucleic acid sequence associated with resistance or tolerance to disease.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tolerance" or "improved tolerance" in a plant to disease conditions is an indication that the plant is less affected by disease conditions with respect to yield, survivability and/or other relevant agronomic measures, compared to a less resistant, more "susceptible" plant. Tolerance is a relative term, indicating that a "tolerant" plant survives and/or produces better yields in disease conditions compared to a different (less tolerant) plant (e.g., a different corn line strain) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance or susceptibility of different plants, plant lines or plant families under disease conditions, and furthermore, will also recognize the phenotypic gradations of "tolerant."

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "sub cloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Yield" is the culmination of all agronomic traits as determined by the productivity per unit area of a particular plant product of commercial value. "Agronomic traits," include the underlying genetic elements of a given plant variety that contribute to yield over the course of growing season.

EXAMPLES

Example 1. Inoculation and Assessment of FSR Resistance Phenotypes

Corn plants were inoculated 10 days after flowering by injecting an internode of each stalk with $2 \times 10^5$ *Fusarium moniliforme* spores suspended in 2 mL of distilled water. Six weeks after inoculation, the severity of *Fusarium* stalk rot in each plant was visually assessed by splitting stalks longitudinally to expose the pith. Internodes at the site of inoculation were examined to determine the percent of the internode showing visual lesions characteristic of the disease (necrosis), as summarized in Table 2. The individual plant scores of each row were then averaged to generate a final score for the row.

TABLE 2

Rating Scale of relative FSR infection resistance phenotypes.

| % Internode Necrosis | Score | Rating |
|---|---|---|
| 0-10% | 1 | Highly resistant |
| 10-20% | 2 | Highly resistant |
| 20-30% | 3 | Resistant |
| 30-40% | 4 | Resistant |
| 40-50% | 5 | Intermediate |
| 50-60% | 6 | Susceptible |
| 60-70% | 7 | Susceptible |
| >80% | 8 | Highly susceptible |
| >80% and necrosis expands to adjacent internode | 9 | Highly susceptible |

Example 2. Assays Useful for Detecting FSR Resistance Genotypes

For convenience, primer sequences for amplifying SNP marker loci linked to FSR-3.01 or FSR-8.01 and the probes used to genotype the corresponding SNP sequences are provided in Table 3. The SNP position within the SEQ ID NO. is given in the second column. Primer and probe synthesis is within the skill of the art once the SNP position in the corn genome is provided. One of skill in the art will also immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Also, configuration of the amplification primers and detection probes can, of course, vary. Thus, the invention is not limited to the primers, probes, or marker sequences specifically recited herein.

TABLE 3

Primers and probes useful for detecting FSR resistance.

| SEQ ID NO. | SNP Pos | SEQ ID NO. | | | |
|---|---|---|---|---|---|
| | | Fwd Primer | Rev Primer | Probe 1 | Probe 2 |
| 1 | 81 | 18 | 35 | 52 | 69 |
| 2 | 46 | 19 | 36 | 53 | 70 |
| 3 | 49 | 20 | 37 | 54 | 71 |
| 4 | 319 | 21 | 38 | 55 | 72 |
| 5 | 96 | 22 | 39 | 56 | 73 |
| 6 | 180 | 23 | 40 | 57 | 74 |
| 7 | 263 | 24 | 41 | 58 | 75 |
| 8 | 132 | 25 | 42 | 59 | 76 |
| 9 | 538 | 26 | 43 | 60 | 77 |
| 10 | 49 | 27 | 44 | 61 | 78 |
| 11 | 139 | 28 | 45 | 62 | 79 |
| 12 | 101 | 29 | 46 | 63 | 80 |
| 13 | 551 | 30 | 47 | 64 | 81 |
| 14 | 101 | 31 | 48 | 65 | 82 |
| 15 | 968 | 32 | 49 | 66 | 83 |
| 16 | 58 | 33 | 50 | 67 | 84 |
| 17 | 101 | 34 | 51 | 68 | 85 |

Illustrative FSR resistance marker DNA sequences SEQ ID NOs: 1, 5, or 14 can be amplified using the primers indicated in Table 3 using SEQ ID NOs: 18 and 35, 22 and 39, or 31 and 48, respectively, and detected with probes indicated in Table 3 as SEQ ID NOs: 52 and 69, 56 and 73, or 65 and 82, respectively.

Example 3. Marker-Trait Association Study

Two replicates of F2-derived F3 individuals and F4 individuals derived from F3 heterozygotes by the cross between a resistant inbred maize line and a susceptible inbred maize line were inoculated and phenotyped for FSR resistance at La Charca and Tlajomulco, Mexico using methods described in Example 1.

DNA was also extracted from each individual in each replicate at each location and genotyped with over 100 SNP markers that were selected to collectively span the maize genome (Table 4). Loci were eliminated from further analysis where they were monomorphic in the subject population studied.

Marker-trait association studies were performed using both single-marker analysis (SMA) and composite interval mapping (CIM). For each marker, the thresholds of Likelihood ratio between full and null models for CIM were based on 1000 permutation tests and the thresholds (p-value) for SMA were based on 10,000 permutation tests (Churchill and Doerge 1994).

TABLE 4

Two replicates of two independent populations derived from FSR resistant and FSR susceptible parents were inoculated with FSR spores, phenotyped for FSR resistance, and genotyped with either 141 or 144 SNP markers.

| Population | Location | No. of Individuals | No. of SNP |
|---|---|---|---|
| 1 | La Charca, Tlajomulco | 299 | 141 |
| 2 | La Charca, Tlajomulco | 179 | 144 |

Detection of FSR-3.01

Table 5 lists the effect estimates on FSR resistance phenotype ratings associated with markers that revealed significant associations with FSR-3.01. Each row provides the SEQ ID NO. of the marker, and the estimated effect that the marker polymorphism had on the FSR phenotype. The statistical significance (p-value) of the association between the marker and the FSR resistance rating in each case was p-val≤0.001.

TABLE 5

Effect estimates on FSR ratings of example markers associated with FSR-3.01.

| SEQ ID NO. | Effect Estimate |
|---|---|
| 1 | 0.56 |
| 2 | 0.67 |
| 3 | 0.2 |
| 4 | 0.55 |
| 5 | 0.52 |

For example, SEQ ID NO: 1 was associated with a 0.56 change in FSR resistance rating by one copy of the favorable allele. SEQ ID NO: 3 was associated with a 0.2 change in FSR resistance rating by one copy of the favorable allele. FSR resistance ratings were generated using the methods described in Example 1.

Table 6 describes the chromosome 3 profile of the FSR-3.01 QTL revealed by the CIM analysis, including the chromosome interval where the Likelihood ratio was within the threshold of p-value≤0.01.

TABLE 6

Results of the composite interval mapping (CIM) analysis on chromosome 3. SEQ ID NO: 1 and SEQ ID NO: 5 mark the ends of the region of the chromosome where the CIM Likelihood ratio remained within the threshold of p-value ≤0.01. The peak of the Likelihood ratio corresponds to the FSR-3.01 locus.

| CIM Profile Feature | CIM Profile Position on MON Map (cM) | Locus/Nearest Marker | Locus/Marker Position† MON Map (cM) | IBM2 Map (IcM) |
|---|---|---|---|---|
| Left Border | 102.2 | SEQ ID NO: 1 | 102.2 | 352.2 |
| Likelihood ratio peak | 112.9 | FSR-3.01 | 112.9 | 392.8 |
| Right Border | 122.8 | SEQ ID NO: 5 | 122.8 | 426.3 |

†cM = centiMorgans, IcM = map units of the IBM2 2008 Neighbors Genetic Map.

Thus, the CIM analysis revealed that markers within the interval flanked by and including markers SEQ ID NO: 1 and SEQ ID NO: 5 were highly associated with FSR-3.01 (p-value≤0.01). Markers bordering FSR-3.01 also find utility with this invention, but their associations with that interval tend to decrease as their locations become further removed from FSR-3.01.

Detection of FSR-8.01

Table 7 lists the effect estimates on FSR resistance phenotype ratings associated with markers that revealed significant associations with FSR-8.01. Each row provides the SEQ ID NO. of the marker, and the estimated effect that the marker polymorphism had on the FSR phenotype. The statistical significance (p-value) of the association between the marker and the FSR resistance rating in each case was p-val≤0.001.

TABLE 7

Effect estimates on FSR ratings of example markers associated with FSR-8.01.

| SEQ ID NO. | Effect Estimate |
| --- | --- |
| 7 | 1.177 |
| 8 | 1.181 |
| 9 | 1.237 |
| 10 | 1.161 |
| 11 | 1.142 |
| 12 | 1.175 |
| 13 | 1.19 |
| 14 | 1.172 |
| 15 | 1.202 |
| 16 | 1.109 |
| 17 | 1.141 |

For example, SEQ ID NO: 9 was associated with a 1.237 change in FSR resistance rating by one copy of the favorable allele. SEQ ID NO: 14 was associated with a 1.172 change in FSR resistance rating by one copy of the favorable allele. FSR resistance ratings were generated using the methods described in Example 1.

Table 8 describes the chromosome 8 profile of the FSR-8.01 QTL revealed by the CIM analysis, including the chromosome interval where the Likelihood ratio was within the threshold of p-value≤0.01.

TABLE 8

Results of the composite interval mapping (CIM) analysis on chromosome 8. SEQ ID NO: 6 and SEQ ID NO: 17 mark the ends of the region of the chromosome where the CIM Likelihood ratio remained within the threshold of p-value ≤0.01. The peak of the Likelihood ratio corresponds to the FSR-8.01 locus.

| CIM Profile Feature | CIM Profile Position on MON Map (cM) | Locus/Nearest Marker | Locus/Marker Position† MON Map cM | IBM2 Map IcM |
| --- | --- | --- | --- | --- |
| Left Boarder | 69.0 | SEQ ID NO: 6 | 69.0 | 233.6 |
| Likelihood ratio peak | 71.0 | FSR-8.01 | 71.0 | 214.9 |
| Right Boarder | 81.7 | SEQ ID NO: 17 | 81.7 | 285.3 |

†cM = centiMorgans, IcM = map units of the IBM2 2008 Neighbors Genetic Map.

Thus, the CIM analysis revealed that markers within the interval flanked by and including markers SEQ ID NO: 6 and SEQ ID NO: 17 were highly associated with FSR-8.01 (p-value≤0.01). Markers bordering FSR-8.01 also find utility with this invention, but their associations with that interval tend to decrease as their locations become further removed from FSR-8.01.

Example 4. Detecting FSR Resistance in a Population of Plants and Monitoring the Introgression of FSR Resistance Loci from One Plant Line into Another Via MAS A population of corn plants can be phenotyped using any method that gauges the effect of FSR infection on a plant trait, including the methods described herein. The genotypes of the plants in the population at one or more markers that map to the FSR-3.01 or FSR-8.01 chromosome intervals, or at one or more markers closely linked to one of those intervals, can also be determined. In one embodiment, statistical associations can then be made between the recorded phenotypes and the genotypes using a variety of methods known in the art, including those described herein.

In one embodiment, genotypes of offspring derived from one or more individuals in the population can be compared to the genotypes of the parents at one or more marker loci linked to the FSR-3.01 or FSR-8.01 genotypes of the parents at those same loci. Individuals that share marker genotypes with the resistant parent at one or more markers can then be selected for advancement in the breeding program. Individuals that do not share marker genotypes with the resistant parent, or individuals that do share marker genotypes with the susceptible parent, can be discarded. This process saves the laborious and time consuming process of phenotyping plants to verify which are resistant or susceptible.

In some embodiments, useful markers comprise any marker that is within or genetically linked to FSR-3.01 or FSR-8.01. In other embodiments, use markers comprise any marker that is between publically available markers psk2 and gpm753d. In other embodiments, useful markers comprise any marker that is between publically available markers umc1790 and mHbrBC384-Mo17. In other embodiments, associations are made between genotypes for one or more SNP markers that map between publically available markers psk2 and gpm753d or umc1790 and mHbrBC384-Mo17.

Selections and assays may be performed on single loci, or simultaneously on multiple loci. For example, a breeder skilled in the art could base advancement decisions on the genotypes of markers linked to FSR-3.01 or FSR-8.01 and genotypes of markers linked to other loci, simultaneously. For instance, a breeder may require that the same plant must exhibit genotypes at one or more markers linked to FSR-3.01 or FSR-8.01 and/or at one or more markers linked to any other locus in order to be advanced. In one embodiment, a breeder may require that the same plant must exhibit genotypes at one or more markers linked to FSR-3.01 and FSR-8.01 in order to be advanced. In other embodiments, a single genotype at only one locus may be sufficient for advancement.

By selecting only those individuals with the desired genotype for advancement in the breeding program, the frequency of desired alleles and desired phenotypes can be increased in future generations.

The introgression of one or more desired loci from a donor line into another is achieved via repeated backcrossing to a recurrent parent accompanied by selection to retain one or more FSR resistance loci from the donor parent. Markers associated with FSR resistance are assayed in progeny and those progeny with one or more FSR resistance markers are selected for advancement. In another aspect, one or more markers can be assayed in the progeny to select for plants with the genotype of the agronomically elite parent. This invention anticipates that trait introgression activities will require more than one generation, wherein progeny are crossed to the recurrent (agronomically elite) parent or selfed. Selections are made based on the presence of one or more FSR resistance markers and can also be made based on the recurrent parent genotype, wherein screening is performed on a genetic marker and/or phenotype basis. In another embodiment, markers of this invention can be used in conjunction with other markers, ideally at least one on each chromosome of the corn genome, to track the introgression of other desired traits as well as FSR resistance loci into elite germplasm. In yet another embodiment, at least 100 SNP markers assorted across the 10 chromosomes of corn will be useful in conjunction with the SNP molecular markers of the present invention to follow the introgression of other desired traits as well as FSR resistance into elite germplasm. In a preferred embodiment, about three hundred fifty SNP markers, distributed every 5 centimorgans across the 10 chromosomes of the corn genetic linkage map, will be useful in conjunction with the SNP molecular markers of the present invention to follow the introgression of other desired traits as well as FSR resistance into elite germplasm. In another embodiment, QTLs associated with FSR resistance will be useful in conjunction with SNP molecular markers of the present invention to combine quantitative and qualitative FSR resistance in the same plant. It is within the scope of this invention to utilize the methods and compositions for trait integration of FSR resistance. It is contemplated that the present invention will be useful for developing commercial varieties with FSR resistance and an agronomically elite phenotype.

For example, one skilled in the art can use one or more markers linked to FSR-3.01 or FSR-8.01, for example, those listed in Table 1a or Table 1b, to select plants for FSR resistance genotypes arising from the donor while selecting for the recipient genotypes in adjacent chromosome regions. In practice, this reduces the amount of linkage drag from the donor genome that maybe associated with undesirable agronomic properties. This backcrossing procedure is implemented at any stage in line development and occurs in conjunction with breeding for superior agronomic characteristics or one or more traits of interest, including transgenic and nontransgenic traits.

Alternatively, a forward breeding approach is employed wherein one or more FSR resistance loci can be monitored for successful introgression following a cross with a susceptible parent with subsequent generations genotyped for one or more FSR resistance loci and for one or more additional traits of interest, including transgenic and non-transgenic traits.

This invention can be used on populations other than those specifically described in this application without altering the methods described herein. Although different parents may have different genotypes at different markers, the method of using this invention is fundamentally identical. Parents are first phenotyped for FSR resistance, genotyped at each marker, and then those genotypes are used to infer resistant or susceptible phenotypes in progeny derived from those parents or in any other population where the genotypes are associated with the same phenotypes.

Example 5. Fine-Mapping of FSR-3.01 by Joint Linkage Analysis

The original QTL identification was from three bi-parental mapping populations. The three bi-parental populations were merged for joint linkage mapping (Table 9). CV056629/CV344635, CV334995/I180580 and CV374246/CV344635. CV344635 is described in U.S. Pat. No. 8,471,127 issued Jun. 25, 2013, which is incorporated herein by reference in its entirety. CV334995 is described in U.S. Pat. No. 7,709,709 issued May 4, 2010, which is incorporated herein by reference in its entirety. I180580 is described in U.S. Pat. No. 7,173,171 issued Feb. 6, 2007, which is incorporated herein by reference in its entirety. CV374246 is described in U.S. Pat. No. 7,875,775 issued Jan. 25, 2011, which is incorporated herein by reference in its entirety. CV344635 was derived from I180580.

TABLE 9

Mapping Populations

| Project ID | Mapping population | Resistant Line | Susceptible Line | Population Type | Population Size |
|---|---|---|---|---|---|
| A | CV056629/CV344635 | CV344635 | CV056629 | F4 | 179 |
| B | CV334995/I180580 | I180580 | CV334995 | F3 | 236 |
| C | CV374246/CV344635 | CV344635 | CV374246 | DH | 242 |
| JOINT | Multi-Origin | I180580_CV344635 | CV056629_CV374246_CV334995 | JNT | 644 |

To increase the marker density in the chromosome interval associated with FSR-3.01, 16 new SNP markers were developed (see Table 10) that collectively spanned 100.8-112.2 cM on chromosome 3 in the maize genome. The SNP position within the SEQ ID NO. is given in the second column. One of skill in the art will recognize that other sequences to either side of the given primers can also be effectively used, so long as they primers can amplify a region that includes the allele to be detected. Further, it will be appreciated that the precise probe to be used for detection can vary, e.g., any probe that can identify the region of a marker amplicon to be detected can be substituted for those examples provided herein. Configuration of the amplification primers and detection probes may also vary. Thus, the invention is not limited to the primers, probes, or marker sequences specifically recited herein.

fine-mapped to a 5.9 cM interval (105-110.9 cM). The QTL effect for one copy of favorable allele was 0.542 rating score. FSR resistance ratings were generated using the methods described in Example 1. The phenotypic variance explained ($R^2$) by this QTL was 21%.

TABLE 11

Summary of LASSO result in fine-mapping of FSR-3.01

| Project ID | Population Type | #Mk | Chr | Left | Right | p-value | Additive | QTL $R^2$ | Total $R^2$ |
|---|---|---|---|---|---|---|---|---|---|
| Joint | Inbred | 329 | 3 | 105 | 110.9 | 0.01 | 0.542 | 0.213 | 0.413 |

Table 12 lists the estimated effects of markers associated with FSR-3.01 in joint linkage mapping by single-marker association (SMA) analysis. Each row provides the SEQ ID NO of the marker, genetic map loci are represented in cM, with position zero being the first (most distal) marker known at the beginning of the chromosome on Monsanto's internal consensus genetic map, F statistical value, p-value and the estimated effect that the marker polymorphism had on the FSR phenotype.

TABLE 10

Primers and probes useful for fine-mapping of FSR-3.01

| | SEQ ID NO. | | | | |
|---|---|---|---|---|---|
| SEQ ID NO. | SNP Position | Fwd Primer | Rev Primer | Probe 1 | Probe 2 |
| 86 | 216 | 102 | 118 | 134 | 150 |
| 1 | 81 | 18 | 35 | 52 | 69 |
| 87 | 151 | 103 | 119 | 135 | 151 |
| 88 | 151 | 104 | 120 | 136 | 152 |
| 89 | 194 | 105 | 121 | 137 | 153 |
| 90 | 101 | 106 | 122 | 138 | 154 |
| 91 | 151 | 107 | 123 | 139 | 155 |
| 92 | 151 | 108 | 124 | 140 | 156 |
| 93 | 151 | 109 | 125 | 141 | 157 |
| 94 | 101 | 110 | 126 | 142 | 158 |
| 95 | 151 | 111 | 127 | 143 | 159 |
| 96 | 180 | 112 | 128 | 144 | 160 |
| 97 | 151 | 113 | 129 | 145 | 161 |
| 98 | 101 | 114 | 130 | 146 | 162 |
| 99 | 101 | 115 | 131 | 147 | 163 |
| 2 | 46 | 19 | 36 | 53 | 70 |
| 100 | 101 | 116 | 132 | 148 | 164 |
| 101 | 200 | 117 | 133 | 149 | 165 |

644 plants were genotyped using the SNP markers shown in Table 10, and the data was combined into previous genotyping information. Marker-trait association studies were performed using both least absolute shrinkage and selection operator (LASSO) (Robert Tibshirani, 1995) model and single-marker association (SMA) analysis. Table 11 provides the Project ID, population type, number of markers used, chromosome position, left and right flanking positions of this QTL on Monsanto's internal consensus genetic map, additive effect, and phenotypic variance of this QTL or Total ($R^2$). The QTL associated with FSR-3.01 was

TABLE 12

Allele effects of markers associated with FSR-3.01 in joint linkage mapping.

| SEQ ID NO. | MON Map cM | Fstat | Permutation testing Probability | Single Allele Effect |
|---|---|---|---|---|
| 86 | 100.8 | 182.3 | 0.001 | 0.56 |
| 1 | 102.2 | 180.9 | 0.001 | 0.56 |
| 87 | 102.5 | 185.1 | 0.001 | 0.56 |
| 88 | 104.0 | 188.3 | 0.001 | 0.57 |
| 89 | 104.2 | 187.4 | 0.001 | 0.56 |
| 90 | 105.0 | 190.5 | 0.001 | 0.57 |
| 91 | 106.2 | 163.1 | 0.001 | 0.54 |
| 92 | 106.2 | 163.7 | 0.001 | 0.54 |
| 93 | 107.1 | 174.7 | 0.001 | 0.56 |
| 94 | 108.5 | 174.0 | 0.001 | 0.56 |
| 95 | 108.7 | 173.1 | 0.001 | 0.55 |
| 96 | 108.8 | 163.1 | 0.001 | 0.54 |
| 97 | 109.0 | 167.4 | 0.001 | 0.55 |
| 98 | 109.3 | 164.6 | 0.001 | 0.55 |
| 99 | 110.3 | 173.0 | 0.001 | 0.56 |
| 2 | 110.9 | 181.8 | 0.001 | 0.57 |
| 100 | 111.8 | 173.1 | 0.001 | 0.55 |
| 101 | 112.2 | 161.9 | 0.001 | 0.53 |

*P-value is based on 10,000 permutation tests.

For example, SEQ ID NO: 86 was associated with a 0.56 change in FSR resistance rating by one copy of the favorable allele.

Example 6. Annotated Genes within FSR-3.01 or FSR-8.01

Table 13 lists annotated coding sequences within the FSR-3.01 and FSR-8.01 regions. Each row provides gene ID, gene annotation, chromosome location, genetic position on Monsanto internal consensus map and physical position based on Arizona Genomics Institute B73 RefGen_v2 sequence which is publicly available. Transgenic maize resistant to *Fusarium* stalk rot can be generated using these annotated genes as described herein.

TABLE 13

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 1 | Histidine kinase 2 n = 1 Tax = Zea mays RepID = Q76H00_MAIZE (0.0); CHASE: CHASE domain (3.9e-68); HisKA: His Kinase A (phosphoacceptor) domain (1.2e-24); HATPase_c: Histidine kinase, DNA gyrase B-, and HSP90-like ATPase (2.9e-31); Response_reg: Response regulator receiver domain (4.5e-25); GO_MF:GO:0016772, transferase activity, transferring phosphorus-containing groups# (0.0); GO_BP:GO:0018106, peptidyl-histidine phosphorylation# (0.0); GO_CC:GO:0016020, membrane# (0.0) | 3 | 102.2 | 158889193 | 158896487 |
| 2 | OSJNBa0053B21.7 protein n = 3 Tax = Oryza sativa RepID = Q7XKR4_ORYSJ (1e-145); CG-1: CG-1 domain (3.6e-78); Ank: Ankyrin repeat (13); Ank: Ankyrin repeat (5e-06); Topo-VIb_trans: Topoisomerase VI B subunit, transducer (0.08); IQ: IQ calmodulin-binding motif (18); IQ: IQ calmodulin-binding motif (0.004); IQ: IQ calmodulin-binding motif (0.0036); GO_MF:GO:0030528, transcription regulator activity# (0.0); GO_BP:GO:0045449, regulation of transcription# (0.0); GO_CC:GO:0005634, nucleus# (0.0) | 3 | 102.2 | 158894821 | 158901970 |
| 3 | HAT family dimerisation domain containing protein n = 4 Tax = Oryza sativa Japonica Group RepID = Q7G4F1_ORYSJ (1e-176); hATC: hAT family dimerisation domain (2.9e-32); GO_MF:GO:0046983, protein dimerization activity# (1e-176); GO_BP:GO:0032196, transposition# (1e-136) | 3 | 102.2 | 158915841 | 158918155 |
| 4 | CBS domain containing protein n = 5 Tax = Poaceae RepID = B6U1W0_MAIZE (0.0); CBS: CBS domain (5.7e-25); CBS: CBS domain (3e-20); PB1: PB1 domain (6.3e-16); GO_MF:GO:0003824, catalytic activity# (3e-55); GO_BP:GO:0008152, metabolic process# (3e-55) | 3 | 102.2 | 158974015 | 158978428 |
| 5 | MADS-box transcription factor 8 n = 3 Tax = Zea mays RepID = B6T9L2_MAIZE (3e-64); SRF-TF: SRF-type transcription factor (DNA-binding and dimerisation domain) (1.8e-25); GO_MF:GO:0043565, sequence-specific DNA binding# (3e-64); GO_BP:GO:0045449, regulation of transcription# (3e-64); GO_CC:GO:0005634, nucleus# (3e-64) | 3 | 102.2 | 158979849 | 159007027 |
| 6 | Transposase n = 1 Tax = Zea mays RepID = A5X2G8_MAIZE (1e-176); hATC: hAT family dimerisation domain (7.1e-29); GO_MF:GO:0046983, protein dimerization activity# (0.0); GO_BP:GO:0006468, protein amino acid phosphorylation# (1e-43) | 3 | 102.2 | 159003437 | 159006179 |
| 7 | Putative uncharacterized protein n = 1 Tax = Zea mays RepID = B6T0P1_MAIZE (9e-21) | 3 | 102.2 | 159169715 | 159170268 |
| 8 | Squamosa promoter-binding-like protein 2 n = 2 Tax = Oryza sativa RepID = SPL2_ORYSJ (6e-67); SBP: SBP domain (1.9e-48); GO_MF:GO:0046872, metal ion binding# (6e-67); GO_BP:GO:0045449, regulation of transcription# (6e-67); GO_CC:GO:0005634, nucleus# (6e-67) | 3 | 102.3 | 159377754 | 159381056 |
| 9 | C/VIF2 n = 2 Tax = Zea mays RepID = B6TMN1_MAIZE (9e-16); PMEI: Plant invertase/pectin methylesterase inhibitor (1.5e-19); GO_MF:GO:0030599, pectinesterase activity# (4e-28); GO_BP:GO:0004857, enzyme inhibitor activity# (4e-28) | 3 | 102.3 | 159479564 | 159480232 |
| 10 | Putative basic helix-loop-helix protein BHLH12 n = 1 Tax = Lotus japonicus RepID = C0IP17_LOTJA (6e-32); HLH: Helix-loop-helix DNA-binding domain (0.0003); GO_MF:GO:0030528, transcription regulator activity# (3e-39); GO_BP:GO:0045449, regulation of transcription# (3e-39); GO_CC:GO:0005634, nucleus# (3e-39) | 3 | 102.3 | 159485166 | 159485874 |
| 11 | Nucleobase ascorbate transporter n = 2 Tax = Populus trichocarpa RepID = B9MYJ5_POPTR (2e-39); Xan_ur_permease: Permease family (0.069); GO_MF:GO:0005215, transporter activity# (3e-52); GO_BP:GO:0055085, transmembrane transport# (3e-52); GO_CC:GO:0016020, membrane# (3e-52) | 3 | 102.3 | 159604854 | 159607076 |
| 12 | 40S ribosomal protein S7 n = 2 Tax = Poaceae RepID = RS7_SECCE (3e-98); Ribosomal_S7e: Ribosomal protein S7e (3.3e-84); GO_MF:GO:0003735, structural constituent of ribosome# (3e-98); GO_BP:GO:0006412, translation# (3e-98); GO_CC:GO:0030529, ribonucleoprotein complex# (3e-98) | 3 | 102.3 | 159608077 | 159610141 |
| 13 | Helicase-like protein n = 1 Tax = Oryza sativa Japonica Group RepID = Q5VR06_ORYSJ (1e-114); GO_MF:GO:0004386, helicase activity# (1e-114) | 3 | 102.3 | 159666647 | 159667759 |
| 14 | Putative retrotransposon protein n = 1 Tax = Phyllostachys edulis RepID = D3IVP0_9POAL (3e-86); DUF889: Eukaryotic protein of unknown function (DUF889) (1.2e-54); GO_MF:GO:0004386, helicase activity# (7e-83) | 3 | 102.3 | 159669204 | 159670250 |
| 15 | Retrotransposon protein n = 1 Tax = Zea mays RepID = B6U894_MAIZE (8e-44); GO_MF:GO:0004386, helicase activity# (1e-28) | 3 | 102.3 | 159670783 | 159673146 |
| 16 | Putative uncharacterized protein n = 1 Tax = Zea mays RepID = B6UBS8_MAIZE (4e-91) | 3 | 102.3 | 159677432 | 159679346 |
| 17 | HAT dimerisation domain-containing protein, putative n = 1 Tax = Oryza sativa Japonica Group RepID = Q84MT5_ORYSJ (3e-32); GO_MF:GO:0046983, protein dimerization activity# (3e-30) | 3 | 102.3 | 159685435 | 159690179 |
| 18 | Putative reverse transcriptase n = 1 Tax = Sorghum bicolor RepID = Q8LJX1_SORBI (2e-49); GO_MF:GO:0003964, RNA-directed DNA polymerase, group II intron encoded# (2e-49); GO_BP:GO:0006278, RNA-dependent DNA replication# (2e-49) | 3 | 102.5 | 159704324 | 159705004 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 19 | Acyl-[acyl-carrier-protein] desaturase, chloroplastic n = 1 Tax = *Elaeis guineensis* RepID = STAD_ELAGV (1e-175); FA_desaturase_2: Fatty acid desaturase (4.5e-244); GO_MF:GO:0009536, transition metal ion binding# (0.0); GO_BP:GO:0055114, oxidation reduction# (0.0); GO_CC:GO:0009536, plastid# (1e-175) | 3 | 103.3 | 160666708 | 160671413 |
| 20 | Hydrolase-like protein n = 1 Tax = *Zea mays* RepID = B6SRX1_MAIZE (1e-163); Abhydrolase_1: alpha/beta hydrolase fold (4.4e-09); GO_MF:GO:0016787, hydrolase activity# (1e-163) | 3 | 103.3 | 160750607 | 160754718 |
| 21 | Probable auxin efflux carrier component 6 n = 4 Tax = Poaceae RepID = PIN6_ORYSJ (1e-159); Mem_trans: Membrane transport protein (1.1e-72); GO_MF:GO:0010329, IDA#auxin efflux transmembrane transporter activity# (3e-43); GO_BP:GO:0055085, transmembrane transport# (1e-159); GO_CC:GO:0016021, integral to membrane# (1e-159) | 3 | 103.35 | 160753025 | 160757157 |
| 22 | OJ1485_B09.11 protein n = 3 Tax = *Oryza sativa* RepID = Q8RZI5_ORYSJ (7e-87); F-box: F-box domain (0.01); Sell: Sell repeat (5.9); Sell: Sell repeat (0.0093); Sell: Sell repeat (0.079); zf-MYND: MYND finger (8.7e-09); GO_MF:GO:0008270, zinc ion binding# (7e-87); GO_CC:GO:0005634, nucleus# (9e-55) | 3 | 103.45 | 159817059 | 159819103 |
| 23 | Putative transformer serine/arginine-rich ribonucleoprotein n = 2 Tax = *Oryza sativa* RepID = Q84QA6_ORYSJ (1e-26); RRM_1: RNA recognition motif. (a.k.a. RRM, RB (7.9e-10); GO_MF:GO:0003676, nucleic acid binding# (5e-29); GO_BP:GO:0008380, RNA splicing# (1e-17); GO_CC:GO:0030529, ribonucleoprotein complex# (1e-17) | 3 | 103.7 | 160563885 | 160566370 |
| 24 | Putative uncharacterized protein n = 1 Tax = *Zea mays* RepID = B6UD01_MAIZE (6e-12) | 3 | 103.75 | 160559981 | 160560684 |
| 25 | Hydrolase-like protein n = 1 Tax = *Zea mays* RepID = B6SRX1_MAIZE (3e-40); GO_MF:GO:0016787, hydrolase activity# (3e-40) | 3 | 103.8 | 160785443 | 160785875 |
| 26 | FK506-binding protein 2-1 n = 3 Tax = Andropogoneae RepID = B4FUK2_MAIZE (3e-69); FKBP_C: FKBP-type peptidyl-prolyl cis-trans isomeras (3.5e-55); GO_MF:GO:0016853, isomerase activity# (3e-69); GO_BP:GO:0006457, protein folding# (3e-69); GO_CC:GO:0005788, endoplasmic reticulum lumen# (8e-54) | 3 | 103.8 | 161953049 | 161955764 |
| 27 | Transcription elongation factor 1 homolog n = 7 Tax = Poaceae RepID = ELOF1_ORYSJ (4e-35); Elf1: Transcription elongation factor Elf1 like (9.3e-48); GO_MF:GO:0046872, metal ion binding# (4e-35); GO_BP:GO:0045449, regulation of transcription# (4e-35); GO_CC:GO:0005634, nucleus# (4e-35) | 3 | 103.9 | 160787852 | 160788759 |
| 28 | Loricrin n = 2 Tax = *Zea mays* RepID = B6SSB2_MAIZE (9e-50) | 3 | 104 | 161893091 | 161894313 |
| 29 | AP-1 complex subunit gamma-2, putative n = 1 Tax = *Ricinus communis* RepID = B9S1S1_RICCO (0.0); Adaptin_N: Adaptin N terminal region (2.7e-57); HEAT: HEAT repeat (9.8e-05); HEAT: HEAT repeat (12); GO_MF:GO:0005515, protein binding# (0.0); GO_BP:GO:0016192, vesicle-mediated transport# (0.0); GO_CC:GO:0030117, membrane coat# (0.0) | 3 | 104.1 | 161847000 | 161856031 |
| 30 | E2 protein isoform 5 n = 2 Tax = *Zea mays* RepID = B6TAW6_MAIZE (2e-48); EnY2: Transcription factor e(y)2 (1.8e-36); GO_MF:GO:0030374, IDA#ligand-dependent nuclear receptor transcription coactivator activity# (4e-17); GO_BP:GO:0051028, mRNA transport# (4e-17); GO_CC:GO:0009941, IDA#chloroplast envelope# (3e-11) | 3 | 104.3 | 160512467 | 160515039 |
| 31 | Putative uncharacterized protein Sb03g043990 n = 2 Tax = Andropogoneae RepID = C5XGA1_SORBI (6e-80); GO_MF:GO:0005515, protein binding# (6e-10); GO_CC:GO:0005886, plasma membrane# (6e-10) | 3 | 104.3 | 160515583 | 160518688 |
| 32 | Dynamin, putative n = 1 Tax = *Ricinus communis* RepID = B9T3E4_RICCO (0.0); MMR_HSR1: GTPase of unknown function (0.0016); Dynamin_N: Dynamin family (1.6e-89); Dynamin_M: Dynamin central region (3.7e-134); GED: Dynamin GTPase effector domain (6e-36); GO_MF:GO:0005525, GTP binding# (0.0); GO_BP:GO:0051301, cell division# (0.0); GO_CC:GO:0016020, membrane# (0.0) | 3 | 104.4 | 160397321 | 160408459 |
| 33 | Catalytic/protein phosphatase type 2C n = 2 Tax = *Zea mays* RepID = B6TWB0_MAIZE (1e-15); GO_MF:GO:0003824, catalytic activity# (1e-15); GO_BP:GO:0004721, phosphoprotein phosphatase activity# (2e-11) | 3 | 104.4 | 160430829 | 160431484 |
| 34 | Catalytic/protein phosphatase type 2C n = 2 Tax = *Zea mays* RepID = B6TWB0_MAIZE (1e-12); GO_MF:GO:0003824, catalytic activity# (1e-12) | 3 | 104.4 | 160431696 | 160432351 |
| 35 | Putative uncharacterized protein 9C20.7 n = 1 Tax = *Zea mays* RepID = Q5NKP3_MAIZE (4e-09) | 3 | 104.4 | 160432563 | 160433166 |
| 36 | Catalytic/protein phosphatase type 2C n = 2 Tax = *Zea mays* RepID = B6TWB0_MAIZE (2e-14); GO_MF:GO:0003824, catalytic activity# (2e-14); GO_BP:GO:0004721, phosphoprotein phosphatase activity# (3e-11) | 3 | 104.4 | 160433431 | 160434086 |
| 37 | Hypersensitivity-induced response-like protein n = 1 Tax = *Cenchrus ciliaris* RepID = Q9AITP0_CENCI (8e-20); GO_MF:GO:0005515, protein binding# (4e-18); GO_CC:GO:0016020, membrane# (2e-18) | 3 | 104.4 | 161765290 | 161765490 |
| 38 | OJ1485_B09.2 protein n = 2 Tax = *Oryza sativa* RepID = Q8RUF2_ORYSJ (8e-92); Nucleotid_trans: Nucleotide-diphospho-sugar transferas (0.036); GO_MF:GO:0003690, IDA#double-stranded DNA binding# (3e-90); GO_BP:GO:0006265, DNA topological change# (3e-90); GO_CC:GO:0005634, nucleus# (9e-58) | 3 | 104.5 | 160303613 | 160305557 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 39 | OJ1485_B09.3 protein n = 1 Tax = Oryza sativa Japonica Group RepID = Q8RZJ3_ORYSJ (1e-82); GO_MF:GO:0003677, DNA binding# (4e-64); GO_BP:GO:0045449, regulation of transcription# (4e-64); GO_CC:GO:0005634, nucleus# (4e-64) | 3 | 104.5 | 160327891 | 160329710 |
| 40 | Putative transposase n = 1 Tax = Zea mays RepID = Q8W0Y1_MAIZE (4e-25) | 3 | 104.5 | 160331611 | 160332429 |
| 41 | Putative uncharacterized protein n = 1 Tax = Zea mays RepID = B6SP05_MAIZE (3e-14) | 3 | 104.6 | 161695642 | 161697306 |
| 42 | Putative uncharacterized protein Sb03g043790 n = 1 Tax = Sorghum bicolor RepID = C5XG81_SORBI (0.0); GO_MF:GO:0003824, catalytic activity## (1e-115) | 3 | 104.6 | 161700194 | 161703481 |
| 43 | Mannosyl-oligosaccharide glucosidase, putative n = 1 Tax = Ricinus communis RepID = B9RMG4_RICCO (0.0); Glyco_hydro_63: Mannosyl oligosaccharide glucosidase (1.9e-60); GO_MF:GO:0004573, mannosyl-oligosaccharide glucosidase activity# (0.0); GO_BP:GO:0009311, IDA#oligosaccharide metabolic process# (0.0); GO_CC:GO:0005783, IDA#endoplasmic reticulum# (1e-177) | 3 | 104.7 | 160074262 | 160087237 |
| 44 | Putative retrotransposon protein n = 1 Tax = Phyllostachys edulis RepID = D3IVT4_9POAL (1e-19); GO_MF:GO:0008270, zinc ion binding# (6e-19); GO_BP:GO:0015074, DNA integration# (6e-19) | 3 | 104.7 | 160113302 | 160113547 |
| 45 | Putative uncharacterized protein Sb04g006710 n = 1 Tax = Sorghum bicolor RepID = C5XXI6_SORBI (1e-124); GO_MF:GO:0003964, RNA-directed DNA polymerase, group II intron encoded# (6e-11); GO_BP:GO:0007165, signal transduction# (5e-12); GO_CC:GO:0005886, plasma membrane# (1e-12) | 3 | 104.7 | 160141479 | 160143346 |
| 46 | OSJNBa0083I11.5 protein n = 1 Tax = Oryza sativa Japonica Group RepID = Q7XM33_ORYSJ (9e-57); RVT_2: Reverse transcriptase (RNA-dependent DNA pol (2.4e-06); GO_MF:GO:0008270, zinc ion binding# (5e-58); GO_BP:GO:0015074, DNA integration# (5e-58); GO_CC:GO:0016021, integral to membrane# (2e-53) | 3 | 104.7 | 160167145 | 160167771 |
| 47 | Protein kinase APK1B, chloroplast, putative n = 1 Tax = Ricinus communis RepID = B9SIV9_RICCO (3e-10); GO_MF:GO:0005524, ATP binding# (4e-10); GO_BP:GO:0006468, protein amino acid phosphorylation# (4e-10) | 3 | 104.7 | 161650237 | 161650694 |
| 48 | Zinc finger CCCH type domain-containing protein ZFN-like 2 n = 3 Tax = Zea mays RepID = B6TK84_MAIZE (1e-166); zf-CCCH: Zinc finger C-x8-C-x5-C-x3 H type (and similar) (1.8e-09); zf-CCCH: Zinc finger C-x8-C-x5-C-x3-H type (and similar) (3.6e-08); zf-CCCH: Zinc finger C-x8-C-x5-C-x3-H type (and similar) (8.5e-11); zf-CCCH: Zinc finger C-x8-C-x5-C-x3-H type (and similar) (3.3e-11); GO_MF:GO:0046872, metal ion binding# (1e-166); GO_BP:GO:0009416, IEP#response to light stimulus# (5e-58); GO_CC:GO:0005634, nucleus# (1e-155) | 3 | 104.75 | 161643342 | 161649531 |
| 49 | Putative uncharacterized protein n = 1 Tax = Zea mays RepID = B6SUB9_MAIZE (1e-69) | 3 | 104.8 | 159990193 | 160008489 |
| 50 | Exostosin-like n = 2 Tax = Andropogoneae RepID = B6UFM1_MAIZE (0.0); Exostosin: Exostosin family (7.5e-96); GO_MF:GO:0016740, transferase activity# (1e-75); GO_BP:GO:0048868, IMP#pollen tube development# (5e-65); GO_CC:GO:0016020, membrane# (0.0) | 3 | 104.8 | 160013230 | 160017242 |
| 51 | Transposon protein CACTA, En/Spm sub-class n = 1 Tax = Zea mays RepID = B6U6W8_MAIZE (2e-43); GO_MF:GO:0046872, metal ion binding# (9e-09); GO_BP:GO:0016070, TAS#RNA metabolic process# (9e-09) | 3 | 104.8 | 160020221 | 160021299 |
| 52 | Putative DNA repair protein rhp54 n = 1 Tax = Oryza sativa Japonica Group RepID = Q7XI63_ORYSJ (3e-34); GO_MF:GO:0005524, ATP binding# (7e-35); GO_BP:GO:0045449, regulation of transcription# (3e-20); GO_CC:GO:0005634, nucleus# (3e-20) | 3 | 104.8 | 161456374 | 161456877 |
| 53 | Putative auxin-independent growth promoter n = 2 Tax = Oryza sativa Japonica Group RepID = Q6Z341_ORYSJ (7e-25) | 3 | 104.8 | 161464517 | 161466445 |
| 54 | ER lumen protein retaining receptor n = 1 Tax = Oryza sativa Japonica Group RepID = B9FES2_ORYSJ (4e-19); GO_MF:GO:0005515, protein binding# (2e-27); GO_BP:GO:0010165, response to X-ray# (2e-27); GO_CC:GO:0005634, nucleus# (2e-27) | 3 | 104.8 | 161558818 | 161562477 |
| 55 | Putative leucine zipper protein n = 1 Tax = Oryza sativa Japonica Group RepID = Q8RZJ0_ORYSJ (0.0); Exo70: Exo70 exocyst complex subunit (5.5e-164); GO_BP:GO:0006887, exocytosis# (0.0); GO_CC:GO:0000145, NAS#exocyst# (0.0) | 3 | 104.85 | 159939500 | 159942907 |
| 56 | Mitochondrial import receptor subunit TOM20 n = 2 Tax = Andropogoneae RepID = B6SZD1_MAIZE (1e-101); TOM20_plant: Plant specific mitochondrial import recep (9.6e-128); GO_MF:GO:0005515, protein binding# (1e-101); GO_BP:GO:0045040, protein import into mitochondrial outer membrane# (1e-101); GO_CC:GO:0005742, mitochondrial outer membrane translocase complex# (1e-101) | 3 | 104.9 | 159873679 | 159879241 |
| 57 | OJ1485_B09.7 protein n = 3 Tax = Oryza sativa RepID = Q8RZJ9_ORYSJ (2e-48); GO_MF:GO:0016301, kinase activity# (4e-29); GO_BP:GO:006301, kinase activity# (4e-29); GO_CC:GO:0009505, IDA#expansin# (6e-29) | 3 | 104.9 | 159936961 | 159938372 |
| 58 | Putative uncharacterized protein n = 1 Tax = Zea mays RepID = C4C41_MAIZE (1e-112); FYVE: FYVE zinc finger (0.083); zf-MIZ: MIZ zinc finger (0.079); zf-C3HC4: Zinc finger, C3HC4 type (RING finger) (6e-09); GO_MF:GO:0046872, metal ion binding# (1e-112) | 3 | 104.95 | 160932864 | 160936118 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 59 | Sucrose-phosphate synthase n = 3 Tax = Andropogoneae RepID = SPS_MAIZE (0.0); Glycos_transf_1: Glycosyl transferases group 1 (8.1e−22); S6PP: Sucrose-6F-phosphate phosphohydrolase (1.1e−05); GO_MF:GO:0046524, sucrose-phosphate synthase activity# (0.0); GO_BP:GO:0009058, biosynthetic process# (0.0); GO_CC:GO:0005886, plasma membrane# (0.0) | 3 | 104.95 | 161252328 | 161258511 |
| 60 | Putative extra sporogenous cells n = 2 Tax = Oryza sativa RepID = Q7F8Q9_ORYSJ (0.0); LRRNT_2: Leucine rich repeat N-terminal domain (3.8e−06); LRR_1: Leucine Rich Repeat (0.94); LRR_1: Leucine Rich Repeat (0.002); LRR_1: Leucine Rich Repeat (4.3); LRR_1: Leucine Rich Repeat (2.3); LRR_1: Leucine Rich Repeat (0.99); LRR_1: Leucine Rich Repeat (8.3); LRR_1: Leucine Rich Repeat (1.7); LRR_1: Leucine Rich Repeat (6.3); LRR_1: Leucine Rich Repeat (12); LRR_1: Leucine Rich Repeat (0.75); LRR_1: Leucine Rich Repeat (5.6); LRR_1: Leucine Rich Repeat (0.64); LRR_1: Leucine Rich Repeat (3.7); LRR_1: Leucine Rich Repeat (2.6); LRR_1: Leucine Rich Repeat (0.91); LRR_1: Leucine Rich Repeat (0.11); LRR_1: Leucine Rich Repeat (54); LRR_1: Leucine Rich Repeat (1.7); LRR_1: Leucine Rich Repeat (1.2); LRR_1: Leucine Rich Repeat (0.34); LRR_1: Leucine Rich Repeat (0.02); LRR_1: Leucine Rich Repeat (8.5); LRR_1: Leucine Rich Repeat (0.78); LRR_1: Leucine Rich Repeat (11); LRR_1: Leucine Rich Repeat (1.8); LRR_1: Leucine Rich Repeat (0.069); LRR_1: Leucine Rich Repeat (14); Pkinase: Protein kinase domain (7.5e−36); Pkinase_Tyr: Protein tyrosine kinase (1.9e−24); GO_MF:GO:0016301, kinase activity# (0.0); GO_BP:GO:0048658, PMID:17727613#tapetal layer development# (0.0); GO_CC:GO:0016021, integral to membrane# (0.0) | 3 | 104.95 | 161580031 | 161583912 |
| 61 | Putative uncharacterized protein n = 1 Tax = Zea mays RepID = COPM38_MAIZE (3e−10); GO_MF:GO:0017111, nucleoside-triphosphatase activity# (3e−10); GO_BP:GO:0009432, SOS response# (3e−10); GO_CC:GO:0005737, cytoplasm# (3e−10) | 3 | 105 | 160872388 | 160877158 |
| 62 | Lysine ketoglutarate reductase trans-splicing related 1-like n = 3 Tax = Oryza sativa RepID = Q5LN0_ORYSJ (1e−148); DUF707: Protein of unknown function (DUF707) (2.8e−205) | 3 | 105 | 160899188 | 160902589 |
| 63 | Putative uncharacterized protein n = 1 Tax = Zea mays RepID = B6T227_MAIZE (1e−09) | 3 | 105 | 161259756 | 161260190 |
| 64 | Zgc:162613 protein n = 3 Tax = Danio rerio RepID = A3KNW8_DANRE (1e−39); DUF647: Protein of unknown function, DUF647 (1.5e−177); GO_MF:GO:0016740, transferase activity# (5e−38); GO_BP:GO:0032502, IMP#developmental process# (1e−166); GO_CC:GO:0005576, extracellular region# (0.0) | 3 | 105 | 161363754 | 161369525 |
| 65 | Zinc finger-like protein (Fragment) n = 1 Tax = Phaseolus vulgaris RepID = Q84U29_PHAVU (8e−15); zf-C3HC4: Zinc finger, C3HC4 type (RING finger) (9.1e−05); GO_MF:GO:0046872, metal ion binding# (1e−102) | 3 | 105 | 161565312 | 161566687 |
| 66 | Wiscott-Aldrich syndrome, C-terminal n = 1 Tax = Zea mays RepID = B6U4M1_MAIZE (7e−48); B12D: B12D protein (2.8e−06); PBD: P21-Rho-binding domain (3.2e−09) | 3 | 105 | 161567574 | 161574608 |
| 67 | TA1 protein (Fragment) n = 1 Tax = Oryza sativa Japonica Group RepID = Q70KS8_ORYSJ (1e−85); HLH: Helix-loop-helix DNA-binding domain (1.1e−07); GO_MF:GO:0030528, transcription regulator activity# (0.0); GO_BP:GO:0045449, regulation of transcription# (0.0); GO_CC:GO:0005634, nucleus# (0.0) | 3 | 107.15 | 162063107 | 162066385 |
| 68 | Os01g0178200 protein n = 2 Tax = Oryza sativa RepID = Q5VRD8_ORYSJ (1e−22); DUF92: Integral membrane protein DUF92 (4.7e−05) | 3 | 107.6 | 162086845 | 162091358 |
| 69 | Putative uncharacterized protein Sb03g043660 n = 1 Tax = Sorghum bicolor RepID = C5XG65_SORBI (8e−63); DUF506: Protein of unknown function (DUF506) (3.8e−50) | 3 | 107.6 | 162095278 | 162096162 |
| 70 | Minor histocompatibility antigen H13, putative n = 1 Tax = Ricinus communis RepID = B9SUL7_RICCO (1e−88); PA: PA domain (1.4e−19); Peptidase_A22B: Signal peptide peptidase (2.3e−26); GO_MF:GO:0004190, penicillopepsin activity# (1e−160); GO_BP:GO:0050819, negative regulation of coagulation# (8e−23); GO_CC:GO:0016021, integral to membrane# (1e−160) | 3 | 107.6 | 162175457 | 162180323 |
| 71 | SH3 domain-containing protein n = 1 Tax = Trifolium repens RepID = D3YBF4_TRIRP (1e−16); GO_MF:GO:0005515, protein binding# (2e−14); GO_CC:GO:0005737, cytoplasm# (2e−14) | 3 | 107.6 | 162280029 | 162280752 |
| 72 | Pentatricopeptide repeat-containing protein, putative n = 1 Tax = Ricinus communis RepID = B9T3T5_RICCO (1e−112); PPR: PPR repeat (3.4); PPR: PPR repeat (0.00045); PPR: PPR repeat (3.8e−11); PPR: PPR repeat (3.3e−06); PPR: PPR repeat (1.9); PPR: PPR repeat (2.5); PPR: PPR repeat (0.59); GO_MF:GO:0005488, binding# (1e−109); GO_BP:GO:0016556, IMP#mRNA modification# (2e−96); GO_CC:GO:0009536, plastid# (2e−96) | 3 | 107.6 | 162296687 | 162298725 |
| 73 | Putative uncharacterized protein Sb03g043620 n = 1 Tax = Sorghum bicolor RepID = C5XG62_SORBI (3e−50); GO_BP:GO:0010375, IMP#stomatal complex patterning# (3e−18) | 3 | 107.6 | 162312872 | 162314047 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 74 | Protein MYG1, putative n = 1 Tax = Ricinus communis RepID = B9RYS8_RICCO (2e-45); UPF0160: Uncharacterised protein family (UPF0160) (4.9e-11); Tryp_alpha_amyl: Protease inhibitor/seed storage/LTP f (0.059); GO_MF:GO:0016151, nickel ion binding# (8e-20); GO_BP:GO:0043473, IMP#pigmentation# (1e-19); GO_CC:GO:0005739, mitochondrion# (2e-48) | 3 | 107.6 | 162317907 | 162323226 |
| 75 | Protease inhibitor/seed storage/LTP family protein n = 4 Tax = Zea mays RepID = B6ST99_MAIZE (2e-14); Metallothio_Pro: Prokaryotic metallothionein (0.05); Tryp_alpha_amyl: Protease inhibitor/seed storage/LTP f (0.07); GO_MF:GO:0008233, peptidase activity# (2e-14) | 3 | 107.6 | 162372177 | 162372497 |
| 76 | OSJNBa0086O06.17 protein n = 2 Tax = Oryza sativa Japonica Group RepID = Q7XLZ2_ORYSJ (2e-99); GO_MF:GO:0004803, transposase activity# (4e-48); GO_BP:GO:0006313, transposition, DNA-mediated# (4e-48) | 3 | 107.6 | 162388373 | 162390026 |
| 77 | Xyloglucan endotransglucosylase/hydrolase protein 32 n = 2 Tax = Zea mays RepID = B6T9H5_MAIZE (1e-22); GO_MF:GO:0016787, hydrolase activity# (1e-22); GO_BP:GO:0006073, cellular glucan metabolic process# (1e-22); GO_CC:GO:0048046, IDA#apoplast# (1e-22) | 3 | 107.6 | 162390710 | 162391087 |
| 78 | Putative uncharacterized protein Sb03g043580 n = 1 Tax = Sorghum bicolor RepID = C5XG58_SORBI (4e-11) | 3 | 107.7 | 162527626 | 162527856 |
| 79 | cDNA clone: J013092F14, full insert sequence n = 2 Tax = Poaceae RepID = B7ECT5_ORYSJ (3e-24); GO_CC:GO:0005886, plasma membrane# (4e-14) | 3 | 107.7 | 162559310 | 162559546 |
| 80 | Putative uncharacterized protein n = 1 Tax = Zea mays RepID = B6TFE5_MAIZE (2e-65); DUF538: Protein of unknown function, DUF538 (3.1e-47); GO_MF:GO:0043565, sequence-specific DNA binding# (5e-20); GO_BP:GO:0045449, regulation of transcription# (5e-20); GO_CC:GO:0005773, IDA#vacuole# (2e-29) | 3 | 107.7 | 162599043 | 162600050 |
| 81 | Putative uncharacterized protein n = 1 Tax = Zea mays RepID = C4IYL7_MAIZE (9e-62) | 3 | 107.7 | 162600661 | 162601008 |
| 82 | Pentatricopeptide repeat-containing protein, putative n = 1 Tax = Ricinus communis RepID = B9RTF6_RICCO (2e-82); TPR_4: Tetratricopeptide repeat (3.8); PPR: PPR repeat (0.0044); TPR_4: Tetratricopeptide repeat (6.6); PPR: PPR repeat (2.1e-07); TPR_4: Tetratricopeptide repeat (21); PPR: PPR repeat (8.3e-06); PPR: PPR repeat (0.91); PPR: PPR repeat (0.49); GO_MF:GO:0005488, binding# (9e-85); GO_BP:GO:0032259, methylation# (7e-78); GO_CC:GO:0005739, mitochondrion# (3e-77) | 3 | 107.7 | 162602021 | 162603645 |
| 83 | Uncharacterized ACR, COG1565 family protein n = 2 Tax = Zea mays RepID = B6TEQ7_MAIZE (0.0); DUF566: Family of unknown function (DUF566) (4.7e-06); Malic_M: Malic enzyme, NAD binding domain (1.2e-06); DUF185: Uncharacterized ACR, COG1565 (1.9e-49); GO_MF:GO:0051287, NAD or NADH binding# (1e-35); GO_BP:GO:0055114, oxidation reduction# (1e-35); GO_CC:GO:0005622, intracellular# (2e-34) | 3 | 107.7 | 162692864 | 162701741 |
| 84 | Heavy meromyosin-like n = 2 Tax = Oryza sativa RepID = Q8S0A4_ORYSJ (0.0) | 3 | 107.7 | 162701976 | 162709719 |
| 85 | Mitochondrial import inner membrane translocase subunit TIM16 n = 4 Tax = Andropogoneae RepID = B6TGT3_MAIZE (1e-60); Pam16: Pam16 (1.4e-13); GO_MF:GO:0005215, transporter activity# (4e-52); GO_BP:GO:0006857, oligopeptide transport# (4e-52); GO_CC:GO:0016020, membrane# (4e-52) | 3 | 107.7 | 162741183 | 162743797 |
| 86 | Regulatory protein viviparous-1 n = 2 Tax = Zea mays RepID = VIV1_MAIZE (0.0); B3: B3 DNA binding domain (2.6e-21); GO_MF:GO:0003677, DNA binding# (0.0); GO_BP:GO:0045449, regulation of transcription# (0.0); GO_CC:GO:0005737, cytoplasm# (0.0) | 3 | 107.7 | 162800024 | 162804983 |
| 87 | Abc transporter, putative n = 1 Tax = Ricinus communis RepID = B9SPK8_RICCO (0.0); ABC_membrane: ABC transporter transmembrane region (4.7e-29); SMC_N: RecF/RecN/SMC N terminal domain (0.03); ABC_tran: ABC transporter (1.5e-57); GO_MF:GO:0004626, ATPase activity, coupled to transmembrane movement of substances# (0.0); GO_BP:GO:0055085, transmembrane transport# (0.0); GO_CC:GO:0016021, integral to membrane# (0.0) | 3 | 107.7 | 162813868 | 162818612 |
| 88 | Ribophorin II, putative n = 1 Tax = Ricinus communis RepID = B9SV32_RICCO (0.0); Ribophorin_II (RPN2) (6.7e-201); GO_MF:GO:0004579, dolichyl-diphosphooligosaccharide-protein glycotransferase activity# (0.0); GO_BP:GO:0018279, protein amino acid N-linked glycosylation via asparagine# (0.0); GO_CC:GO:0008250, oligosaccharyltransferase complex# (0.0) | 3 | 107.7 | 162825595 | 162831853 |
| 89 | Calcium binding atopy-related autoantigen 1 n = 2 Tax = Andropogoneae RepID = B6SL16_MAIZE (6e-35); efhand: EF hand (0.0033); GO_MF:GO:0005509, calcium ion storage activity# (6e-35) | 3 | 107.8 | 163070674 | 163078478 |
| 90 | F-box domain containing protein n = 1 Tax = Zea mays RepID = B6U9Q3_MAIZE (0.0); F-box: F-box domain (0.001); FBD: FBD (0.0025) | 3 | 107.8 | 163085351 | 163088065 |
| 91 | Putative uncharacterized protein n = 2 Tax = Zea mays RepID = B6SQJ7_MAIZE (6e-36) | 3 | 107.8 | 163330774 | 163332783 |
| 92 | Putative uncharacterized protein n = 2 Tax = Zea mays RepID = B6SQJ7_MAIZE (6e-36) | 3 | 107.8 | 163443609 | 163445618 |
| 93 | Putative gag-pol polyprotein n = 1 Tax = Zea mays RepID = Q8SA91_MAIZE (4e-25); GO_MF:GO:0004190, penicillopepsin activity# (4e-25); GO_BP:GO:0015074, DNA integration# (4e-25); GO_CC:GO:0005634, nucleus# (4e-25) | 3 | 107.9 | 163652562 | 163657461 |
| 94 | Putative uncharacterized protein n = 1 Tax = Zea mays RepID = B6T8G3_MAIZE (2e-18) | 3 | 107.9 | 163658731 | 163660184 |
| 95 | DEAD-box ATP-dependent RNA helicase 30 n = 2 Tax = Oryza sativa Japonica Group RepID = RH30_ORYSJ (0.0); GRP: Glycine rich protein family (0.0024); ResIII: Type III restriction enzyme, res subunit (0.048); DEAD: DEAD/DEAH box helicase (1.2e-70); Helicase_C: Helicase | 3 | 107.9 | 163743628 | 163748000 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 96 | conserved C-terminal domain (3.4e−34); GO_MF:GO:0016787, hydrolase activity# (0.0); GO_BP:GO:0042254, ribosome biogenesis# (0.0); GO_CC:GO:0005634, nucleus# (0.0) | | | | |
| 96 | Putative uncharacterized protein n = 2 Tax = Zea mays RepID = B4FJK2_MAIZE (2e−44); GO_MF:GO:0003677, DNA binding# (2e−44); GO_BP:GO:0045449, regulation of transcription# (2e−44); GO_CC:GO:0005634, nucleus# (2e−44) | 3 | 107.9 | 163748547 | 163749188 |
| 97 | SCAR-like protein 2 n = 3 Tax = Oryza sativa Japonica Group RepID = SCRL2_ORYSJ (2e−24); GO_MF:GO:0003779, actin binding# (2e−24); GO_CC:GO:0005856, cytoskeleton# (2e−24) | 3 | 107.9 | 163751314 | 163751773 |
| 98 | Putative uncharacterized protein Sb05g000810 n = 1 Tax = Sorghum bicolor RepID = C5Y329_SORBI (4e−20); GO_MF:GO:0003725, IDA#double-stranded RNA binding# (1e−15); GO_CC:GO:0005622, intracellular# (1e−15) | 3 | 107.9 | 163754714 | 163755373 |
| 99 | EH-domain-containing protein 1 n = 3 Tax = Andropogoneae RepID = B6U193_MAIZE (1e−52); GO_MF:GO:0005525, GTP binding# (1e−52); GO_BP:GO:0004872, receptor activity# (5e−40); GO_CC:GO:0016020, membrane# (8e−25) | 3 | 107.9 | 163862316 | 163863436 |
| 100 | Lipoprotein n = 1 Tax = Zea mays RepID = B6SKL9_MAIZE (5e−60) | 3 | 108 | 163993324 | 163995044 |
| 101 | Lysine ketoglutarate reductase trans-splicing related 1 n = 3 Tax = Andropogoneae RepID = B6TPP1_MAIZE (0.0); DUF707: Protein of unknown function (DUF707) (6e−235) | 3 | 108 | 163995909 | 164000076 |
| 102 | Protein phosphatase 2c, putative n = 1 Tax = Ricinus communis RepID = B9SVM2_RICCO (2e−78); DUF868: Plant protein of unknown function (DUF868) (6.5e−117); O_MF:GO:0046872, metal ion binding# (2e−78); GO_BP:GO:0006470, protein amino acid dephosphorylation# (2e−78); GO_CC:GO:0008287, protein serine/threonine phosphatase complex# (2e−78) | 3 | 108 | 164171419 | 164172810 |
| 103 | Putative uncharacterized protein Sb03g043370 n = 1 Tax = Sorghum bicolor RepID = C5XFK5_SORBI (1e−104) | 3 | 108 | 164174099 | 164192802 |
| 104 | Putative uncharacterized protein n = 1 Tax = Zea mays RepID = B61XB0_MAIZE (0.0); MRP-S28: Mitochondrial ribosomal subunit protein (2.4e−08); GO_CC:GO:0005829, DA#cytosol# (1e−120) | 3 | 108 | 164251551 | 164255647 |
| 105 | Putative uncharacterized protein Sb10g021032 (Fragment) n = 1 Tax = Sorghum bicolor RepID = C5Z404_SORBI (4e−65) | 3 | 108 | 164319175 | 164320946 |
| 106 | Retrotransposon gag protein n = 1 Tax = Asparagus officinalis RepID = Q2AA53_ASPOF (9e−49); Retrotrans_gag: Retrotransposon gag protein (2.3e−09); GO_MF:GO:0004523, ribonuclease H activity# (1e−44); GO_BP:GO:0015074, DNA integration# (1e−44); GO_CC:GO:0005634, nucleus# (1e−44) | 3 | 108 | 164343946 | 164347214 |
| 107 | OSJNBa0091D06.8 protein n = 1 Tax = Oryza sativa RepID = Q7XU13_ORYSA (2e−30); IRF: Interferon regulatory factor transcription factor (0.1); GO_MF:GO:0004523, ribonuclease H activity# (1e−30); GO_BP:GO:0015074, DNA integration# (1e−30); GO_CC:GO:0005634, nucleus# (2e−30) | 3 | 108 | 164347526 | 164348056 |
| 108 | Endoribonuclease Dicer homolog 3a n = 1 Tax = Oryza sativa Japonica Group RepID = DCL3A_ORYSJ (0.0); Helicase_C: Helicase conserved C-terminal domain (7.3e−18); dsrm: Double-stranded RNA binding motif (0.032); dsRNA_bind: Double stranded RNA binding domain (1.2e−18); PAZ: PAZ domain (1.8e−07); Ribonuclease_3: RNase3 domain (8.5e−34); Ribonuclease_3: RNase3 domain (2.6e−43); dsrm: Double-stranded RNA binding motif (0.23); dsrm: Double-stranded RNA binding motif (0.31); GO_MF:GO:0046872, metal ion binding# (0.0); GO_BP:GO:0031047, IMP#gene silencing by RNA# (0.0); GO_CC:GO:0005634, nucleus# (0.0) | 3 | 108 | 164365769 | 164375526 |
| 109 | HD2 type histone deacetylase HDA106 n = 1 Tax = Zea mays RepID = Q94F81_MAIZE (1e−109); GO_MF:GO:0046872, metal ion binding# (1e−28); GO_BP:GO:0045449, regulation of transcription# (1e−28); GO_CC:GO:0005730, IDA#nucleolus# (1e−28) | 3 | 108 | 164377535 | 164380957 |
| 110 | Harpin-induced protein n = 1 Tax = Zea mays RepID = B6UDA2_MAIZE (1e−124); Hin1: Harpin-induced protein 1 (Hin1) (7.5e−27) | 3 | 108 | 164390945 | 164392443 |
| 111 | Integrator complex subunit 9 homolog n = 1 Tax = Nematostella vectensis RepID = INT9_NEMVE (8e−38); GO_MF:GO:0005515, protein binding# (1e−32); GO_BP:GO:0016180, snRNA processing# (1e−32); GO_CC:GO:0005634, nucleus# (8e−38) | 3 | 108.1 | 164476703 | 164482132 |
| 112 | Mitochondrial transcription termination factor-like n = 2 Tax = Oryza sativa Japonica Group RepID = Q67UH1_ORYSJ (2e−79); mTERF: mTERF (5.4e−09); GO_MF:GO:0005524, ATP binding# (5e−71); GO_BP:GO:0006468, protein amino acid phosphorylation# (5e−71) | 3 | 108.1 | 164502626 | 164504224 |
| 113 | Copine III-like n = 3 Tax = Oryza sativa RepID = Q5N628_ORYSJ (0.0); Copine: Copine (3e−93); zfP11: P-11 zinc finger (0.093); zfC3HC4: Zinc finger, C3HC4 type (RING finger) (0.0026); GO_MF:GO:0046872, metal ion binding# (0.0); GO_BP:GO:0009850, IMP#auxin metabolic process# (1e−156); GO_CC:GO:0016020, membrane# (1e−156) | 3 | 108.1 | 164580643 | 164584828 |
| 114 | Proline transport protein-like n = 2 Tax = Oryza sativa RepID = Q8L431_ORYSJ (0.0); Aa_trans: Transmembrane amino acid transporter protein (3e−50); GO_MF:GO:0015193, IG#L-proline transmembrane transporter activity# (1e−89); GO_BP:GO:0015824, proline transport# (1e−89); GO_CC:GO:0016021, integral to membrane# (0.0) | 3 | 108.1 | 164586510 | 164589297 |
| 115 | Putative uncharacterized protein n = 1 Tax = Zea mays RepID = B6SP05_MAIZE (2e−14) | 3 | 108.1 | 164663433 | 164687249 |

TABLE 13-continued

Annotated coding sequences within the FSR-3.01 and FSR-8.01 regions.

| Gene ID | Annotation | Chr | MON Map cM[†] | Physical Map Position bp[††] Start | End |
|---|---|---|---|---|---|
| 116 | Retrotransposon protein, putative, unclassified n = 1 Tax = Oryza sativa Japonica Group RepID = Q2QUP3_ORYSJ (4e-40); zf-CCHC: Zinc knuckle (3.8e-05); zf-CCHC: Zinc knuckle (4.2e-06); GO_MF:GO:0003964, RNA-directed DNA polymerase, group II intron encoded# (4e-40); GO_BP:GO:0006278, RNA-dependent DNA replication# (4e-40) | 3 | 108.1 | 164765422 | 164771885 |
| 117 | Hsp70 molecular chaperone (Fragment) n = 72 Tax = Bradyrhizobium RepID = A5A9H9_9BRAD (2e-23); GO_MF:GO:0005524, ATP binding# (8e-26); GO_BP:GO:0006950, response to stress# (4e-25); GO_CC:GO:0005739, mitochondrion# (4e-23) | 3 | 108.1 | 164773452 | 164773959 |
| 118 | P0497A05.17 protein n = 2 Tax = Oryza sativa Japonica RepID = Q8L4S2_ORYSJ (1e-116); CorA: CorA-like Mg2+ transporter protein (2.4e-31); GO_MF:GO:0046873, metal ion transmembrane transporter activity# (8e-66); GO_BP:GO:0055085, transmembrane transport# (8e-66); GO_CC:GO:0016020, membrane# (8e-66) | 3 | 108.15 | 164884487 | 164898704 |
| 119 | HAT family dimerisation domain containing protein n = 3 Tax = Oryza sativa Japonica Group RepID = Q2QPA8_ORYSJ (5e-11); GO_MF:GO:0046983, protein dimerization activity# (3e-15); GO_BP:GO:0005975, carbohydrate metabolic process# (1e-13); GO_CC:GO:0005622, intracellular# (1e-13) | 3 | 108.2 | 164907013 | 164907497 |
| 120 | Putative uncharacterized protein Sb02g031755 (Fragment) n = 1 Tax = Sorghum bicolor RepID = C5X711_SORBI (1e-40); GO_MF:GO:0003677, DNA binding# (4e-36); GO_BP:GO:0015074, DNA integration# (2e-09) | 3 | 108.2 | 164918544 | 164918859 |
| 121 | Putative uncharacterized protein n = 2 Tax = Zea mays RepID = B4FIS6_MAIZE (1e-22); zf-C2HC_plant: Protein of unknown function, DUF1544 (2.5e-15); GO_MF:GO:0003677, DNA binding# (1e-22) | 3 | 108.2 | 164918884 | 164960006 |
| 122 | Protein-S-isoprenylcysteine O-methyltransferase n = 2 Tax = Zea mays RepID = B6TWA2_MAIZE (1e-107); ICMT: Isoprenylcysteine carboxyl methyltransferase (ICMT) family (6e-39); GO_MF:GO:0016740, transferase activity# (1e-107); GO_BP:GO:0006481, C-terminal protein amino acid methylation# (1e-107); GO_CC:GO:0016021, integral to membrane# (1e-107) | 3 | 108.2 | 164967420 | 164969981 |
| 123 | Protein binding protein, putative n = 1 Tax = Ricinus communis RepID = B9RAQ1_RICCO (2e-56); zf-TAZ: TAZ zinc finger (0.099); GO_MF:GO:0008270, zinc ion binding# (1e-114); GO_BP:GO:0006355, regulation of transcription, DNA-dependent# (1e-114); GO_CC:GO:0005634, nucleus# (1e-114) | 3 | 108.2 | 164974619 | 164978606 |
| 124 | Putative uncharacterized protein Sb05g019060 n = 1 Tax = Sorghum bicolor RepID = C5Y2V6_SORBI (6e-18) | 3 | 108.2 | 165056085 | 165059577 |
| 125 | Protein terminal ear1 n = 1 Tax = Zea mays RepID = TE1_MAIZE (0.0); RRM_1: RNA recognition motif (a.k.a. RRM, RB (0.0065); RRM_1: RNA recognition motif (a.k.a. RRM, RB (0.00023); RRM_2: RNA recognition motif 2 (4e-39); GO_MF:GO:0003723, RNA binding# (0.0); GO_BP:GO:0007275, TAS#multicellular organismal development# (0.0) | 3 | 108.2 | 165174172 | 165178071 |
| 126 | B1358B12.21 protein n = 4 Tax = Oryza sativa RepID = Q7XUS3_ORYSJ (3e-22); GO_MF:GO:0004803, transposase activity# (3e-21); GO_BP:GO:0006313, transposition, DNA-mediated# (3e-21) | 3 | 108.3 | 165300798 | 165301802 |
| 127 | Putative polyprotein n = 1 Tax = Oryza sativa Japonica Group RepID = Q6UUL5_ORYSJ (6e-39); GO_MF:GO:0003700, transcription factor activity# (6e-39); GO_BP:GO:0045449, regulation of transcription# (6e-39) | 3 | 108.3 | 165394588 | 165395472 |
| 128 | P0497A05.6 protein n = 1 Tax = Oryza sativa Japonica Group RepID = Q8LIW5_ORYSJ (2e-14) | 3 | 108.4 | 165456958 | 165457869 |
| 129 | Nucleic acid binding protein, putative n = 1 Tax = Ricinus communis RepID = B9RAP0_RICCO (1e-140); JmjN: jmjN domain (1.3e-15); JmjC: JmjC domain (5e-54); DUF1126: Repeat of unknown function (DUF1126) (0.019); GO_MF:GO:0008270, zinc ion binding# (0.0); GO_BP:GO:0048366, TAS#leaf development# (1e-139); GO_CC:GO:0005622, intracellular# (0.0) | 3 | 108.5 | 165450429 | 165455337 |
| 130 | BCL-2 binding anthanogene-1 n = 3 Tax = Andropogoneae RepID = B6TXB6_MAIZE (2e-66); GO_MF:GO:0005515, protein binding# (2e-26); GO_BP:GO:0006915, apoptosis# (2e-26) | 3 | 108.5 | 165460350 | 165461480 |
| 131 | P0497A05.3 protein n = 3 Tax = Oryza sativa RepID = Q8LIW8_ORYSJ (0.0); TPR_1: Tetratricopeptide repeat (0.0011); TPR_2: Tetratricopeptide repeat (8.1e-05); TPR_4: Tetratricopeptide repeat (0.87); TPR_1: Tetratricopeptide repeat (0.42); TPR_2: Tetratricopeptide repeat (0.39); TPR_1: Tetratricopeptide repeat (2e-06); TPR_2: Tetratricopeptide repeat (0.015); TPR_2: Tetratricopeptide repeat (1.4e-06); TPR_4: Tetratricopeptide repeat (9.2); TPR_1: Tetratricopeptide repeat (3.4); TPR_2: Tetratricopeptide repeat (1.3); TPR_1: Tetratricopeptide repeat (4.7); TPR_2: Tetratricopeptide repeat (26); TPR_1: Tetratricopeptide repeat (0.0017); TPR_2: Tetratricopeptide repeat (0.0013); TPR_4: Tetratricopeptide repeat (2.8); GO_MF:GO:0005488, binding# (0.0); GO_BP:GO:0006508, proteolysis# (7e-21); GO_CC:GO:0005622, intracellular# (7e-21) | 3 | 108.5 | 165463587 | 165478472 |
| 132 | Ceramide glucosyltransferase, putative n = 1 Tax = Ricinus communis RepID = B9RKH1_RICCO (2e-20); GO_MF:GO:0016757, transferase activity, transferring glycosyl groups# (4e-21) | 3 | 108.55 | 165653906 | 165669525 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 133 | Cysteine endopeptidase n = 5 Tax = Oryza sativa RepID = Q7F3A8_ORYSJ (1e–148); Inhibitor_I29: Cathepsin propeptide inhibitor domain ((2.9e–14); DUF1918: Domain of unknown function (DUF1918) (0.073); Peptidase C1: Papain family cysteine protease (1.1e–129); GO_MF:GO:0016787, hydrolase activity# (1e–177); GO_BP:GO:0006508, proteolysis# (1e–177); GO_CC:GO:0005788, endoplasmic reticulum lumen# (1e–117). | 3 | 108.6 | 165445237 | 165446893 |
| 134 | Nucleic acid binding protein, putative n = 1 Tax = Ricinus communis RepID = B9RAP0_RICCO (1e–15); GO_MF:GO:0008270, zinc ion binding# (3e–33); GO_BP:GO:0048366, TAS#leaf development# (6e–12); GO_CC:GO:0005622, intracellular# (3e–33) | 3 | 108.6 | 165448724 | 165450566 |
| 135 | Putative uncharacterized protein n = 2 Tax = Zea mays RepID = Q5GAU8_MAIZE (7e–17) | 3 | 108.6 | 165551858 | 165552144 |
| 136 | Putative uncharacterized protein n = 1 Tax = Zea mays RepID = C0PLF6_MAIZE (1e–13) | 3 | 108.6 | 165668072 | 165668383 |
| 137 | Fructose-bisphosphate aldolase cytoplasmic isozyme n = 18 Tax = commelinids RepID = ALF_ORYSJ (0.0); Glycolytic: Fructose-bisphosphate aldolase class-I (2.1e–259); GO_MF:GO:0016829, lyase activity# (0.0); GO_BP:GO:0008152, metabolic process# (0.0); GO_CC:GO:0005737, cytoplasm# (0.0) | 3 | 108.6 | 165723021 | 165725581 |
| 138 | PSRP4 n = 2 Tax = Andropogoneae RepID = B6T2D1_MAIZE (8e–18) | 3 | 108.8 | 165725766 | 165728006 |
| 139 | Protein binding protein, putative n = 1 Tax = Ricinus communis RepID = B9RMQ0_RICCO (4e–68); zfC3HC4: Zinc finger, C3HC4 type (RING finger) (0.0001); GO_MF:GO:0046872, metal ion binding# (1e–122) | 3 | 108.8 | 165728771 | 165731884 |
| 140 | Putative uncharacterized protein Sb03g043110 n = 1 Tax = Sorghum bicolor RepID = C5XFH4_SORBI (0.0); B3: B3 DNA binding domain (1.4e–10); B3: B3 DNA binding domain (0.00015); GO_MF:GO:0003677, DNA binding# (1e–125); GO_BP:GO:0045449, regulation of transcription# (1e–125); GO_CC:GO:0005634, nucleus# (1e–125) | 3 | 109 | 165855198 | 165857792 |
| 141 | Exo70 exocyst complex subunit family protein n = 2 Tax = Zea mays RepID = B6SWM6_MAIZE (0.0); Exo70: Exo70 exocyst complex subunit (7.5e–78); GO_BP:GO:0006887, exocytosis# (0.0); GO_CC:GO:0000145, NAS#exocyst## (0.0) | 3 | 109 | 165857827 | 165860040 |
| 142 | Putative transposase n = 1 Tax = Oryza sativa Japonica Group RepID = Q8L516_ORYSJ (1e–84); Plant_tran: Plant transposon protein (5e–05); GO_MF:GO:0005524, ATP binding# (1e–78); GO_BP:GO:0006468, protein amino acid phosphorylation# (1e–78) | 3 | 109.1 | 165874313 | 165876275 |
| 143 | Two-component response regulator ARR11 n = 2 Tax = Andropogoneae RepID = B6UC09_MAIZE (0.0); Response_reg: Response regulator receiver domain (1.2e–27); Myb_DNA-binding: Myb-like DNA-binding domain (7.9e–11); GO_MF:GO:0003677, DNA binding# (0.0); GO_BP:GO:0045449, regulation of transcription# (0.0); GO_CC:GO:0005634, nucleus# (0.0) | 3 | 109.1 | 165897223 | 165901241 |
| 144 | Putative uncharacterized protein Sb03g043070 n = 1 Tax = Sorghum bicolor RepID = C5XFH0_SORBI (0.0) | 3 | 109.1 | 165903035 | 165912074 |
| 145 | E3 SUMO-protein ligase SIZ2 n = 2 Tax = Oryza sativa RepID = SIZ2_ORYSJ (3e–11); GO_MF:GO:0046872, metal ion binding# (3e–11); GO_CC:GO:0005634, nucleus# (3e–11) | 3 | 109.1 | 165921011 | 165921870 |
| 146 | Putative uncharacterized protein n = 1 Tax = Zea mays RepID = C4IYH0_MAIZE (2e–21) | 3 | 109.3 | 165985310 | 165986062 |
| 147 | B1065G12.33 protein n = 4 Tax = Oryza sativa RepID = Q8RZ62_ORYSJ (4e–32); DUF971: Protein of unknown function (DUF971) (2.3e–41); GO_MF:GO:0016853, isomerase activity# (3e–21) | 3 | 109.3 | 166019231 | 166033766 |
| 148 | Protein kinase n = 3 Tax = Andropogoneae RepID = B6SS49_MAIZE (0.0); GO_CC:GO:0005886, plasma membrane# (8e–39) | 3 | 109.3 | 166071796 | 166094047 |
| 149 | Gibberellin response modulator-like protein n = 2 Tax = Oryza sativa RepID = Q8RZ73_ORYSJ (1e–174); GRAS: GRAS family transcription factor (1.2e–119); GO_MF:GO:0005515, protein binding# (2e–47); GO_BP:GO:0045449, regulation of transcription# (1e–174); GO_CC:GO:0005634, nucleus# (8e–50) | 3 | 109.5 | 166151703 | 166153319 |
| 150 | Transposon protein, putative, CACTA, En/Spm sub-class n = 1 Tax = Oryza sativa Japonica Group RepID = Q2QWY8_ORYSJ (3e–59); GO_MF:GO:0004803, transposase activity# (3e–36); GO_BP:GO:0006313, transposition, DNA-mediated# (3e–36) | 3 | 109.7 | 166196959 | 166197693 |
| 151 | Peptide transporter PTR2 n = 2 Tax = Zea mays RepID = B6SXM6_MAIZE (0.0); MFS_1: Major Facilitator Superfamily (5.7e–05); PTR2: POT family (2.4e–118); GO_MF:GO:0005215, transporter activity# (0.0); GO_BP:GO:0006857, oligopeptide transport# (0.0); GO_CC:GO:0016021, integral to membrane# (0.0) | 3 | 109.7 | 166199666 | 166202898 |
| 152 | B1065G12.16 protein n = 2 Tax = Oryza sativa RepID = Q8RZ79_ORYSJ (0.0); Abhydrolase_3: alpha/beta hydrolase fold (3.1e–75); GO_MF:GO:0016787, hydrolase activity# (0.0); GO_BP:GO:0008152, metabolic process# (0.0); GO_CC:GO:0005634, nucleus# (9e–30) | 3 | 109.8 | 166243856 | 166246747 |
| 153 | Endopeptidase-like protein n = 1 Tax = Oryza sativa Japonica Group RepID = Q8RZ80_ORYSJ (0.0); Peptidase_M: Peptidase family M3 (1.1e–91); GO_MF:GO:0016787, hydrolase activity# (0.0); GO_BP:GO:0006508, proteolysis# (0.0); GO_CC:GO:0005737, cytoplasm# (1e–109) | 3 | 109.85 | 166247016 | 166254397 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 154 | Acid phosphatase/vanadium-dependent haloperoxidase related n = 3 Tax = Andropogoneae RepID = B6SYG4_MAIZE (2e−52); DUF212: Divergent PAP2 family (7.6e−44); GO_MF:GO:0004601, peroxidase activity# (2e−52) | 3 | 110 | 166377306 | 166379640 |
| 155 | Putative uncharacterized protein n = 1 Tax = Zea mays RepID = B6SGD8_MAIZE (9e−28) | 3 | 110.1 | 166319780 | 166320127 |
| 156 | VTC2 n = 2 Tax = Zea mays RepID = B6T940_MAIZE (0.0); GO_MF:GO:0080048, IDA#GDP-D-glucose phosphorylase activity# (1e−105); GO_BP:GO:0019853, L-ascorbic acid biosynthetic process# (1e−105) | 3 | 110.3 | 166381511 | 166384098 |
| 157 | DNA repair protein recA n = 3 Tax = Andropogoneae RepID = B6TNM4_MAIZE (0.0); RecA: recA bacterial DNA recombination protei (4.6e−179); Rad51: Rad51 (8e−05); MipZ: ATPase MipZ (0.089); GO_MF:GO:0017111, nucleoside-triphosphatase activity# (0.0); GO_BP:GO:0009432, SOS response# (0.0); GO_CC:GO:0005737, cytoplasm# (0.0) | 3 | 110.3 | 166384292 | 166391067 |
| 158 | B1065G12.5 protein n = 1 Tax = Oryza sativa Japonica Group RepID = Q7F1X9_ORYSJ (0.0); U-box: U-box domain (1.6e−20); Arm: Armadillo/beta-catenin-like repeat (0.24); Arm: Armadillo/beta-catenin-like repeat (1.7); Arm: Armadillo/beta-catenin-like repeat (2.2); GO_MF:GO:0005488, binding# (0.0); GO_BP:GO:0016567, IGI#protein ubiquitination# (0.0); GO_CC:GO:0000151, ubiquitin ligase complex# (0.0) | 3 | 110.3 | 166431215 | 166436430 |
| 159 | Cysteine-type peptidase, putative n = 1 Tax = Ricinus communis RepID = B9T7Q4_RICCO (3e−54); OTU: OTU-like cysteine protease (2.1e−30); GO_MF:GO:0016874, ligase activity# (1e−56); GO_BP:GO:0009058, biosynthetic process# (1e−56) | 3 | 110.6 | 166446402 | 166449258 |
| 160 | Helix-loop-helix DNA-binding domain containing protein n = 1 Tax = Zea mays RepID = B6TUA5_MAIZE (1e−160); HLH: Helix-loop-helix DNA-binding domain (3.4e−08); GO_MF:GO:0030528, transcription regulator activity# (1e−160); GO_BP:GO:0045449, regulation of transcription# (1e−160); GO_CC:GO:0005634, nucleus# (1e−160) | 3 | 110.6 | 166448058 | 166452009 |
| 161 | Transposon protein Pong sub-class n = 1 Tax = Zea mays RepID = B6TCG7_MAIZE (0.0); Plant_tran: Plant transposon protein (4.3e−56); GO_MF:GO:0016740, transferase activity# (1e−105); GO_CC:GO:0005840, ribosome# (1e−107) | 3 | 110.7 | 166486192 | 166487676 |
| 162 | L-asparaginase 2 n = 1 Tax = Phaseolus vulgaris RepID = Q2PW34_PHAVU (2e−19); GO_MF:GO:0016787, hydrolase activity# (6e−57) | 3 | 110.8 | 166526151 | 166529874 |
| 163 | Putative DAD1 n = 3 Tax = Oryza sativa Japonica Group RepID = Q8SID9_ORYSJ (0.0); Lipase (class 3) (5.3e−53); Lipase: Thioesterase domain (0.096); GO_MF:GO:0004806, triglyceride lipase activity# (1e−171); GO_BP:GO:0006629, lipid metabolic process# (1e−171); GO_CC:GO:0009507, chloroplast# (1e−108) | 3 | 110.9 | 166596752 | 166598153 |
| 164 | Glycosyltransferase n = 3 Tax = Andropogoneae RepID = Q5QPY6_SORBI (0.0); DUF563: Protein of unknown function (DUF563) (1.5e−133); GO_MF:GO:0016757, transferase activity, transferring glycosyl groups# (0.0) | 3 | 110.9 | 166689883 | 166692410 |
| 165 | Streptococcal hemagglutinin-like protein n = 2 Tax = Oryza sativa Japonica Group RepID = Q6EN70_ORYSJ (1e−116); DUF566: Family of unknown function (DUF566) (9.5e−81); GO_MF:GO:0008017, IDA#microtubule binding# (3e−27); GO_BP:GO:0051301, cell division# (3e−27); GO_CC:GO:0005880, IDA#nuclear microtubule# (3e−27) | 3 | 110.9 | 166997433 | 167001364 |
| 166 | S-adenosylmethionine-dependent methyltransferase, putative n = 1 Tax = Ricinus communis RepID = B9SX25_RICCO (1e−128); DUF248: Putative methyltransferase (9.1e−213); methyltransf_11: Methyltransferase domain (0.00061); GO_MF:GO:0016740, transferase activity# (1e−128); GO_BP:GO:0016301, kinase activity# (1e−119); GO_CC:GO:0005794, IDA#Golgi apparatus# (1e−112) | 3 | 110.9 | 167004322 | 167007358 |
| 167 | Putative Pto kinase interactor 1 n = 1 Tax = Oryza sativa Japonica Group RepID = Q69IN5_ORYSJ (1e−138); Pkinase_Tyr: Protein tyrosine kinase (2.6e−25); Pkinase: Protein kinase domain (2.6e−19); GO_MF:GO:0005524, ATP binding# (1e−169); GO_BP:GO:0006468, protein amino acid phosphorylation# (1e−169); GO_CC:GO:0005886, plasma membrane# (1e−139) | 3 | 110.9 | 167008810 | 167013529 |
| 168 | Probable mannan synthase 2 n = 1 Tax = Oryza sativa Japonica Group RepID = CSLA2_ORYSI (1e−26); GO_MF:GO:0016757, transferase activity, transferring glycosyl groups# (1e−26); GO_BP:GO:0007047, cellular cell wall organization# (1e−26); GO_CC:GO:0016021, integral to membrane# (1e−26) | 3 | 110.9 | 167017762 | 167018749 |
| 169 | OSJNBa0071G03.3 protein n = 3 Tax = Oryza sativa RepID = Q7XX26_ORYSJ (8e−14); DUF1685: Protein of unknown function (DUF1685) (1.7e−34) | 3 | 110.9 | 167049453 | 167052175 |
| 170 | Ovule development aintegumenta-like protein BNM3 n = 1 Tax = Oryza sativa RepID = Q8LGQ3_ORYSA (1e−135); AP2: AP2 domain (1.2e−09); AP2: AP2 domain (1.6e−14); GO_MF:GO:0003700, transcription factor activity# (1e−128); GO_BP:GO:0045449, regulation of transcription# (1e−128); GO_CC:GO:0005634, nucleus# (1e−128) | 3 | 110.95 | 166793205 | 166797397 |
| 171 | diacylglycerol lipase beta n = 2 Tax = Gallus gallus RepID = UPI0000ECAA58 (4e−12); Lipase 3: Lipase (class 3) (3.3e−06); GO_MF:GO:0004806, triglyceride lipase activity# (0.0); GO_BP:GO:0006629, lipid metabolic process# (0.0) | 3 | 111 | 166663041 | 166670528 |
| 172 | Protein binding protein, putative n = 1 Tax = Ricinus communis RepID = B9S8S6_RICCO (1e−18); GO_MF:GO:0005515, protein binding# (3e−55) | 3 | 111 | 166675147 | 166675905 |
| 173 | Putative uncharacterized protein Sb03g042790 n = 3 Tax = Andropogoneae RepID = C5XFE3_SORBI (0.0) | 3 | 111 | 166811247 | 166817387 |
| 174 | Putative uncharacterized protein Sb03g042800 n = 1 Tax = Sorghum bicolor RepID = C5XFE4_SORBI (3e−78); Pollen_Ole_e_I: Pollen proteins Ole e I family (5.7e−10); Extensin_2: Extensin-like region (0.48); Extensin_2: Extensin-like region (0.65); Extensin_2: Extensin-like region (0.4) | 3 | 111.05 | 166798399 | 166800620 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 175 | Patatin, putative n = 1 Tax = *Ricinus communis* RepID = B9R7G2_RICCO (1e−76); Patatin: Patatin-like phospholipase (4.1e−05); GO_MF:GO:0016787, hydrolase activity# (1e−177); GO_BP:GO:0008152, metabolic process# (1e−177); GO_CC:GO:0016020, membrane# (6e−60) | 3 | 111.05 | 167072867 | 167075108 |
| 176 | Putative integral membrane protein n = 1 Tax = *Zea mays* RepID = Q5GAV3_MAIZE (1e−27); GO_MF:GO:0016758, transferase activity, transferring hexosyl groups# (6e−31); GO_BP:GO:0008152, metabolic process# (6e−31); GO_CC:GO:0016020, membrane# (1e−27) | 3 | 111.1 | 166801413 | 166807981 |
| 177 | Kiaa0078 protein (Fragment) n = 1 Tax = *Oryza sativa* RepID = Q9XFD8_ORYSA (6e−92); Rad21/Rec8 like protein (4.6e−14); GO_MF:GO:0005515, protein binding# (2e−33); GO_BP:GO:0007062, protein (3.1e−66); Rad21_Rec8: Conserved region of Rad21/Rec8 like protein; Rad21_Rec8_N: N terminus of Rad21/Rec8 like protein; NAS#sister chromatid cohesion# (1e−83); GO_CC:GO:0000228, nuclear chromosome# (0.0) | 3 | 111.2 | 167362932 | 167372276 |
| 178 | Formin-like protein 1 n = 1 Tax = *Oryza sativa Japonica* Group RepID = FH1_ORYSJ (0.0); FH2: Formin Homology 2 Domain (1.8e−167); GO_MF:GO:0003779, actin binding# (0.0); GO_MF:GO:0030036, actin cytoskeleton organization# (0.0); GO_CC:GO:0016021, integral to membrane# (0.0) | 3 | 111.4 | 167430557 | 167434529 |
| 179 | Beta-glucosidase 4 n = 2 Tax = *Oryza sativa* RepID = BGL04_ORYSJ (8e−45); GO_MF:GO:0043169, cation binding# (3e−51); GO_BP:GO:0005975, carbohydrate metabolic process# (3e−51); GO_CC:GO:0022626, IDA#cytosolic ribosome# (1e−22) | 3 | 111.75 | 167437055 | 167437918 |
| 180 | Beta-glucosidase 4 n = 2 Tax = *Oryza sativa* RepID = BGL04_ORYSJ (0.0); Glyco_hydro_1: Glycosyl hydrolase family 1 (1.6e−130); GO_MF:GO:0043169, cation binding# (0.0); GO_BP:GO:0005975, carbohydrate metabolic process# (0.0); GO_CC:GO:0005576, extracellular region# (2e−98) | 3 | 111.8 | 167442292 | 167446542 |
| 181 | Retrotransposon protein, putative, Ty1-copia subclass n = 1 Tax = *Oryza sativa Japonica* Group RepID = Q2QSG2_ORYSJ (4e−55); Retrotransposon_gag: Retrotransposon gag protein (0.0017); GO_MF:GO:0003677, DNA binding# (4e−55); GO_BP:GO:0015074, DNA integration# (4e−55) | 3 | 111.8 | 167449115 | 167449852 |
| 182 | Pentatricopeptide repeat protein n = 2 Tax = *Oryza sativa* RepID = A0IBX0_ORYSJ (1e−142); PPR: PPR repeat (0.14); PPR: PPR repeat (0.82); PPR: PPR repeat (0.62); PPR: PPR repeat (0.00036); PPR: PPR repeat (5.4e−07); PPR: PPR repeat (7.9e−07); PPR: PPR repeat (2e−11); GO_MF:GO:0005488, binding# (1e−142); GO_BP:GO:0006952, defense response# (1e−26); GO_CC:GO:0005739, mitochondrion# (2e−99) | 3 | 111.8 | 167472698 | 167474938 |
| 183 | 50S ribosomal protein L13 n = 2 Tax = Andropogoneae RepID = B6TQ75_MAIZE (4e−09); GO_MF:GO:0003735, structural constituent of ribosome# (3e−09); GO_BP:GO:0006412, translation# (3e−09); GO_CC:GO:0005840, ribosome# (3e−09) | 3 | 111.8 | 167479089 | 167479298 |
| 184 | 50S ribosomal protein L13 n = 2 Tax = Andropogoneae RepID = B6TQ75_MAIZE (1e−49); Ribosomal_L13: Ribosomal protein L13 (2.3e−07); GO_MF:GO:0003735, structural constituent of ribosome# (1e−49); GO_BP:GO:0006412, translation# (1e−49); GO_CC:GO:0005840, ribosome# (1e−49) | 3 | 111.8 | 167486399 | 167488255 |
| 185 | Ribonuclease 2 n = 2 Tax = *Zea mays* RepID = B6TDK4_MAIZE (1e−149); Ribonuclease_T2: Ribonuclease T2 family (8.8e−55); GO_MF:GO:0003897, ribonuclease T2 activity## (1e−149); GO_BP:GO:0006950, response to stress# (2e−60); GO_CC:GO:0005773, IDA#vacuole# (2e−60) | 3 | 111.8 | 167682817 | 167685987 |
| 186 | Ribonuclease 2 n = 2 Tax = *Zea mays* RepID = B6TGK1_MAIZE (1e−146); Ribonuclease_T2: Ribonuclease T2 family (3.1e−57); GO_MF:GO:0003897, ribonuclease T2 activity## (1e−146); GO_BP:GO:0006950, response to stress# (6e−69); GO_CC:GO:0005773, IDA#vacuole# (6e−69) | 3 | 111.8 | 167686841 | 167690777 |
| 187 | Glycosyltransferase n = 1 Tax = *Populus trichocarpa* RepID = B9N4D7_POPTR (1e−120); Glyco_transf_8: Glycosyl transferase family 8 (1.5e−38); GO_MF:GO:0016757, transferase activity, transferring glycosyl groups# (1e−137); GO_BP:GO:0006468, protein amino acid phosphorylation# (3e−58); GO_CC:GO:0005886, plasma membrane# (6e−65) | 3 | 111.8 | 167711919 | 167713615 |
| 188 | OSJNBa0063C18.6 protein n = 1 Tax = *Oryza sativa Japonica* Group RepID = Q7X6Q9_ORYSJ (3e−14); GO_MF:GO:0008234, cysteine-type peptidase activity## (3e−14); GO_BP:GO:0006508, proteolysis# (3e−14); GO_CC:GO:0030529, ribonucleoprotein complex# (5e−10) | 3 | 111.8 | 167715238 | 167717735 |
| 189 | DNA helicase homolog, putative n = 1 Tax = *Musa acuminata* RepID = Q1EPC6_MUSAC (0.0); DUF889: Eukaryotic protein of unknown function (DUF889) (7.1e−70); GO_MF:GO:0005524, ATP binding# (6e−36); GO_BP:GO:0048366, TAS#leaf development# (8e−91); GO_CC:GO:0005678, IPI#chromatin assembly complex# (8e−91) | 3 | 111.8 | 167729335 | 167732914 |
| 190 | Helicase-like protein n = 1 Tax = *Oryza sativa Japonica* Group RepID = Q9AYF0_ORYSJ (7e−24); GO_MF:GO:0004386, helicase activity# (7e−24) | 3 | 111.8 | 167732923 | 167734044 |
| 191 | Sec20 family protein n = 4 Tax = Andropogoneae RepID = B6TQD1_MAIZE (4e−46) | 3 | 111.8 | 167734979 | 167735405 |
| 192 | MPPN domain containing protein n = 1 Tax = *Zea mays* RepID = B6UAH6_MAIZE (4e−17); Sec20: Sec20 (0.03); MPPN: MPPN (rrm-like) domain (0.022); GO_MF:GO:0004576, oligosaccharyl transferase activity# (1e−12); GO_BP:GO:0006486, protein amino acid glycosylation# (1e−12); GO_CC:GO:0016020, membrane# (1e−12) | 3 | 111.8 | 167744313 | 167750012 |
| 193 | P0696G06.27 protein n = 2 Tax = *Oryza sativa* RepID = Q8L4W8_ORYSJ (0.0); Rhodanese: Rhodanese-like domain (0.0041); GO_MF:GO:0004872, receptor activity# (1e−14); GO_BP:GO:0004872, receptor activity# (1e−14); GO_CC:GO:0009507, chloroplast# (4e−63) | 3 | 111.8 | 168290364 | 168298568 |
| 194 | Chromatin assembly factor-1 n = 3 Tax = *Oryza sativa* RepID = B2ZX90_ORYSJ (0.0); ToIA: ToIA protein (0.0032); DUF1154: Protein of unknown function (DUF1154) (0.023); GO_MF:GO:0005524, ATP binding# (6e−36); GO_BP:GO:0048366, TAS#leaf development# (8e−91) | 3 | 111.8 | 168301241 | 168308101 |
| 195 | Putative mutator-like transposase n = 2 Tax = *Oryza sativa Japonica* Group RepID = Q75IN8_ORYSJ (1e−27) | 3 | 111.8 | 168301382 | 168301870 |
| 196 | Putative ribosomal protein n = 1 Tax = *Oryza sativa* RepID = Q8SB40_ORYSA (5e−48); Plant_tran: Plant transposon protein (5.9e−23); GO_MF:GO:0016740, transferase activity# (5e−25); GO_CC:GO:0005840, ribosome# (5e−48) | 3 | 111.8 | 168363189 | 168363859 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 197 | Putative ribosomal protein n = 1 Tax = *Oryza sativa* RepID = Q8SB40_ORYSA (3e−09); GO_CC:GO:0005840, ribosome# (3e−09) | 3 | 111.8 | 168363866 | 168364830 |
| 198 | Putative uncharacterized protein n = 2 Tax = *Zea mays* RepID = B6TTS0_MAIZE (3e−46) | 3 | 111.8 | 168429303 | 168429952 |
| 199 | ATP binding protein n = 3 Tax = Andropogoneae RepID = B6SYS4_MAIZE (3e−13); DUF1296: Protein of unknown function (DUF1296) (0.0017); GO_MF:GO:0005524, ATP binding# (3e−13); GO_BP:GO:0006468, protein amino acid phosphorylation# (3e−13) | 3 | 111.8 | 168430535 | 168434782 |
| 200 | Alpha-2,8-sialyltransferase 8b, putative n = 1 Tax = *Ricinus communis* RepID = B9RA86_RICCO (1e−70); GO_MF:GO:0008373, sialyltransferase activity# (1e−103); GO_BP:GO:0006486, protein amino acid glycosylation# (1e−103); GO_CC:GO:0030173, integral to Golgi membrane# (1e−103) | 3 | 111.8 | 168438932 | 168440345 |
| 201 | Zinc finger protein n = 1 Tax = *Zea mays* RepID = B6SJ02_MAIZE (1e−80); Trigger_N: Bacterial trigger factor protein (TF) (0.019); zf-C3HC4: Zinc finger, C3HC4 type (RING finger) (2.2e−15); GO_MF:GO:0008270, zinc ion binding# (1e−80); GO_BP:GO:0015031, protein transport# (1e−109); GO_CC:GO:0009570, IDA#chloroplast stroma# (1e−21) | 3 | 111.8 | 168480872 | 168487707 |
| 202 | Selenoprotein n = 4 Tax = Andropogoneae RepID = B6T325_MAIZE (5e−81); Sep15_SelM: Sep15/SelM redox domain (6.7e−40); GO_MF:GO:0008430, selenium binding# (9e−16); GO_BP:GO:0051084, IDA#'de novo' posttranslational protein folding# (9e−16); GO_CC:GO:0005788, endoplasmic reticulum lumen# (9e−16) | 3 | 111.8 | 168489946 | 168492960 |
| 203 | Fructokinase-1 n = 8 Tax = Poaceae RepID = SCRK1_ORYSJ (1e−166); PfkB: pfkB family carbohydrate kinase (4.3e−107); GO_MF:GO:0016740, transferase activity# (1e−166); GO_CC:GO:0005886, plasma membrane# (1e−136) | 3 | 111.8 | 168523210 | 168526249 |
| 204 | Putative uncharacterized protein n = 1 Tax = *Zea mays* RepID = B8A0T9_MAIZE (1e−38) | 3 | 111.9 | 167786045 | 167789878 |
| 205 | Retrotransposon protein, putative, unclassified n = 1 Tax = *Oryza sativa Japonica* Group RepID = Q10PF2_ORYSJ (0.0); zf-H2C2: His(2)-Cys(2) zinc finger (0.011); rve: Integrase core domain (6.9e−18); Chromo: 'chromo' (CHRomatin Organisation MOd (5.5e−11); GO_MF:GO:0003964, RNA-directed DNA polymerase, group II intron encoded# (0.0); GO_BP:GO:0015074, DNA integration# (0.0); GO_CC:GO:0005634, nucleus# (0.0) | 3 | 111.9 | 167790427 | 167792988 |
| 206 | Putative polyprotein, 5′-partial (Fragment) n = 1 Tax = *Oryza sativa* RepID = Q94GF8_ORYSA (4e−54); RVP_2: Retroviral aspartyl protease (0.00023); GO_MF:GO:0003964, RNA-directed DNA polymerase, group II intron encoded# (2e−56); GO_BP:GO:0015074, DNA integration# (2e−56); GO_CC:GO:0005634, nucleus# (2e−56) | 3 | 111.9 | 167793124 | 167793873 |
| 207 | Putative uncharacterized protein n = 2 Tax = *Zea mays* RepID = B8A0T9_MAIZE (2e−73); PPR: PPR repeat (1.9); PPR: PPR repeat (0.089); GO_MF:GO:0008270, zinc ion binding# (7e−29); GO_CC:GO:0009507, chloroplast# (7e−29) | 3 | 111.9 | 167797246 | 167802786 |
| 208 | Putative uncharacterized protein n = 1 Tax = *Zea mays* RepID = C0PFS4_MAIZE (0.0); GO_MF:GO:0043565, sequence-specific DNA binding# (4e−46); GO_BP:GO:0006355, regulation of transcription, DNA-dependent# (4e−46) | 3 | 111.9 | 167805773 | 167810540 |
| 209 | Membrane-associated 30 kDa protein n = 3 Tax = Andropogoneae RepID = B6T6V3_MAIZE (1e−122); PspA_IM30: PspA/D430 family (2.3e−25); Snf7: Snf7 (0.096); GO_BP:GO:0044419, interspecies interaction between organisms# (1e−115); GO_CC:GO:0016020, membrane# (1e−115) | 3 | 111.9 | 168368220 | 168373431 |
| 210 | HAT family dimerisation domain containing protein n = 1 Tax = *Oryza sativa Japonica* Group RepID = Q2QRD1_ORYSJ (8e−22); GO_MF:GO:0046983, protein dimerization activity# (2e−23) | 3 | 111.9 | 168405403 | 168405915 |
| 211 | Eukaryotic translation initiation factor 3 subunit 2 n = 2 Tax = Andropogoneae RepID = B6SSB6_MAIZE (1e−09); GO_MF:GO:0003743, protein-synthesizing GTPase activity, initiation# (1e−09); GO_BP:GO:0003743, protein-synthesizing GTPase activity, initiation# (1e−09) | 3 | 111.9 | 168609417 | 168609826 |
| 212 | AP-3 complex subunit sigma-2 n = 3 Tax = Andropogoneae RepID = B4FA26_MAIZE (4e−26); Clat_adaptor_s: Clathrin adaptor complex small chain (3.2e−09); GO_MF:GO:0008565, protein transporter activity# (4e−26); GO_BP:GO:0016192, vesicle-mediated transport# (4e−26); GO_CC:GO:0030117, membrane coat# (4e−26) | 3 | 111.9 | 168611405 | 168613025 |
| 213 | Phenylalanine ammonia-lyase n = 22 Tax = Poaceae RepID = PAL2_ORYSJ (4e−46); PAL: Phenylalanine and histidine ammonia-lyase (0.0036); GO_MF:GO:0016841, ammonia-lyase activity# (4e−46); GO_BP:GO:0009698, phenylpropanoid metabolic process# (4e−46); GO_CC:GO:0005737, cytoplasm# (4e−46) | 3 | 111.9 | 168620337 | 168620882 |
| 214 | Leukotriene A-4 hydrolase, putative n = 1 Tax = *Ricinus communis* RepID = B9SD61_RICCO (1e−17); GO_MF:GO:0016787, hydrolase activity# (6e−36); GO_BP:GO:0019370, leukotriene biosynthetic process# (6e−36) | 3 | 111.9 | 168661556 | 168662161 |
| 215 | Putative uncharacterized protein n = 1 Tax = *Zea mays* RepID = C0PAB7_MAIZE (1e−14) | 3 | 112 | 167912639 | 167932679 |
| 216 | Putative uncharacterized protein n = 1 Tax = *Zea mays* RepID = C0PAB7_MAIZE (7e−18) | 3 | 112 | 167933809 | 167934006 |
| 217 | Putative HOBBIT n = 1 Tax = *Oryza sativa Japonica* Group RepID = Q69XV2_ORYSJ (0.0); TPR_1: Tetratricopeptide repeat (1.5); TPR_2: Tetratricopeptide repeat (5.6); TPR_1: Tetratricopeptide repeat (9.8e−06); TPR_2: Tetratricopeptide repeat (0.002); TPR_1: Tetratricopeptide repeat (2.6e−05); TPR_2: Tetratricopeptide repeat (0.21); TPR_1: Tetratricopeptide repeat (2.1e−05); TPR_1: Tetratricopeptide repeat (1.8e−06); TPR_1: Tetratricopeptide repeat (0.013); TPR_2: Tetratricopeptide repeat (0.0028); TPR_1: Tetratricopeptide repeat (4e−08); TPR_2: Tetratricopeptide repeat (3.8); TPR_2: Tetratricopeptide repeat (1.6); TPR_1: Tetratricopeptide repeat (0.12); TPR_2: Tetratricopeptide repeat (0.65); | 3 | 112 | 168003055 | 168013349 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| | GO_MF:GO:0005488, binding# (0.0); GO_BP:GO:0051510, IGI#regulation of unidimensional cell growth# (0.0); GO_CC:GO:0009504, IDA#cell plate# (0.0) | | | | |
| 218 | Putative transposable element n = 1 Tax = *Oryza sativa Japonica* Group RepID = Q8LNC1_ORYSJ (1e-151); MuDR: MuDR family transposase (5.6e-27); Transposase_mut: Transposase, Mutator family (0.05); MULE: MULE transposase domain (2.2e-11); SWIM: SWIM zinc finger (3.4e-08); GO_MF:GO:0008270, zinc ion binding# (0.0); GO_BP:GO:0006313, transposition, DNA-mediated# (0.0) | 3 | 112.1 | 168015671 | 168017677 |
| 219 | DNA-directed RNA polymerase n = 2 Tax = *Oryza sativa Japonica* Group RepID = Q0DKN9_ORYSJ (2e-35); RNA_pol_Rpb1_2: RNA polymerase Rpb1, domain 2 (1.4e-05); GO_MF:GO:0016779, nucleotidyltransferase activity# (2e-35); GO_BP:GO:0006366, transcription from RNA polymerase II promoter# (2e-35); GO_CC:GO:0005665, DNA-directed RNA polymerase II, core complex# (2e-35) | 3 | 112.1 | 168021045 | 168024149 |
| 220 | Putative uncharacterized protein Sb04g025980 n = 1 Tax = *Sorghum bicolor* RepID = C5XXM9_SORBI (2e-32) | 3 | 112.1 | 168854887 | 168856209 |
| 221 | P0696G06.7 protein n = 3 Tax = *Oryza sativa* RepID = Q7F447_ORYSJ (0.0); Metallophos: Calcineurin-like phosphoesterase (4.9e-09); GO_MF:GO:0016787, hydrolase activity# (0.0); GO_BP:GO:0006396, RNA processing# (0.0); GO_CC:GO:0005622, intracellular# (0.0) | 3 | 112.1 | 168858815 | 168863872 |
| 222 | Putative uncharacterized protein Sb10g008520 n = 1 Tax = *Sorghum bicolor* RepID = C5XH02_SORBI (1e-10) | 3 | 112.1 | 168866726 | 168869485 |
| 223 | Aspartokinase n = 1 Tax = *Sorghum bicolor* RepID = C5Z7H3_SORBI (6e-30); AA_kinase: Amino acid kinase family (0.016); GO_MF:GO:0016740, transferase activity# (9e-30); GO_BP:GO:0016301, kinase activity# (9e-30); GO_CC:GO:0009536, plastid# (2e-26) | 3 | 112.2 | 168901191 | 168909642 |
| 224 | Protein binding protein, putative n = 1 Tax = *Ricinus communis* RepID = B9T840_RICCO (1e-109); BTB: BTB/POZ domain (0.00015); zf-TAZ: TAZ zinc finger (0.0094); GO_MF:GO:0008270, zinc ion binding# (0.0); GO_BP:GO:0006355, regulation of transcription, DNA-dependent## (0.0); GO_CC:GO:0005634, nucleus# (0.0) | 3 | 112.2 | 168918994 | 168923530 |
| 225 | DNA binding protein n = 1 Tax = *Zea mays* RepID = B6T3S3_MAIZE (3e-28); SRF-TF: SRF-type transcription factor (DNA-binding and dimerisation domain) (6.5e-15); GO_MF:GO:0043565, sequence-specific DNA binding# (2e-63); GO_BP:GO:0045449, regulation of transcription# (2e-63); GO_CC:GO:0005634, nucleus# (2e-63) | 3 | 112.2 | 168925201 | 168926167 |
| 226 | Ankyrin-kinase, putative n = 1 Tax = *Ricinus communis* RepID = B9SV01_RICCO (1e-164); Ank: Ankyrin repeat (4.3e-11); Pkinase: Protein kinase domain (7.3e-25); Pkinase_Tyr: Protein tyrosine kinase (9.1e-17); GO_MF:GO:0016301, kinase activity# (0.0); GO_BP:GO:0016301, kinase activity# (0.0); GO_CC:GO:0005737, cytoplasm# (1e-95) | 3 | 112.2 | 168959249 | 168962676 |
| 227 | PAE n = 1 Tax = *Litchi chinensis* RepID = B3V945_LITCN (6e-50); PAE: Pectinacetylesterase (8.5e-71); GO_MF:GO:0016787, hydrolase activity# (1e-56); GO_CC:GO:0016020, membrane# (2e-50) | 3 | 112.3 | 169031162 | 169033726 |
| 228 | PAE n = 1 Tax = *Litchi chinensis* RepID = B3V945_LITCN (1e-33); PAE: Pectinacetylesterase (7e-10); GO_MF:GO:0016787, hydrolase activity# (2e-41) | 3 | 112.3 | 169034338 | 169035344 |
| 229 | PAE n = 1 Tax = *Litchi chinensis* RepID = B3V945_LITCN (1e-92); PAE: Pectinacetylesterase (3.1e-190); GO_MF:GO:0016787, hydrolase activity# (1e-123); GO_CC:GO:0016020, membrane# (1e-93) | 3 | 112.3 | 169044021 | 169046721 |
| 230 | NADP-dependent oxidoreductase P1 n = 3 Tax = Andropogoneae RepID = B6TFG1_MAIZE (1e-110); Glyco_hydro_28: Glycosyl hydrolases family 28 (3.8e-13); GO_MF:GO:0016798, hydrolase activity, acting on glycosyl bonds# (0.0); GO_BP:GO:0055114, oxidation reduction# (0.0) | 3 | 112.3 | 169071070 | 169080582 |
| 231 | Putative uncharacterized protein n = 1 Tax = *Zea mays* RepID = B6UD01_MAIZE (5e-12) | 3 | 112.3 | 169081463 | 169082314 |
| 232 | Putative transformer serine/arginine-rich ribonucleoprotein n = 2 Tax = *Oryza sativa* RepID = Q84QA6_ORYSJ (6e-28); RRM_1: RNA recognition motif. (a.k.a. RRM, RBD (1.2e-09); GO_MF:GO:0003676, nucleic acid binding# (1e-30); GO_BP:GO:0008380, RNA splicing# (4e-19); GO_CC:GO:0030529, ribonucleoprotein complex# (4e-19) | 3 | 112.3 | 169085515 | 169087999 |
| 233 | Putative uncharacterized protein n = 1 Tax = *Zea mays* RepID = B4FSH8_MAIZE (2e-51); IQ: IQ calmodulin-binding motif (0.00029); IQ: IQ calmodulin-binding motif (0.8) | 3 | 112.35 | 169093629 | 169095183 |
| 234 | TPR repeat n = 1 Tax = *Medicago truncatula* RepID = AQ5X4_MEDTR (4e-41); TPR_2: Tetratricopeptide repeat (18); SPO22: Meiosis protein SPO22/ZIP4 like (1e-49); TPR_2: Tetratricopeptide repeat (14); TPR_2: Tetratricopeptide repeat (11); TPR_2: Tetratricopeptide repeat (2.3); GO_MF:GO:0005488, binding# (0.0) | 3 | 112.4 | 169113781 | 169117194 |
| 235 | Protein IAL1 n = 3 Tax = *Zea mays* RepID = IAL1_MAIZE (3e-98); DUF260: Protein of unknown function DUF260 (3.6e-64); GO_MF:GO:0005515, protein binding# (7e-44); GO_BP:GO:0007275, TAS#multicellular organismal development# (3e-98); GO_CC:GO:0005634, nucleus# (3e-98) | 3 | 112.5 | 169217653 | 169220962 |
| 236 | Putative uncharacterized protein n = 1 Tax = *Zea mays* RepID = COP2N4_MAIZE (3e-38) | 3 | 112.6 | 169313187 | 169317616 |
| 237 | Retrotransposon protein, putative, LINE subclass n = 1 Tax = *Oryza sativa Japonica* Group RepID = Q7XET4_ORYSJ (1e-09); GO_MF:GO:0004190, penicillopepsin activity# (4e-09); GO_BP:GO:0015074, DNA integration# (4e-09); GO_CC:GO:0005634, nucleus# (4e-09) | 3 | 112.6 | 169348963 | 169349896 |
| 238 | Putative uncharacterized protein n = 1 Tax = *Zea mays* RepID = B7ZZD5_MAIZE (2e-56) | 3 | 113.2 | 169538753 | 169539943 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 239 | Mitogen-activated protein kinase kinase-like n = 1 Tax = Oryza sativa Japonica Group RepID = Q5ZE15_ORYSJ (6e–22); GO_MF:GO:0016301, kinase activity# (6e–22); GO_BP:GO:0016301, kinase activity# (6e–22); GO_CC:GO:0005737, cytoplasm# (6e–11) | 3 | 113.2 | 169539810 | 169540145 |
| 240 | Protein ycf2 n = 2 Tax = Asteraceae RepID = YCF2_GUIAB (2e–32); GO_MF:GO:0017111, nucleoside-triphosphatase activity# (2e–32); GO_BP:GO:0032259, methylation# (2e–31); GO_CC:GO:0005739, mitochondrion# (8e–64) | 3 | 113.3 | 169573423 | 169574052 |
| 241 | DNA binding protein, putative n = 1 Tax = Ricinus communis RepID = B9R9V4_RICCO (1e–26); RNA_pol_Rpc4: RNA polymerase III RPC4 (4.4e–23); GO_MF:GO:0003899, DNA-directed RNA polymerase III activity# (1e–158); GO_BP:GO:0006383, transcription from RNA polymerase III promoter# (1e–158); GO_CC:GO:0005666, DNA-directed RNA polymerase III complex# (1e–158) | 3 | 113.3 | 169576810 | 169579768 |
| 242 | Mitogen-activated protein kinase kinase-like n = 1 Tax = Oryza sativa Japonica Group RepID = Q5ZE15_ORYSJ (4e–62); Pkinase: Protein kinase domain (1.8e–25); Pkinase_Tyr: Protein tyrosine kinase (1e–09); GO_MF:GO:0005524, ATP binding# (3e–62); GO_BP:GO:0006468, protein amino acid phosphorylation# (3e–62); GO_CC:GO:0005886, plasma membrane# (1e–29) | 3 | 113.3 | 169582103 | 169583032 |
| 243 | Signal recognition particle subunit srp72, putative n = 1 Tax = Ricinus communis RepID = B9RMK3_RICCO (1e–113); GO_MF:GO:0008312, 7S RNA binding# (1e–179); GO_BP:GO:0006614, SRP-dependent cotranslational protein targeting to membrane# (1e–179); GO_CC:GO:0048500, signal recognition particle# (1e–179) | 3 | 113.45 | 169617037 | 169619993 |
| 244 | Serine/threonine-protein kinase RIO2 n = 1 Tax = Zea mays RepID = B6SHM1_MAIZE (0.0); Rio2_N: Rio2, N-terminal (9.9e–52); Kdo: Lipopolysaccharide kinase (Kdo) (0.0053); APH: Phosphotransferase enzyme family (0.0048); RIO1: RIO1 family (1.6e–72); GO_MF:GO:0016301, kinase activity# (0.0); GO_CC:GO:0005737, cytoplasm# (1e–110) | 3 | 113.6 | 169743475 | 169748165 |
| 245 | MLO-like protein 1 n = 1 Tax = Zea mays RepID = Q94CG7_MAIZE (1e–151); GO_BP:GO:0008219, TAS#cell death# (0.0); GO_CC:GO:0016021, integral to membrane# (0.0) | 3 | 113.7 | 169873245 | 169877270 |
| 246 | NAC domain-containing protein, putative n = 1 Tax = Ricinus communis RepID = B9S056_RICCO (9e–49); NAM: No apical meristem (NAM) protein (8.6e–35); IDA#calmodulin binding# (1e–130); GO_BP:GO:0045449, regulation of transcription# (1e–130); GO_CC:GO:0005634, nucleus# (2e–27) | 3 | 113.7 | 170022867 | 170025687 |
| 247 | ATRAD3, putative n = 1 Tax = Ricinus communis RepID = B9S061_RICCO (1e–110); Methyltransf_11: Methyltransferase domain (1.8e–07); Methyltransf_12: Methyltransferase domain (3.1e–06); GO_MF:GO:0008168, methyltransferase activity# (1e–107); GO_BP:GO:0008152, metabolic process# (1e–107); GO_CC:GO:0005886, plasma membrane# (2e–44) | 3 | 113.8 | 170063542 | 170064940 |
| 248 | PHD finger protein n = 4 Tax = Zea mays RepID = B6TYP6_MAIZE (1e–110); C1_3: C1-like domain (0.063); PHD: PHD-finger (1.7e–11); GO_MF:GO:0046872, metal ion binding# (1e–110); GO_BP:GO:0046961, proton-transporting ATPase activity, rotational mechanism# (2e–72); GO_CC:GO:0005634, nucleus# (5e–74) | 3 | 113.9 | 170106397 | 170110892 |
| 249 | Peptide chain release factor, putative n = 1 Tax = Ricinus communis RepID = B9S081_RICCO (8e–54); RF-1: Peptidyl-tRNA hydrolase domain (1.9e–06); GO_MF:GO:0003747, translation release factor activity# (1e–78); GO_BP:GO:0006415, translational termination# (1e–78); GO_CC:GO:0005737, cytoplasm# (2e–12) | 3 | 113.9 | 170111448 | 170114501 |
| 250 | Putative 2-C-methyl-D-erythritol 4-phosphate cytidylyltransferase n = 2 Tax = Oryza sativa RepID = Q5N8G1_ORYSJ (1e–125); IspD: Uncharacterized protein family UPF0007 (1.2e–55); NTP_transferase: Nucleotidyl transferase (0.1); GO_MF:GO:0050518, 2-C-methyl-D-erythritol 4-phosphate cytidylyltransferase activity# (1e–125); GO_BP:GO:0016114 terpenoid biosynthetic process# (1e–125); GO_CC:GO:0009570, IDA#chloroplast stroma# (5e–91) | 3 | 113.9 | 170115790 | 170118780 |
| 251 | Zgc:162613 protein n = 3 Tax = Danio rerio RepID = A3KNW8_DANRE (3e–30); DUF647: Protein of unknown function, DUF647 (9.6e–153); GO_MF:GO:0003674, ND#molecular function# (3e–26); GO_BP:GO:0010224, response to UV-B# (2e–29); GO_CC:GO:0016021, integral to membrane# (6e–30) | 3 | 113.9 | 170119830 | 170125020 |
| 252 | Putative uncharacterized protein n = 1 Tax = Zea mays RepID = C0HGN3_MAIZE (1e–23) | 3 | 113.9 | 170144285 | 170144599 |
| 253 | Putative uncharacterized protein n = 1 Tax = Zea mays RepID = Q6JAD6_MAIZE (3e–09) | 3 | 114 | 170148931 | 170218903 |
| 254 | AP2 domain containing protein n = 1 Tax = Zea mays RepID = B6UDE8_MAIZE (1e–103); AP2: AP2 domain (2.5e–20); GO_MF:GO:0003700, transcription factor activity# (1e–103); GO_BP:GO:0045449, regulation of transcription# (1e–103); GO_CC:GO:0005634, nucleus# (1e–103) | 3 | 114.1 | 170221982 | 170223800 |
| 255 | Putative uncharacterized protein Sb03g042100 n = 2 Tax = Andropogoneae RepID = C5XEN6_SORBI (1e–26); GO_MF:GO:0051082, unfolded protein binding# (3e–20); GO_BP:GO:0006457, protein folding# (3e–20) | 3 | 114.1 | 170248244 | 170251095 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 256 | Nucleic acid binding protein, putative n = 1 Tax = Ricinus communis RepID = B9SKB5_RICCO (9e−97); GO_MF:GO:0003723, RNA binding# (1e−132); GO_BP:GO:0030154, cell differentiation# (4e−30); GO_CC:GO:0005634, nucleus# (7e−81) | 3 | 114.1 | 170277042 | 170281693 |
| 257 | M25 protein (Fragment) n = 2 Tax = Zea mays RepID = Q84V73_MAIZE (1e−112); SRF-TF: SRF-type transcription factor (DNA-binding and dimerisation domain) (6.2e−31); K-box: K-box region (3.6e−42); GO_MF:GO:0043565, sequence-specific DNA binding# (1e−112); GO_BP:GO:0045449, regulation of transcription# (1e−112); GO_CC:GO:0005634, nucleus# (1e−112) | 3 | 114.3 | 170365225 | 170381998 |
| 258 | Pentatricopeptide repeat protein PPR986-2 n = 1 Tax = Ricinus communis RepID = B6SPB1_MAIZE (7e−29); PPR: PPR repeat (0.01); GO_MF:GO:0004553, hydrolase activity, hydrolyzing O-glycosyl compounds# (2e−43); GO_BP:GO:0005975, carbohydrate metabolic process# (2e−43); GO_CC:GO:0009507, chloroplast# (2e−15) | 3 | 114.3 | 170382014 | 170383688 |
| 259 | Transcriptional factor TINY n = 1 Tax = Zea mays RepID = B6SP65_MAIZE (2e−67); AP2: AP2 domain (5.6e−17); GO_MF:GO:0003700, transcription factor activity# (2e−67); GO_BP:GO:0045449, regulation of transcription# (2e−67); GO_CC:GO:0005634, nucleus# (2e−67) | 3 | 114.4 | 170423568 | 170424380 |
| 260 | Leucoanthocyanidin reductase n = 1 Tax = Zea mays RepID = B6T842_MAIZE (4e−65); GO_MF:GO:0050662, coenzyme binding# (4e−65); GO_BP:GO:0044237, cellular metabolic process# (4e−65); GO_CC:GO:0005694, chromosome# (2e−40) | 3 | 114.4 | 170426281 | 170428946 |
| 261 | Phosphoinositide 5-phosphatase, putative n = 1 Tax = Ricinus communis RepID = B9RR38_RICCO (2e−52) | 3 | 114.4 | 170431126 | 170433790 |
| 262 | Hydrolase-like protein n = 2 Tax = Oryza sativa RepID = Q5N8H1_ORYSJ (1e−164); PGAP1: PGAP1-like protein (0.016); Thioesterase: Thioesterase domain (0.0067); Abhydrolase_1: alpha/beta hydrolase fold (1.3e−07); GO_MF:GO:0016788, hydrolase activity, acting on ester bonds# (1e−164); GO_BP:GO:0009058, biosynthetic process# (1e−164); GO_CC:GO:0005739, mitochondrion# (8e−42) | 3 | 114.4 | 170440239 | 170445382 |
| 263 | Cytochrome c n = 5 Tax = Magnoliophyta Rep ID = CYC_ORYSJ (4e−58); Cytochrom_C: Cytochrome c (8.1e−34); GO_MF:GO:0046872, metal ion binding# (4e−58); GO_BP:GO:0022900, electron transport chain# (4e−58); GO_CC:GO:0070469, respiratory chain# (4e−58) | 3 | 114.5 | 170498763 | 170503087 |
| 264 | DNA glycosylase n = 1 Tax = Micromonas pusilla CCMP1545 RepID = C1MR64_9CHLO (2e−47); SNARE_assoc: SNARE associated Golgi protein (1.5e−48); GO_MF:GO:0005524, ATP binding# (3e−19); GO_BP:GO:0006915, apoptosis# (3e−19); GO_CC:GO:0009507, chloroplast# (2e−77) | 3 | 114.5 | 170535675 | 170538882 |
| 265 | Pentatricopeptide (PPR) repeat-containing protein-like protein n = 2 Tax = Oryza sativa Japonica Group RepID = Q6ZIP5_ORYSJ (1e−101); TPR_4: Tetratricopeptide repeat (12); PPR: PPR repeat (2e−08); PPR: PPR repeat (1.5e−06); PPR: PPR repeat (6.5e−09); TPR_4: Tetratricopeptide repeat (1.4); PPR: PPR repeat (2.5); GO_BP:GO:0005488, binding# (1e−141); GO_CC:GO:0005739, mitochondrion# (1e−102) | 3 | 114.5 | 170538931 | 170540493 |
| 266 | Putative uncharacterized protein n = 1 Tax = Zea mays RepID = B6SSE8_MAIZE (7e−84) | 3 | 114.5 | 170545652 | 170548181 |
| 267 | Transposon protein Pong sub-class n = 1 Tax = Zea mays RepID = B6TCG7_MAIZE (1e−29); Plant_tran: Plant transposon protein (1.1e−06); GO_CC:GO:0005840, ribosome# (2e−28) | 3 | 114.6 | 170678312 | 170678644 |
| 268 | Putative polyprotein n = 1 Tax = Zea mays RepID = Q8SA93_MAIZE (1e−118); GO_MF:GO:0003964, RNA-directed DNA polymerase, group II intron encode# (1e−118); GO_BP:GO:0015074, DNA integration# (1e−118); GO_CC:GO:0005634, nucleus# (1e−118) | 3 | 114.6 | 170703404 | 170704531 |
| 269 | Protein binding protein, putative n = 1 Tax = Ricinus communis RepID = B9SG36_RICCO (1e−157); U-box: U-box domain (9.8e−24); Plus-3: Plus-3 domain (2.3e−24); GO_MF:GO:0046872, metal ion binding# (7e−84); GO_BP:GO:0016570, histone modification# (7e−84); Arm: Armadillo/beta-catenin-like repeat (4.9e−09); Arm: Armadillo/beta-catenin-like repeat (0.003); Arm: Armadillo/beta-catenin-like repeat (8e−05); Arm: Armadillo/beta-catenin-like repeat (1.9e−09); Arm: Armadillo/beta-catenin-like repeat (0.01); Arm: Armadillo/beta-catenin-like repeat (0.66); GO_CC:GO:0005634, nucleus# (7e−84) | 3 | 114.6 | 170707230 | 170710209 |
| 270 | Putative uncharacterized protein Sb03g041940 n = 1 Tax = Sorghum bicolor RepID = C5XEM1_SORBI (1e−44); GYF: GYF domain (1.2e−05); GO_MF:GO:0046872, metal ion binding# (6e−11); GO_BP:GO:0016570, histone modification# (6e−11); GO_CC:GO:0005634, nucleus# (6e−11) | 3 | 114.6 | 170732741 | 170733199 |
| 271 | Ubiquitin-protein ligase, putative n = 1 Tax = Ricinus communis RepID = B9SS21_RICCO (5e−27); SWIB: SWIB/MDM2 domain (0.0017); Plus-3: Plus-3 domain (2.3e−24); GO_MF:GO:0005488, binding# (7e−84); GO_BP:GO:0016567, IGI#protein ubiquitination# (0.0); GO_CC:GO:000151, ubiquitin ligase complex# (0.0) | 3 | 114.7 | 170771543 | 170775469 |
| 272 | NAC domain-containing protein 48 n = 1 Tax = Zea mays RepID = B6TI55_MAIZE (1e−153); NAM: No apical meristem (NAM) protein (1.9e−83); GO_MF:GO:0036677, DNA binding# (1e−151); GO_BP:GO:0045449, regulation of transcription# (1e−151); GO_CC:GO:0005634, nucleus# (1e−130) | 3 | 114.7 | 170820468 | 170822609 |
| 273 | Ankyrin-like protein n = 1 Tax = Zea mays RepID = B6U1Y2_MAIZE (2e−35); GO_MF:GO:006740, transferase activity# (7e−32); GO_BP:GO:0055114, oxidation reduction# (9e−23); GO_CC:GO:0005794, IDA#Golgi apparatus# (5e−36) | 3 | 114.8 | 170867201 | 170867947 |
| 274 | Gibberellin 20 oxidase 2 n = 16 Tax = Oryza RepID = GAOX2_ORYSJ (1e−162); 2OG-FeII_Oxy: 2OG-Fe(II) oxygenase superfamily (1.4e−48); GO_MF:GO:0046872, metal ion binding# (1e−162); GO_BP:GO:0055114, oxidation reduction# (1e−162); GO_CC:GO:0005737, cytoplasm# (1e−103) | 3 | 114.8 | 170899605 | 170902451 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 275 | Retrotransposon protein, putative, unclassified n = 1 Tax = Oryza sativa Japonica Group RepID = Q2QSH2_ORYSJ (5e-13); GO_MF:GO:0004523, ribonuclease H activity# (5e-13); GO_BP:GO:0006278, RNA-dependent DNA replication# (5e-13) | 3 | 114.8 | 170908908 | 170925761 |
| 276 | B1248C03.3 protein n = 1 Tax = Oryza sativa Japonica Group RepID = Q7FAL2_ORYSJ (1e-63); GO_MF:GO:0003964, RNA-directed DNA polymerase, group II intron encoded# (1e-63); GO_BP:GO:0006278, RNA-dependent DNA replication# (1e-63) | 3 | 114.8 | 170909162 | 170909755 |
| 277 | Exosome complex exonuclease rrp45, putative n = 1 Tax = Ricinus communis RepID = B9SYQ9_RICCO (2e-49); RNase_PH_C: 3′ exoribonuclease family, domain 2 (1.5e-09); GO_MF:GO:0003723, RNA binding# (2e-67); GO_BP:GO:0006396, RNA processing# (2e-67); GO_CC:GO:0005737, cytoplasm# (3e-48) | 3 | 114.8 | 170912362 | 170916073 |
| 278 | PHD finger protein-like n = 2 Tax = Oryza sativa RepID = Q5N7H9_ORYSJ (4e-23); PHD: PHD-finger (2.3e-05); zf-C3HC4: Zinc finger, C3HC4 type (RING finger) (0.014); PHD: PHD-finger (3.1e-07); GO_MF:GO:0046872, metal ion binding# (9e-28); GO_CC:GO:0016021, integral to membrane# (1e-20) | 3 | 114.9 | 171032370 | 171032891 |
| 279 | Unknow protein n = 1 Tax = Oryza sativa Japonica Group RepID = Q60EP7_ORYSJ (1e-40) | 3 | 114.9 | 171147903 | 171155837 |
| 280 | Unknow protein n = 1 Tax = Oryza sativa Japonica Group RepID = Q60EP7_ORYSJ (3e-29) | 3 | 114.9 | 171149713 | 171151352 |
| 281 | Putative uncharacterized protein n = 1 Tax = Zea mays RepID = O48967_MAIZE (2e-17) | 3 | 114.9 | 171379246 | 171381120 |
| 282 | MADS-box transcription factor 2 n = 5 Tax = Poaceae RepID = MADS2_ORYSJ (1e-110); SRF-TF: SRF-type transcription factor (DNA-binding and dimerisation domain) (9.6e-31); K-box: K-box region (1.5e-28); GO_MF:GO:0043565, sequence-specific DNA binding# (1e-110); GO_BP:GO:0045449, regulation of transcription# (1e-110); GO_CC:GO:0005634, nucleus# (1e-110) | 3 | 114.9 | 171427699 | 171430664 |
| 283 | Amino acid carrier n = 2 Tax = Andropogoneae RepID = B6T9X6_MAIZE (0.0); Aa_trans: Transmembrane amino acid transporter protein (1.4e-146); Phage_holin_3: Phage holin family (Lysis protein S) (0.063); GO_MF:GO:0015293, symporter activity# (0.0); GO_BP:GO:0015804, neutral amino acid transport# (0.0); GO_CC:GO:0016021, integral to membrane# (0.0) | 3 | 114.9 | 171435067 | 171438501 |
| 284 | Putative dual-specific kinase DSK1 n = 1 Tax = Oryza sativa Japonica Group RepID = Q5N7J0_ORYSJ (0.0); Pkinase_Tyr: Protein tyrosine kinase (7.5e-18); Pkinase: Protein kinase domain (1.5e-26); GO_MF:GO:0005524, ATP binding# (0.0); GO_BP:GO:0006468, protein amino acid phosphorylation# (0.0); GO_CC:GO:0005886, plasma membrane# (4e-85) | 3 | 114.9 | 171639409 | 171646343 |
| 285 | F-box/LRR-repeat protein 2 n = 2 Tax = Andropogoneae RepID = B4G0B1_MAIZE (0.0); LRR_1: Leucine Rich Repeat (71); LRR_1: Leucine Rich Repeat (17); LRR_1: Leucine Rich Repeat (8.1); LRR_1: Leucine Rich Repeat (94); LRR_1: Leucine Rich Repeat (1e+02); GO_MF:GO:0005515, protein binding# (1e-158); GO_BP:GO:0051603, proteolysis involved in cellular protein catabolic process# (1e-106); GO_CC:GO:0000151, ubiquitin ligase complex# (2e-13) | 3 | 114.9 | 171709202 | 171713046 |
| 286 | DNA ligase-like n = 1 Tax = Oryza sativa Japonica Group RepID = Q8RZQ7_ORYSJ (0.0); DRMBL: DNA repair metallo-beta-lactamase (7.1e-11); GO_MF:GO:0016874, ligase activity# (0.0); GO_BP:GO:0006468, protein amino acid phosphorylation# (1e-105); GO_CC:GO:0005634, nucleus# (4e-20) | 3 | 114.9 | 171714003 | 171716849 |
| 287 | NADH dehydrogenase I subunit N n = 2 Tax = Andropogoneae RepID = B4FKX8_MAIZE (7e-93); GO_MF:GO:0016655, oxidoreductase activity, acting on NADH or NADPH, quinone or similar compound as acceptor# (1e-121); GO_BP:GO:0055114, oxidation reduction# (1e-121); GO_CC:GO:0016020, membrane# (1e-121) | 3 | 115 | 171441464 | 171443435 |
| 288 | Non-imprinted in Prader-Willi/Angelman syndrome region protein, putative n = 1 Tax = Ricinus communis RepID = B9SSN6_RICCO (1e-134); DUF6: Integral membrane protein DUF6 (0.055); DUF803: Protein of unknown function (DUF803) (6e-208); GO_CC:GO:0005886, plasma membrane# (2e-90) | 3 | 115 | 171443315 | 171448732 |
| 289 | Putative leucine-rich repeat receptor-like kinase n = 1 Tax = Oryza sativa Indica Group RepID = Q66QA8_ORYSJ (2e-84); LRR_1: Leucine Rich Repeat (2.1); LRR_1: Leucine Rich Repeat (0.23); LRR_1: Leucine Rich Repeat (0.026); LRR_1: Leucine Rich Repeat (4.5); LRR_1: Leucine Rich Repeat (9.6); LRR_1: Leucine Rich Repeat (26); LRR_1: Leucine Rich Repeat (0.14); LRR_1: Leucine Rich Repeat (1.2e+02); GO_MF:GO:0005524, ATP binding# (1e-86); GO_BP:GO:0006468, protein amino acid phosphorylation# (1e-86) | 3 | 115 | 171466052 | 171469839 |
| 290 | Seven-transmembrane-domain protein 1 n = 2 Tax = Zea mays RepID = B6SU55_MAIZE (7e-72); MtN3_slv: MtN3/sativa family (3.5e-22); MtN3_slv: MtN3/sativa family (2.3e-15); GO_MF:GO:0008270, zinc ion binding# (7e-39); GO_BP:GO:0010208, IMP#pollen wall assembly# (6e-37); GO_CC:GO:0016021, integral to membrane# (1e-105) | 3 | 115 | 171748802 | 171752467 |
| 291 | CDPK-related protein kinase n = 5 Tax = Poaceae RepID = B6SHU9_MAIZE (1e-55); GO_MF:GO:0005524, ATP binding# (3e-57); GO_BP:GO:006301, kinase activity# (1e-55); GO_CC:GO:0016020, membrane# (2e-39) | 3 | 115 | 171777495 | 171778056 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 292 | Pentatricopeptide repeat protein PPR868-14 n = 2 Tax = Andropogoneae RepID = B6U7N3_MAIZE (0.0); PPR: PPR repeat (0.00083); TPR_4: Tetratricopeptide repeat (6.3); TPR_4: Tetratricopeptide repeat (5.4); PPR: PPR repeat (1.2e-05); TPR_4: Tetratricopeptide repeat (1.5); PPR: PPR repeat (1.2e-08); PPR: PPR repeat (0.79); PPR: PPR repeat (2.5e-10); PPR: PPR repeat (0.18); TPR_4: Tetratricopeptide repeat (41); PPR: PPR repeat (0.057); PPR: PPR repeat (5.2); GO_MF:GO:0005488, binding# (4e-91); GO_CC:GO:0009536, plastid# (8e-89) | 3 | 115.1 | 171779387 | 171781432 |
| 293 | Importin beta-1, putative n = 1 Tax = Ricinus communis RepID = B9SKY7_RICCO (2e-13); GO_MF:GO:0008565, protein transporter activity# (8e-17); GO_BP:GO:0008565, protein transporter activity# (8e-17); GO_CC:GO:0009507, chloroplast# (6e-15) | 3 | 115.1 | 171815263 | 171816887 |
| 294 | Phytochrome B n = 8 Tax = Sorghum RepID = PHYB_SORBI (2e-49); GO_MF:GO:0042803, protein homodimerization activity# (2e-49); GO_BP:GO:0050896, response to stimulus# (2e-49); GO_CC:GO:0016020, membrane# (2e-49) | 3 | 115.15 | 171817584 | 171822908 |
| 295 | Pectinesterase n = 2 Tax = Oryza sativa RepID = Q8LJK2_ORYSJ (0.0); Pectinesterase: Pectinesterase (3e-143); GO_MF:GO:0045330, aspartyl esterase activity# (0.0); GO_BP:GO:0042545, cell wall modification# (0.0); GO_CC:GO:0005618, IDA#cell wall# (0.0) | 3 | 115.3 | 171894912 | 171898201 |
| 296 | Nitroreductase family protein, putative n = 1 Tax = Oryza sativa Japonica Group RepID = Q8LMV1_ORYSJ (0.0); GO_MF:GO:0016491, oxidoreductase activity# (0.0) | 3 | 115.3 | 171898843 | 171903374 |
| 297 | Glycogenin-like protein n = 4 Tax = Oryza sativa RepID = Q5NA53_ORYSJ (0.0); Glyco_transf_8: Glycosyl transferase family 8 (2.7e-61); GO_MF:GO:0016757, transferase activity, transferring glycosyl groups# (0.0) | 3 | 115.7 | 172050750 | 172055326 |
| 298 | OSJNBa0095H06.12 protein n = 1 Tax = Oryza sativa Japonica Group RepID = Q7XS07_ORYSJ (3e-51); GO_MF:GO:0004386, helicase activity# (8e-47) | 3 | 115.9 | 172179901 | 172180535 |
| 299 | Putative retrotransposon protein n = 1 Tax = Phyllostachys edulis RepID = D3IVP0_9POAL (1e-123); GO_MF:GO:0004386, helicase activity# (1e-115) | 3 | 115.9 | 172188829 | 172189985 |
| 300 | AT hook motif-containing protein, putative n = 2 Tax = Oryza sativa Japonica Group RepID = Q2R0Z1_ORYSJ (0.0); DUF889: Eukaryotic protein of unknown function (DUF889) (6.4e-84); GO_MF:GO:0004386, helicase activity# (0.0) | 3 | 115.9 | 172189989 | 172196219 |
| 301 | Putative uncharacterized protein Sb03g041650 n = 1 Tax = Sorghum bicolor RepID = C5XRE3_SORBI (4e-52); DUF506: Protein of unknown function (DUF506) (3.7e-36); GO_MF:GO:0005515, protein binding# (8e-20); GO_CC:GO:0005634, nucleus# (8e-20) | 3 | 115.9 | 172198615 | 172200295 |
| 302 | Beta-glucanase-like protein n = 1 Tax = Oryza sativa Japonica Group RepID = Q5N9F8_ORYSJ (0.0); Glyco_hydro_43: Glycosyl hydrolases family 43 (0.002); GO_MF:GO:0004553, hydrolase activity, hydrolyzing O-glycosyl compounds# (0.0); GO_BP:GO:0005975, carbohydrate metabolic process# (0.0); GO_CC:GO:0030529, ribonucleoprotein complex# (0.0) | 3 | 115.9 | 172257039 | 172260656 |
| 303 | Putative uncharacterized protein Sb07g027290 n = 1 Tax = Sorghum bicolor RepID = C5YTM6_SORBI (9e-16) | 3 | 116 | 172150745 | 172150990 |
| 304 | 4,5-DOPA dioxygenase extradiol n = 2 Tax = Zea mays RepID = B4FQS1_MAIZE (1e-142); LigB: Catalytic LigB subunit of aromatic ring-opening dioxygenase (5e-96); GO_MF:GO:0016702, oxidoreductase activity, acting on single donors with incorporation of molecular oxygen, incorporation of two atoms of oxygen# (1e-142); GO_BP:GO:0055114, oxidation reduction# (1e-142); GO_CC:GO:0005737, cytoplasm# (2e-72) | 3 | 116 | 172333476 | 172336038 |
| 305 | Catalytic/protein phosphatase type 2C n = 2 Tax = Zea mays RepID = B6TWB0_MAIZE (6e-21); GO_MF:GO:0003824, catalytic activity# (6e-21); GO_BP:GO:0004721, phosphoprotein phosphatase activity# (2e-17); GO_CC:GO:0005886, plasma membrane# (2e-11) | 3 | 116 | 172348756 | 172349196 |
| 306 | Leucine-rich receptor protein kinase-like protein n = 1 Tax = Oryza sativa Japonica Group RepID = Q5N9G1_ORYSJ (1e-149); LRR_1: Leucine Rich Repeat (5.5); LRR_1: Leucine Rich Repeat (0.11); LRR_1: Leucine Rich Repeat (13); Pkinase: Protein kinase domain (3.8e-40); Pkinase_Tyr: Protein tyrosine kinase (6.1e-18); LRR_1: Leucine Rich Repeat (2.3e+02); GO_MF:GO:0016301, kinase activity# (0.0); GO_BP:GO:0016301, kinase activity# (0.0); GO_CC:GO:0016021, integral to membrane# (1e-120) | 3 | 116 | 172374729 | 172376996 |
| 307 | Putative uncharacterized protein n = 2 Tax = Zea mays RepID = B6TK95_MAIZE (1e-52) | 3 | 116.1 | 172441684 | 172443173 |
| 308 | Beta-1,3-galactosyltransferase sqv-2 n = 1 Tax = Zea mays RepID = B6TIX7_MAIZE (1e-47); GO_MF:GO:0016757, transferase activity, transferring glycosyl groups# (1e-47); GO_BP:GO:0006486, protein amino acid glycosylation# (1e-47); GO_CC:GO:0016021, integral to membrane# (1e-47) | 3 | 116.1 | 172444363 | 172445137 |
| 309 | Beta-1,3-galactosyltransferase sqv-2 n = 1 Tax = Zea mays RepID = B6TIX7_MAIZE (3e-26); GO_MF:GO:0016757, transferase activity, transferring glycosyl groups# (3e-26); GO_BP:GO:0006486, protein amino acid glycosylation# (3e-26); GO_CC:GO:0016021, integral to membrane# (3e-26) | 3 | 116.1 | 172445592 | 172446433 |
| 310 | Mitotic checkpoint protein n = 1 Tax = Zea mays RepID = B6U4F6_MAIZE (0.0); MAD: Mitotic checkpoint protein (3.1e-128); Pox_A_type_inc: Viral A-type inclusion protein repeat (69); Pox_A_type_inc: Viral A-type inclusion protein repeat (14); Pox_A_type_inc: Viral A-type inclusion protein repeat (20); Pox_A_type_inc: Viral A-type inclusion protein repeat (5.7); Pox_A_type_inc: Viral A-type inclusion protein repeat (19); GO_MF:GO:0005515, protein binding# (1e-16); GO_BP:GO:0051301, cell division# (1e-16); GO_CC:GO:0005856, cytoskeleton# (1e-16) | 3 | 116.15 | 172447355 | 172477549 |
| 311 | Putative uncharacterized protein n = 1 Tax = Zea mays RepID = C0PES4_MAIZE (1e-130) | 3 | 116.3 | 172522488 | 172546848 |
| 312 | SnRK1-interacting protein 1 n = 2 Tax = Zea mays RepID = B6TIS1_MAIZE (1e-103); GO_MF:GO:0050897, IDA#cobalt ion binding# (2e-53); GO_CC:GO:0009507, chloroplast# (7e-31) | 3 | 116.35 | 172566013 | 172574173 |

TABLE 13-continued

Annotated coding sequences within the FSR-3.01 and FSR-8.01 regions.

| Gene ID | Annotation | Chr | MON Map cM† | Physical Map Position bp†† Start | Physical Map Position bp†† End |
|---|---|---|---|---|---|
| 313 | Putative RRM-containing protein SEB-4 n = 2 Tax = Oryza sativa RepID = Q5N8W4_ORYSJ (1e−139); RRM_1: RNA recognition motif. (a.k.a. RRM, RB (2.1e−17); GO_MF:GO:0003676, nucleic acid binding# (1e−139) | 3 | 116.5 | 172624870 | 172629189 |
| 314 | Galactosyltransferase-like protein n = 1 Tax = Oryza sativa Japonica Group RepID = Q5N8W6_ORYSJ (8e−54); RRM_1: RNA recognition motif. (a.k.a. RRM, RB (9.2e−16); GO_MF:GO:0003676, nucleic acid binding# (4e−55) | 3 | 116.5 | 172675337 | 172678828 |
| 315 | SUN4 n = 1 Tax = Zea mays RepID = D3KCC3_MAIZE (0.0); F5_F8_type_C: F5/8 type C domain (0.068); Sad1_UNC: Sad1/UNC-like C-terminal (5.9e−59); GO_CC:GO:0016021, integral to membrane# (2e−32) | 3 | 116.5 | 172806294 | 172809079 |
| 316 | ATP binding protein n = 1 Tax = Zea mays RepID = B6U192_MAIZE (1e−147); Kinesin: Kinesin motor domain (3.7e−37); Nodulin-like: Nodulin-like (2.5e−09); GO_MF:GO:0005524, ATP binding# (1e−147); GO_CC:GO:0005874, microtubule# (1e−147); GO_BP:GO:0007018, microtubule-based movement# (1e−147) | 3 | 116.5 | 172813626 | 172817058 |
| 317 | Putative auxin-regulated protein n = 1 Tax = Oryza sativa Japonica Group RepID = Q6YYY6_ORYSJ (6e−14); DUF966: Domain of unknown function (DUF966) (5.9e−06) | 3 | 116.5 | 172822909 | 172824557 |
| 318 | Serine endopeptidase degp2, putative n = 1 Tax = Ricinus communis RepID = B9S3X1_RICCO (2e−09); GO_MF:GO:0032440, 2-alkenal reductase activity# (2e−09); GO_BP:GO:0055114, oxidation reduction# (2e−09); GO_CC:GO:0016020, membrane# (8e−09) | 3 | 116.5 | 172826631 | 172828767 |
| 319 | Pyrimidine-specific ribonucleoside hydrolase rihA n = 4 Tax = Andropogoneae RepID = B6T5H3_MAIZE (4e−34); GO_MF:GO:0006787, hydrolase activity# (4e−34); GO_BP:GO:0008152, metabolic process# (2e−20); GO_CC:GO:0005829, IDA#cytosol# (1e−15) | 3 | 116.5 | 172847460 | 172847835 |
| 320 | ATP binding protein n = 4 Tax = Zea mays RepID = B6U8U2_MAIZE (0.0); GO_MF:GO:0005524, ATP binding# (0.0); GO_BP:GO:0006468, protein amino acid phosphorylation# (0.0) | 3 | 116.5 | 172890112 | 172896927 |
| 321 | Putative uncharacterized protein Sb02g036510 n = 1 Tax = Sorghum bicolor RepID = C5XBL8_SORBI (3e−15) | 3 | 116.5 | 172900980 | 172902970 |
| 322 | Putative uncharacterized protein Sb03g032780 n = 1 Tax = Sorghum bicolor RepID = C5XI97_SORBI (1e−115); GO_BP:GO:0006998, cell wall macromolecule catabolic process# (9e−23) | 3 | 116.5 | 172903355 | 172904665 |
| 323 | F-box protein interaction domain containing protein n = 2 Tax = Zea mays RepID = B6TT97_MAIZE (1e−163); F-box: F-box domain (0.00082); GO_MF:GO:0016301, kinase activity# (4e−20); GO_BP:GO:0016301, kinase activity# (4e−20) | 3 | 116.5 | 172905270 | 172906947 |
| 324 | Putative chloride channel n = 2 Tax = Oryza sativa RepID = Q5N8W8_ORYSJ (0.0); Voltage_CLC: Voltage gated chloride channel (6.3e−82); DUF2062: Uncharacterized protein conserved in (0.084); TAT_signal: TAT (twin-arginine translocation) pat (0.092); CBS: CBS domain (1.1e−08); GO_MF:GO:0005247, voltage-gated chloride channel activity# (0.0); GO_BP:GO:0055085, transmembrane transport# (0.0); GO_CC:GO:0016021, integral to membrane# (0.0) | 3 | 116.8 | 172852406 | 172855470 |
| 325 | P0648C09.24 protein n = 1 Tax = Oryza sativa Japonica Group RepID = Q8RYX6_ORYSJ (1e−147); DUF266: Arabidopsis protein of unknown function, DUF266 (3.9e−185); GO_MF:GO:0008375, acetylglucosaminyltransferase activity# (0.0); GO_CC:GO:0016020, membrane# (0.0) | 3 | 116.8 | 173002202 | 173004319 |
| 326 | DnaJ protein n = 2 Tax = Zea mays RepID = B6T720_MAIZE (1e−144); DnaJ: DnaJ domain (4.2e−18); DnaJ_C: DnaJ C terminal region (6.8e−10); GO_MF:GO:0051082, unfolded protein binding# (1e−162); GO_BP:GO:0006457, protein folding# (1e−162) | 3 | 116.8 | 173004861 | 173007364 |
| 327 | Beta-galactosidase n = 2 Tax = Andropogoneae RepID = B6L0W2_MAIZE (0.0); Glyco_hydro_35: Glycosyl hydrolases family 35 (2.8e−170); Glyco_hydro_2_N: Glycosyl hydrolases family 2, sugar binding domain (0.08); Gal_Lectin: Galactose binding lectin domain (0.00035); GO_MF:GO:0043169, cation binding# (0.0); GO_BP:GO:0008152, metabolic process# (0.0); GO_CC:GO:0048046, IDA#apoplast# (0.0) | 3 | 116.8 | 173015374 | 173022743 |
| 328 | Signal recognition particle receptor alpha subunit, putative n = 1 Tax = Ricinus communis RepID = B9STS5_RICCO (1e−54); SRP54: SRP54-type protein, GTPase domain (5.7e−05); GO_MF:GO:0017111, nucleoside-triphosphatase activity# (2e−58); GO_BP:GO:0006614, SRP-dependent cotranslational protein targeting to membrane# (2e−58); GO_CC:GO:0005783, IDA#endoplasmic reticulum# (2e−53) | 3 | 117.1 | 173134957 | 173135803 |
| 329 | Beta-galactosidase n = 1 Tax = Oryza sativa Indica Group RepID = B2Z6M9_ORYSI (0.0); Glyco_hydro_35: Glycosyl hydrolases family 35 (2.2e−162); Glyco_hydro_42: Beta-galactosidase (0.025); Glyco_hydro_2_N: Glycosyl hydrolases family 2, sugar binding domain (0.043); Gal_Lectin: Galactose binding lectin domain (1.1e−24); GO_MF:GO:0043169, cation binding# (0.0); GO_BP:GO:0008152, metabolic process# (0.0); GO_CC:GO:0048046, IDA#apoplast# (0.0) | 3 | 117.1 | 173201293 | 173208931 |
| 330 | Src2-like protein n = 1 Tax = Zea mays RepID = B6TF82_MAIZE (9e−24); XYPPX: XYPPX repeat (1e+02); XYPPX: XYPPX repeat (1.7e+02); XYPPX repeat (1e+02); XYPPX: XYPPX repeat (1.2e+02); XYPPX: XYPPX repeat (1e+02); XYPPX: XYPPX repeat (25); XYPPX: XYPPX repeat (1.2e+02) | 3 | 117.3 | 173284946 | 173285813 |
| 331 | OSJNBa0009P12.18 protein n = 3 Tax = Oryza sativa RepID = Q5VSV8_ORYSA (1e−34); GO_MF:GO:0017076, purine nucleotide binding# (1e−34); GO_BP:GO:0006094, gluconeogenesis# (1e−34); GO_CC:GO:0032040, small-subunit processome# (5e−22) | 3 | 117.3 | 173287877 | 173288635 |
| 332 | Putative uncharacterized protein n = 1 Tax = Zea mays RepID = C0PKR7_MAIZE (9e−69) | 3 | 117.5 | 173371885 | 173373794 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 333 | 1-phosphatidylinositol-3-phosphate 5-kinase FAB1-like protein n = 1 Tax = *Oryza sativa Japonica* Group RepID = Q6H5I5_ORYSJ (1e-122); GO_MF:GO:0016307, phosphatidylinositol phosphate kinase activity# (1e-161); GO_BP:GO:0046488, phosphatidylinositol metabolic process# (1e-161); GO_CC:GO:0005739, mitochondrion# (1e-37) | 3 | 117.5 | 173396687 | 173400469 |
| 334 | DNA polymerase I n = 4 Tax = Andropogoneae RepID = B6U7X8_MAIZE (1e-166); 5_3_exonuc_N: 5′-3′ exonuclease, N-terminal resolvase-like domain (1.1e–12); 5_3_exonuc: 5′-3′ exonuclease, C-terminal SAM fold (4.2e–06); GO_MF:GO:0008409, 5′-3′ exonuclease activity# (1e-166); GO_BP:GO:0006281, DNA repair# (8e-20); GO_CC:GO:0005622, intracellular# (8e-20) | 3 | 117.5 | 173468914 | 173471177 |
| 335 | HAT family dimerisation domain containing protein n = 1 Tax = *Oryza sativa Japonica* Group RepID = Q2QRD1_ORYSJ (1e-78); GO_MF:GO:0046983, protein dimerization activity# (4.1e–25); hATC: hAT family dimerisation domain (4.1e–25); GO_MF:GO:0046983, protein dimerization activity# (1e-78) | 3 | 117.8 | 173511054 | 173512633 |
| 336 | Myb transcription factor n = 3 Tax = *Oryza sativa* RepID = Q5TKI8_ORYSJ (3e-84); Myb_DNA-binding: Myb-like DNA-binding domain (6.9e–11); GO_MF:GO:0003677, DNA binding# (1e-118); GO_BP:GO:0045449, regulation of transcription# (1e-118); GO_CC:GO:0005634, nucleus# (1e-118) | 3 | 117.9 | 173520319 | 173521525 |
| 337 | ATP binding protein n = 1 Tax = *Zea mays* RepID = B6U6Y9_MAIZE (0.0); dNK: Deoxynucleoside kinase (3.7e–29); GO_MF:GO:0016773, phosphotransferase activity, alcohol group as acceptor# (0.0); GO_BP:GO:0006139, nucleobase, nucleoside, nucleotide and nucleic acid metabolic process# (0.0); GO_CC:GO:0005634, nucleus# (1e-171) | 3 | 118.3 | 173585707 | 173590684 |
| 338 | HAT family dimerisation domain containing protein n = 1 Tax = *Oryza sativa Japonica* Group RepID = Q2QRD1_ORYSJ (1e-16); zf-BED: BED zinc finger (0.0026); GO_MF:GO:0046983, protein dimerization activity# (1e-16) | 3 | 118.3 | 173654679 | 173655715 |
| 339 | Putative uncharacterized protein Sb01g029380 n = 1 Tax = *Sorghum bicolor* RepID = C5WSG6_SORBI (2e-27); GO_MF:GO:0046983, protein dimerization activity# (3e-10); GO_CC:GO:0016021, integral to membrane# (4e-10) | 3 | 118.3 | 173681345 | 173682358 |
| 340 | OSJNBa0088K19.7 protein n = 3 Tax = *Oryza sativa* RepID = Q7XU24_ORYSJ (1e-116); DUF668: Protein of unknown function (DUF668) (4e-54); GO_MF:GO:0016301, kinase activity# (1e-119); GO_CC:GO:0005886, plasma membrane# (1e-162) | 3 | 118.3 | 173688595 | 173699327 |
| 341 | Erythroid differentiation-related factor 1-like protein n = 2 Tax = *Oryza sativa* RepID = Q5N730_ORYSJ (0.0); GO_MF:GO:0005515, protein binding# (1e-25); GO_BP:GO:0045449, regulation of transcription# (4e-35); GO_CC:GO:0005886, plasma membrane# (0.0) | 3 | 118.3 | 173735061 | 173741621 |
| 342 | Amidophosphoribosyltransferase n = 2 Tax = Andropogoneae RepID = B6SRU6_MAIZE (0.0); GATase_2: Glutamine amidotransferases class-II (3.4e–35); Pribosyltran: Phosphoribosyl transferase domain (2.8e–15); GO_MF:GO:0016757, transferase activity, transferring glycosyl groups# (0.0); GO_BP:GO:0009116, nucleoside metabolic process# (0.0); GO_CC:GO:0005618, IDA#cell wall# (1e-166) | 3 | 118.3 | 173801435 | 173803391 |
| 343 | 3-phosphoinositide-dependent protein kinase 1 n = 4 Tax = Andropogoneae RepID = B6UBV8_MAIZE (0.0); Pkinase_Tyr: Protein tyrosine kinase (2.5e–10); Pkinase: Protein kinase domain (3.3e–83); GO_MF:GO:0016301, kinase activity# (0.0); GO_CC:GO:0016023, cytoplasmic membrane-bounded vesicle# (2e-83) | 3 | 118.4 | 174059840 | 174064980 |
| 344 | SKP1-like protein 1A n = 1 Tax = *Zea mays* RepID = B6UDE5_MAIZE (4e-64); Skp1_POZ: Skp1 family, tetramerisation domain (3.6e–23); Skp1: Skp1 family, dimerisation domain (2.9e–38); GO_MF:GO:0005515, protein binding# (4e-64); GO_BP:GO:0006511, ubiquitin-dependent protein catabolic process# (4e-64); GO_CC:GO:0005634, nucleus# (2e-42) | 3 | 118.4 | 174067213 | 174067846 |
| 345 | Malic enzyme (Fragment) n = 1 Tax = *Oryza sativa Japonica* Group RepID = Q53RP5_ORYSJ (1e-140); FAR1: FAR1 family (2.9e–27); MULE: MULE transposase domain (2.5e–19); GO_MF:GO:0051287, NAD or NADH binding# (1e-140); GO_BP:GO:0055114, oxidation reduction# (1e-140); GO_CC:GO:0005622, intracellular# (1e-137) | 3 | 118.4 | 174149824 | 174151436 |
| 346 | Putative uncharacterized protein n = 1 Tax = *Zea mays* RepID = C4JA86_MAIZE (2e-11) | 3 | 118.4 | 174214742 | 174215602 |
| 347 | Putative uncharacterized protein n = 1 Tax = *Zea mays* RepID = C0PNM6_MAIZE (1e-35) | 3 | 118.4 | 174215246 | 174250947 |
| 348 | Putative cytochrome P450 monooxygenase n = 2 Tax = *Oryza sativa* RepID = Q6K6C8_ORYSJ (2e-39); GO_MF:GO:0046872, metal ion binding# (1e-52); GO_BP:GO:0055114, oxidation reduction# (1e-52) | 3 | 118.4 | 174269792 | 174270437 |
| 349 | POT family protein n = 1 Tax = *Zea mays* RepID = B6ST62_MAIZE (0.0); MFS_1: Major Facilitator Superfamily (0.035); PTR2: POT family (3.1e–47); GO_MF:GO:0005215, transporter activity# (0.0); GO_BP:GO:0006857, oligopeptide transport# (0.0); GO_CC:GO:0016020, membrane# (0.0) | 3 | 118.4 | 174335482 | 174341351 |
| 350 | Peptide transporter PTR2-B n = 2 Tax = *Zea mays* RepID = B6SWT0_MAIZE (0.0); MFS_1: Major Facilitator Superfamily (0.0021); PTR2: POT family (2.6e–80); GO_MF:GO:0005215, transporter activity# (0.0); GO_BP:GO:0006857, oligopeptide transport# (0.0); GO_CC:GO:0016020, membrane# (0.0) | 3 | 118.4 | 174361364 | 174363736 |
| 351 | Aspartate aminotransferase n = 3 Tax = Andropogoneae RepID = B6TK79_MAIZE (0.0); Aminotran_1_2: Aminotransferase class I and II (2.6e–88); GO_MF:GO:0030170, pyridoxal phosphate binding# (0.0); GO_BP:GO:0016847, 1-aminocyclopropane-1-carboxylate synthase activity# (0.0); GO_CC:GO:0009507, chloroplast# (1e-179) | 3 | 118.4 | 174367844 | 174371254 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 352 | NPH3 family protein n = 3 Tax = *Oryza sativa Japonica* Group RepID = Q6AST7_ORYSJ (1e−36); GO_MF:GO:0005515, protein binding# (6e−37); GO_BP:GO:0009416, IEP#response to light stimulus# (6e−37); GO_CC:GO:0005634, nucleus# (4e−33) | 3 | 118.4 | 174448279 | 174454420 |
| 353 | Nucleic acid binding protein n = 4 Tax = *Zea mays* RepID = B6THI3_MAIZE (0.0); zf-C2H2: Zinc finger, C2H2 type (2.3e−05); zf-C2H2: Zinc finger, C2H2 type (0.48); zf-C2H2: Zinc finger, C2H2 type (1.9); GO_MF:GO:0008270, zinc ion binding# (0.0); GO_BP:GO:0045449, regulation of transcription# (0.0); GO_CC:GO:0005622, intracellular# (0.0) | 3 | 118.4 | 174461545 | 174465281 |
| 354 | Embryogenesis-associated protein EMB8 n = 2 Tax = Andropogoneae RepID = B6U4K5_MAIZE (0.0); Abhydrolase_1: alpha/beta hydrolase fold (3.6e−05); GO_MF:GO:0016787, hydrolase activity# (0.0); GO_BP:GO:0008150, ND#biological_process# (9e−44); GO_CC:GO:0016021, integral to membrane# (9e−44) | 3 | 118.4 | 174533708 | 174546586 |
| 355 | OSJNBa0079C19.15 protein n = 1 Tax = *Oryza sativa* Japonica Group RepID = Q7FA01_ORYSA (6e−45); GO_MF:GO:0004803, transposase activity# (6e−45); GO_BP:GO:0006313, transposition, DNA-mediated# (6e−45); GO_CC:GO:0005783, IDA#endoplasmic reticulum# (1e−34) | 3 | 118.4 | 174548132 | 174548512 |
| 356 | Gag-pol polyprotein, putative n = 1 Tax = *Asparagus officinalis* RepID = Q2A9Z5_ASPOF (4e−12); GO_MF:GO:0003964, RNA-directed DNA polymerase, group II intron encoded# (4e−12); GO_BP:GO:0006278, RNA-dependent DNA replication# (4e−12); GO_CC:GO:0005634, nucleus# (3e−10) | 3 | 118.4 | 174679875 | 174680057 |
| 357 | Retrotransposon protein, putative, Ty3-gypsy subclass n = 2 Tax = *Oryza sativa* Japonica RepID = Q7YG23_ORYSJ (2e−54); GO_MF:GO:0008270, zinc ion binding# (4e−55); GO_BP:GO:0015074, DNA integration# (4e−55); GO_CC:GO:0005634, nucleus# (2e−54) | 3 | 118.4 | 174680227 | 174681046 |
| 358 | X-ray repair cross complementing protein 2, xrcc2, putative n = 1 Tax = *Ricinus communis* RepID = B9RPZ1_RICCO (3e−38); GO_MF:GO:0003677, DNA binding# (5e−49); GO_BP:GO:0006506, TAS#GPI anchor biosynthetic process# (7e−73); GO_CC:GO:0016021, integral to membrane# (7e−73) | 3 | 118.4 | 174688476 | 174694367 |
| 359 | MATE efflux protein-like n = 2 Tax = *Oryza sativa* RepID = Q5N7N1_ORYSJ (3e−15); GO_MF:GO:0015297, antiporter activity# (1e−61); GO_BP:GO:0055085, transmembrane transport# (1e−61); GO_CC:GO:0016020, membrane# (1e−61) | 3 | 118.4 | 174696169 | 174699186 |
| 360 | Probable ion channel DMI1, chloroplastic n = 5 Tax = *Oryza sativa* RepID = DMI1_ORYSJ (0.0); TrkA_N: TrkA-N domain (0.023); DUF1012: Protein of unknown function (DUF1012) (4.7e−05); GO_MF:GO:0005488, binding# (0.0); GO_BP:GO:0008152, metabolic process# (0.0); GO_CC:GO:0031969, IDA#chloroplast membrane# (0.0) | 3 | 118.4 | 174760419 | 174769602 |
| 361 | Serine/threonine-protein kinase SAPK4 n = 5 Tax = Poaceae RepID = SAPK4_ORYSJ (1e−123); Pkinase: Protein kinase domain (1.4e−64); Pkinase_Tyr: Protein tyrosine kinase (2.4e−12); GO_MF:GO:0016740, transferase activity# (1e−123); GO_BP:GO:0016301, kinase activity# (1e−123); GO_CC:GO:0005634, nucleus# (1e−108) | 3 | 118.4 | 174770228 | 174775694 |
| 362 | Photosystem II 22 kDa protein n = 3 Tax = Andropogoneae RepID = B6TKD1_MAIZE (1e−107); Chloroa_b-bind: Chlorophyll A-B binding protein (1.6e−17); GO_MF:GO:0051738, TAS#xanthophyll binding# (3e−70); GO_BP:GO:0015979, photosynthesis# (3e−74); GO_CC:GO:0016021, integral to membrane# (3e−74) | 3 | 118.4 | 174825207 | 174827767 |
| 363 | P-type ATPase (Fragment) n = 1 Tax = *Hordeum vulgare* RepID = Q94IM9_HORVU (5e−50); Hydrolase: haloacid dehalogenase-like hydrolase (0.034); GO_MF:GO:0015662, ATPase activity, coupled to transmembrane movement of ions, phosphorylative mechanism# (5e−50); GO_BP:GO:0015662, ATPase activity, coupled to transmembrane movement of ions, phosphorylative mechanism# (5e−50); GO_CC:GO:0016021, integral to membrane# (5e−50) | 3 | 118.4 | 174893873 | 174896216 |
| 364 | Putative uncharacterized protein Sb04g024240 n = 1 Tax = *Sorghum bicolor* RepID = C5XWC2_SORBI (1e−20); zf-CCHC: Zinc knuckle (0.0001) | 3 | 118.4 | 174915097 | 174915526 |
| 365 | Putative uncharacterized protein n = 1 Tax = *Zea mays* RepID = C0PGF1_MAIZE (7e−17) | 3 | 118.7 | 175096376 | 175096756 |
| 366 | Androgen induced inhibitor of proliferation (A63)pds5, putative n = 1 Tax = *Ricinus communis* RepID = B9RJ83_RICCO (3e−29); GO_MF:GO:0005488, binding# (8e−55); GO_BP:GO:0008152, metabolic process# (2e−16); GO_CC:GO:0009507, chloroplast# (4e−19) | 3 | 118.7 | 175099942 | 175103297 |
| 367 | Putative retroelement protein n = 1 Tax = *Sorghum bicolor* RepID = B3VTC3_SORBI (8e−19); GO_MF:GO:0003682, chromatin binding# (8e−19); GO_BP:GO:0006333, chromatin assembly or disassembly# (8e−19); GO_CC:GO:0005634, nucleus# (8e−19) | 3 | 118.7 | 175105093 | 175105440 |
| 368 | Androgen induced inhibitor of proliferation (A63)pds5, putative n = 1 Tax = *Ricinus communis* RepID = B9RJ83_RICCO (2e−89); HEAT: HEAT repeat (7.1); HEAT: HEAT repeat (16); HEAT: HEAT repeat (4.5); HEAT: HEAT repeat (8.5); GO_MF:GO:0005488, binding# (1e−130); GO_BP:GO:0006278, RNA-dependent DNA replication# (1e−95); GO_CC:GO:0005634, nucleus# (6e−18) | 3 | 118.7 | 175123678 | 175125164 |
| 369 | Putative uncharacterized protein Sb03g041085 (Fragment) n = 1 Tax = *Sorghum bicolor* RepID = C5XR84_SORBI (5e−56); GO_MF:GO:0005488, binding# (8e−26) | 3 | 118.8 | 175183345 | 175192059 |
| 370 | NPL4 family protein n = 4 Tax = Andropogoneae RepID = B4FHK5_MAIZE (0.0); NPL4: NPL4 family (7.3e−135); GO_MF:GO:0005488, binding# (7e−97); GO_CC:GO:0005783, IDA#endoplasmic reticulum# (0.0) | 3 | 118.9 | 175281852 | 175287153 |
| 371 | OSJNBa0065J03.2 protein n = 1 Tax = *Oryza sativa* Japonica Group RepID = Q7Y7Y2_ORYSJ (2e−18); GO_MF:GO:0004190, penicillopepsin activity# (2e−18); GO_BP:GO:0015074, DNA integration# (2e−18); GO_CC:GO:0005634, nucleus# (2e−18) | 3 | 119 | 175317626 | 175318015 |
| 372 | Protein disulfide isomerase n = 2 Tax = Andropogoneae RepID = Q5EUD0_MAIZE (1e−46); GO_MF:GO:0016853, isomerase activity# (1e−46); GO_BP:GO:0045454, cell redox homeostasis# (1e−46); GO_CC:GO:0005783, IDA#endoplasmic reticulum# (2e−13) | 3 | 119 | 175325155 | 175326673 |
| 373 | Zeamatin, putative n = 1 Tax = *Ricinus communis* RepID = B9SZE5_RICCO (7e−28); Thaumatin family (0.00013); GO_MF:GO:0005515, protein binding# (2e−10); GO_BP:GO:0046686, IEP#response to cadmium ion# (2e−10); GO_CC:GO:0005618, IDA#cell wall# (5e−24) | 3 | 119 | 175338982 | 175339505 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 374 | Ribonuclease P n = 3 Tax = Andropogoneae RepID = B6T1F1_MAIZE (1e−17); GO_MF:GO:0003676, nucleic acid binding# (1e−17); GO_BP:GO:0006468, protein amino acid phosphorylation# (1e−09) | 3 | 119 | 175340760 | 175343653 |
| 375 | Retrotransposon protein SINE subclass n = 3 Tax = Zea mays RepID = B6T9S6_MAIZE (6e−36); GO_MF:GO:0016787, hydrolase activity# (6e−36); GO_BP:GO:0006629, lipid metabolic process# (6e−36); GO_CC:GO:0005773, IDA#vacuole# (2e−20) | 3 | 119 | 175343828 | 175348081 |
| 376 | OSJNBa0064G10.15 protein n = 1 Tax = Oryza sativa Japonica Group RepID = Q7XKB6_ORYSJ (5e−37); DUF639: Plant protein of unknown function (DUF639) (5.3e−258); Reticulon: Reticulon (0.013) | 3 | 119 | 175348514 | 175374260 |
| 377 | Retrotransposon protein, putative, Ty1-copia subclass n = 1 Tax = Oryza sativa Japonica Group RepID = Q2QSG2_ORYSJ (1e−13); GO_MF:GO:0003677, DNA binding# (1e−13); GO_BP:GO:0015074, DNA integration# (1e−13) | 3 | 119 | 175372096 | 175372675 |
| 378 | DNA polymerase n = 1 Tax = Sorghum bicolor RepID = C5XR76_SORBI (0.0); DNA_pol_B_exo: DNA polymerase family B, exonuclease domain (1.6e−12); zf-DHHC: DHHC zinc finger domain (9.6e−30); DNA_pol_B: DNA Polymerase alpha zinc finger (1.6e−09); GO_MF:GO:0016779, nucleotidyltransferase activity# (0.0); GO_BP:GO:0006273, ISS#lagging strand elongation# (0.0); GO_CC:GO:0005634, nucleus# (0.0) | 3 | 119.2 | 175498364 | 175514524 |
| 379 | Palmitoyltransferase ZDHHC9 n = 3 Tax = Andropogoneae RepID = B6T1T8_MAIZE (1e−113); GO_MF:GO:0046872, metal ion binding# (1e−113); GO_BP:GO:0006412, translation# (3e−87); GO_CC:GO:0016021, integral to membrane# (1e−84) | 3 | 119.2 | 175517630 | 175524776 |
| 380 | Tubulin gamma-1 chain n = 28 Tax = Embryophyta RepID = TBG1_ARATH (5e−29); GO_MF:GO:0050660, FAD binding# (3e−33); GO_BP:GO:0055114, oxidation reduction# (3e−33); GO_CC:GO:0043234, protein complex# (3e−33) | 3 | 119.2 | 175525450 | 175528545 |
| 381 | AP2 domain transcription factor-like n = 2 Tax = Oryza sativa RepID = Q5N965_ORYSJ (2e−34); AP2: AP2 domain (2.1e−20); GO_MF:GO:0003700, transcription factor activity# (2e−34); GO_BP:GO:0045449, regulation of transcription# (2e−34); GO_CC:GO:0005634, nucleus# (2e−34) | 3 | 119.2 | 175549184 | 175552449 |
| 382 | Membrane protein COV-like n = 5 Tax = Poaceae RepID = Q8SIP4_ORYSJ (1e−136); DUF502: Protein of unknown function (DUF502) (2.5e−36) | 3 | 119.2 | 175556827 | 175563188 |
| 383 | Yip1 domain containing protein n = 1 Tax = Tetrahymena thermophila SB210 RepID = Q22B55_TETTH (6e−09); Yip1: Yip1 domain (0.0016) | 3 | 119.2 | 175566419 | 175569742 |
| 384 | Sterol 3-beta-glucosyltransferase n = 3 Tax = Andropogoneae RepID = B6SKE1_MAIZE (0.0); Glyco_transf_28: Glycosyltransferase family 28 N-terminal domain (1.2e−46); GO_MF:GO:0016758, transferase activity, transferring hexosyl groups# (0.0); GO_BP:GO:0030259, lipid glycosylation# (0.0); GO_CC:GO:0005886, plasma membrane# (0.0) | 3 | 119.2 | 175571486 | 175589373 |
| 385 | G-box-binding factor 4 n = 3 Tax = Andropogoneae RepID = B6SKU0_MAIZE (7e−73); GO_MF:GO:0046983, protein dimerization activity# (7e−73); GO_BP:GO:0006355, regulation of transcription, DNA-dependent# (7e−73); GO_CC:GO:0005634, nucleus# (7e−73) bZIP_1: bZIP transcription factor (3.1e−11); bZIP_2: Basic region leucine zipper (5.6e−09); | 3 | 119.3 | 175629663 | 175633484 |
| 386 | Putative uncharacterized protein Sb03g040960 n = 2 Tax = Andropogoneae RepID = C5XQN1_SORBI (0.0); GO_MF:GO:0005524, ATP binding# (1e−94); GO_BP:GO:0006437, tyrosyl-tRNA aminoacylation# (1e−94); GO_CC:GO:0005737, cytoplasm# (1e−94) | 3 | 119.3 | 175633118 | 175637510 |
| 387 | Transferase n = 2 Tax = Zea mays RepID = B6TPL4_MAIZE (0.0); Transferase: Transferase family (3.6e−106); GO_MF:GO:0016747, transferase activity, transferring acyl groups other than amino-acyl groups# (0.0) | 3 | 119.4 | 175686325 | 175689363 |
| 388 | Tubby-like protein n = 3 Tax = Andropogoneae RepID = B6U1N5_MAIZE (0.0); F-box: F-box domain (6.4e−06); Tub: Tub family (1.6e−168); GO_MF:GO:0016787, hydrolase activity# (1e−113); GO_BP:GO:0045449, regulation of transcription# (1e−154); GO_CC:GO:0005886, plasma membrane# (1e−154) | 3 | 119.4 | 175691664 | 175696010 |
| 389 | Snrnp sm protein, putative n = 6 Tax = Embryophyta RepID = B9T2G3_RICCO (5e−10) | 3 | 119.4 | 175701107 | 175701619 |
| 390 | BolA-like protein n = 4 Tax = Poaceae RepID = Q5N9F3_ORYSJ (1e−29); BolA: BolA-like protein (6.9e−31) | 3 | 119.4 | 175705359 | 175706614 |
| 391 | Fructose-1,6-bisphosphatase, cytosolic n = 5 Tax = Poaceae RepID = F1G6P2_ORYCO (0.0); FBPase: Fructose-1-6-bisphosphatase (5.4e−204); GO_MF:GO:0046872, metal ion binding# (0.0); GO_BP:GO:0042132, fructose 1,6-bisphosphate 1-phosphatase activity# (0.0); GO_CC:GO:0005737, cytoplasm# (0.0) | 3 | 119.4 | 175707507 | 175710858 |
| 392 | VAMP-like protein YKT62 n = 3 Tax = Zea mays RepID = B6TVP5_MAIZE (7e−69); GO_MF:GO:0042578, phosphoric ester hydrolase activity# (7e−58); GO_BP:GO:0016192, vesicle-mediated transport# (7e−69); GO_CC:GO:0016021, integral to membrane# (7e−69) | 3 | 119.6 | 175779152 | 175780870 |
| 393 | Histone H3 n = 1 Tax = Oryza sativa Japonica Group RepID = Q53NE3_ORYSJ (6e−23); GO_CC:GO:0005694, chromosome# (6e−23); GO_MF:GO:0003677, DNA binding# (6e−23); GO_BP:GO:0006334, nucleosome assembly# (6e−23); GO_CC:GO:0005694, chromosome# (6e−23) | 3 | 119.8 | 175868598 | 175869269 |
| 394 | Peptidase M48, Ste24p n = 1 Tax = Zea mays RepID = B6TA12_MAIZE (3e−60); Peptidase_M48: Peptidase family M48 (7.1e−07); Peptidase_M56: BlaR1 peptidase M56 (0.0091); Peptidase_C12: Ubiquitin carboxyl-terminal hydrolase, family 1 (0.00015); SapB_1: Saposin-like type B, region 1 (2.8e−05); SapB_2: Saposin-like type B, region 2 (0.028); GO_BP:GO:0006508, proteolysis# (3e−60); GO_CC:GO:0016020, membrane# (3e−60) | 3 | 120 | 175926976 | 175931743 |
| 395 | Surfactant protein B containing protein n = 3 Tax = Zea mays RepID = B6T8B6_MAIZE (2e−62); GO_BP:GO:0006629, lipid metabolic process# (2e−62); GO_CC:GO:0005764, lysosome# (2e−15) | 3 | 120.05 | 175931839 | 175935637 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 396 | RING-H2 finger protein ATL3C n = 1 Tax = Zea mays RepID = B6ST75_MAIZE (2e−54); zf-C3HC4: Zinc finger, C3HC4 type (RING finger) (6.2e−06); GO_MF:GO:0046872, metal ion binding# (2e−54); GO_CC:GO:0016021, integral to membrane# (2e−15) | 3 | 120.1 | 175936649 | 175937454 |
| 397 | Dof zinc finger protein 9 n = 1 Tax = Hordeum vulgare subsp. vulgare RepID = A5HWF8_HORVD (2e−39); zf-Dof: Dof domain, zinc finger (1.2e−35); GO_MF:GO:0008270, zinc ion binding# (2e−39); GO_BP:GO:0045449, regulation of transcription# (2e−39); GO_CC:GO:0005634, nucleus# (2e−26) | 3 | 120.2 | 175965582 | 175974373 |
| 398 | Dof zinc finger protein 9 n = 1 Tax = Hordeum vulgare subsp. vulgare RepID = A5HWF8_HORVD (2e−48); GO_MF:GO:0008270, zinc ion binding# (2e−56); GO_BP:GO:0045449, regulation of transcription# (2e−56) | 3 | 120.2 | 175965975 | 175966855 |
| 399 | Anthocyanidin 3-O-glucosyltransferase n = 2 Tax = Andropogoneae RepID = B6SU01_MAIZE (0.0); UDPGT: UDP-glucuronosyl and UDP-glucosyl transferase (1e−07); GO_MF:GO:0016758, transferase activity, transferring hexosyl groups# (0.0); GO_BP:GO:0008152, metabolic process# (0.0) | 3 | 120.3 | 175998910 | 176000677 |
| 400 | Anthocyanidin 3-O-glucosyltransferase n = 2 Tax = Andropogoneae RepID = B6SU01_MAIZE (0.0); UDPGT: UDP-glucuronosyl and UDP-glucosyl transferase (2.4e−07); GO_MF:GO:0016758, transferase activity, transferring hexosyl groups# (0.0); GO_BP:GO:0008152, metabolic process# (0.0) | 3 | 120.3 | 176038345 | 176039880 |
| 401 | Anthocyanidin 3-O-glucosyltransferase n = 2 Tax = Andropogoneae RepID = B6TRK5_MAIZE (0.0); UDPGT: UDP-glucuronosyl and UDP-glucosyl transferase (3.2e−07); Glyco_tran_28_C: Glycosyltransferase family 28 C-terminal domain (0.042); GO_MF:GO:0016758, transferase activity, transferring hexosyl groups# (0.0); GO_BP:GO:0008152, metabolic process# (0.0) | 3 | 120.3 | 176043286 | 176045138 |
| 402 | Putative uncharacterized protein Sb06g011810 n = 1 Tax = Sorghum bicolor RepID = C5YEB3_SORBI (6e−11) | 3 | 120.3 | 176051207 | 176051446 |
| 403 | Photoreceptor-interacting protein-like n = 4 Tax = Andropogoneae RepID = B6T0F2_MAIZE (2e−36); NPH3: NPH3 family (0.0099); GO_MF:GO:0004871, signal transducer activity## (7e−37); GO_BP:GO:0009416, IEP#response to light stimulus# (7e−37); GO_CC:GO:0005886, plasma membrane# (4e−09) | 3 | 120.3 | 176070424 | 176071202 |
| 404 | Uricase n = 1 Tax = Zea mays RepID = B4G1P7_MAIZE (1e−149); Uricase: Uricase (7.8e−48); Uricase (3.1e−20); GO_MF:GO:0016491, oxidoreductase activity## (1e−131); GO_BP:GO:0055114, oxidation reduction# (1e−131); GO_CC:GO:0005777, IDA#peroxisome# (4e−86) | 3 | 120.3 | 176257559 | 176261095 |
| 405 | Retrotransposon protein, putative, Ty1-copia subclass n = 1 Tax = Oryza sativa Japonica Group RepID = Q2QSO2_ORYSJ (2e−24); GO_MF:GO:0008270, zinc ion binding## (2e−24); GO_BP:GO:0015074, DNA integration## (2e−24); GO_CC:GO:0005622, intracellular# (9e−19) | 3 | 120.3 | 176264306 | 176264540 |
| 406 | Serine/threonine-protein kinase Nek5 n = 2 Tax = Oryza sativa RepID = NEK5_ORYSJ (0.0); Pkinase: Protein kinase domain (1.4e−75); Pkinase_Tyr: Protein tyrosine kinase (2.9e−16); Kdo: Lipopolysaccharide kinase (Kdo) (0.024); GO_MF:GO:0016740, transferase activity## (0.0); GO_BP:GO:0016301, kinase activity## (0.0); GO_CC:GO:0055028, IDA#cortical microtubule# (1e−156) | 3 | 120.5 | 176289474 | 176295510 |
| 407 | Syntaxin, plant, putative n = 1 Tax = Ricinus communis RepID = B9T2S1_RICCO (4e−20); Hin1: Harpin-induced protein 1 (Hin1) (1.1e−34); GO_MF:GO:0000156, two-component response regulator activity## (6e−11); Kdo: Lipopolysaccharide kinase (Kdo) (0.024); GO_BP:GO:0051607, IMP#defense response to virus# (4e−20); GO_CC:GO:0005886, plasma membrane# (4e−20) | 3 | 120.5 | 176296694 | 176297398 |
| 408 | Harpin-induced protein 1 n = 1 Tax = Bruguiera gymnorhiza RepID = B1Q4T2_9ROSI (7e−14); Hin1: Harpin-induced protein 1 (Hin1) (3.4e−19); GO_BP:GO:0051707, IEP#response to other organism# (1e−12); GO_CC:GO:0009507, chloroplast# (1e−12) | 3 | 120.6 | 176301641 | 176302213 |
| 409 | Harpin-inducing protein n = 1 Tax = Casuarina glauca RepID = B0ZC11_CASGL (4e−21); Hin1: Harpin-induced protein 1 (Hin1) (1.1e−42); GO_MF:GO:0005515, protein binding# (3e−10); GO_BP:GO:0051607, IMP#defense response to virus# (1e−16); GO_CC:GO:0005886, plasma membrane# (1e−16) | 3 | 120.6 | 176302930 | 176304103 |
| 410 | Putative uncharacterized protein Sb03g040780 n = 1 Tax = Sorghum bicolor RepID = C5XQL0_SORBI (1e−18) | 3 | 120.9 | 176322098 | 176322610 |
| 411 | Ovate protein n = 1 Tax = Zea mays RepID = B6SI20_MAIZE (3e−11); DUF623: Protein of unknown function, DUF623 (1.4e−34) | 3 | 121 | 176332104 | 176333800 |
| 412 | OSJNBa0088H09.12 protein n = 3 Tax = Oryza sativa RepID = Q7XPU4_ORYSJ (2e−14); DUF623: Protein of unknown function, DUF623 (1.1e−30) | 3 | 121.3 | 176354609 | 176356292 |
| 413 | Putative uncharacterized protein n = 1 Tax = Zea mays RepID = B6TX28_MAIZE (2e−38) | 3 | 121.5 | 176365418 | 176366596 |
| 414 | RNA binding protein n = 3 Tax = Andropogoneae RepID = B6T390_MAIZE (1e−09); PAM2: Ataxin-2 C-terminal region (3.8e−05); GO_MF:GO:0003723, RNA binding## (1e−09); GO_BP:GO:0006396, RNA processing## (1e−09); GO_CC:GO:0030529, ribonucleoprotein complex# (1e−09) | 3 | 121.5 | 176373937 | 176374758 |
| 415 | Putative gag-pol polyprotein n = 1 Tax = Zea mays RepID = Q8HGI4_MAIZE (1e−56); GO_MF:GO:0008270, zinc ion binding# (1e−56); GO_BP:GO:0015074, DNA integration# (1e−56) | 3 | 121.5 | 176425086 | 176425704 |
| 416 | DNA binding protein n = 2 Tax = Andropogoneae RepID = B6U2E0_MAIZE (1e−50); Myb_DNA-binding: Myb-like DNA-binding domain (0.043); Myb_DNA-binding: Myb-like DNA-binding domain (3.3e−12); GO_MF:GO:0003677, DNA binding# (9e−59); GO_BP:GO:0045449, regulation of transcription# (1e−39); GO_CC:GO:0005634, nucleus# (1e−54) | 3 | 121.5 | 176433983 | 176435494 |
| 417 | Sorting nexin 3, putative n = 1 Tax = Ricinus communis RepID = B9SWH8_RICCO (1e−168); PX: PX domain (1.7e−32); Vps5: Vps5 C terminal like (5e−15); GO_MF:GO:0035091, IMP#phosphoinositide binding# (0.0); GO_BP:GO:0007154, cell communication# (0.0); GO_CC:GO:0030904, retromer complex# (1e−163) | 3 | 121.6 | 176446897 | 176451221 |
| 418 | Putative uncharacterized protein Sb03g040710 n = 2 Tax = Andropogoneae RepID = C5XQK3_SORBI (6e−76); DUF584: Protein of unknown function, DUF584 (1.5e−17) | 3 | 121.65 | 176451411 | 176452570 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 419 | NAC transcription factor-like protein n = 2 Tax = Oryza sativaRepID = Q94CW0_ORYSJ (3e-69); NAM: No apical meristem (NAM) protein (2.1e-47); GO_MF:GO:0003677, DNA binding#; GO_BP:GO:0045449, regulation of transcription# (3e-69); GO_CC:GO:0005634, nucleus# (7e-51) | 3 | 122.15 | 176510723 | 176512231 |
| 420 | Putative uncharacterized protein Sb03g040650 n = 1 Tax = Sorghum bicolor RepID = C5XQJ7_SORBI (1e-35) | 3 | 122.15 | 176553306 | 176554086 |
| 421 | Putative uncharacterized protein n = 1 Tax = Zea mays RepID = B6TW48_MAIZE (2e-76) | 3 | 122.2 | 176556622 | 176558892 |
| 422 | Catalytic/hydrolase n = 1 Tax = Zea mays RepID = B6SJL9_MAIZE (0.0); PGAP1: PGAP1-like protein (0.071); Abhydrolase_1: alpha/beta hydrolase fold (0.00056); GO_MF:GO:0016787, hydrolase activity# (0.0); GO_BP:GO:0006066, alcohol metabolic process# (1e-154); GO_CC:GO:0005739, mitochondrion# (1e-105) | 3 | 122.25 | 176523462 | 176526731 |
| 423 | Phospholipase D alpha 1 n = 2 Tax = Andropogoneae RepID = PLDA1_MAIZE (9e-28); PPR: PPR repeat (0.01); Glyco_hydro_9: Glycosyl hydrolase family 9 (1.6e-05); GO_MF:GO:0004553, hydrolase activity, hydrolyzing O-glycosyl compounds# (0.0); GO_BP:GO:0005975, carbohydrate metabolic process# (0.0); GO_CC:GO:0016020, membrane# (9e-28) | 3 | 122.3 | 176528107 | 176529876 |
| 424 | Putative uncharacterized protein Sb03g040660 n = 1 Tax = Sorghum bicolor RepID = C5XQJ8_SORBI (0.0); Hemerythrin: Hemerythrin (0.015); Hemerythrin: Hemerythrin (2.3); DUF1054: Protein of unknown function (DUF1054) (0.016); GO_MF:GO:0005515, protein binding# (1e-35) | 3 | 122.3 | 176529882 | 176533815 |
| 425 | Hevamine-A n = 1 Tax = Zea mays RepID = B6TVA3_MAIZE (1e-145); Glyco_hydro_18: Glycosyl hydrolases family 18 (1.5e-51); GO_MF:GO:0043169, cation binding (1e-145); GO_BP:GO:0008152, metabolic process# (1e-145); GO_CC:GO:0005773, IDA#vacuole# (1e-97) | 3 | 122.4 | 176569917 | 176571499 |
| 426 | Class III chitinase n = 1 Tax = Panax ginseng RepID = Q19AL0_PANGI (1e-102); Glyco_hydro_18: Glycosyl hydrolases family 18 (3.9e-44); GO_MF:GO:0043169, cation binding# (1e-133); GO_BP:GO:0008152, metabolic process# (1e-133); GO_CC:GO:0005615, extracellular space# (1e-96) | 3 | 122.4 | 176597593 | 176598560 |
| 427 | Class III chitinase n = 1 Tax = Panax ginseng RepID = Q19AL0_PANGI (1e-105); Glyco_hydro_18: Glycosyl hydrolases family 18 (2.9e-52); GO_MF:GO:0043169, cation binding# (1e-137); GO_BP:GO:0008152, metabolic process# (1e-137); GO_CC:GO:0005618, IDA#cell wall# (2e-97) | 3 | 122.4 | 176599914 | 176600977 |
| 428 | Heat shock protein binding protein n = 1 Tax = Zea mays RepID = B6U723_MAIZE (5e-32); GO_MF:GO:0031072, heat shock protein binding# (5e-32); GO_BP:GO:0006950, response to stress# (5e-32) | 3 | 122.4 | 176777440 | 176778989 |
| 429 | Putative uncharacterized protein Sb02g037540 n = 2 Tax = Andropogoneae RepID = C5XCF9_SORBI (6e-17) | 3 | 122.4 | 176778705 | 176782511 |
| 430 | F-box protein-like n = 4 Tax = Poaceae RepID = Q8RZ32_ORYSJ (0.0); F-box: F-box domain (0.0046) | 3 | 122.4 | 176783173 | 176791091 |
| 431 | Putative uncharacterized protein Sb02g042500 n = 1 Tax = Sorghum bicolor RepID = C5X4Y2_SORBI (1e-17); PPR: PPR repeat (1e-06) | 3 | 122.4 | 176788513 | 176788932 |
| 432 | Glucan endo-1,3-beta-glucosidase 7 n = 2 Tax = Andropogoneae RepID = B6T478_MAIZE (1e-179); Glyco_hydro_17: Glycosyl hydrolases family 17 (1.7e-96); GO_MF:GO:0043169, cation binding# (1e-179); GO_BP:GO:0008152, metabolic process# (1e-179); GO_CC:GO:0046658, anchored to plasma membrane# (1e-107) | 3 | 122.45 | 176562644 | 176565454 |
| 433 | Liguleless2-like protein n = 2 Tax = Zea mays RepID = Q84UA5_MAIZE (0.0); bZIP_2: Basic region leucine zipper (0.01); bZIP_1: bZIP transcription factor (0.003); GO_MF:GO:0046983, protein dimerization activity# (0.0); GO_BP:GO:0006355, regulation of transcription, DNA-dependent# (0.0); GO_CC:GO:0005634, nucleus# (0.0) | 3 | 122.75 | 176800252 | 176808864 |
| 434 | Putative uncharacterized protein n = 2 Tax = Zea mays RepID = B6U713_MAIZE (0.0); GO_BP:GO:0055114, oxidation reduction# (0.0); GO_MF:GO:0016491, oxidoreductase activity# (0.0); 2OG-FeII_Oxy: 2OG-Fe(II) oxygenase superfamily (0.018); | 8 | 69 | 66655758 | 66661595 |
| 435 | Phragmoplastin n = 1 Tax = Camellia sinensis RepID = A2T1L8_CAMSI (0.0); MMR_HSR1: GTPase of unknown function (0.00019); Dynamin_N: Dynamin family (5.5e-88); Dynamin_M: Dynamin central region (1.2e-103); GED: Dynamin GTPase effector domain (3.3e-38); GO_MF:GO:0005525, GTP binding# (0.0); GO_BP:GO:0051301, cell division# (0.0); GO_CC:GO:0009524, IDA#phragmoplast# (0.0) | 8 | 69 | 66662515 | 66672012 |
| 436 | Dopamine beta-monooxygenase n = 3 Tax = Andropogoneae RepID = B6TH76_MAIZE (0.0); DOMON: DOMON domain (0.025); DUF2427: Domain of unknown function (DUF2427) (0.082); GO_MF:GO:0004500, dopamine beta-monooxygenase activity# (0.0); GO_BP:GO:0006548, histidine catabolic process# (0.0); GO_CC:GO:0016021, integral to membrane# (1e-44) | 8 | 69 | 66829804 | 66832512 |
| 437 | Dopamine beta-monooxygenase n = 3 Tax = Andropogoneae RepID = B6TH76_MAIZE (0.0); DOMON: DOMON domain (0.025); DUF2427: Domain of unknown function (DUF2427) (0.082); GO_MF:GO:0004500, dopamine beta-monooxygenase activity# (0.0); GO_BP:GO:0006548, histidine catabolic process# (0.0); GO_CC:GO:0016021, integral to membrane# (1e-44) | 8 | 69 | 66856185 | 66858893 |
| 438 | Putative uncharacterized protein n = 1 Tax = Zea mays RepID = C0HDR6_MAIZE (1e-126); DUF1639: Protein of unknown function (DUF1639) (9.5e-29) | 8 | 69 | 66988051 | 66992509 |
| 439 | Putative uncharacterized protein n = 1 Tax = Zea mays RepID = C4I1U2_MAIZE (4e-10) | 8 | 69 | 66992846 | 66993175 |
| 440 | Chloroplast nucleoid DNA binding protein-like n = 1 Tax = Oryza sativa Japonica Group RepID = Q5QM88_ORYSJ (8e-82); Asp: Eukaryotic aspartyl protease (0.00063); GO_MF:GO:0016787, hydrolase activity# (1e-163); GO_BP:GO:0006508, proteolysis# (1e-163) | 8 | 69 | 67202702 | 67205538 |
| 441 | Putative uncharacterized protein Sb09g028090 n = 2 Tax = Andropogoneae RepID = C5YVF9_SORBI (0.0); GO_CC:GO:0009507, chloroplast# (1e-102) | 8 | 69 | 67353996 | 67357167 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 442 | RNA Binding Protein-like n = 2 Tax = Oryza sativa Japonica Group RepID = Q7EZ58_ORYSJ (3e–43); RAM_1: RNA recognition motif (a.k.a. RRM, RB (0.06); RRM_1: RNA recognition motif (a.k.a. RRM, RB (0.011); GO_MF:GO:0003676, nucleic acid binding# (8e–62) | 8 | 69 | 67374077 | 67376254 |
| 443 | Glycoside hydrolase, family 28 n = 2 Tax = Andropogoneae RepID = B6TX01_MAIZE (2e–39); GO_MF:GO:0016798, hydrolase activity, acting on glycosyl bonds# (2e–39); GO_BP:GO:0008152, metabolic process# (2e–39); GO_CC:GO:0016021, integral to membrane# (1e–21) | 8 | 69 | 67378682 | 67379061 |
| 444 | Ubiquitin-conjugating enzyme E2 n = 3 Tax = Andropogoneae RepID = Q5RLI8_MAIZE (1e–162); GO_BP:GO:0051246, regulation of protein metabolic process# (0.0) GO_MF:GO:0019787, small conjugating protein ligase activity# (0.0); GO_BP:GO:0016567, protein ubiquitination# (2e–101); UQ_con: Ubiquitin-conjugating enzyme (1.6e–28); | 8 | 69 | 67380589 | 67387935 |
| 445 | Pirin-like protein n = 1 Tax = Solanum lycopersicum RepID = PIRL_SOLLC (4e–26); Pirin: Pirin (4.2e–19); GO_MF:GO:0005516, IDA#calmodulin binding# (2e–21); GO_BP:GO:0007018, microtubule-based movement# (4e–18); GO_CC:GO:0005634, nucleus# (4e–26) | 8 | 69 | 67407549 | 67407962 |
| 446 | Pirin-like protein n = 3 Tax = Zea mays RepID = B6TS20_MAIZE (2e–72); Pirin_C: Pirin C-terminal region (3.7e–38); GO_MF:GO:0005516, IDA#calmodulin binding# (1e–44); GO_BP:GO:0009738, IMP#abscisic acid mediated signaling pathway# (7e–43); GO_CC:GO:0005634, nucleus# (5e–50) | 8 | 69 | 67407993 | 67410918 |
| 447 | Putative uncharacterized protein n = 1 Tax = Zea mays RepID = C0P2F7_MAIZE (1e–22) | 8 | 69 | 67415431 | 67415880 |
| 448 | PHD-type zinc finger protein-like n = 1 Tax = Oryza sativa Japonica Group RepID = Q84NP5_ORYSJ (2e–19); GO_MF:GO:0008080, N-acetyltransferase activity# (2e–22); GO_BP:GO:0008152, metabolic process# (2e–22) | 8 | 69 | 67417257 | 67417523 |
| 449 | TPR domain containing protein n = 2 Tax = Andropogoneae RepID = B6SI86_MAIZE (5e–66); GO_MF:GO:0005488, binding# (2e–16) | 8 | 69 | 67445895 | 67448009 |
| 450 | 50S ribosomal protein L21 n = 4 Tax = Andropogoneae RepID = C5YVG2_SORBI (1e–54); Ribosomal_L21p:Ribosomal prokaryotic L21 protein (2.8e–27); GO_MF:GO:0019843, rRNA binding# (5e–43); GO_BP:GO:0006412, translation# (5e–43); GO_CC:GO:0030529, ribonucleoprotein complex# (1e–43) | 8 | 69 | 67491320 | 67495907 |
| 451 | Structural constituent of ribosome n = 1 Tax = Zea mays RepID = B6SGX4_MAIZE (0.0); GO_MF:GO:0003723, RNA binding# (0.0); GO_BP:GO:0006396, RNA processing# (0.0); GO_CC:GO:0016020, membrane# (7e–50) | 8 | 69 | 67500034 | 67501797 |
| 452 | 40S ribosomal protein S4 n = 17 Tax = commelinids RepID = RS4_ORYSJ (1e–30); Ribosomal_S4e: Ribosomal family S4e (6e–17); KOW: KOW motif (5.9e–05); GO_MF:GO:0003735, structural constituent of ribosome# (3e–33); GO_BP:GO:0006412, translation# (3e–33); GO_CC:GO:0005840, ribosome# (3e–33) | 8 | 69 | 67556204 | 67557043 |
| 453 | Transposon protein, putative, CACTA, En/Spm sub-class n = 1 Tax = Oryza sativa Japonica Group RepID = Q2R337_ORYSJ (2e–41); GO_MF:GO:0005524, ATP binding# (5e–24); GO_BP:GO:0006468, protein amino acid phosphorylation# (5e–24) | 8 | 69 | 70615005 | 70615933 |
| 454 | Transposon protein, putative, CACTA, En/Spm sub-class n = 1 Tax = Oryza sativa Japonica Group RepID = Q2QWY8_ORYSJ (1e–54); GO_MF:GO:0005524, ATP binding# (8e–45); GO_BP:GO:0006468, protein amino acid phosphorylation# (2e–45) | 8 | 69 | 70616774 | 70617362 |
| 455 | CACTA TnpD transposase n = 1 Tax = Zea mays RepID = A0EVI2_MAIZE (8e–71); GO_MF:GO:0003677, DNA binding# (1e–35); GO_BP:GO:0015074, DNA integration# (1e–35) | 8 | 69 | 70621129 | 70622573 |
| 456 | Ubiquitin ligase protein cop1, putative n = 1 Tax = Ricinus communis RepID = B9RCP1_RICCO (0.0); Pkinase:Protein kinase domain (0.0091); WD40: WD domain, G-beta repeat (1.2); WD40: WD domain, G-beta repeat (0.016); WD40: WD domain, G-beta repeat (1.8e–07); WD40: WD domain, G-beta repeat (0.087); WD40: WD domain, G-beta repeat (5.4e–06); WD40: WD domain, G-beta repeat (5.1); GO_MF:GO:0032440, 2-alkenal reductase activity# (0.0); GO_BP:GO:0055114, oxidation reduction# (0.0); GO_CC:GO:0016607, IDA#nuclear speck# (0.0) | 8 | 69 | 72174759 | 72182919 |
| 457 | Protein disulfide isomerase n = 2 Tax = Andropogoneae RepID = Q5EUD6_MAIZE (2e–63); Thioredoxin: Thioredoxin (7.5e–13); ERp29: Endoplasmic reticulum protein ERp29, C-te (0.035); GO_MF:GO:0016853, isomerase activity# (2e–63); GO_BP:GO:0045454, cell redox homeostasis# (2e–63); GO_CC:GO:0005783, IDA#endoplasmic reticulum# (2e–63) | 8 | 69 | 73202962 | 73205959 |
| 458 | UPF0737 protein 7 n = 3 Tax = Andropogoneae RepID = U7377_MAIZE (0.0); GO_MF:GO:0003676, nucleic acid binding# (6e–09); GO_BP:GO:0006810, transport# (6e–09); GO_CC:GO:0005634, nucleus# (0.0) | 8 | 69.1 | 67718099 | 67723430 |
| 459 | Os02g0140101 protein n = 4 Tax = Poaceae RepID = Q6ZZX5_ORYSJ (3e–13); DPM2: Dolichol phosphate-mannose biosynthesis regu (9.5e–51); GO_MF:GO:0016757, transferase activity, transferring glycosyl groups# (3e–13) | 8 | 69.1 | 67723481 | 67729604 |
| 460 | Exosome complex exonuclease RRP41 n = 6 Tax = Poaceae RepID = B6T763_MAIZE (1e–105); RNase_PH: 3' exoribonuclease family, domain 1 (1.3e–21); RNase_PH_C: 3'exoribonuclease family, domain 2 (2.9e–10); GO_MF:GO:0004527, exonuclease activity# (1e–105); GO_BP:GO:0006396, RNA processing# (1e–105); GO_CC:GO:0005737, cytoplasm# (3e–43) | 8 | 69.1 | 67729947 | 67735083 |
| 461 | OSJNBa0008M17.5 protein n = 1 Tax = Oryza sativa Japonica Group RepID = Q7XN10_ORYSJ (5e–36) | 8 | 69.1 | 70603256 | 70603871 |
| 462 | Putative transposase n = 1 Tax = Zea mays RepID = Q945K3_MAIZE (1e–133); Transposase_11: Transposase DDE domain (0.001); Plant_tran: Plant transposon protein (0.0001); GO_MF:GO:0004803, transposase activity# (1e–133); GO_BP:GO:0006313, transposition, DNA-mediated# (1e–133) | 8 | 69.1 | 73227996 | 73229586 |
| 463 | 60S acidic ribosomal protein P2A n = 11 Tax = Andropogoneae RepID = RLA2A_MAIZE (5e–27); Ribosomal_60s: 60s Acidic ribosomal protein (8e–38); GO_MF:GO:0003735, structural constituent of ribosome# (5e–27); GO_BP:GO:0006414, translational elongation# (5e–27); GO_CC:GO:0030529, ribonucleoprotein complex# (5e–27) | 8 | 69.1 | 73231852 | 73233748 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 464 | Retrotransposon protein, putative, unclassified n = 2 Tax = Oryza sativa Japonica Group RepID = Q10HY9_ORYSJ (2e−15); GO_MF:GO:0008270, zinc ion binding# (2e−19); GO_BP:GO:0006278, RNA-dependent DNA replication# (2e−15) | 8 | 69.2 | 71728584 | 71730308 |
| 465 | Acyltransferase, putative n = 1 Tax = Ricinus communis RepID = B9RBF7_RICCO (0.0); Chal_sti_synt_N: Chalcone and stilbene synthases, N-te (0.075); FAE1_CUT1_RppA: FAE1/Type III polyketide synthase-lik (8.4e−226); ACP_syn_III_C: 3-Oxoacyl-[acyl-carrier-protein] (ACP) (0.0054); Chal_sti_synt_C: Chalcone and stilbene synthases, C-te (1.2e−05); ACP_syn_III_C: 3-Oxoacyl-[acyl-carrier-protein] (ACP) (3.1e−07); GO_MF:GO:0016747, transferase activity, transferring acyl groups other than amino-acyl groups# (0.0); GO_BP:GO:0008610, lipid biosynthetic process# (0.0); GO_CC:GO:0016020, membrane# (0.0) | 8 | 69.4 | 71791503 | 71793883 |
| 466 | Glycerol kinase n = 2 Tax = Andropogoneae RepID = B6TZ71_MAIZE (9e−20); GO_MF:GO:0016773, phosphotransferase activity, alcohol group as acceptor# (9e−20); GO_BP:GO:0016301, kinase activity# (9e−20) | 8 | 69.4 | 71808569 | 71809069 |
| 467 | DRE-binding protein DREB1 n = 1 Tax = Cymbidium insigne RepID = A6YT27_9ASPA (5e−24); AP2: AP2 domain (3.8e−20); GO_MF:GO:0003700, transcription factor activity# (2e−67); GO_BP:GO:0045449, regulation of transcription# (2e−67); GO_CC:GO:0005634, nucleus# (2e−67) | 8 | 69.5 | 72423591 | 72424384 |
| 468 | ATP binding protein, putative n = 1 Tax = Ricinus communis RepID = B9RC18_RICCO (0.0); AAA_3: ATPase family associated with various (0.0048); AAA: ATPase family associated with various cellular activities (AAA) (2.5e−78); AAA_5: ATPase family associated with various (0.0016); GO_MF:GO:0017111, nucleoside-triphosphatase activity# (0.0); GO_BP:GO:0051301, cell division# (0.0) | 8 | 69.6 | 75066604 | 75072021 |
| 469 | BRASSINOSTEROID INSENSITIVE 1-associated receptor kinase 1, putative n = 1 Tax = Ricinus communis RepID = B9T3S1_RICCO (9e−25); GO_MF:GO:0005524, ATP binding# (3e−28); GO_BP:GO:0006468, protein amino acid phosphorylation# (3e−28); GO_CC:GO:0016021, integral to membrane# (9e−25) | 8 | 69.6 | 75073037 | 75075203 |
| 470 | Transposon protein, putative, Mutator sub-class n = 2 Tax = Oryza sativa Japonica Group RepID = Q10FB0_ORYSJ (7e−16); GO_MF:GO:0008270, zinc ion binding# (8e−16) | 8 | 69.6 | 75165143 | 75165609 |
| 471 | Putative uncharacterized protein Sb09g029910 n = 2 Tax = Sorghum bicolor RepID = C5YWJ1_SORBI (6e−16); GO_BP:GO:0055085, transmembrane transport# (2e−12); GO_CC:GO:0016021, integral to membrane# (2e−12) | 8 | 69.6 | 75187314 | 75187850 |
| 472 | Cyclin G-associated kinase-like protein n = 2 Tax = Oryza sativa RepID = Q69L76_ORYSJ (3e−74); GO_MF:GO:0016301, kinase activity# (3e−74); GO_BP:GO:0016301, kinase activity# (3e−74) | 8 | 69.65 | 74162123 | 74163697 |
| 473 | Putative uncharacterized protein n = 1 Tax = Zea mays RepID = B4FS85_MAIZE (1e−29) | 8 | 69.7 | 72479615 | 72480599 |
| 474 | Potassium transporter n = 3 Tax = Phragmites australis RepID = Q1T759_PHRAU (4e−13); GO_MF:GO:0015079, potassium ion transmembrane transporter activity# (4e−13); GO_BP:GO:0015079, potassium ion transmembrane transporter activity# (4e−13); GO_CC:GO:0016020, membrane# (4e−13) | 8 | 69.7 | 74163982 | 74164446 |
| 475 | Formamidase n = 1 Tax = Lupinus albus RepID = B9VXW6_LUPAL (4e−37); FmdA_AmdA: Acetamidase/Formamidase family (0.063); GO_MF:GO:0016811, hydrolase activity, acting on carbon-nitrogen (but not peptide) bonds, in linear amides# (4e−77); GO_BP:GO:0008152, metabolic process# (4e−77); GO_CC:GO:0005773, IDA#vacuole# (3e−38) | 8 | 69.75 | 71844016 | 71846415 |
| 476 | Protein Rf1, mitochondrial n = 2 Tax = Oryza sativa Indica Group RepID = RF1_ORYSI (0.0); PPR: PPR repeat (5.7); PPR: PPR repeat (0.69); PPR: PPR repeat (0.00073); PPR: PPR repeat (8.3e−12); PPR: PPR repeat (4.7e−10); PPR: PPR repeat (5.4e−13); PPR: PPR repeat (7e−10); PPR: PPR repeat (0.034); PPR: PPR repeat (9.4e−10); PPR: PPR repeat (2.9e−09); PPR: PPR repeat (2e−08); PPR: PPR repeat (1.6e−05); PPR: PPR repeat (1.9e−10); PPR: PPR repeat (1.3e−09); PPR: PPR repeat (0.00031); PPR: PPR repeat (5.3e−08); PPR: PPR repeat (3.6e−08); PPR: PPR repeat (4.8e−06); PPR: PPR repeat (4.6); GO_MF:GO:0008415, acyltransferase activity# (0.0); GO_BP:GO:0008152, metabolic process# (0.0); GO_CC:GO:0005739, mitochondrion# (0.0) | 8 | 69.8 | 77089017 | 77091404 |
| 477 | IMP dehydrogenase/GMP reductase, putative n = 1 Tax = Medicago truncatula RepID = A2Q539_MEDTR (2e−11); GO_MF:GO:0003677, DNA binding# (1e−117) | 8 | 69.8 | 77095435 | 77098145 |
| 478 | WRKY transcription factor 19 n = 3 Tax = Oryza sativa Japonica Group RepID = Q6IER2_ORYSJ (7e−41); WRKY: WRKY DNA-binding domain (9.4e−30); GO_MF:GO:0043565, sequence-specific DNA binding# (7e−41); GO_BP:GO:0045449, regulation of transcription# (7e−41); GO_CC:GO:0005634, nucleus# (7e−41) | 8 | 70.05 | 72382890 | 72384377 |
| 479 | 60S acidic ribosomal protein P2A n = 11 Tax = Andropogoneae RepID = RLA2A_MAIZE (1e−38); Ribosomal_60s: 60s Acidic ribosomal protein (1.2e−38); GO_MF:GO:0003735, structural constituent of ribosome# (4e−30); GO_BP:GO:0006414, translational elongation# (4e−30); GO_CC:GO:0030529, ribonucleoprotein complex# (4e−30) | 8 | 70.05 | 73386619 | 73388908 |
| 480 | Mitochondrial chaperone BCS1 n = 3 Tax = Andropogoneae RepID = B6SVD2_MAIZE (1e−178); AAA: ATPase family associated with various cellular activities (AAA) (3.8e−10); AAA_5: ATPase family associated with various (0.014); GO_MF:GO:0017111, nucleoside-triphosphatase activity# (1e−178); GO_CC:GO:0005739, mitochondrion# (1e−106) | 8 | 70.05 | 77133844 | 77135045 |
| 481 | Mitogen-activated protein kinase 9 n = 3 Tax = Oryza sativa RepID = MPK9_ORYSJ (1e−136); Pkinase: Protein kinase domain (0.0014); GO_MF:GO:0016740, transferase activity# (1e−136); GO_BP:GO:0016301, kinase activity# (1e−136); GO_CC:GO:0005886, plasma membrane# (3e−95) | 8 | 70.1 | 74681545 | 74688835 |
| 482 | Putative polyprotein n = 1 Tax = Zea mays RepID = Q8SA93_MAIZE (1e−28); GO_MF:GO:0003964, RNA-directed DNA polymerase, group II intron encoded# (1e−28); GO_BP:GO:0006355, regulation of transcription, DNA-dependent# (2e−29); GO_CC:GO:0005634, nucleus# (2e−29) | 8 | 70.1 | 76985420 | 76985803 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 483 | Mitochondrial chaperone BCS1 n = 3 Tax = Andropogoneae RepID = B6SVD2_MAIZE (0.0); AAA: ATPase family associated with various cellular activities (AAA) (7.7e−11); AAA_5: ATPase family associated with various (0.028); GO_MF:GO:0017111, nucleoside-triphosphatase activity# (0.0); GO_CC:GO:0005739, mitochondrion# (1e−106) | 8 | 70.1 | 76990850 | 76992377 |
| 484 | Mitochondrial chaperone BCS1 n = 3 Tax = Andropogoneae RepID = B6SVD2_MAIZE (2e−41); GO_MF:GO:0017111 nucleoside-triphosphatase activity# (2e−41) | 8 | 70.1 | 77135050 | 77135358 |
| 485 | IMP dehydrogenase/GMP reductase, putative n = 1 Tax = Medicago truncatula RepID = A2Q539_MEDTR (5e−18); Myb_DNA-binding: Myb-like DNA-binding domain (0.072); GO_MF:GO:0003677, DNA binding# (0.0) | 8 | 70.15 | 76983379 | 76988331 |
| 486 | Tetratricopeptide repeat protein, tpr, putative n = 1 Tax = Ricinus communis RepID = B9R838_RICCO (7e−20); efhand: EF hand (3.9e−05); GO_MF:GO:0008270, zinc ion binding# (3e−24); GO_BP:GO:0006508, proteolysis# (2e−14); GO_CC:GO:0000502, proteasome complex# (7e−19) | 8 | 70.2 | 72620245 | 72622319 |
| 487 | Probable protein phosphatase 2C 51 n = 3 Tax = Oryza sativa RepID = P2C51_ORYSJ (2e−93); PP2C: Protein phosphatase 2C (1.1e−76); GO_MF:GO:0046872, metal ion binding# (1e−161); GO_BP:GO:0006470, protein amino acid dephosphorylation# (1e−161); GO_CC:GO:0008287, protein serine/threonine phosphatase complex# (1e−161) | 8 | 70.2 | 72623215 | 72631055 |
| 488 | ATP10 protein n = 1 Tax = Zea mays RepID = B6TN8_MAIZE (1e−139); ATP-synt_10: ATP10 protein (3.7e−06); GO_MF:GO:0008236, serine-type peptidase activity# (1e−47); GO_BP:GO:0033615, mitochondrial proton-transporting ATP synthase complex assembly# (1e−139); GO_CC:GO:0005743, mitochondrial inner membrane# (1e−139) | 8 | 70.2 | 80037657 | 80046134 |
| 489 | Cell division protein kinase, putative n = 1 Tax = Ricinus communis RepID = B9TSN4_RICCO (7e−82); Pkinase_Tyr: Protein tyrosine kinase (1e−04); Pkinase: Protein kinase domain (5.4e−21); GO_MF:GO:0005524, ATP binding# (2e−95); GO_BP:GO:0006468, protein amino acid phosphorylation# (2e−95); GO_CC:GO:0005886, plasma membrane# (3e−82) | 8 | 70.25 | 80024603 | 80025821 |
| 490 | DNA binding protein n = 3 Tax = Andropogoneae RepID = B6TCD9_MAIZE (9e−75); SRF-TF: SRF-type transcription factor (DNA-binding and dimerisation domain) (8.5e−21); GO_MF:GO:0043565, sequence-specific DNA binding# (9e−75); GO_BP:GO:0045449, regulation of transcription# (9e−75); GO_CC:GO:0005634, nucleus# (9e−75) | 8 | 70.3 | 72653910 | 72654861 |
| 491 | F-box domain containing protein n = 3 Tax = Andropogoneae RepID = B6U5X4_MAIZE (6e−90) | 8 | 70.3 | 72664145 | 72664967 |
| 492 | DNA-binding protein WRKY3-like n = 2 Tax = Oryza sativa Japonica Group RepID = Q5ZEB2_ORYSJ (3e−37); WRKY: WRKY DNA-binding domain (4.7e−30); GO_MF:GO:0043565, sequence-specific DNA binding# (8e−48); GO_BP:GO:0045449, regulation of transcription# (8e−48); GO_CC:GO:0005634, nucleus# (8e−48) | 8 | 70.35 | 74902354 | 74903632 |
| 493 | Lactoylglutathione lyase n = 1 Tax = Zea mays RepID = B4FQ23_MAIZE (1e−109); Glyoxalase: Glyoxalase/Bleomycin resistance protein/Dioxygenase superfamily (2.6e−11); GO_MF:GO:0016829, lyase activity# (1e−109) | 8 | 70.35 | 80291813 | 80295002 |
| 494 | Nucleoside diphosphate kinase n = 3 Tax = Zea mays RepID = B6TKC5_MAIZE (2e−72); NDK: Nucleoside diphosphate kinase (6e−65); GO_MF:GO:0016740, transferase activity# (2e−72); GO_BP:GO:0005737, cytoplasm# (2e−72); GO_MF:GO:0016301, kinase activity# (2e−72); GO_CC:GO:0005737, cytoplasm# (2e−72) | 8 | 70.4 | 79074614 | 79075596 |
| 495 | Alpha-N-arabinofuranosidase A n = 2 Tax = Zea mays RepID = B6T9B9_MAIZE (2e−78); GO_MF:GO:0046556, alpha-N-arabinofuranosidase activity# (2e−78); GO_BP:GO:0046373, L-arabinose metabolic process# (2e−78); GO_CC:GO:0005578, proteinaceous extracellular matrix# (6e−54) | 8 | 70.4 | 80019137 | 80024134 |
| 496 | ATP binding protein n = 2 Tax = Andropogoneae RepID = B6SXM5_MAIZE (0.0); Kinesin: Kinesin motor domain (1.1e−125); GO_MF:GO:0005524, ATP binding# (0.0); GO_BP:GO:0007018, microtubule-based movement# (0.0); GO_CC:GO:0005874, microtubule# (0.0) | 8 | 70.45 | 83046589 | 83087386 |
| 497 | CTP synthase n = 1 Tax = Zea mays RepID = B6SXZ9_MAIZE (0.0); CTP_synth_N: CTP synthase N-terminus (4.4e−201); GATase: Glutamine amidotransferase class-I (3.3e−78); GO_MF:GO:0003883, CTP synthase activity# (0.0); GO_BP:GO:0006221, pyrimidine nucleotide biosynthetic process# (0.0); GO_CC:GO:0005829, IDA#cytosol# (1e−175) | 8 | 70.5 | 72744835 | 72751237 |
| 498 | OSJNBa0029I02.20 protein n = 1 Tax = Oryza sativa RepID = Q7XMR7_ORYSA (6e−29); GO_MF:GO:0004523, ribonuclease H activity# (6e−29); GO_BP:GO:0045449, regulation of transcription# (6e−29) | 8 | 70.5 | 82966507 | 82967100 |
| 499 | Putative uncharacterized protein n = 1 Tax = Zea mays RepID = B7ZYQ1_MAIZE (1e−15) | 8 | 70.5 | 83080991 | 83081326 |
| 500 | Transposon protein, putative, CACTA, En/Spm sub-class n = 1 Tax = Oryza sativa Japonica Group RepID = Q2R1M9_ORYSJ (8e−60); GO_MF:GO:0004803, transposase activity# (2e−66); GO_BP:GO:0006313, transposition, DNA-mediated# (2e−66) | 8 | 70.55 | 74905264 | 74907420 |
| 501 | Tubulin beta chain, putative n = 1 Tax = Ricinus communis RepID = B9SB77_RICCO (2e−34); GO_MF:GO:0005525, GTP binding# (2e−34); GO_BP:GO:0051258, protein polymerization# (2e−34); GO_CC:GO:0043234, protein complex# (2e−34) | 8 | 70.6 | 77234145 | 77234873 |
| 502 | Serine hydroxymethyltransferase n = 5 Tax = Poaceae RepID = Q7Y1F0_ORYSJ (2e−94); SHMT: Serine hydroxymethyltransferase (2.4e−30); Tubulin: Tubulin/FtsZ family, GTPase domain (6.3e−06); GO_MF:GO:0030170, pyridoxal phosphate binding# (2e−94); GO_BP:GO:0006730, one-carbon metabolic process# (2e−94); GO_CC:GO:0048046, IDA#apoplast# (2e−89) | 8 | 70.6 | 77234886 | 77237194 |
| 503 | Catalytic/protein phosphatase type 2C n = 1 Tax = Zea mays RepID = B6U289_MAIZE (9e−52); GO_MF:GO:0003824, catalytic activity# (9e−52); GO_CC:GO:0005886, plasma membrane# (4e−38); GO_BP:GO:0004721, phosphoprotein phosphatase activity# (4e−38); GO_CC:GO:0005886, plasma membrane# (1e−19) | 8 | 70.7 | 72381917 | 72382396 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 504 | Putative uncharacterized protein n = 1 Tax = Zea mays RepID = Q69V9_MAIZE (1e–21) | 8 | 70.7 | 74850214 | 74850548 |
| 505 | VIP2 protein n = 1 Tax = Avena fatua RepID = Q9M4C5_AVEFA (1e–101); GO_MF:GO:0046872, metal ion binding# (1e–101) | 8 | 70.7 | 82851656 | 82853989 |
| 506 | Chaperone protein dnaJ, putative n = 1 Tax = Ricinus communis RepID = B9RNG7_RICCO (1e–142); DnaJ: DnaJ domain (1.2e–35); DnaJ_C: DnaJ C terminal region (4.3e–18); GO_MF:GO:0051082, unfolded protein binding# (1e–145); GO_BP:GO:0006457, protein folding# (1e–145); GO_CC:GO:0005886, plasma membrane# (1e–138) | 8 | 70.8 | 79424401 | 79433056 |
| 507 | OSJNBa0065O17.7 protein n = 1 Tax = Oryza sativa Japonica Group RepID = Q7XPS4_ORYSJ (6e–39); GO_MF:GO:0003964, RNA-directed DNA polymerase, group II intron encoded# (6e–39); GO_BP:GO:0015074, DNA integration# (6e–39); GO_CC:GO:0005634, nucleus# (9e–34) | 8 | 70.85 | 76769570 | 76770143 |
| 508 | MAPK activating protein-like n = 5 Tax = Oryza sativa RepID = Q5N8F0_ORYSI (8e–25); DUF292: Eukaryotic protein of unknown function, DUF292 (0.0041); GO_MF:GO:0005524, ATP binding# (2e–12); GO_BP:GO:0006438, valyl-tRNA aminoacylation# (2e–12); GO_CC:GO:0005737, cytoplasm# (2e–12) | 8 | 70.9 | 76754358 | 76755616 |
| 509 | OSJNBa0065O17.7 protein n = 1 Tax = Oryza sativa Japonica Group RepID = Q7XPS4_ORYSJ (8e–25); GO_MF:GO:0003964, RNA-directed DNA polymerase, group II intron encoded# (8e–25); GO_BP:GO:0015074, DNA integration# (8e–25) | 8 | 70.9 | 76766268 | 76769413 |
| 510 | Protein SEY1, putative n = 1 Tax = Ricinus communis RepID = B9RQ05_RICCO (9e–72); RHD3: Root hair defective 3 GTP-binding protein (RHD3) (0.013); GO_MF:GO:0016787, hydrolase activity# (1e–101); GO_CC:GO:0016021, integral to membrane# (1e–101) | 8 | 70.9 | 83123484 | 83125993 |
| 511 | Serine/threonine-protein phosphatase n = 2 Tax = Andropogoneae RepID = C5Z0I0_SORBI (1e–175); Metallophos: Calcineurin-like phosphoesterase (7.6e–45); GO_MF:GO:0016787, hydrolase activity# (1e–161); GO_BP:GO:0004721, phosphoprotein phosphatase activity# (1e–161); GO_CC:GO:0016459, myosin complex# (1e–127) | 8 | 70.95 | 83126356 | 83130765 |
| 512 | Triosephosphate isomerase n = 1 Tax = Zea mays RepID = B6SMV7_MAIZE (1e–67); TIM: Triosephosphate isomerase (1.6e–33); ABC_membrane_2: ABC transporter transmembrane region (0.025); GO_MF:GO:0016853, isomerase activity# (1e–67); GO_BP:GO:0008152, metabolic process# (1e–67); GO_CC:GO:0005737, cytoplasm# (9e–60) | 8 | 71 | 82634448 | 82642435 |
| 513 | AT hook motif-containing protein, putative n = 2 Tax = Oryza sativa Japonica Group RepID = Q2R0Z1_ORYSJ (0.0); CXC: Tesmin/TSO1-like CXC domain (0.0019); GO_MF:GO:0004386, helicase activity# (0.0) | 8 | 71 | 83131432 | 83138464 |
| 514 | AT hook motif-containing protein, putative n = 2 Tax = Oryza sativa Japonica Group RepID = Q2R0Z1_ORYSJ (1e–109); DUF889: Eukaryotic protein of unknown function (DUF889) (5.9e–09); GO_MF:GO:0004386, helicase activity# (1e–109) | 8 | 71.05 | 83138621 | 83139769 |
| 515 | SIN3 component, histone deacetylase complex n = 1 Tax = Populus trichocarpa RepID = B9HLV3_POPTR (5e–18); GO_MF:GO:0016564, transcription repressor activity# (2e–18); GO_BP:GO:0006355, regulation of transcription, DNA-dependent# (6e–57); GO_CC:GO:0005634, nucleus# (6e–57) | 8 | 71.1 | 76691823 | 76693893 |
| 516 | Clathrin heavy chain, putative; 28833-19741 n = 14 Tax = Magnoliophyta RepID = Q9SRM1_ARATH (9e–60); GO_MF:GO:0005515, protein binding# (3e–64); GO_BP:GO:0016192, vesicle-mediated transport# (3e–64); GO_CC:GO:0030132, clathrin coat of coated pit# (3e–64) | 8 | 71.1 | 82584615 | 82587189 |
| 517 | Galactosyltransferase family n = 3 Tax = Andropogoneae RepID = B6SXL2_MAIZE (3e–44); GO_MF:GO:0016757, transferase activity, transferring glycosyl groups# (3e–44); GO_BP:GO:0006486, protein amino acid glycosylation# (3e–44); GO_CC:GO:0016021, integral to membrane# (3e–44) | 8 | 71.1 | 82619337 | 82620998 |
| 518 | OSIGBa0135L04.1 protein n = 1 Tax = Oryza sativa RepID = Q01M88_ORYSA (4e–97); GO_MF:GO:0004386, helicase activity# (6e–74) | 8 | 71.1 | 83140523 | 83144235 |
| 519 | Putative uncharacterized protein Sb09g030240 n = 2 Tax = Sorghum bicolor RepID = C5YWM1_SORBI (8e–72) | 8 | 71.2 | 76647177 | 76648354 |
| 520 | SIN3 component, histone deacetylase complex n = 1 Tax = Populus trichocarpa RepID = B9HU88_POPTR (2e–10); GO_BP:GO:0006355, regulation of transcription, DNA- dependent# (1e–17); GO_CC:GO:0005634, nucleus# (1e–17) | 8 | 71.2 | 76656395 | 76657117 |
| 521 | ATP binding protein n = 1 Tax = Zea mays RepID = B6U0Y9_MAIZE (8e–40); GO_MF:GO:0016597, amino acid binding# (8e–40); GO_BP:GO:0008152, metabolic process# (8e–40); GO_CC:GO:0005829, IDA#cytosol# (2e–20) | 8 | 71.2 | 79379493 | 79380654 |
| 522 | UvrB/uvrC motif family protein n = 3 Tax = Andropogoneae RepID = B6TZ52_MAIZE (1e–149); UVR: UvrB/uvrC motif (0.011); UVR: UvrB/uvrC motif (0.02); DUF525: Protein of unknown function (DUF525) (6.7e–46); GO_MF:GO:0004518, nuclease activity# (1e–149); GO_BP:GO:0006289, IGI#nucleotide-excision repair# (1e–149) | 8 | 71.25 | 80438068 | 80441429 |
| 523 | Cytochrome c oxidase polypeptide Vb n = 1 Tax = Zea mays RepID = B6U4H2_MAIZE (3e–52); COX5B: Cytochrome c oxidase subunit Vb (1e–16); zf-CHCC: Zinc-finger domain (0.00083); GO_MF:GO:0004129, cbb3-type cytochrome c oxidase# (3e–52); GO_BP:GO:0004129, cbb3-type cytochrome c oxidase# (3e–52) | 8 | 71.3 | 76641925 | 76644716 |
| 524 | Putative uncharacterized protein n = 1 Tax = Zea mays RepID = B6IYK4_MAIZE (2e–69); GO_CC:GO:0009507, chloroplast## (3e–21) | 8 | 71.3 | 82495083 | 82495878 |
| 525 | Putative uncharacterized protein Sb09g029710 n = 1 Tax = Sorghum bicolor RepID = C5YWG5_SORBI (9e–40); BSP: Plant Basic Secretory Protein (2.8e–35) | 8 | 71.4 | 74660646 | 74662000 |
| 526 | HAT family dimerisation domain containing protein n = 1 Tax = Oryza sativa Japonica Group RepID = Q2QRD1_ORYSI (3e–90); zf-BED: BED zinc finger (4.9e–06); GO_MF:GO:0046983, protein dimerization activity# (3e–90); GO_BP:GO:0006350, transcription# (9e–29) | 8 | 71.5 | 76561092 | 76562289 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 527 | LOB domain protein 25 n = 2 Tax = Zea mays RepID = B6U340_MAIZE (3e−42); DUF260: Protein of unknown function DUF260 (2.1e−62); GO_MF:GO:0005515, protein binding# (1e−41); GO_BP:GO:0010016, IMP#shoot morphogenesis# (1e−29); GO_CC:GO:0016020, membrane# (2e−42) | 8 | 71.5 | 82375676 | 82377525 |
| 528 | Putative uncharacterized protein Sb09g004930 n = 2 Tax = Andropogoneae RepID = C5Z1I2_SORBI (4e−88); PIG-H: GPI-GlcNAc transferase complex, PIG-H compon (2.3e−22); GO_MF:GO:0016788, hydrolase activity, acting on ester bonds# (1e−38) | 8 | 71.5 | 82378172 | 82390011 |
| 529 | Lysophospholipase 2-like n = 3 Tax = Oryza sativa RepID = Q5ZBI5_ORYSJ (1e−100); Abhydrolase_2: Phospholipase/Carboxylesterase (1.5e−37); GO_MF:GO:0016787, hydrolase activity# (1e−107) | 8 | 71.65 | 76522603 | 76529857 |
| 530 | Cyclin type B-like n = 1 Tax = Zea mays RepID = O24584_MAIZE (4e−15); GO_CC:GO:0005634, nucleus# (4e−15) | 8 | 71.7 | 76501653 | 76501981 |
| 531 | Peptide chain release factor 2 n = 1 Tax = Zea mays RepID = B6UHD9_MAIZE (4e−74); PCRF: PCRF domain (1.4e−08); RF-1: Peptidyl-tRNA hydrolase domain (2.4e−05); GO_MF:GO:0016149, translation release factor activity, codon specific# (2e−79); GO_BP:GO:0016149, translation release factor activity, codon specific# (2e−79); GO_CC:GO:0005737, cytoplasm# (2e−79) | 8 | 71.7 | 76502731 | 76505082 |
| 532 | Zinc finger protein 7 n = 1 Tax = Zea mays RepID = B6U599_MAIZE (2e−41); GO_MF:GO:0008270, zinc ion binding# (2e−41); GO_CC:GO:0005622, intracellular# (2e−41) | 8 | 71.7 | 76509380 | 76510008 |
| 533 | Putative uncharacterized protein Sb09g030180 n = 1 Tax = Sorghum bicolor RepID = C5YWM2_SORBI (2e−13) | 8 | 71.7 | 76516695 | 76517305 |
| 534 | Putative homeobox-leucine zipper protein HOX26 n = 2 Tax = Oryza sativa RepID = HOX26_ORYSJ (7e−15); Homeobox: Homeobox domain (1.2e−05); GO_MF:GO:0043565, sequence-specific DNA binding# (2e−84); GO_BP:GO:0045449, regulation of transcription# (2e−84); GO_CC:GO:0016021, integral to membrane# (2e−84) | 8 | 71.7 | 80678089 | 80680549 |
| 535 | Putative ribulose-1,5 bisphosphate carboxylase/oxygenase large subunit N-methyltransferase, chloroplast n = 1 Tax = Oryza sativa Japonica Group RepID = Q6ESK6_ORYSJ (2e−09); SET: SET domain (4.5e−08); Rubis-subs-bind: Rubisco LSMT substrate-binding (0.0073); GO_MF:GO:0016740, transferase activity# (2e−21); GO_CC:GO:0009507, chloroplast# (2e−09) | 8 | 71.75 | 76493297 | 76498315 |
| 536 | Plasminogen activator inhibitor 1 RNA-binding protein n = 2 Tax = Andropogoneae RepID = B6T4Q3_MAIZE (1e−102); GRP: Glycine rich protein family (0.088); Sm1_N: Sm1 (0.024); HABP4_PAI-RBP1: Hyaluronan/mRNA binding family (7.3e−41); GO_CC:GO:0005737, cytoplasm# (6e−23) | 8 | 71.8 | 77429944 | 77433247 |
| 537 | Putative ubiquitin n = 1 Tax = Oryza sativa Japonica Group RepID = Q6L557_ORYSJ (1e−177); ubiquitin: Ubiquitin family (1.1e−12); ubiquitin: Ubiquitin family (0.00026); PI3_PI4_kinase: Phosphatidylinositol 3- and 4-kinase (6.6e−80); GO_MF:GO:0016773, phosphotransferase activity, alcohol group as acceptor# (0.0); GO_BP:GO:0016301, kinase activity# (1e−149); GO_CC:GO:0005777, IDA#peroxisome# (1e−149) | 8 | 71.8 | 77432348 | 77435177 |
| 538 | Dihydrolipoyl dehydrogenase n = 4 Tax = Poaceae RepID = C5Z0L0_SORBI (0.0); HI0933_like: HI0933-like protein (0.056); DAO: FAD dependent oxidoreductase (0.0028); FAD_binding_2: FAD binding domain (0.0017); GIDA: Glucose inhibited division protein A (0.002); Pyr_redox_2: Pyridine nucleotide-disulphide oxidored (6.3e−48); Pyr_redox: Pyridine nucleotide-disulphide oxidore (4.2e−23); Pyr_redox_dim: Pyridine nucleotide-disulphide oxidor (1.8e−41); GO_MF:GO:0050660, FAD binding# (0.0); GO_BP:GO:0055114, oxidation reduction# (0.0); GO_CC:GO:0043234, protein complex# (0.0) | 8 | 71.85 | 79300397 | 79307530 |
| 539 | 60S acidic ribosomal protein P2A n = 11 Tax = Andropogoneae RepID = RLA2A_MAIZE (3e−24); Ribosomal_60s: 60s Acidic ribosomal protein (2.2e−38); GO_MF:GO:0003735, structural constituent of ribosome# (3e−24); GO_BP:GO:0006414, translational elongation# (3e−24); GO_CC:GO:0030529, ribonucleoprotein complex# (3e−24) | 8 | 71.9 | 73686297 | 73688554 |
| 540 | Catalytic, putative n = 1 Tax = Ricinus communis RepID = B9RL97_RICCO (1e−125); Peptidase_S9: Prolyl oligopeptidase family (0.07); Abhydrolase_3: alpha/beta hydrolase fold (1.3e−05); GO_MF:GO:0016787, hydrolase activity# (1e−130); GO_CC:GO:0016020, membrane# (1e−130) | 8 | 71.9 | 73689972 | 73694162 |
| 541 | H0702G05.5 protein n = 1 Tax = Oryza sativa RepID = Q25AI8_ORYSA (1e−41); cwf21: cwf21 family (3.2e−22); GO_MF:GO:0003677, DNA binding# (2e−13) | 8 | 71.9 | 73724531 | 73725644 |
| 542 | ATP binding protein n = 1 Tax = Zea mays RepID = B6U656_MAIZE (1e−170); Pkinase: Protein kinase domain (2.7e−38); Pkinase_Tyr: Protein tyrosine kinase (5.8e−32); GO_MF:GO:0005524, ATP binding# (1e−170); GO_BP:GO:0006468, protein amino acid phosphorylation# (1e−170); GO_CC:GO:0005886, plasma membrane# (1e−113) | 8 | 71.9 | 73726676 | 73730357 |
| 543 | Putative uncharacterized protein Sb09g029450 n = 2 Tax = Andropogoneae RepID = C5YW44_SORBI (1e−175) | 8 | 71.9 | 73731498 | 73738039 |
| 544 | Dihydroflavonol-4-reductase n = 3 Tax = Andropogoneae RepID = B6TK03_MAIZE (1e−167); adh_short: short chain dehydrogenase (0.0004); Epimerase: NAD dependent epimerase/dehydratase family (1.3e−05); 3Beta_HSD: 3-beta hydroxysteroid dehydrogenase/isomerase family (2.3e−06); NAD_binding_4: Male sterility protein (0.04); GO_MF:GO:0005488, binding# (1e−167); GO_BP:GO:0008152, metabolic process# (1e−167) | 8 | 71.9 | 73846714 | 73852084 |
| 545 | Putative polygalacturonase n = 1 Tax = Oryza sativa Japonica Group RepID = Q6L5E7_ORYSJ (1e−155); Glyco_hydro_28: Glycosyl hydrolases family 28 (1e−87); GO_MF:GO:0016798, hydrolase activity, acting on glycosyl bonds# (0.0); GO_BP:GO:0008152, metabolic process# (0.0); GO_CC:GO:0005618, IDA#cell wall# (4e−79) | 8 | 71.9 | 73851064 | 73854409 |
| 546 | Ribonuclease P n = 3 Tax = Andropogoneae RepID = B6T7F1_MAIZE (5e−25); Prefoldin_2: Prefoldin subunit (0.0025); GO_MF:GO:0003676, nucleic acid binding# (5e−25); GO_BP:GO:0006508, proteolysis# (2e−24); GO_CC:GO:0016272, prefoldin complex# (4e−22) | 8 | 71.9 | 73872086 | 73875838 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 547 | Calmodulin binding protein n = 2 Tax = Andropogoneae RepID = B6U170_MAIZE (2e−96); GO_MF:GO:0005516, IDA#calmodulin binding# (2e−11) | 8 | 71.9 | 73875938 | 73878129 |
| 548 | PnFL-2 n = 3 Tax = Andropogoneae RepID = B6T7Q6_MAIZE (2e−40) | 8 | 71.9 | 73881273 | 73881812 |
| 549 | GATA transcription factor 19 n = 1 Tax = Zea mays RepID = B6TS85_MAIZE (2e−32); GATA: GATA zinc finger (1.6e−19); GO_MF:GO:0046872, metal ion binding#; GO_BP:GO:0006355, regulation of transcription, DNA-dependent# (2e−32); GO_CC:GO:0005634, nucleus# (1e−14) | 8 | 71.9 | 73894507 | 73895669 |
| 550 | Sugar transporter protein n = 1 Tax = Ananas comosus RepID = A4GXC8_ANACO (0.0); Sugar_tr: Sugar (and other) transporter (3.9e−104); MFS_1: Major Facilitator Superfamily (5.9e−13); GO_MF:GO:0022891, substrate-specific transmembrane transporter activity# (0.0); GO_BP:GO:0055085, transmembrane transport# (0.0); GO_CC:GO:0016021, integral to membrane# (0.0) | 8 | 71.9 | 73900392 | 73906519 |
| 551 | Putative uncharacterized protein n = 1 Tax = Zea mays RepID = C4I377_MAIZE (4e−09) | 8 | 71.9 | 74125695 | 74125928 |
| 552 | Potassium transporter 10 n = 2 Tax = Andropogoneae RepID = B6SS13_MAIZE (3e−79); K_trans: K+ potassium transporter (2e−09); GO_MF:GO:0015079, potassium ion transmembrane transporter activity# (3e−79); GO_BP:GO:0015079, potassium ion transmembrane transporter activity# (3e−79); GO_CC:GO:0016020, membrane# (3e−79) | 8 | 71.9 | 74129720 | 74130514 |
| 553 | 10A19I.4 n = 3 Tax = Oryza sativa Japonica Group RepID = Q9XHW2_ORYSJ (1e−107); HhH-GPD: HhH-GPD superfamily base excision DNA repair protein (3.9e−22); GO_MF:GO:0003824, catalytic activity# (1e−136); GO_BP:GO:0006284, base-excision repair# (1e−136); GO_CC:GO:0005634, nucleus# (2e−81) | 8 | 71.9 | 74131792 | 74133362 |
| 554 | Pentatricopeptide repeat-containing protein, putative n = 1 Tax = Ricinus communis RepID = B9S8W1_RICCO (1e−117); PPR: PPR repeat (0.15); TPR_4: Tetratricopeptide repeat (4.2); PPR: PPR repeat (7.8e−05); TPR_4: Tetratricopeptide repeat (0.2); TPR_4: Tetratricopeptide repeat (14); PPR: PPR repeat (0.018); TPR_4: Tetratricopeptide repeat (18); PPR: PPR repeat (4.1e−07); PPR: PPR repeat (3.6e−11); PPR: PPR repeat (3.7); PPR: PPR repeat (2.4); TPR_4: Tetratricopeptide repeat (25); GO_MF:GO:0005488, binding# (0.0) | 8 | 71.9 | 74249467 | 74251973 |
| 555 | Ulp1 protease family, C-terminal catalytic domain containing protein n = 2 Tax = Oryza sativa Japonica Group RepID = Q109R5_ORYSJ (2e−19); GO_MF:GO:0008234, cysteine-type peptidase activity# (9e−67); GO_BP:GO:0006508, proteolysis# (9e−67) | 8 | 71.9 | 74301564 | 74303726 |
| 556 | Putative uncharacterized protein n = 1 Tax = Zea mays RepID = C0PMZ8_MAIZE (2e−34); GO_MF:GO:0008234, cysteine-type peptidase activity# (2e−34); GO_BP:GO:0006508, proteolysis# (2e−34) | 8 | 71.9 | 74304167 | 74304498 |
| 557 | RuBisCo subunit binding-protein beta subunit (Fragment) n = 1 Tax = Zea mays RepID = Q6B7Q9_MAIZE (5e−62); GO_MF:GO:0005524, ATP binding# (5e−60); GO_BP:GO:0044267, cellular protein metabolic process# (5e−60); GO_CC:GO:0009536, plastid# (5e−60) | 8 | 71.9 | 74307088 | 74308237 |
| 558 | DNA helicase homolog, putative n = 1 Tax = Musa acuminata RepID = Q1EPC6_MUSAC (2e−93); DUF889: Eukaryotic protein of unknown function (DUF889) (6.5e−15); GO_MF:GO:0004386, helicase activity# (2e−93) | 8 | 71.9 | 74311462 | 74312484 |
| 559 | DNA helicase homolog, putative n = 1 Tax = Musa acuminata RepID = Q1EPC6_MUSAC (4e−10); GO_MF:GO:0004386, helicase activity# (4e−10) | 8 | 71.9 | 74315968 | 74320576 |
| 560 | UPF0737 protein 1 n = 1 Tax = Zea mays RepID = U7J7I1_MAIZE (1e−36); GO_CC:GO:0005634, nucleus# (1e−36) | 8 | 71.9 | 74320992 | 74321396 |
| 561 | Late-embryogenesis-abundant protein n = 4 Tax = Andropogoneae RepID = C7E3V1_SACOF (2e−85); LEA_2: Late embryogenesis abundant protein (6.6e−90); GO_BP:GO:0009269, response to desiccation# (1e−73); GO_CC:GO:0005886, plasma membrane# (5e−49) | 8 | 71.9 | 74938506 | 74939595 |
| 562 | Putative uncharacterized protein n = 1 Tax = Zea mays RepID = B6U8E7_MAIZE (8e−50) | 8 | 71.9 | 74989358 | 74990328 |
| 563 | BRASSINOSTEROID INSENSITIVE 1-associated receptor kinase 1, putative n = 1 Tax = Ricinus communis RepID = B9T3S1_RICCO (1e−26); GO_MF:GO:0005524, ATP binding# (5e−32); GO_BP:GO:0006468, protein amino acid phosphorylation# (5e−32); GO_CC:GO:0016021, integral to membrane# (1e−26) | 8 | 71.9 | 75004267 | 75006457 |
| 564 | ATP binding protein, putative n = 1 Tax = Ricinus communis RepID = B9RIQ4_RICCO (0.0); AAA_3: ATPase family associated with various (0.0048); AAA: ATPase family associated with various cellular activities (AAA) (2.5e−78); AAA_5: ATPase family associated with various (0.0016); GO_MF:GO:0017111, nucleoside-triphosphatase activity# (0.0); GO_BP:GO:0051301, cell division# (0.0) | 8 | 71.9 | 75007473 | 75012890 |
| 565 | Putative uncharacterized protein Sb01g044750 n = 1 Tax = Sorghum bicolor RepID = C5WUV8_SORBI (2e−32); GO_MF:GO:0046983, protein dimerization activity# (8e−10); GO_BP:GO:0006355, regulation of transcription, DNA-dependent# (8e−10); GO_CC:GO:0005634, nucleus# (8e−10) | 8 | 71.9 | 82154905 | 82155374 |
| 566 | CCT motif family protein n = 2 Tax = Zea mays RepID = B6U5M8_MAIZE (1e−114) | 8 | 71.95 | 79070986 | 79074301 |
| 567 | Hexose transporter (Fragment) n = 5 Tax = Zea mays RepID = Q9LLD9_MAIZE (3e−10); GO_MF:GO:0022891, substrate-specific transmembrane transporter activity# (3e−10); GO_BP:GO:0055085, transmembrane transport# (3e−10); GO_CC:GO:0016021, integral to membrane# (3e−10) | 8 | 72 | 73478314 | 73479582 |
| 568 | Latex-abundant protein n = 2 Tax = Andropogoneae RepID = B4FNB7_MAIZE (1e−17); GO_MF:GO:0004197, cysteine-type endopeptidase activity# (1e−27); GO_BP:GO:0006508, proteolysis# (1e−27) | 8 | 72 | 73520240 | 73520491 |
| 569 | Putative uncharacterized protein Sb09g029410 n = 1 Tax = Sorghum bicolor RepID = C5YW40_SORBI (7e−66); DUF617: Protein of unknown function, DUF617 (2.2e−15) | 8 | 72 | 73636991 | 73637806 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 570 | Putative uncharacterized protein n = 1 Tax = Zea mays RepID = C0PAB7_MAIZE (2e–19) | 8 | 72 | 75282999 | 75292186 |
| 571 | Tubulin gamma-1 chain n = 28 Tax = Embryophyta RepID = TBG1_ARATH (0.0); Tubulin: Tubulin/FtsZ family, GTPase domain (8e–94); Tubulin_C: Tubulin/FtsZ family, C-terminal domain (2.6e–59); GO_MF:GO:0005525, GTP 708cellular localization# (0.0); GO_CC:GO:0043234, protein complex# (0.0) | 8 | 72.05 | 79279716 | 79285737 |
| 572 | Inorganic phosphate transporter 1-7 n = 3 Tax = Andropogoneae RepID = B6TXX9_MAIZE (8e–61); GO_MF:GO:0005315, inorganic phosphate transmembrane transporter activity# (8e–61); GO_BP:GO:0006817, phosphate transport# (8e–61); GO_CC:GO:0016021, integral to membrane# (8e–61) | 8 | 72.05 | 80685551 | 80686059 |
| 573 | Zeon1 gag protein n = 3 Tax = Zea mays RepID = Q7XBD3_MAIZE (8e–19) | 8 | 72.1 | 82026765 | 82028638 |
| 574 | Putative uncharacterized protein Sb09g004280 n = 2 Tax = Andropogoneae RepID = C5Z0J2_SORBI (8e–44) | 8 | 72.1 | 83245239 | 83247221 |
| 575 | Putative uncharacterized protein n = 1 Tax = Andropogoneae RepID = B4F8F2_MAIZE (1e–77); GO_MF:GO:0003676, nucleic acid binding# (4e–35) | 8 | 72.3 | 76316289 | 76317707 |
| 576 | Probable protein phosphatase 2C 52 n = 2 Tax = Oryza sativa RepID = P2C52_ORYSJ (2e–91); PP2C: Protein phosphatase 2C (8.4e–46); GO_MF:GO:0046872, metal ion binding# (1e–96); GO_BP:GO:0006470, protein amino acid dephosphorylation# (1e–96); GO_CC:GO:0008287, protein serine/threonine phosphatase complex# (1e–96) | 8 | 72.3 | 76319202 | 76324609 |
| 577 | Probable protein phosphatase 2C 52 n = 2 Tax = Oryza sativa RepID = P2C52_ORYSJ (3e–20); GO_MF:GO:0046872, metal ion binding# (5e–75); GO_BP:GO:0006470, protein amino acid dephosphorylation# (5e–75); GO_CC:GO:0008287, protein serine/threonine phosphatase complex# (5e–75) | 8 | 72.3 | 76331266 | 76331972 |
| 578 | NADH-ubiquinone oxidoreductase 10.5 kDa subunit n = 4 Tax = Andropogoneae RepID = B6TDN0_MAIZE (6e–31); L51_S25_CI-B8: Mitochondrial ribosomal protein L51/S25/CI-B8 domain (1.6e–10); GO_MF:GO:0016491, oxidoreductase activity# (1e–17); GO_BP:GO:0055114, oxidation reduction# (1e–17); GO_CC:GO:0045271, IDA#respiratory chain complex I# (4e–23) | 8 | 72.35 | 80681445 | 80685001 |
| 579 | Putative uncharacterized protein n = 1 Tax = Zea mays RepID = B6TGL0_MAIZE (3e–75) | 8 | 72.4 | 81880838 | 81881973 |
| 580 | Putative seryl-tRNA synthetase n = 1 Tax = Oryza sativa Japonica Group RepID = Q5JKQ2_ORYSJ (1e–41); Seryl_tRNA_N: Seryl-tRNA synthetase N-terminal domain (0.0053); GO_MF:GO:0016874, ligase activity# (1e–49); GO_BP:GO:0006434, seryl-tRNA aminoacylation# (1e–49); GO_CC:GO:0005737, cytoplasm# (1e–49) | 8 | 72.55 | 74456288 | 74459537 |
| 581 | BC10 protein n = 2 Tax = Oryza sativa RepID = Q65XS5_ORYSJ (2e–60); DUF266: Arabidopsis protein of unknown function, DUF266 (4.2e–18); GO_MF:GO:0008375, acetylglucosaminyltransferase activity# (7e–68); GO_CC:GO:0016020, membrane# (7e–68) | 8 | 72.65 | 80791555 | 80798628 |
| 582 | Probable protein ABIL4 n = 3 Tax = Oryza sativa RepID = ABIL4_ORYSJ (2e–33); GO_CC:GO:0005856, cytoskeleton# (2e–80); GO_MF:GO:0005515, protein binding# (2e–37); GO_BP:GO:0045010, PMID: 11559594#actin nucleation# (2e–33); GO_CC:GO:0005856, cytoskeleton# (2e–80) | 8 | 72.7 | 75598612 | 75601628 |
| 583 | Putative calcium-dependent protein kinase n = 1 Tax = Oryza sativa Japonica Group RepID = Q5ZE73_ORYSJ (0.0); Kdo: Lipopolysaccharide kinase (Kdo) (0.082); Pkinase: Protein kinase domain (8.6e–103); Pkinase_Tyr: Protein tyrosine kinase (5.2e–11); efhand: EF hand (2.8e–07); efhand: EF hand (5.7e–06); efhand: EF hand (1.1e–06); efhand: EF hand (8.3e–09); GO_MF:GO:0016740, transferase activity# (0.0); GO_BP:GO:0016301, kinase activity# (0.0); GO_CC:GO:0005886, plasma membrane# (0.0) | 8 | 72.7 | 75601806 | 75605555 |
| 584 | OSJNBa0039G19.7 protein n = 1 Tax = Oryza sativa Japonica Group RepID = Q7XXD1_ORYSJ (1e–166); PPR: PPR repeat (6.7e–06); PPR: PPR repeat (2.6); PPR: PPR repeat (6.5); GO_MF:GO:0005488, binding# (8e–89); GO_BP:GO:0006306, DNA methylation# (8e–89); GO_CC:GO:0005739, mitochondrion# (6e–72) | 8 | 72.7 | 77588398 | 77590631 |
| 585 | Dihydrolipoyl dehydrogenase n = 4 Tax = Poaceae RepID = C5Z0L0_SORBI (0.0); H0933_like: H0933-like protein (0.056); DAO: FAD dependent oxidoreductase (0.0028); FAD_binding_2: FAD binding domain (0.0017); GIDA: Glucose inhibited division protein A (0.002); Pyr_redox_2: Pyridine nucleotide-disulphide oxidore (6.3e–48); Pyr_redox: Pyridine nucleotide-disulphide oxidore (4.2e–23); Pyr_redox_dim: Pyridine nucleotide-disulphide oxidore (1.8e–41); GO_MF:GO:0050660, FAD binding# (0.0); GO_BP:GO:0055114, oxidation reduction# (0.0); GO_CC:GO:0043234, protein complex# (0.0) | 8 | 72.7 | 79203447 | 79210580 |
| 586 | OSJNBa0070M12.5 protein n = 2 Tax = Oryza sativa RepID = Q7XTM0_ORYSJ (6e–25); GO_MF:GO:0046872, metal ion binding# (6e–25) | 8 | 72.7 | 80934925 | 80936751 |
| 587 | Disease resistance protein-like n = 2 Tax = Oryza sativa RepID = Q9AXB2_ORYSJ (1e–143); GO_MF:GO:0043565, sequence-specific DNA binding# (2e–59); GO_BP:GO:0045449, regulation of transcription# (2e–59); GO_CC:GO:0031224, intrinsic to membrane# (2e–59) | 8 | 72.75 | 75641962 | 75645944 |
| 588 | Serine-threonine protein kinase, putative n = 1 Tax = Ricinus communis RepID = B9RCP0_RICCO (1e–136); DUF1221: Protein of unknown function (DUF1221) (4.1e–108); Pkinase: Protein kinase domain (5.4e–22); Pkinase_Tyr: Protein tyrosine kinase (6.3e–17); GO_MF:GO:0005524, ATP binding# (0.0); GO_BP:GO:0006468, protein amino acid phosphorylation# (0.0); GO_CC:GO:0016020, membrane# (6e–26) | 8 | 72.8 | 75648367 | 75650800 |
| 589 | BC10 protein n = 2 Tax = Oryza sativa RepID = Q65XS5_ORYSJ (2e–89); DUF266: Arabidopsis protein of unknown function, DUF266 (3e–19); GO_MF:GO:0008375, acetylglucosaminyltransferase activity# (2e–89); GO_CC:GO:0016020, membrane# (2e–89) | 8 | 72.85 | 80822276 | 80825863 |
| 590 | Polygalacturonase n = 2 Tax = Oryza sativa RepID = B6TDS0_MAIZE (0.0); Glyco_hydro_28: Glycosyl hydrolases family 28 (1.7e–10); Pec_lyase_C: Pectate lyase (0.078); GO_MF:GO:0016798, hydrolase activity, acting on glycosyl bonds# (0.0); GO_BP:GO:0008152, metabolic process# (0.0); GO_CC:GO:0005773, IDA#vacuole# (1e–111) | 8 | 72.9 | 76128003 | 76130303 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 591 | Gag-pol n = 1 Tax = Zea mays RepID = Q8W1D1_MAIZE (3e−51); GO_MF:GO:0008270, zinc ion binding# (3e−51); GO_BP:GO:0015074, DNA integration# (3e−51); GO_CC:GO:0005634, nucleus# (3e−51) | 8 | 72.9 | 79636242 | 79636718 |
| 592 | Gag-pol n = 1 Tax = Zea mays RepID = Q8W1D1_MAIZE (6e−18); GO_MF:GO:0008270, zinc ion binding# (6e−18); GO_BP:GO:0015074, DNA integration# (6e−18); GO_CC:GO:0005634, nucleus# (6e−18) | 8 | 72.9 | 79636906 | 79637138 |
| 593 | Ribosomal protein L18 n = 16 Tax = Poaceae RepID = Q5WMY3_ORYSJ (3e−85); Ribosomal_L18e: Eukaryotic ribosomal protein L18 (2.3e−103); GO_MF:GO:0003735, structural constituent of ribosome# (3e−85); GO_BP:GO:0006412, translation# (3e−85); GO_CC:GO:0030529, ribonucleoprotein complex# (3e−85) | 8 | 72.9 | 83335693 | 83339014 |
| 594 | Probable cellulose synthase A catalytic subunit 1 [UDP-forming] n = 15 Tax = Poaceae RepID = CESA1_ORYSJ (0.0); PHD: PHD-finger (0.015); zf-C3HC4: Zinc finger, C3HC4 type (RING finger) (0.094); Cellulose_synt: Cellulose synthase (0); GO_MF:GO:0046872, metal ion binding# (0.0); GO_BP:GO:0030244, cellulose biosynthetic process# (0.0); GO_CC:GO:0016021, integral to membrane# (0.0) | 8 | 73 | 80220199 | 80226474 |
| 595 | Putative uncharacterized protein n = 2 Tax = Zea mays RepID = C0PM59_MAIZE (1e−127) | 8 | 73.05 | 79163688 | 79167287 |
| 596 | Mitochondrial carrier-like protein n = 1 Tax = Solanum tuberosum RepID = Q2PYY0_SOLTU (7e−19); Mito_carr: Mitochondrial carrier protein (6.3e−05); GO_MF:GO:0030528, transcription regulator activity# (3e−24); GO_BP:GO:0055085, transmembrane transport# (3e−24); GO_CC:GO:0016021, integral to membrane# (3e−24) | 8 | 73.1 | 75821743 | 75822198 |
| 597 | Extra-large G-protein-like n = 2 Tax = Oryza sativa RepID = Q6K2T0_ORYSJ (2e−61); GO_CC:GO:0005886, plasma membrane# (5e−56) | 8 | 73.2 | 76036061 | 76039111 |
| 598 | DNA binding protein n = 1 Tax = Zea mays RepID = B6TXV7_MAIZE (2e−89); HLH: Helix-loop-helix DNA-binding domain (4.6e−11); GO_MF:GO:0030528, transcription regulator activity# (2e−89); GO_BP:GO:0045449, regulation of transcription# (2e−89); GO_CC:GO:0005634, nucleus# (2e−89) | 8 | 73.2 | 79141710 | 79142884 |
| 599 | Ring finger protein, putative n = 1 Tax = Ricinus communis RepID = B9RS17_RICCO (3e−28); PHD: PHD-finger (0.05); zf-C3HC4: Zinc finger, C3HC4 type (RING finger) (2.2e−07); GO_MF:GO:0046872, metal ion binding# (7e−57); GO_BP:GO:0004842, NAS#ubiquitin-protein ligase activity# (2e−28); GO_CC:GO:0016021, integral to membrane# (9e−30) | 8 | 73.2 | 79149486 | 79150526 |
| 600 | Putative uncharacterized protein orfI05-e n = 1 Tax = Zea mays RepID = Q6R991_MAIZE (2e−18); GO_CC:GO:0005739, mitochondrion# (2e−18) | 8 | 73.2 | 80827284 | 80827898 |
| 601 | Putative uncharacterized protein n = 2 Tax = Oryza sativa RepID = Q851R1_ORYSJ (2e−19) | 8 | 73.2 | 81415796 | 81417430 |
| 602 | Catalytic/protein phosphatase type 2C n = 4 Tax = Andropogoneae RepID = B6T119_MAIZE (7e−10); GO_MF:GO:0003824, catalytic activity# (6e−10) | 8 | 73.25 | 79934413 | 79935030 |
| 603 | C4-dicarboxylate transporter-like protein n = 2 Tax = Oryza sativa RepID = Q8L4G8_ORYSJ (1e−131); C4dic_mal_tran: C4-dicarboxylate transporter/malic acid transport protein (8.9e−63); GO_MF:GO:0046872, metal ion binding# (4e−26); GO_BP:GO:0055085, transmembrane transport# (1e−177); GO_CC:GO:0016021, integral to membrane# (1e−177) | 8 | 73.3 | 75414377 | 75470871 |
| 604 | HAT family dimerisation domain containing protein n = 1 Tax = Oryza sativa Japonica Group RepID = Q53M48_ORYSJ (5e−71); GO_MF:GO:0046983, protein dimerization activity# (5e−86) | 8 | 73.3 | 75955890 | 75956803 |
| 605 | Probable indole-3-acetic acid-amido synthetase GH3.5 n = 3 Tax = Oryza sativa RepID = GH35_ORYSJ (0.0); GH3: GH3 auxin-responsive promoter (2e−284); tRNA_int_endo_N: tRNA intron endonuclease, N-terminal domain (0.096); GO_MF:GO:0016874, ligase activity# (0.0); GO_BP:GO:0009733, IEP#response to auxin stimulus# (0.0); GO_CC:GO:0005773, IDA#vacuole# (0.0) | 8 | 73.4 | 75985652 | 75990570 |
| 606 | DNA binding protein, putative n = 1 Tax = Ricinus communis RepID = B9RWI9_RICCO (9e−78); HLH: Helix-loop-helix DNA-binding domain (7.3e−15); GO_MF:GO:0030528, transcription regulator activity# (1e−112); GO_BP:GO:0045449, regulation of transcription# (1e−112); GO_CC:GO:0005634, nucleus# (1e−112) | 8 | 73.4 | 75990716 | 75992165 |
| 607 | Protein phosphatase 2C ABI2 n = 2 Tax = Zea mays RepID = B6TN97_MAIZE (0.0); PP2C: Protein phosphatase 2C (1.7e−76); GO_MF:GO:0046872, metal ion binding# (0.0); GO_BP:GO:0006470, protein amino acid dephosphorylation# (0.0); GO_CC:GO:0008287, protein serine/threonine phosphatase complex# (0.0) | 8 | 73.4 | 77983697 | 77986868 |
| 608 | Putative gag-pol polyprotein n = 1 Tax = Zea mays RepID = Q8SA91_MAIZE (4e−24); GO_MF:GO:0004190, penicillopepsin activity# (4e−24); GO_BP:GO:0015074, DNA integration# (4e−24); GO_CC:GO:0005634, nucleus# (4e−24) | 8 | 73.4 | 78039378 | 78039764 |
| 609 | Translation initiation factor n = 1 Tax = Pisum sativum RepID = Q8HGS8_PEA (0.0); GTP_EFTU: Elongation factor Tu GTP binding domain (1.5e−42); MMR_HSR1: GTPase of unknown function (7.4e−05); GTP_EFTU_D2: Elongation factor Tu domain 2 (8.5e−05); GO_MF:GO:0005525, GTP binding# (0.0); GO_BP:GO:0003743, protein-synthesizing GTPase activity, initiation# (0.0); GO_CC:GO:0005829, IDA#cytosol# (0.0) | 8 | 73.4 | 78073256 | 78079737 |
| 610 | ATP binding protein, putative n = 1 Tax = Ricinus communis RepID = B9SAN5_RICCO (2e−38); AAA: ATPase family associated with various cellular activities (AAA) (1.2e−05); GO_MF:GO:0017111, nucleoside-triphosphatase activity# (4e−39); GO_BP:GO:0009229, thiamin diphosphate biosynthetic process# (3e−37) | 8 | 73.4 | 78114912 | 78115537 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 611 | DNA binding protein, putative n = 1 Tax = *Ricinus communis* RepID = B9S516_RICCO (1e-107); GO_MF:GO:0003677, DNA binding# (0.0); GO_CC:GO:0005634, nucleus# (1e-107) | 8 | 73.4 | 78189173 | 78208974 |
| 612 | Pepsin A n = 2 Tax = *Zea mays* RepID = B6SWN4_MAIZE (0.0); Asp: Eukaryotic aspartyl protease (4.6e-63); GO_MF:GO:0004190, penicillopepsin activity# (0.0); GO_BP:GO:0006508, proteolysis# (0.0) | 8 | 73.4 | 79126285 | 79128196 |
| 613 | Boron transporter n = 5 Tax = *Oryza sativa* RepID = Q1ZYR7_ORYSJ (0.0); HCO3_cotransp: HCO3-transporter family (4.2e-16); BCCT: BCCT family transporter (0.092); GO_MF:GO:0015380, anion exchanger activity# (0.0); GO_CC:GO:0016021, integral to membrane# (0.0) | 8 | 73.4 | 79936497 | 79940559 |
| 614 | Putative uncharacterized protein Sb09g005260 n = 1 Tax = *Sorghum bicolor* RepID = C5Z151_SORBI (3e-37); Alba: Alba (1.1e-20); GO_MF:GO:0003676, nucleic acid binding# (6e-35) | 8 | 73.4 | 80385418 | 80386690 |
| 615 | Nucleotide sugar translocator BT2A n = 4 Tax = *Zea mays* RepID = B2LWG5_MAIZE (0.0); Mito_carr: Mitochondrial carrier protein (1.7e-27); Mito_carr: Mitochondrial carrier protein (3.3e-34); Mito_carr: Mitochondrial carrier protein (4.6e-33); GO_MF:GO:0005488, binding# (0.0); GO_BP:GO:0055085, transmembrane transport# (0.0); GO_CC:GO:0016021, integral to membrane# (0.0) | 8 | 73.4 | 80386832 | 80390311 |
| 616 | ANAC075 n = 3 Tax = Andropogoneae RepID = B6UC12_MAIZE (2e-26); NAM: No apical meristem (NAM) protein (1.2e-06); GO_MF:GO:0003677, DNA binding# (1e-51); GO_BP:GO:0045449, regulation of transcription# (1e-51); GO_CC:GO:0005634, nucleus# (1e-27) | 8 | 73.4 | 80621133 | 80624343 |
| 617 | Chaperone clpb, putative n = 1 Tax = *Ricinus communis* RepID = B9SJA7_RICCO (6e-18); GO_MF:GO:0017111, nucleoside-triphosphatase activity# (2e-19); GO_BP:GO:0019538, protein metabolic process# (2e-19); GO_CC:GO:0009570, IDA#chloroplast stroma# (6e-18) | 8 | 73.4 | 80627876 | 80629816 |
| 618 | Putative uncharacterized protein Sb03g023091 (Fragment) n = 1 Tax = *Sorghum bicolor* RepID = C5XM85_SORBI (1e-23) | 8 | 73.4 | 80662391 | 80663581 |
| 619 | AP2 domain containing protein n = 1 Tax = *Zea mays* RepID = B6SQ62_MAIZE (1e-115); AP2: AP2 domain (2.9e-18); GO_MF:GO:0003700, transcription factor activity# (1e-115); GO_BP:GO:0045449, regulation of transcription# (1e-115); GO_CC:GO:0005634, nucleus# (1e-115) | 8 | 73.4 | 80979506 | 80980774 |
| 620 | Endo-1,3;1,4-beta-D-glucanase n = 1 Tax = *Zea mays* RepID = B4FTK9_MAIZE (1e-134); DLH: Dienelactone hydrolase family (2.3e-13); GO_MF:GO:0016787, hydrolase activity# (4e-77); GO_BP:GO:0009651, IEP#response to salt stress# (2e-72); GO_CC:GO:0048046, IDA#apoplast# (2e-72) | 8 | 73.4 | 88889056 | 88893568 |
| 621 | DNA binding protein, putative n = 1 Tax = *Ricinus communis* RepID = B9S516_RICCO (1e-130); HSA: HSA (1.4e-13); GO_MF:GO:0003677, DNA binding# (0.0); GO_CC:GO:0005634, nucleus# (1e-130) | 8 | 73.45 | 78209319 | 78257571 |
| 622 | GPI-anchored protein n = 2 Tax = *Zea mays* RepID = B6TM89_MAIZE (2e-33); X8: X8 domain (1.7e-48); GO_MF:GO:0016787, hydrolase activity# (6e-33); GO_BP:GO:0008152, metabolic process# (3e-26) | 8 | 73.5 | 74621022 | 74622720 |
| 623 | UV-damaged DNA binding protein n = 3 Tax = *Oryza sativa* RepID = Q9FS08_ORYSJ (9e-53); GO_MF:GO:0003676, nucleic acid binding# (9e-53); GO_BP:GO:0016481, negative regulation of transcription# (3e-50); GO_CC:GO:0005634, nucleus# (9e-53) | 8 | 73.5 | 77723776 | 77724872 |
| 624 | Putative vacuolar ATP synthase subunit C (Fragment) n = 1 Tax = *Oryza sativa Japonica* Group RepID = Q84PC1_ORYSJ (0.0); V-ATPase_C: V-ATPase subunit C (1.3e-192); GO_MF:GO:0016820, hydrolase activity, acting on acid anhydrides, catalyzing transmembrane movement of substances# (0.0); GO_BP:GO:0016820, hydrolase activity, acting on acid anhydrides, catalyzing transmembrane movement of substances# (0.0); GO_CC:GO:0033180, proton-transporting V-type ATPase, V1 domain# (0.0) | 8 | 73.5 | 77746144 | 77752266 |
| 625 | CCAAT-box-binding transcription factor-like protein n = 3 Tax = *Oryza sativa* RepID = Q6YU01_ORYSJ (6e-33); GO_MF:GO:0005488, binding# (8e-22); GO_BP:GO:0010197, IMP#polar nucleus fusion# (3e-20); GO_CC:GO:0005730, IDA# nucleolus# (3e-20) | 8 | 73.5 | 79688507 | 79689087 |
| 626 | GDP dissociation inhibitor n = 7 Tax = Brassicaceae RepID = Q8LBY8_ARATH (4e-99); GDI: GDP dissociation inhibitor (8.8e-37); GO_MF:GO:0043087, regulation of GTPase activity# (1e-105); GO_BP:GO:0043087, regulation of GTPase activity# (1e-105); GO_CC:GO:0005737, cytoplasm# (1e-56) | 8 | 73.5 | 79689525 | 79691113 |
| 627 | Putative uncharacterized protein Sb09g004360 n = 4 Tax = Andropogoneae RepID = C5Z0K3_SORBI (1e-104) | 8 | 73.5 | 79694403 | 79697709 |
| 628 | Integral membrane protein like n = 1 Tax = *Zea mays* RepID = B6SMU5_MAIZE (1e-127); Nuc_sug_transp: Nucleotide-sugar transporter (0.033); DUF6: Integral membrane protein DUF6 (0.04); TPT: Triose-phosphate Transporter family (6.1e-49); GO_BP:GO:0009624, IEP#response to nematode# (1e-36); GO_CC:GO:0016021, integral to membrane# (1e-110) | 8 | 73.5 | 81159846 | 81164547 |
| 629 | Leucine Rich Repeat family protein n = 1 Tax = *Oryza sativa Japonica* Group RepID = Q2R0X3_ORYSJ (0.0); LRR_1: Leucine Rich Repeat (1.4); LRR_1: Leucine Rich Repeat (2.4); LRR_1: Leucine Rich Repeat (0.24); LRR_1: Leucine Rich Repeat (51); LRR_1: Leucine Rich Repeat (19); LRR_1: Leucine Rich Repeat (1.1); LRR_1: Leucine Rich Repeat (16); LRR_1: Leucine Rich Repeat (4.3); LRR_1: Leucine Rich Repeat (0.65); LRR_1: Leucine Rich Repeat (0.47); LRR_1: Leucine Rich Repeat (3.3); LRR_1: Leucine Rich Repeat (1.1); LRR_1: Leucine Rich Repeat (1.4); LRR_1: Leucine Rich Repeat (9.9); LRR_1: Leucine Rich Repeat (4.6); LRR_1: Leucine Rich Repeat (3.4); LRR_1: Leucine Rich Repeat (2.6); LRR_1: Leucine Rich Repeat (46); Pkinase: Protein kinase domain (3.9e-34); Pkinase_Tyr: Protein tyrosine kinase (1.3e-15); GO_MF:GO:0005524, ATP binding# (0.0); GO_BP:GO:0006468, protein amino acid phosphorylation# (0.0); GO_CC:GO:0016021, integral to membrane# (0.0) | 8 | 73.5 | 81244208 | 81248033 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 630 | HIRA-interacting protein, putative n = 1 Tax = Ricinus communis RepID = B9SG71_RICCO (3e−94); Nfu_N: Scaffold protein NfuNitU N terminal (2.3e−57); NifU: NifU-like domain (5.2e−29); GO_MF:GO:0051536, iron-sulfur cluster binding# (1e−104); GO_BP:GO:0016226, iron-sulfur cluster assembly# (1e−104); GO_CC:GO:0005739, mitochondrion# (1e−92) | 8 | 73.5 | 83396432 | 83400437 |
| 631 | Importin subunit alpha-1b n = 5 Tax = Poaceae RepID = IMA1B_ORYSJ (0.0); IBB: Importin beta binding domain (4.6e−26); Arm: Armadillo/beta-catenin-like repeat (3.1); HEAT: HEAT repeat (26); Arm: Armadillo/beta-catenin-like repeat (5.1e−11); HEAT: HEAT repeat (5.1); Arm: Armadillo/beta-catenin-like repeat (7.9e−14); HEAT: HEAT repeat (0.002); Arm: Armadillo/beta-catenin-like repeat (2.5e−08); Arm: Armadillo/beta-catenin-like repeat (2.1e−06); HEAT: HEAT repeat (1.6); Arm: Armadillo/beta-catenin-like repeat (2.1e−10); HEAT: HEAT repeat (1.5); Arm: Armadillo/beta-catenin-like repeat (8e−11); HEAT: HEAT repeat (9.3); Arm: Armadillo/beta-catenin-like repeat (1.6e−13); HEAT: HEAT repeat (30); Arm: Armadillo/beta-catenin-like repeat (4.5e−07); HEAT: HEAT repeat (37); GO_MF:GO:0008565, protein transporter activity# (0.0); GO_BP:GO:0015031, protein transport# (0.0); GO_CC:GO:0048471, ISS#perinuclear region of cytoplasm# (0.0) | 8 | 73.5 | 83435940 | 83441077 |
| 632 | Eukaryotic translation initiation factor 3 subunit (EIF-3)-like n = 3 Tax = Oryza sativa RepID = Q6ZGV8_ORYSJ (5e−81); GO_MF:GO:0005488, binding# (5e−81); GO_BP:GO:0003743, protein-synthesizing GTPase activity, initiation# (5e−81); GO_CC:GO:0005634, nucleus# (1e−36) | 8 | 73.5 | 83489976 | 83493185 |
| 633 | D8Erd354e protein, putative n = 2 Tax = Oryza sativa RepID = Q53NA2_ORYSJ (8e−41); DUF2261: Uncharacterized conserved protein (DU (4e−09); GO_MF:GO:0005488, binding# (3e−71); GO_BP:GO:0005975, carbohydrate metabolic process# (1e−28) | 8 | 73.5 | 83733935 | 83740029 |
| 634 | Cinnamic acid 4-hydroxylase n = 4 Tax = Andropogoneae RepID = Q94IP1_SORBI (0.0); p450: Cytochrome P450 (5.7e−134); GO_MF:GO:0046872, metal ion binding# (0.0); GO_BP:GO:0055114, oxidation reduction# (0.0); GO_CC:GO:0016020, membrane# (0.0) | 8 | 73.5 | 83792776 | 83796118 |
| 635 | GRP: Glycine rich protein family (0.038) | 8 | 73.5 | 83798547 | 83800359 |
| 636 | Ankyrin like protein n = 1 Tax = Zea mays RepID = B6U4R6_MAIZE (0.0); DUF248: Putative methyltransferase (3.6e−284); Methyltransf_11: Methyltransferase domain (3.2e−07); Methyltransf_12: Methyltransferase domain (0.04); GO_MF:GO:0046872, metal ion binding# (1e−128); GO_CC:GO:0005794, IDA#Golgi apparatus# (0.0) | 8 | 73.5 | 83916814 | 83921399 |
| 637 | F6D8.18 protein n = 11 Tax = rosids RepID = Q9SSR2_ARATH (7e−86); Peptidase_S24: Peptidase family S24 (1.5e−08); GO_MF:GO:0008233, peptidase activity# (1e−92); GO_BP:GO:0006508, proteolysis# (1e−92); GO_CC:GO:0016020, membrane# (1e−92) | 8 | 73.5 | 84066155 | 84070657 |
| 638 | Mom(Plant), putative n = 1 Tax = Ricinus communis RepID = B9STU6_RICCO (6e−17); GO_MF:GO:0046872, metal ion binding# (5e−21); GO_BP:GO:0006333, chromatin assembly or disassembly# (5e−21); GO_CC:GO:0005634, nucleus# (5e−21) | 8 | 73.5 | 84130984 | 84132037 |
| 639 | Elongation factor 1-alpha n = 112 Tax = Embryophyta RepID = EF1A_ARATH (0.0); GTP_EFTU_D3: Elongation factor Tu GTP binding domain (1.3e−111); MMR_HSR1: GTPase of unknown function (0.002); GTP_EFTU_D2: Elongation factor Tu domain 2 (8e−25); GTP_EFTU_D3: Elongation factor Tu C-terminal domain (8.5e−60); GO_MF:GO:0005525, GTP binding# (0.0); GO_BP:GO:0046686, IEP#response to cadmium ion# (0.0); GO_CC:GO:0016020, membrane# (0.0) | 8 | 73.5 | 84356485 | 84359671 |
| 640 | Putative uncharacterized protein Sb08g000470 n = 5 Tax = Andropogoneae RepID = C5YQ14_SORBI (5e−22) | 8 | 73.5 | 84404874 | 84411025 |
| 641 | Kelch motif family protein n = 1 Tax = Zea mays RepID = B6TNH4_MAIZE (7e−32); GO_MF:GO:0016874, ligase activity# (2e−13); GO_CC:GO:0005634, nucleus# (7e−17) | 8 | 73.5 | 84412206 | 84412417 |
| 642 | Putative polyprotein n = 1 Tax = Oryza sativa Japonica Group RepID = Q68IL2_ORYSJ (1e−50); GO_MF:GO:0003677, DNA binding# (1e−50); GO_BP:GO:0015074, DNA integration# (1e−50) | 8 | 73.5 | 84501053 | 84501763 |
| 643 | Retrotransposon protein, putative, unclassified n = 1 Tax = Oryza sativa Japonica Group RepID = Q2QMU2_ORYSJ (4e−59); Retrotrans_gag: Retrotransposon gag protein (0.014); GO_MF:GO:0003677, DNA binding# (2e−43); GO_BP:GO:0015074, DNA integration# (2e−43) | 8 | 73.5 | 84501783 | 84503163 |
| 644 | Retrotransposon protein, putative, unclassified n = 1 Tax = Oryza sativa Japonica Group RepID = Q2QUJ7_ORYSJ (2e−21); GO_MF:GO:0003676, nucleic acid binding# (2e−21); GO_BP:GO:0006278, RNA-dependent DNA replication# (2e−20) | 8 | 73.5 | 84594422 | 84594682 |
| 645 | Elongation factor 1-alpha n = 112 Tax = Embryophyta RepID = EF1A_ARATH (0.0); GTP_EFTU: Elongation factor Tu GTP binding domain (1.3e−111); MMR_HSR1: GTPase of unknown function (0.002); GTP_EFTU_D2: Elongation factor Tu domain 2 (1.8e−24); GTP_EFTU_D3: Elongation factor Tu C-terminal domain (8.5e−60); GO_MF:GO:0005525, GTP binding# (0.0); GO_BP:GO:0046686, IEP#response to cadmium ion# (0.0); GO_CC:GO:0016020, membrane# (0.0) | 8 | 73.5 | 84595221 | 84610050 |
| 646 | GDP-mannose transporter, putative n = 1 Tax = Ricinus communis RepID = B9SA23_RICCO (2e−31); GO_MF:GO:0031072, heat shock protein binding# (8e−39); GO_BP:GO:0015784, IGH#GDP-mannose transport# (2e−29); GO_CC:GO:0016021, integral to membrane# (1e−42) | 8 | 73.5 | 84635631 | 84637805 |
| 647 | Putative gypsy-type retrotransposon n = 1 Tax = Zea mays RepID = Q7XBE0_MAIZE (2e−33) | 8 | 73.5 | 84730931 | 84731620 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 648 | RNA binding protein n = 1 Tax = Zea mays RepID = B6UFA0_MAIZE (1e-175); RRM_1: RNA recognition motif (a.k.a. RRM, RB (6.8e-10); RRM_1: RNA recognition motif (a.k.a. RRM, RB (1.1e-18); RRM_1: RNA recognition motif (a.k.a. RRM, RB (1.3e-20); GO_MF:GO:0003723, RNA binding# (0.0); GO_BP:GO:0006397, mRNA processing# (2e-63); GO_CC:GO:0030529, ribonucleoprotein complex# (0.0) | 8 | 73.5 | 84784663 | 84789837 |
| 649 | FOG: TPR repeat (ISS) n = 1 Tax = Ostreococcus tauri RepID = Q01R5_OSTTA (7e-09); TPR_1: Tetratricopeptide repeat (0.034); GO_MF:GO:0031072, heat shock protein binding# (1e-178) | 8 | 73.5 | 84943635 | 84947592 |
| 650 | DNAJ heat shock N-terminal domain-containing protein n = 1 Tax = Polysphondylium pallidum PN500 RepID = D3AYV5_POLPA (8e-28); TPR_1: Tetratricopeptide repeat (0.64); TPR_2: Tetratricopeptide repeat (0.23); TPR_1: Tetratricopeptide repeat (0.00055); TPR_2: Tetratricopeptide repeat (0.18); TPR_1: Tetratricopeptide repeat (0.26); TPR_2: Tetratricopeptide repeat (0.74); DnaJ: DnaJ domain (1.5e-26); GO_MF:GO:0031072, heat shock protein binding# (1e-149); GO_BP:GO:0006457, protein folding# (5e-26); GO_CC:GO:0045335, IDA#phagocytic vesicle# (3e-24) | 8 | 73.5 | 84946695 | 84987693 |
| 651 | Putative uncharacterized protein Sb09g007350 n = 1 Tax = Sorghum bicolor RepID = C5YV43_SORBI (1e-40) | 8 | 73.5 | 84958603 | 84960030 |
| 652 | Lichenase-2 n = 2 Tax = Zea mays RepID = B6T391_MAIZE (1e-159); Glyco_hydro_17: Glycosyl hydrolases family 17 (1.4e-175); GO_MF:GO:0043169, cation binding# (1e-159); GO_BP:GO:0008152, metabolic process# (1e-159); GO_CC:GO:0005615, extracellular space# (1e-79) | 8 | 73.5 | 85097445 | 85103507 |
| 653 | Putative uncharacterized protein n = 1 Tax = Zea mays RepID = C0PE12_MAIZE (0.0); GO_MF:GO:0005488, binding# (0.0); GO_BP:GO:0008152, metabolic process# (0.0); GO_CC:GO:0016020, membrane# (2e-72) | 8 | 73.5 | 85120975 | 85124053 |
| 654 | Calcineurin B-like protein 2 n = 18 Tax = Magnoliophyta RepID = CNBL2_ORYSJ (1e-37); GO_MF:GO:0005509, calcium ion storage activity# (1e-37); GO_BP:GO:0019722, IMP#calcium-mediated signaling# (7e-33); GO_CC:GO:0032578, aleurone grain membrane# (1e-37) | 8 | 73.5 | 85274355 | 85274697 |
| 655 | Ribonuclease 3-like protein 2 n = 1 Tax = Oryza sativa Japonica Group RepID = RTL2_ORYSJ (1e-133); dsrm: Double-stranded RNA binding motif (2.2e-29); Ribonuclease_3: RNase3 domain (2.2e-29); dsrm: Double-stranded RNA binding motif (5.7e-09); GO_MF:GO:0046872, metal ion binding# (1e-133); GO_BP:GO:0006396, RNA processing# (1e-133); GO_CC:GO:0005622, intracellular# (1e-133) | 8 | 73.5 | 85306646 | 85317194 |
| 656 | Zgc:92172 n = 2 Tax = Danio rerio RepID = Q5U399_DANRE (4e-33); GO_MF:GO:0016818, hydrolase activity, acting on acid anhydrides, in phosphorus-containing anhydrides# (4e-45); GO_BP:GO:0006139, nucleobase, nucleoside, nucleotide and nucleic acid metabolic process# (4e-45); GO_CC:GO:0016021, integral to membrane# (0.0) | 8 | 73.5 | 85398753 | 85399187 |
| 657 | Zgc:92172 n = 2 Tax = Danio rerio RepID = Q5U399_DANRE (4e-45); GO_MF:GO:0016818, hydrolase activity, acting on acid anhydrides, in phosphorus-containing anhydrides# (3e-94); GO_BP:GO:0006139, nucleobase, nucleoside, nucleotide and nucleic acid metabolic process# (3e-94); GO_CC:GO:0005634, nucleus# (3e-94) | 8 | 73.5 | 85414178 | 85415861 |
| 658 | Putative uncharacterized protein Sb10g008850 n = 3 Tax = Andropogoneae RepID = C5Z7L1_SORBI (2e-10); GO_MF:GO:0047334, diphosphate-fructose-6-phosphate 1-phosphotransferase activity# (2e-10); GO_BP:GO:0047334, diphosphate-fructose-6-phosphate 1-phosphotransferase activity# (2e-10); GO_CC:GO:0005945, 6-phosphofructokinase complex# (2e-10) | 8 | 73.5 | 85423276 | 85423801 |
| 659 | CCT motif family protein n = 2 Tax = Zea mays RepID = B6U5M8_MAIZE (8e-11); GO_MF:GO:0051082, unfolded protein binding# (4e-09); GO_BP:GO:0006950, response to stress# (4e-09) | 8 | 73.5 | 85657079 | 85668765 |
| 660 | Cation proton exchanger (Fragment) n = 2 Tax = Populus trichocarpa RepID = B9HXD0_POPTR (0.0); Na_H_Exchanger: Sodium/hydrogen exchanger family (5.8e-83); GO_MF:GO:0015299, solute:hydrogen antiporter activity# (0.0); GO_BP:GO:0055085, transmembrane transport# (0.0); GO_CC:GO:0016021, integral to membrane# (0.0) | 8 | 73.5 | 85863835 | 85866511 |
| 661 | Putative uncharacterized protein n = 2 Tax = Zea mays RepID = B4FIH8_MAIZE (3e-62) | 8 | 73.5 | 86063082 | 86064559 |
| 662 | Putative uncharacterized protein Sb01g038930 n = 2 Tax = Andropogoneae RepID = C5WP90_SORBI (3e-23) | 8 | 73.5 | 86316923 | 86317888 |
| 663 | Chloroplast pentatricopeptide repeat protein 10 n = 2 Tax = Andropogoneae RepID = B8Y6I0_MAIZE (3e-17); PPR: PPR repeat (8.9e-06) | 8 | 73.5 | 86570622 | 86571155 |
| 664 | Pectinesterase n = 1 Tax = Sorghum bicolor RepID = C5YWT6_SORBI (0.0); Got1: Got1-like family (0.057); PMEI: Plant invertase/pectin methylesterase inhibitor (8.5e-22); Pectinesterase: Pectinesterase (2.1e-191); GO_MF:GO:0045330, aspartyl esterase activity# (0.0); GO_BP:GO:0042545, cell wall modification# (0.0); GO_CC:GO:0005618, IDA#cell wall# (0.0) | 8 | 73.5 | 86579079 | 86586531 |
| 665 | Protein binding protein n = 2 Tax = Zea mays RepID = B4FIH4_MAIZE (1e-35); GO_MF:GO:0008270, zinc ion binding# (1e-35) | 8 | 73.5 | 86661357 | 86661949 |
| 666 | Gag-pol n = 1 Tax = Zea mays RepID = Q8W1D1_MAIZE (2e-83); rve: Integrase core domain (3.6e-15); GO_MF:GO:0008270, zinc ion binding# (2e-83); GO_BP:GO:0015074, DNA integration# (2e-83); GO_CC:GO:0005634, nucleus# (2e-83) | 8 | 73.5 | 86670796 | 86671275 |
| 667 | Pentatricopeptide repeat-containing protein, putative n = 1 Tax = Ricinus communis RepID = B9RZB6_RICCO (1e-104); PfkB: pfkB family carbohydrate kinase (8.2e-12); GO_MF:GO:0004747, ribokinase activity# (1e-166); GO_BP:GO:0006014, D-ribose metabolic process# (1e-166); GO_CC:GO:0005622, intracellular# (6e-25) | 8 | 73.5 | 86861705 | 86871530 |

TABLE 13-continued

Annotated coding sequences within the FSR-3.01 and FSR-8.01 regions.

| Gene ID | Annotation | Chr | MON Map cM† | Physical Map Position bp†† Start | Physical Map Position bp†† End |
|---|---|---|---|---|---|
| 668 | Catalytic/protein phosphatase type 2C n = 2 Tax = Zea mays RepID = B6TWB0_MAIZE (4e-25); GO_MF:GO:0003824, catalytic activity# (4e-25); GO_BP:GO:0004721, phosphoprotein phosphatase activity# (2e-22); GO_CC:GO:0005886, plasma membrane# (7e-14) | 8 | 73.5 | 88963912 | 88965293 |
| 669 | DNA primase n = 1 Tax = Zea mays RepID = B6T4S3_MAIZE (0.0); DNA_primase_S: DNA primase small subunit (1.6e-52); GO_MF:GO:0016740, transferase activity# (0.0); GO_BP:GO:0006269, DNA replication, synthesis of RNA primer# (0.0); GO_CC:GO:0005658, alpha DNA polymerase:primase complex# (0.0) | 8 | 73.5 | | |
| 670 | WRKY67-superfamily of TFs having WRKY and zinc finger domains n = 2 Tax = Zea mays RepID = B6T4Y9_MAIZE (6e-83); FAR1: FAR1 family (0.018); WRKY: WRKY DNA-binding domain (1.7e-36); GO_MF:GO:0043565, sequence-specific DNA binding# (6e-83); GO_BP:GO:0045449, regulation of transcription# (6e-83); GO_CC:GO:0005634, nucleus# (6e-83) | 8 | 73.6 | 78314202 | 78314952 |
| 671 | Transposon protein, putative, CACTA, En/Spm sub-class n = 1 Tax = Oryza sativa Japonica Group RepID = Q53MW6_ORYSJ (2e-16); GO_MF:GO:0004803, transposase activity# (1e-22); GO_BP:GO:0006313, transposition, DNA-mediated# (1e-22) | 8 | 73.7 | 78314968 | 78316948 |
| 672 | Transposon protein, putative, CACTA, En/Spm sub-class n = 1 Tax = Oryza sativa Japonica Group RepID = Q53MW6_ORYSJ (3e-30); GO_MF:GO:0004803, transposase activity# (8e-24); GO_BP:GO:0006313, transposition, DNA-mediated# (8e-24) | 8 | 73.7 | | |
| 673 | F-box domain containing protein n = 2 Tax = Oryza sativa RepID = Q7XH06_ORYSJ (7e-43); F-box: F-box domain (1.8e-05); GO_MF:GO:0008270, zinc ion binding# (2e-50); GO_CC:GO:0005622, intracellular# (2e-50) | 8 | 73.7 | 86905453 | 86908820 |
| 674 | H0215A08.3 protein n = 1 Tax = Oryza sativa RepID = Q01N39_ORYSA (1e-115); RVT_1: Reverse transcriptase (RNA-dependent DN (7e-37); GO_MF:GO:0003964, RNA-directed DNA polymerase, group II intron encoded# (1e-115); GO_BP:GO:0006278, RNA-dependent DNA replication# (1e-115); GO_CC:GO:0005634, nucleus# (1e-115) | 8 | 73.8 | 78350122 | 78351597 |
| 675 | Non-cyanogenic beta-glucosidase n = 2 Tax = Zea mays RepID = B6SKG0_MAIZE (9e-27); GO_MF:GO:0043169, cation binding# (9e-27); GO_BP:GO:0005975, carbohydrate metabolic process# (9e-27); GO_CC:GO:0005773, IDA#vacuole# (2e-13) | 8 | 73.8 | 86911578 | 86914687 |
| 676 | Cysteine-type peptidase n = 6 Tax = Poaceae RepID = B6ST73_MAIZE (1e-16) | 8 | 73.8 | 86920313 | 86927376 |
| 677 | Putative uncharacterized protein n = 1 Tax = Zea mays RepID = B4FS85_MAIZE (3e-11) | 8 | 73.8 | 86941607 | 86942715 |
| 678 | Putative polyprotein n = 1 Tax = Oryza sativa Japonica Group RepID = Q6AIH7_ORYSJ (1e-51); GO_MF:GO:0004523, ribonuclease H activity# (1e-51); GO_BP:GO:0045449, regulation of transcription# (1e-51) | 8 | 73.8 | 86981943 | 86982509 |
| 679 | Monoglyceride lipase n = 2 Tax = Andropogoneae RepID = B4FRE0_MAIZE (1e-146); Abhydrolase_1: alpha/beta hydrolase fold (4e-05); GO_MF:GO:0047372, acylglycerol lipase activity# (1e-131); GO_CC:GO:0005886, plasma membrane# (1e-132) | 8 | 73.8 | 87027773 | 87035014 |
| 680 | UDP-D-glucuronate decarboxylase (Fragment) n = 1 Tax = Hordeum vulgare RepID = Q6B6L9_HORVU (1e-180); Rm1D_sub_bind: Rm1D substrate binding domain (7.8e-05); Epimerase: NAD dependent epimerase/dehydratase family (7.9e-56); Polysacc_synt_2: Polysaccharide biosynthesis protein (0.00074); 3Beta_HSD: 3-beta hydroxysteroid dehydrogenase/isomerase family (1.7e-05); NAD_binding_4: Male sterility protein (3.5e-07); GO_MF:GO:0050662, coenzyme binding# (0.0); GO_BP:GO:0044237, cellular metabolic process# (0.0); GO_CC:GO:0016020, membrane# (1e-153) | 8 | 73.8 | 87033480 | 87038152 |
| 681 | OSJNBa0093O08.9 protein n = 3 Tax = Oryza sativa RepID = Q7XTN8_ORYSJ (1e-30); GO_MF:GO:0017111, nucleoside-triphosphatase activity# (1e-30) | 8 | 73.8 | 87151830 | 87152641 |
| 682 | Nucleic acid binding protein n = 3 Tax = Andropogoneae RepID = B6U4M2_MAIZE (1e-35); GO_MF:GO:0003676, nucleic acid binding# (1e-35); GO_CC:GO:0005622, intracellular# (1e-35) | 8 | 73.8 | 87152728 | 87154011 |
| 683 | Catalytic/oxidoreductase, acting on NADH or NADPH n = 3 Tax = Zea mays RepID = B6T0D7_MAIZE (6e-20); Complex1_LYR: Complex 1 protein (LYR family) (0.00071) | 8 | 73.8 | 87238623 | 87243402 |
| 684 | Putative uncharacterized protein n = 1 Tax = Zea mays RepID = C0HEY7_MAIZE (4e-89) | 8 | 73.8 | 87334958 | 87340970 |
| 685 | Inner membrane lipoprotein n = 6 Tax = Escherichia RepID = B7MNA9_ECO45 (1e-103); GO_BP:GO:0009405, ice nucleation activity# (2e-56); GO_CC:GO:0016020, membrane# (1e-120) | 8 | 73.8 | 87361662 | 87362393 |
| 686 | Inner membrane lipoprotein n = 6 Tax = Escherichia RepID = B7LGB2_ECO55 (1e-125); DiS_P_DiS: Bacterial Peptidase A24 N-terminal domai (2.1e-48); GO_MF:GO:0004190, penicillopepsin activity# (9e-89); GO_BP:GO:0009405, ice nucleation activity# (2e-55); GO_CC:GO:0016020, membrane# (1e-126) | 8 | 73.8 | 87362416 | 87364280 |
| 687 | General secretion pathway protein C n = 18 Tax = Escherichia RepID = D3QRC8_ECOLX (1e-128); GspL: General secretion pathway protein L (GspL) (1e-47); FliL: Flagellar basal body-associated protein FliL (0.022); GspM: General secretion pathway, M protein (8.2e-71); GspT: General secretion pathway protein T (GspT), protein transporter activity# (1e-135); GO_BP:GO:0015628, protein secretion by the type II secretion system# (1e-135); GO_CC:GO:0042597, periplasmic space# (1e-135) | 8 | 73.8 | 87364807 | 87367103 |
| 688 | Nucleoside permease (Fragment) n = 1 Tax = Escherichia coli RepID = B8ZYJ8_ECOLX (1e-106); Nuc_H_symport: Nucleoside H+ symporter (4e-34); GO_MF:GO:0005337, nucleoside transmembrane transporter activity# (1e-107); GO_BP:GO:0015858, IMP#nucleoside transport# (1e-107); GO_CC:GO:0016021, integral to membrane# (1e-107) | 8 | 73.8 | 87368603 | 87369175 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 689 | Ornithine decarboxylase isozyme n = 5 Tax = *Klebsiella* RepID = C4WZ59_KLEPN (0.0); OKR_DC_1_N: Orn/Lys/Arg decarboxylase, N-terminal domain (6.5e–33); OKR_DC_1: Orn/Lys/Arg decarboxylase, major domain (1.4e–257); OKR_DC_1_C: Orn/Lys/Arg decarboxylase, C-terminal domain (0.0023); GO_MF:GO:0030170, pyridoxal phosphate binding# (0.0); GO_BP:GO:0006520, cellular amino acid metabolic process# (0.0); GO_CC:GO:0005737, cytoplasm# (0.0) | 8 | 73.8 | 87369320 | 87371362 |
| 690 | YqgA n = 31 Tax = *Salmonella enterica* RepID = B4T5M5_SALNS (5e–25); DUF554: Protein of unknown function (DUF554) (6.2e–05); GO_MF:GO:0005216, ion channel activity# (2e–12); GO_BP:GO:0005216, ion channel activity# (2e–12); GO_CC:GO:0016021, integral to membrane# (9e–32) | 8 | 73.8 | 87372130 | 87372343 |
| 691 | Chromodomain helicase DNA binding protein, putative n = 1 Tax = *Ricinus communis* RepID = B9SYQ4_RICCO (2e–19); Chromo: 'chromo' (CHRomatin Organisation MOd (1.8e–12); GO_MF:GO:0005524, ATP binding# (3e–27); GO_BP:GO:0006333, chromatin assembly or disassembly# (3e–27); GO_CC:GO:0005634, nucleus# (3e–27) | 8 | 73.8 | 87478622 | 87479964 |
| 692 | Putative uncharacterized protein Sb07g027880 n = 1 Tax = *Sorghum bicolor* RepID = C5YIT8_SORBI (3e–26) | 8 | 73.8 | 87482396 | 87483166 |
| 693 | Chaperone protein dnaJ, putative n = 1 Tax = *Ricinus communis* RepID = B9RT65_RICCO (1e–74); DnaJ: DnaJ domain (2e–30); DUF1977: Domain of unknown function (DUF1977) (4.7e–27); GO_MF:GO:0051082, unfolded protein binding# (1e–130); GO_BP:GO:0006457, protein folding# (1e–130); GO_CC:GO:0016021, integral to membrane# (1e–55) | 8 | 73.8 | 87494732 | 87498179 |
| 694 | MLO-like protein 4 n = 3 Tax = Andropogoneae RepID = B6TXU3_MAIZE (1e–145); Mlo: Mlo family (3.8e–45); Clathrin: Region in Clathrin and VPS (1.8e–15); GO_MF:GO:0005515, protein binding# (7e–97); GO_BP:GO:0008219, TAS#cell death# (1e–145); GO_CC:GO:0016021, integral to membrane# (1e–145) | 8 | 73.8 | 87517374 | 87524631 |
| 695 | Phytochrome A-associated F-box protein, putative n = 1 Tax = *Ricinus communis* RepID = B9SAQ8_RICCO (8e–71); GO_MF:GO:0003676, nucleic acid binding# (2e–69); GO_BP:GO:0048573, IMP#photoperiodism, flowering# (2e–60); GO_CC:GO:0005634, nucleus# (2e–60) | 8 | 73.8 | 87544180 | 87545930 |
| 696 | Hemolysin n = 1 Tax = *Zea mays* RepID = B6SV17_MAIZE (1e–107); DUF21: Domain of unknown function DUF21 (2.4e–42); CBS: CBS domain (5.6e–07); GO_MF:GO:0003677, DNA binding# (1e–148); GO_BP:GO:0015074, DNA integration# (1e–148); GO_CC:GO:0005739, mitochondrion# (1e–153) | 8 | 73.8 | 87676566 | 87726869 |
| 697 | HAT family dimerisation domain containing protein n = 1 Tax = *Phyllostachys edulis* RepID = D3IVP0_9POAL (0.0); GO_MF:GO:0005524, ATP binding# (0.0); GO_BP:GO:0007018, microtubule-based movement# (0.0); GO_CC:GO:0005622, intracellular# (7e–12) | 8 | 73.8 | 87692227 | 87692768 |
| 698 | Putative uncharacterized protein Sb0010s003460 n = 1 Tax = *Sorghum bicolor* RepID = C6IRI0_SORBI (1e–26); zf-CCHC: Zinc knuckle (0.0081); zf-CCHC: Zinc knuckle (0.00027); GO_MF:GO:0043565, sequence-specific DNA binding# (5e–11); GO_BP:GO:0045449, regulation of transcription# (5e–11); GO_CC:GO:0005634, nucleus# (5e–11) | 8 | 73.8 | 87707935 | 87722864 |
| 699 | Retrotransposon protein, putative, unclassified n = 1 Tax = *Oryza sativa Japonica* Group RepID = Q2QXX8_ORYSJ (2e–10); GO_MF:GO:0003677, DNA binding# (2e–10); GO_BP:GO:0015074, DNA integration# (2e–10) | 8 | 73.8 | 87722867 | 87723474 |
| 700 | Putative polyprotein n = 1 Tax = *Oryza sativa Japonica* Group RepID = Q688L2_ORYSJ (3e–30); rve: Integrase core domain (0.004); GO_MF:GO:0003677, DNA binding# (2e–30); GO_BP:GO:0015074, DNA integration# (2e–30) | 8 | 73.8 | 87723686 | 87724030 |
| 701 | Putative uncharacterized protein Sb09g019530 n = 1 Tax = *Sorghum bicolor* RepID = C5YXL1_SORBI (2e–17) | 8 | 73.8 | 87727511 | 87728085 |
| 702 | Retrotransposon protein n = 1 Tax = *Zea mays* RepID = B6U894_MAIZE (1e–100); DUF889: Eukaryotic protein of unknown function (DUF889) (8.1e–22); GO_MF:GO:0004386, helicase activity# (1e–57) | 8 | 73.8 | 87772742 | 87776398 |
| 703 | OSJNBa0095H06.12 protein n = 1 Tax = *Oryza sativa Japonica* Group RepID = Q7XS07_ORYSJ (1e–21); GO_MF:GO:0004386, helicase activity# (1e–19) | 8 | 73.8 | 87776524 | 87776994 |
| 704 | Putative retrotransposon protein n = 1 Tax = *Phyllostachys edulis* RepID = D3IVP0_9POAL (0.0); GO_MF:GO:0004386, helicase activity# (1e–148) | 8 | 73.8 | 87777078 | 87782262 |
| 705 | Kinesin-4 n = 1 Tax = *Zea mays* RepID = B6U113_MAIZE (0.0); Kinesin: Kinesin motor domain (3.3e–157); GO_MF:GO:0005524, ATP binding# (0.0); GO_BP:GO:0007018, microtubule-based movement# (0.0); GO_CC:GO:0005874, microtubule# (0.0) | 8 | 73.8 | 87802577 | 87807005 |
| 706 | Putative uncharacterized protein Sb03g045470 n = 1 Tax = *Sorghum bicolor* RepID = CXXHR9_SORBI (3e–22); GO_MF:GO:0016787, hydrolase activity# (1e–18); GO_CC:GO:0016020, membrane# (3e–13) | 8 | 73.85 | 78352728 | 78353780 |
| 707 | Putative uncharacterized protein n = 1 Tax = *Zea mays* RepID = B6T065_MAIZE (2e–16) | 8 | 73.85 | 87763115 | 87797399 |
| 708 | FtsH4 n = 3 Tax = Triticeae RepID = C6ERB5_AEGTA (0.0); FtsH_ext: FtsH Extracellular (0.015); AAA_2: ATPase family associated with various (0.021); AAA: ATPase family associated with various cellular activities (AAA) (6.7e–94); AAA_5: ATPase family associated with various (4.5e–05); Peptidase_M41: Peptidase family M41 (2e–111); GO_MF:GO:0004672, metal ion binding# (0.0); GO_BP:GO:0030163, protein catabolic process# (0.0); GO_CC:GO:0016020, membrane# (0.0) | 8 | 73.9 | 78358305 | 78365508 |
| 709 | Retrotransposon protein, putative, unclassified n = 1 Tax = *Oryza sativa Japonica* Group RepID = Q10QE5_ORYSJ (4e–13); GO_MF:GO:0003964, RNA-directed DNA polymerase, group II intron encoded# (4e–13); GO_BP:GO:0006278, RNA-dependent DNA replication# (4e–13) | 8 | 73.9 | 78363973 | 78364305 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 710 | Serine-threonine protein kinase, plant-type, putative n = 1 Tax = Ricinus communis RepID = B9RTG0_RICCO (4e-22); GO_MF:GO:0005524, ATP binding# (7e-62); GO_BP:GO:0016998, cell wall macromolecule catabolic process# (7e-63) | 8 | 73.9 | 78365952 | 78366617 |
| 711 | PR-1-like protein (Fragment) n = 1 Tax = Zea mays RepID = D0EJL7_MAIZE (1e-37); SCP: SCP-like extracellular protein (6.5e-29); GO_BP:GO:0009607, response to biotic stimulus# (2e-21); GO_CC:GO:0005576, extracellular region# (3e-49) | 8 | 73.9 | 79003686 | 79004902 |
| 712 | HYP1 n = 2 Tax = Andropogoneae RepID = B6SS81_MAIZE (0.0); DUF221: Domain of unknown function DUF221 (3.6e-138); GO_CC:GO:0016020, membrane# (0.0) | 8 | 73.9 | 79005811 | 79011465 |
| 713 | OSJNBa0033G05.13 protein n = 1 Tax = Oryza sativa Japonica Group RepID = Q7XTM9_ORYSJ (5e-44); rve: Integrase core domain (7.3e-08); GO_MF:GO:0046872, metal ion binding# (4e-44); GO_BP:GO:0015074, DNA integration# (4e-44); GO_CC:GO:0005622, intracellular# (2e-43) | 8 | 73.9 | 87867597 | 87868246 |
| 714 | Oxidoreductase, 2OG-Fe oxygenase family protein n = 1 Tax = Zea mays RepID = B6ST02_MAIZE (2e-58); GO_MF:GO:0016491, oxidoreductase activity# (3e-71); GO_BP:GO:0055114, oxidation reduction# (2e-58); GO_CC:GO:0005622, intracellular# (2e-17) | 8 | 73.9 | 88039846 | 88047578 |
| 715 | Putative uncharacterized protein n = 1 Tax = Zea mays RepID = B6U3C1_MAIZE (2e-42) | 8 | 73.9 | 88139482 | 88142331 |
| 716 | Putative uncharacterized protein n = 1 Tax = Zea mays RepID = B6U3C1_MAIZE (1e-26) | 8 | 73.9 | 88149082 | 88149658 |
| 717 | H0512B01.8 protein n = 1 Tax = Oryza sativa RepID = Q25AF6_ORYSA (2e-84); zf-CCHC: Zinc knuckle (0.0019); GO_MF:GO:0046872, metal ion binding# (2e-84); GO_BP:GO:0015074, DNA integration# (2e-84) | 8 | 73.9 | 88172438 | 88173775 |
| 718 | Retrotransposon protein, putative, Ty3-gypsy subclass n = 1 Tax = Oryza sativa Japonica Group RepID = Q109Z1_ORYSJ (1e-123); zf-CCHC: Zinc knuckle (8.1e-06); GO_MF:GO:0008270, zinc ion binding# (1e-123); GO_BP:GO:0015074, DNA integration# (1e-121); GO_CC:GO:0005634, nucleus# (1e-117) | 8 | 73.9 | 88184506 | 88186242 |
| 719 | Putative uncharacterized protein Sb09g019730 n = 1 Tax = Sorghum bicolor RepID = C5YXN0_SORBI (2e-55); GO_MF:GO:0005509, calcium ion storage activity# (2e-50); GO_BP:GO:0015979, photosynthesis# (2e-50); GO_CC:GO:0019898, ISS#extrinsic to membrane# (2e-50) | 8 | 73.9 | 88275115 | 88276667 |
| 720 | ATP synthase subunit alpha, mitochondrial n = 51 Tax = Eukaryota RepID = ATPAM_ARATH (2e-54); ATP-synt_ab: ATP synthase alpha/beta family, nucleotide-binding domain (3e-09); GO_MF:GO:0046961, proton-transporting ATPase activity, rotational mechanism# (2e-54); GO_BP:GO:0046961, proton-transporting ATPase activity, rotational mechanism# (2e-54); GO_CC:GO:0045261, proton-transporting ATP synthase complex, catalytic core F(1)# (2e-54) | 8 | 73.9 | 88341941 | 88342255 |
| 721 | PnFL-2 n = 3 Tax = Andropogoneae RepID = B6T7Q6_MAIZE (2e-29) | 8 | 73.9 | 88398162 | 88398597 |
| 722 | Beta-propeller domains of methanol dehydrogenase type n = 2 Tax = Andropogoneae RepID = B6U4G5_MAIZE (1e-129); DUF477: Protein of unknown function (DUF477) (1.2e-26); GO_CC:GO:0016021, integral to membrane# (6e-95) | 8 | 73.9 | 88438855 | 88440306 |
| 723 | Basic endochitinase A n = 1 Tax = Zea mays RepID = B6TR38_MAIZE (1e-155); Chitin_bind_1: Chitin recognition protein (2e-16); Glyco_hydro_19: Chitinase class I (2.5e-172); GO_MF:GO:0016798, hydrolase activity, acting on glycosyl bonds# (1e-155); GO_BP:GO:0016998, cell wall macromolecule catabolic process# (1e-155); GO_CC:GO:0005576, extracellular region# (1e-111) | 8 | 73.9 | 88812632 | 88814171 |
| 724 | Calmodulin binding protein n = 1 Tax = Zea mays RepID = B6SPC3_MAIZE (1e-139); GO_BP:GO:0010200, IEP#response to chitin# (1e-115) | 8 | 74 | 78407583 | 78408959 |
| 725 | Histone H2A n = 7 Tax = Spermatophyta RepID = A5AKG7_VITVI (3e-43); Histone: Core histone H2A/H2B/H3/H4 (3.2e-15); GO_MF:GO:0003677, DNA binding# (3e-43); GO_BP:GO:0006334, nucleosome assembly# (3e-43); GO_CC:GO:0005694, chromosome# (3e-43) | 8 | 74 | 78891417 | 78892066 |
| 726 | Nodulin-like protein n = 2 Tax = Oryza sativa RepID = Q6ZG27_ORYSJ (3e-33); Nodulin-like: Nodulin-like (4.5e-83); GO_MF:GO:0031072, heat shock protein binding# (2e-26); GO_BP:GO:0055085, transmembrane transport# (7e-42); GO_CC:GO:0005634, nucleus# (5e-30) | 8 | 74 | 78939868 | 78940608 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 727 | Cobalt ion transporter, putative n = 1 Tax = *Ricinus communis* RepID = B9RST4_RICCO (1e−86); CbiQ: Cobalt transport protein (3e−09); GO_MF:GO:0015087, cobalt ion transmembrane transporter activity# (1e−118); GO_BP:GO:0015087, cobalt ion transmembrane transporter activity# (1e−118); GO_CC:GO:0016021, integral to membrane# (2e−77) | 8 | 74 | 88546267 | 88567647 |
| 728 | Heat shock protein 90 n = 6 Tax = *Oryza sativa* RepID = Q5Z9N8_ORYSJ (2e−70); GO_MF:GO:0051082, unfolded protein binding# (2e−70); GO_BP:GO:0006950, response to stress## (2e−70); GO_CC:GO:0005737, cytoplasm# (2e−70) | 8 | 74 | 88673927 | 88675485 |
| 729 | Plasma membrane associated protein n = 2 Tax = Andropogoneae RepID = B6UGF3_MAIZE (1e−83); AWPM-19: AWPM-19-like family (4e−86); GO_CC:GO:0016021, integral to membrane# (1e−12) | 8 | 74 | 88678931 | 88680028 |
| 730 | Serine/threonine-protein kinase, putative n = 1 Tax = *Ricinus communis* RepID = B9RQT0_RICCO (0.0); Pkinase: Protein kinase domain (8.7e−80); Pkinase_Tyr: Protein tyrosine kinase (1.5e−12); Pkinase_C: Protein kinase C terminal domain (7.4e−09); GO_MF:GO:0016740, transferase activity# (0.0); GO_BP:GO:0016301, kinase activity# (0.0); GO_CC:GO:0005886, plasma membrane# (1e−179) | 8 | 74 | 89080382 | 89093271 |
| 731 | Putative uncharacterized protein n = 1 Tax = *Zea mays* RepID = B6TUN3_MAIZE (5e−29) | 8 | 74 | 89154975 | 89158300 |
| 732 | BZIP transcription factor bZIP109 n = 3 Tax = *Glycine max* RepID = Q0GPG4_SOYBN (6e−33); DUF1664: Protein of unknown function (DUF1664) (2.4e−11) | 8 | 74 | 89257256 | 89260917 |
| 733 | Late embryogenesis abundant protein n = 3 Tax = *Zea mays* RepID = B6TTU1_MAIZE (1e−47) | 8 | 74 | 89528694 | 89529652 |
| 734 | Putative uncharacterized protein n = 1 Tax = *Zea mays* RepID = C4JA86_MAIZE (9e−23) | 8 | 74 | 89583965 | 89643253 |
| 735 | OSJNBa0022H21.18 protein n = 2 Tax = *Oryza sativa Japonica* Group RepID = Q7XKT9_ORYSJ (3e−36); Thiolase_N: Thiolase, N-terminal domain (0.042); GO_MF:GO:0048038, quinone binding# (3e−40); GO_BP:GO:0055114, oxidation reduction# (3e−40); GO_CC:GO:0005777, IDA#peroxisome# (2e−24) | 8 | 74 | 89643922 | 89646684 |
| 736 | Putative polyprotein n = 1 Tax = *Oryza sativa Japonica* Group RepID = Q6L559_ORYSJ (4e−79); rve: Integrase core domain (2.2e−07); GO_MF:GO:0008270, zinc ion binding# (4e−79); GO_BP:GO:0015074, DNA integration# (4e−79); GO_CC:GO:0005840, ribosome# (4e−78) | 8 | 74 | 89691497 | 89692201 |
| 737 | Gag and Pol n = 1 Tax = *Zea mays* RepID = Q8LSK0_MAIZE (2e−31); GO_MF:GO:0008270, zinc ion binding# (2e−31); GO_BP:GO:0015074, DNA integration# (2e−31); GO_CC:GO:0005840, ribosome# (2e−28) | 8 | 74 | 89692947 | 89693332 |
| 738 | Putative uncharacterized protein n = 3 Tax = *Zea mays* RepID = B6SLL9_MAIZE (6e−31) | 8 | 74 | 89825230 | 89825970 |
| 739 | Retrotransposon protein, putative, unclassified n = 2 Tax = *Oryza sativa* RepID = Q10KN1_ORYSJ (1e−15); GO_MF:GO:0003964, RNA-directed DNA polymerase, group II intron encoded# (1e−15); GO_BP:GO:0006278, RNA-dependent DNA replication# (1e−15); GO_CC:GO:0005634, nucleus# (3e−14) | 8 | 74 | 89924962 | 89925156 |
| 740 | Putative polyprotein (Fragment) n = 1 Tax = *Zea mays* RepID = Q8SA93_MAIZE (1e−34); GO_MF:GO:0004190, penicillopepsin activity## (1e−34); GO_BP:GO:0006508, proteolysis# (1e−34); GO_CC:GO:0005634, nucleus# (1e−34) | 8 | 74 | 89925251 | 89925643 |
| 741 | Heat shock 70 kDa protein n = 1 Tax = *Zea mays* RepID = B6SV64_MAIZE (0.0); HSP70: Hsp70 protein (1.9e−120); GO_MF:GO:0005524, ATP binding# (0.0); GO_BP:GO:0006950, response to stress# (0.0); GO_CC:GO:0005737, cytoplasm# (1e−127) | 8 | 74 | 89964273 | 89967960 |
| 742 | Casein kinase I-like n = 4 Tax = Poaceae RepID = Q8LR51_ORYSJ (0.0); Pkinase: Protein kinase domain (1.1e−42); Pkinase_Tyr: Protein tyrosine kinase (1.5e−05); GO_MF:GO:0005524, ATP binding# (0.0); GO_BP:GO:0006468, protein amino acid phosphorylation# (0.0); GO_CC:GO:0005886, plasma membrane# (0.0) | 8 | 74.05 | 78409210 | 78414387 |
| 743 | NF protein (Fragment) n = 1 Tax = *Oryza sativa Japonica* Group RepID = Q70KT0_ORYSJ (2e−30); GO_MF:GO:0016301, kinase activity# (7e−14); GO_BP:GO:0016301, kinase activity## (7e−14); GO_CC:GO:0031588, AMP-activated protein kinase complex# (1e−09) | 8 | 74.1 | 78827462 | 78829082 |
| 744 | Fb2 n = 3 Tax = *Zea mays* RepID = B6SGL8_MAIZE (2e−68); Di19: Drought induced 19 protein (Di19) (1.9e−08); GO_MF:GO:0008270, zinc ion binding# (7e−13); GO_CC:GO:0005622, intracellular# (1e−12) | 8 | 74.1 | 78831850 | 78832799 |
| 745 | Os05g0594500 protein n = 3 Tax = *Oryza sativa* RepID = Q5TKG2_ORYSJ (0.0) | 8 | 74.1 | 78853024 | 78857808 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 746 | Heat shock 70 kDa protein 4 n = 4 Tax = Andropogoneae RepID = B6U237_MAIZE (0.0); HSP70: Hsp70 protein (4.8e-162); GO_MF:GO:0005524, ATP binding# (0.0); GO_BP:GO:0006950, response to stress# (0.0); GO_CC:GO:0005737, cytoplasm# (1e-166) | 8 | 74.1 | 90052425 | 90060314 |
| 747 | Nucleic acid binding f n = 1 Tax = Zea mays RepID = B6T2M0_MAIZE (3e-79); GO_MF:GO:0046872, metal ion binding# (3e-79) | 8 | 74.1 | 90062911 | 90064339 |
| 748 | Early fruit mRNA n = 3 Tax = Andropogoneae RepID = B6TAC1_MAIZE (2e-20) | 8 | 74.1 | 90360744 | 90364222 |
| 749 | Dehydration-responsive protein-like n = 2 Tax = Oryza sativa RepID = Q653G1_ORYSJ (4e-69); DUF248: Putative methyltransferase (7.8e-21); tRNA_m1G_MT: tRNA (Guanine-1)-methyltransferase (0.00014); GO_MF:GO:0016740, transferase activity# (5e-55); GO_BP:GO:0016301, kinase activity# (2e-38); GO_CC:GO:0009505, IDA#apoplast# (3e-37) | 8 | 74.15 | 78437055 | 78440172 |
| 750 | 163k15.5 n = 1 Tax = Zea mays RepID = Q8S457_MAIZE (2e-30); MULE: MULE transposase domain (4.2e-17); GO_MF:GO:0008270, zinc ion binding# (2e-30); GO_BP:GO:0004867, chymotrypsin inhibitor activity# (6e-25) | 8 | 74.15 | 90126416 | 90136807 |
| 751 | Putative uncharacterized protein n = 1 Tax = Zea mays RepID = C0PHV5_MAIZE (4e-12) | 8 | 74.2 | 78462451 | 78462840 |
| 752 | OSJNBa0055H05.12 protein n = 2 Tax = Oryza sativa Japonica Group RepID = Q7XRD0_ORYSJ (1e-104); GO_MF:GO:0046872, metal ion binding# (1e-114) | 8 | 74.2 | 78784972 | 78787336 |
| 753 | NEDD8-activating enzyme E1 catalytic subunit n = 3 Tax = Andropogoneae RepID = B6TJH0_MAIZE (5e-32); RRM_1: RNA recognition motif (a.k.a. RRM, RB (0.037); GO_MF:GO:0016881, acid-amino acid ligase activity# (5e-32); GO_BP:GO:0045116, protein neddylation# (5e-32); GO_CC:GO:0005634, nucleus# (1e-18) | 8 | 74.2 | 90141945 | 90143462 |
| 754 | Receptor-like protein kinase n = 2 Tax = Zea mays RepID = B6TPE6_MAIZE (1e-179); LRR_1: Leucine Rich Repeat (4); LRR_1: Leucine Rich Repeat (29); LRR_1: Leucine Rich Repeat (3e+02); LRR_1: Leucine Rich Repeat (9); LRR_1: Leucine Rich Repeat (4.5); LRR_1: Leucine Rich Repeat (1.6); LRR_1: Leucine Rich Repeat (21); GO_MF:GO:0016301, kinase activity# (1e-179); GO_BP:GO:0016301, kinase activity# (1e-179); GO_CC:GO:0009505, IDA#expansin# (1e-111) | 8 | 74.2 | 90187637 | 90189879 |
| 755 | Annexin p35 (Fragment) n = 1 Tax = Oryza sativa Indica Group RepID = C5IDU2_ORYSI (6e-10); GO_MF:GO:0005544, calcium-dependent phospholipid binding# (2e-13); GO_BP:GO:0046686, IEP#response to cadmium ion# (9e-09); GO_CC:GO:0048046, IDA#apoplast# (9e-09) | 8 | 74.2 | 90190973 | 90191783 |
| 756 | Transcription factor, putative n = 1 Tax = Ricinus communis RepID = B9SB74_RICCO (4e-32); GO_BP:GO:0051301, cell division# (7e-19); GO_CC:GO:0005634, nucleus# (7e-19) | 8 | 74.2 | 90262045 | 90264571 |
| 757 | Putative uncharacterized protein n = 1 Tax = Zea mays RepID = B6UGB2_MAIZE (7e-61) | 8 | 74.2 | 90425639 | 90426136 |
| 758 | HAT family dimerisation domain containing protein n = 1 Tax = Oryza sativa Japonica Group RepID = Q2QRD1_ORYSJ (1e-74); GO_MF:GO:0046983, protein dimerization activity# (1e-74) | 8 | 74.2 | 90465136 | 90466806 |
| 759 | Putative GDA2 protein n = 2 Tax = Oryza sativa RepID = Q5JK83_ORYSJ (2e-92); Dev_Cell_Death: Development and cell death domain (3.6e-84); GO_MF:GO:0016779, nucleotidyltransferase activity# (5e-34) | 8 | 74.3 | 78649300 | 78651403 |
| 760 | Calcium/proton exchanger CAX1-like protein n = 3 Tax = Zea mays RepID = Q9LKW7_MAIZE (0.0); Na_Ca_ex: Sodium/calcium exchanger protein (5.1e-25); Na_Ca_ex: Sodium/calcium exchanger protein (4.7e-31); GO_MF:GO:0008324, cation transmembrane transporter activity# (0.0); GO_BP:GO:0055085, transmembrane transport# (0.0); GO_CC:GO:0016021, integral to membrane# (0.0) | 8 | 74.3 | 78653714 | 78658162 |
| 761 | Putative uncharacterized protein n = 1 Tax = Zea mays RepID = C0P6T6_MAIZE (6e-38) | 8 | 74.3 | 90528889 | 90529392 |
| 762 | 3-N-debenzoyltaxol N-benzoyltransferase-like n = 2 Tax = Oryza sativa RepID = Q9LGF6_ORYSJ (1e-165); Transferase: Transferase family (1.3e-50); GO_MF:GO:0016747, transferase activity, transferring acyl groups other than amino-acyl groups# (0.0) | 8 | 74.3 | 90577557 | 90579826 |
| 763 | Putative uncharacterized protein Sb09g005455 n = 1 Tax = Sorghum bicolor RepID = C5Z172_SORBI (3e-10); DVL: DVL family (1.1e-08) | 8 | 74.4 | 90669153 | 90669662 |
| 764 | Leucine zipper factor-like n = 1 Tax = Oryza sativa Japonica Group RepID = Q5N7Y0_ORYSJ (4e-20); PWWP: PWWP domain (0.046); Sas10_Utp3: Sas10/Utp3 family (2.1e-14) | 8 | 74.4 | 90687922 | 90692251 |
| 765 | Ras-related protein RGP2 n = 7 Tax = Poaceae RepID = RGP2_ORYSJ (1e-112); Arf: ADP-ribosylation factor family (0.00043); MMR_HSR1: GTPase of unknown function | 8 | 74.4 | 90789253 | 90791725 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
|  | (0.0016); Miro: Miro-like protein (5.9e-24); Ras: Ras family (1.2e-96); GTP_EFTU: Elongation factor Tu GTP binding domain (0.069); GO_MF:GO:0005525, GTP binding# (1e-112); GO_BP:GO:0015031, protein transport# (1e-112); GO_CC:GO:0016020, membrane# (1e-112) |  |  |  |  |
| 766 | Protein kinase APK1B, chloroplast, putative n = 1 Tax = Ricinus communis RepID = B9SPN3_RICCO (9e-90); Pkinase: Protein kinase domain (1.5e-30); Pkinase_Tyr: Protein tyrosine kinase (3.4e-17); APH: Phosphotransferase enzyme family (0.0022); GO_MF:GO:0005524, ATP binding# (0.0); GO_BP:GO:0006468, protein amino acid phosphorylation# (0.0); GO_CC:GO:0005576, extracellular region# (1e-76) | 8 | 74.4 | 90833086 | 90835652 |
| 767 | UDP-sulfoquinovose synthase n = 1 Tax = Solanum lycopersicum RepID = C0LIR3_SOLLC (0.0); Epimerase: NAD dependent epimerase/dehydratase family (1.6e-39); GO_MF:GO:0050662, coenzyme binding# (0.0); GO_BP:GO:0044237, cellular metabolic process# (0.0); GO_CC:GO:0009536, plastid# (0.0) | 8 | 74.5 | 90964519 | 90967651 |
| 768 | Phosphatidylinositol transfer protein CSR1 n = 2 Tax = Zea mays RepID = B6TMQ2_MAIZE (5e-62); CRAL_TRIO_N: CRAL/TRIO, N-terminus (0.0023); GO_MF:GO:0005215, transporter activity# (1e-29); GO_BP:GO:0006810, transport# (1e-29); GO_CC:GO:0005622, intracellular# (1e-29) | 8 | 74.5 | 90968485 | 90972591 |
| 769 | Putative uncharacterized protein n = 1 Tax = Zea mays RepID = B6T777_MAIZE (3e-86) | 8 | 74.5 | 91022431 | 91023673 |
| 770 | Putative uncharacterized protein n = 1 Tax = Zea mays RepID = B6TWE0_MAIZE (8e-14) | 8 | 74.7 | 91235607 | 91235966 |
| 771 | Putative uncharacterized protein Sb09g019020 n = 1 Tax = Sorghum bicolor RepID = C5YXE2_SORBI (1e-106) | 8 | 74.7 | 91312779 | 91313513 |
| 772 | Putative uncharacterized protein Sb02g039805 (Fragment) n = 1 Tax = Sorghum bicolor RepID = C5X2J3_SORBI (6e-13) | 8 | 74.7 | 91361119 | 91361355 |
| 773 | Mitochondria fission 1 protein n = 1 Tax = Zea mays RepID = B6T224_MAIZE (2e-63); GO_MF:GO:0005488, binding# (2e-63); GO_BP:GO:0016301, kinase activity# (1e-41); GO_CC:GO:0009507, chloroplast# (5e-41) | 8 | 74.7 | 91385174 | 91386308 |
| 774 | Putative glycerol 3-phosphate permease n = 1 Tax = Zea mays RepID = Q7FS87_MAIZE (1e-139); GO_MF:GO:0003964, RNA-directed DNA polymerase, group II intron encoded# (1e-139); GO_BP:GO:0055085, transmembrane transport# (1e-139); GO_CC:GO:0005634, nucleus# (1e-51) | 8 | 74.7 | 91402660 | 91403709 |
| 775 | Annexin-like protein RJ4 n = 1 Tax = Zea mays RepID = B6SUM2_MAIZE (1e-111); Annexin: Annexin (7.4e-20); Annexin (3.3e-05); Annexin: Annexin (0.001); Annexin: Annexin (6.8e-21); GO_MF:GO:0005544, calcium-dependent phospholipid binding# (1e-118); GO_BP:GO:0009651, IEP#response to salt stress# (4e-58); GO_CC:GO:0005773, IDA#vacuole# (4e-58) | 8 | 74.7 | 91421508 | 91423145 |
| 776 | Putative uncharacterized protein n = 2 Tax = Zea mays RepID = B6TSZ8_MAIZE (2e-50) | 8 | 74.7 | 91443937 | 91447409 |
| 777 | Putative uncharacterized protein n = 2 Tax = Zea mays RepID = B6TSZ8_MAIZE (2e-25) | 8 | 74.7 | 91450931 | 91451101 |
| 778 | CM0216.540.nc protein (Fragment) n = 1 Tax = Lotus japonicus RepID = B0BL99_LOTJA (3e-72) | 8 | 74.7 | 91467894 | 91483313 |
| 779 | HAT family dimerisation domain containing protein n = 1 Tax = Oryza sativa Japonica Group RepID = Q2QP95_ORYSJ (8e-77); DUF659: Protein of unknown function (DUF 659) (4.7e-71); hATC: hAT family dimerisation domain (0.0008); GO_MF:GO:0046983, protein dimerization activity# (1e-102); GO_BP:GO:0006278, RNA-dependent DNA replication# (2e-79); GO_CC:GO:0005622, intracellular# (8e-87) | 8 | 74.7 | 91476796 | 91479291 |
| 780 | Glucosamine 6-phosphate N-acetyltransferase n = 2 Tax = Andropogoneae RepID = B6TIB6_MAIZE (1e-13); GO_MF:GO:0016740, transferase activity# (1e-13); GO_BP:GO:0008152, metabolic process# (1e-13); GO_CC:GO:0016020, membrane# (5e-10) | 8 | 74.8 | 91498648 | 91501917 |
| 781 | Polcalcin Jun o 2 n = 2 Tax = Zea mays RepID = B6SGX1_MAIZE (4e-75); SPARC_Ca_bdg: Secreted protein acidic and rich in cys (0.031); efhand: EF hand (5.6e-07); efhand: EF hand (5.9e-07); efhand: EF hand (3.9e-06); efhand: EF hand (1.2e-06); GO_MF:GO:0005509, calcium ion storage activity# (4e-75); GO_BP:GO:0055114, oxidation reduction# (4e-35); GO_CC:GO:0005737, cytoplasm# (6e-33) | 8 | 74.8 | 91616373 | 91617428 |
| 782 | Putative permease 1 n = 1 Tax = Oryza sativa Japonica Group RepID = Q6Z257_ORYSJ (0.0); Xan_ur_permease: Permease family (5.6e-55); GO_MF:GO:0005215, transporter activity# (0.0); GO_BP:GO:0055085, transmembrane transport# (0.0); GO_CC:GO:0016020, membrane# (0.0) | 8 | 74.8 | 91674953 | 91678496 |
| 783 | Protein aq_1857 n = 3 Tax = Andropogoneae RepID = B6T2K9_MAIZE (4e-80); Fe—S_biosyn: Iron-sulphur cluster biosynthesis (1.9e-21); GO_MF:GO:0051536, iron-sulfur cluster binding# (4e-80); GO_BP:GO:0016226, iron-sulfur cluster assembly# (4e-80); GO_CC:GO:0005739, mitochondrion# (3e-38) | 8 | 74.8 | 91681514 | 91689201 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 784 | Ubiquinone biosynthesis protein ubiB n = 3 Tax = Andropogoneae RepID = B6UDS6_MAIZE (0.0); ABC1: ABC1 family (1.2e-36); APH: Phosphotransferase enzyme family (0.0072); GO_MF:GO:0005524, ATP binding# (0.0); GO_BP:GO:0006468, protein amino acid phosphorylation# (0.0); GO_CC:GO:0010287, IDA#plastoglobule# (0.0) | 8 | 74.8 | 91775984 | 91779470 |
| 785 | Superoxide dismutase [Mn] 3.1, mitochondrial n = 9 Tax = Andropogoneae RepID = SODM1_MAIZE (2e-81); Sod_Fe_N: Iron/manganese superoxide dismutases, (2e-42); Sod_Fe_C: Iron/manganese superoxide dismutases, C-term (3.7e-13); GO_MF:GO:0046872, metal ion binding# (2e-81); GO_BP:GO:0055114, oxidation reduction# (2e-81); GO_CC:GO:0005759, IEP#mitochondrial matrix# (2e-81); | 8 | 74.8 | 91831542 | 91837848 |
| 786 | Superoxide dismutase [Mn] 3.1, mitochondrial n = 9 Tax = Andropogoneae RepID = SODM1_MAIZE (6e-26); Sod_Fe_C: Iron/manganese superoxide dismutases, C-term (6.3e-09); GO_MF:GO:0046872, metal ion binding# (6e-26); GO_BP:GO:0055114, oxidation reduction# (6e-26); GO_CC:GO:0005759, IEP#mitochondrial matrix# (6e-26) | 8 | 74.8 | 91843588 | 91844328 |
| 787 | Ovate protein n = 1 Tax = Solanum lycopersicum RepID = Q8GSM4_SOLLC (5e-14); DUF623: Protein of unknown function, DUF623 (2.6e-31); GO_MF:GO:0016564, transcription repressor activity# (1e-16); GO_CC:GO:0005856, cytoskeleton# (1e-16) | 8 | 74.8 | 91861669 | 91862649 |
| 788 | Coatomer subunit beta'-1 n = 4 Tax = BEP clade RepID = COB21_ORYSJ (1e-27); Coatomer_WDAD: Coatomer WD associated region (0.0034); GO_MF:GO:0005515, protein binding# (1e-27); GO_BP:GO:0016192, vesicle-mediated transport# (1e-27); GO_CC:GO:0031410, IDA#cytoplasmic vesicle# (1e-27) | 8 | 74.8 | 91863984 | 91867269 |
| 789 | Integral membrane protein n = 2 Tax = Andropogoneae RepID = B4F879_MAIZE (2e-50) | 8 | 74.8 | 91867446 | 91868065 |
| 790 | Putative uncharacterized protein n = 1 Tax = Zea mays RepID = B4FYW0_MAIZE (1e-36) | 8 | 74.8 | 92026555 | 92027132 |
| 791 | Basic helix-loop-helix protein-like n = 2 Tax = Oryza sativa RepID = Q5SMX5_ORYSJ (6e-21); HLH: Helix-loop-helix DNA-binding domain (5.5e-11); GO_MF:GO:0030528, transcription regulator activity# (6e-21); GO_BP:GO:0045449, regulation of transcription# (6e-21); GO_CC:GO:0005634, nucleus# (6e-21) | 8 | 74.8 | 92199625 | 92200983 |
| 792 | Thioredoxin-like 6 n = 3 Tax = Zea mays RepID = B6TGT1_MAIZE (4e-96); Thioredoxin: Thioredoxin (1.9e-09); GO_MF:GO:0016671, oxidoreductase activity, acting on sulfur group of donors, disulfide as acceptor# (2e-52); GO_BP:GO:0045454, cell redox homeostasis# (4e-96); GO_CC:GO:0031969, IDA#chloroplast membrane# (2e-52) | 8 | 74.8 | 92487005 | 92499851 |
| 793 | Putative uncharacterized protein n = 2 Tax = Zea mays RepID = B6TKW9_MAIZE (1e-105) | 8 | 74.8 | 92699771 | 92700945 |
| 794 | Putative uncharacterized protein Sb10g022510 n = 1 Tax = Sorghum bicolor RepID = C5Z520_SORBI (4e-10) | 8 | 74.8 | 92746543 | 92746869 |
| 795 | HAT family dimerisation domain containing protein n = 1 Tax = Oryza sativa Japonica Group RepID = Q2QP95_ORYSJ (9e-53); zf-C2HC_plant: Protein of unknown function, DUF1544 (1.8e-12); DUF659: Protein of unknown function (DUF 659) (6.9e-35); GO_MF:GO:0046983, protein dimerization activity# (2e-76); GO_BP:GO:0015074, DNA integration# (1e-60); GO_CC:GO:0005622, intracellular# (1e-63) | 8 | 74.8 | 92869580 | 92872255 |
| 796 | Putative uncharacterized protein Sb07g028390 n = 1 Tax = Sorghum bicolor RepID = C5YJ87_SORBI (1e-09) | 8 | 74.8 | 92884891 | 92885225 |
| 797 | Carboxy-terminal domain RNA polymerase II polypeptide A small phosphatase, putative n = 1 Tax = Ricinus communis RepID = B9S8F4_RICCO (6e-53); NIF: NLI interacting factor-like phosphatase (4.7e-52); GO_MF:GO:0016791, phosphatase activity# (2e-67); GO_BP:GO:0016791, phosphatase activity# (2e-67) | 8 | 74.8 | 93132760 | 93134234 |
| 798 | 60S ribosomal protein L17 n = 19 Tax = Poaceae RepID = RL17_MAIZE (3e-90); Ribosomal_L22: Ribosomal protein L22p/L17e (2.4e-76); GO_MF:GO:0003735, structural constituent of ribosome# (3e-90); GO_BP:GO:0006412, translation# (3e-90); GO_CC:GO:0030529, ribonucleoprotein complex# (3e-90) | 8 | 74.8 | 93176442 | 93179884 |
| 799 | Putative uncharacterized protein n = 1 Tax = Zea mays RepID = B6SQE3_MAIZE (3e-45) | 8 | 74.8 | 93196973 | 93197774 |
| 800 | Transposon protein, putative, CACTA, En/Spm sub-class n = 2 Tax = Oryza sativa RepID = Q7XGX1_ORYSJ (1e-17); GO_MF:GO:0004803, transposase activity# (1e-17); GO_BP:GO:0006313, transposition, DNA-mediated# (1e-17) | 8 | 74.8 | 93223318 | 93223659 |
| 801 | OSJNBa0089K21.9 protein n = 2 Tax = Oryza sativa RepID = Q7XQM7_ORYSJ (3e-52); Plant_tran: Plant transposon protein (0.017); GO_MF:GO:0004803, transposase activity# (7e-55); GO_BP:GO:0006313, transposition, DNA-mediated# (7e-55) | 8 | 74.8 | 93241056 | 93242205 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 802 | P0696G06.8 protein n = 1 Tax = Oryza sativa Japonica Group RepID = Q7F446_ORYSJ (4e-16); GO_MF:GO:0004803, transposase activity# (7e-20); GO_BP:GO:0006313, transposition, DNA-mediated# (7e-20) | 8 | 74.8 | 93242275 | 93242629 |
| 803 | UNE1-like protein n = 1 Tax = Gossypioides kirkii RepID = B2ZAS0_9ROSI (1e-47); DUF641: Plant protein of unknown function (DUF641) (3.8e-47); GO_BP:GO:0009567, IMP#double fertilization forming a zygote and endosperm# (9e-47); GO_CC:GO:0005886, plasma membrane# (3e-37) | 8 | 74.8 | 93251576 | 93253289 |
| 804 | Fyve finger-containing phosphoinositide kinase, fyv1, putative n = 1 Tax = Ricinus communis RepID = B9RR30_RICCO (5e-30); GO_MF:GO:0016307, phosphatidylinositol phosphate kinase activity# (9e-41); GO_BP:GO:0046488, phosphatidylinositol metabolic process# (9e-41); GO_CC:GO:0005739, mitochondrion# (1e-26) | 8 | 74.8 | 93468937 | 93469554 |
| 805 | 60S ribosomal protein L12 n = 1 Tax = Zea mays RepID = B6T1W9_MAIZE (5e-18); Ribosomal_L11_N: Ribosomal protein L11, N-terminal domain (7.3e-07); GO_MF:GO:0003735, structural constituent of ribosome# (5e-18); GO_BP:GO:0006412, translation# (5e-18); GO_CC:GO:0030529, ribonucleoprotein complex# (5e-18) | 8 | 74.8 | 93482587 | 93484032 |
| 806 | Serine/threonine-specific protein kinase-like protein n = 3 Tax = Glycine max RepID = C6ZRT4_SOYBN (1e-145); Pkinase: Protein kinase domain (5.5e-42); Pkinase_Tyr: Protein tyrosine kinase (6.4e-32); APH: Phosphotransferase enzyme family (0.023); GO_MF:GO:0016301, kinase activity# (1e-169); GO_BP:GO:0016301, kinase activity# (1e-169); GO_CC:GO:0005886, plasma membrane# (1e-140) | 8 | 74.8 | 93489504 | 93495397 |
| 807 | AT hook motif-containing protein, putative n = 2 Tax = Oryza sativa Japonica Group RepID = Q2R0Z1_ORYSJ (3e-78); DUF889: Eukaryotic protein of unknown function (DUF889) (9.6e-63); GO_MF:GO:0004386, helicase activity# (6e-78) | 8 | 74.8 | 93539713 | 93544827 |
| 808 | Mitochondrial 2-oxoglutarate/malate carrier protein n = 5 Tax = Andropogoneae RepID = B6T8M6_MAIZE (2e-32); GO_BP:GO:0055085, transmembrane transport# (2e-32); GO_CC:GO:0016021, integral to membrane# (2e-32); Mito_carr: Mitochondrial carrier protein (0.0017); GO_MF:GO:0005488, binding# (2e-32) | 8 | 74.8 | 93569802 | 93571933 |
| 809 | Mitochondrial 2-oxoglutarate/malate carrier protein n = 5 Tax = Andropogoneae RepID = B6T8M6_MAIZE (5e-34); Mito_carr: Mitochondrial carrier protein (4.6e-15); GO_MF:GO:0005488, binding# (5e-34); GO_BP:GO:0055085, transmembrane transport# (5e-34); GO_CC:GO:0016021, integral to membrane# (5e-34) | 8 | 74.8 | 93572131 | 93572687 |
| 810 | 3-5 exonuclease, putative n = 1 Tax = Ricinus communis RepID = B9RFH0_RICCO (7e-95); GO_MF:GO:0008408, 3'-5' exonuclease activity# (1e-165); GO_BP:GO:0006139, nucleobase, nucleoside, nucleotide and nucleic acid metabolic process# (1e-165); GO_CC:GO:0005622, intracellular# (1e-165) | 8 | 74.8 | 93674259 | 93677433 |
| 811 | Mitochondrial carrier protein, putative n = 1 Tax = Ricinus communis RepID = B9SAW7_RICCO (2e-98); Mito_carr: Mitochondrial carrier protein (2.4e-28); Mito_carr: Mitochondrial carrier protein (2.6e-32); GO_MF:GO:0005488, binding# (1e-122); GO_BP:GO:0055085, transmembrane transport# (1e-122); GO_CC:GO:0016021, integral to membrane# (1e-122) | 8 | 74.8 | 93795543 | 93801583 |
| 812 | Ubiquitin-protein ligase/zinc ion binding protein n = 1 Tax = Zea mays RepID = B6TFQ4_MAIZE (1e-23); GO_MF:GO:0016874, ligase activity# (1e-23); GO_BP:GO:0016567, IGI#protein ubiquitination# (1e-23); GO_CC:GO:0005634, nucleus# (1e-23) | 8 | 74.8 | 93883059 | 93884132 |
| 813 | CsPK3 n = 1 Tax = Cucumis sativus RepID = Q9XGL2_CUCSA (2e-27); Pkinase: Protein kinase domain (0.0073); GO_MF:GO:0005524, ATP binding# (1e-48); GO_BP:GO:0006468, protein amino acid phosphorylation# (1e-48); GO_CC:GO:0005886, plasma membrane# (6e-22) | 8 | 74.8 | 93918308 | 93919077 |
| 814 | Subtilisin-chymotrypsin inhibitor CI-1C n = 1 Tax = Zea mays RepID = B6SLR8_MAIZE (2e-33); potato_inhibit: Potato inhibitor I family (5e-29); GO_MF:GO:0004867, chymotrypsin inhibitor activity# (2e-33); GO_BP:GO:0009611, IEP#response to wounding# (2e-33); GO_CC:GO:0005576, extracellular region# (4e-09) | 8 | 74.8 | 93920061 | 93920505 |
| 815 | Putative polyprotein n = 1 Tax = Zea mays RepID = Q8SA93_MAIZE (5e-18); GO_CC:GO:0005634, nucleus# (5e-18); GO_BP:GO:0015074, DNA integration# (5e-18); GO_MF:GO:0003964, RNA-directed DNA polymerase, group II intron encoded# (5e-18) | 8 | 74.8 | 93932449 | 93932886 |
| 816 | HAT family dimerisation domain containing protein n = 1 Tax = Oryza sativa Japonica Group RepID = Q2QRD1_ORYSJ (2e-24); Herpes_UL3: Herpesvirus UL3 protein (0.065); zf-BED: BED zinc finger (0.00035); GO_MF:GO:0046983, protein dimerization activity# (2e-24) | 8 | 74.8 | 94180820 | 94181657 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 817 | Potassium-chloride cotransporter n = 3 Tax = Poaceae RepID = Q6Z0E2_ORYSJ (3e–18); GO_MF:GO:0015377, TAS#cation:chloride symporter activity# (3e–18); GO_BP:GO:0055085, transmembrane transport## (3e–18); GO_CC:GO:0016021, integral to membrane# (3e–18) | 8 | 74.8 | 94299038 | 94299217 |
| 818 | Potassium-chloride cotransporter n = 3 Tax = Poaceae RepID = Q6Z0E2_ORYSJ (0.0); AA_permease: Amino acid permease (2e–08); DUF2074: Predicted permease (DUF2074) (0.028); GO_MF:GO:0015377, TAS#cation:chloride symporter activity# (0.0); GO_BP:GO:0055085, transmembrane transport# (0.0); GO_CC:GO:0016021, integral to membrane# (0.0) | 8 | 74.8 | 94300293 | 94309786 |
| 819 | Potassium-chloride cotransporter n = 3 Tax = Poaceae RepID = Q6Z0E2_ORYSJ (0.0); GO_MF:GO:0015377, TAS#cation:chloride symporter activity# (0.0); GO_BP:GO:0055085, transmembrane transport# (0.0); GO_CC:GO:0016021, integral to membrane# (0.0) | 8 | 74.8 | 94316729 | 94318509 |
| 820 | 60S ribosomal protein L29 n = 9 Tax = Andropogoneae RepID = B6U0G5_MAIZE (2e–24); Ribosomal_L29e: Ribosomal L29e protein family (1.3e–17); GO_MF: GO:0003735, structural constituent of ribosome# (2e–24); GO_BP:GO:0006412, translation# (2e–24); GO_CC:GO:0005840, ribosome# (2e–24) | 8 | 74.8 | 94325768 | 94326837 |
| 821 | Putative polyprotein n = 1 Tax = Zea mays RepID = Q8SA93_MAIZE (3e–35); GO_MF:GO:0003964, RNA-directed DNA polymerase, group II intron encoded# (3e–35); GO_BP:GO:0015074, DNA integration# (3e–35); GO_CC:GO:0005634, nucleus# (3e–35) | 8 | 74.8 | 94353354 | 94353677 |
| 822 | ATP binding protein n = 2 Tax = Andropogoneae RepID = B6TPY7_MAIZE (0.0); PPR: PPR repeat (0.46); PPR: PPR repeat (0.0027); PPR: PPR repeat (5e–08); PPR: PPR repeat (5.4e–05); PPR: PPR repeat (8.6e–11); PPR: PPR repeat (1.3e–07); PPR: PPR repeat (1.1e–06); PPR: PPR repeat (2.7); PPR: PPR repeat (1.1e–06); GO_MF:GO:0005488, binding# (1e–159); GO_BP:GO:0006350, transcription# (1e–159); GO_CC:GO:0005739, mitochondrion# (1e–142) | 8 | 74.8 | 94438246 | 94440138 |
| 823 | ATP binding protein n = 2 Tax = Andropogoneae RepID = B6TPY7_MAIZE (2e–19) | 8 | 74.8 | | |
| 824 | Catalytic/protein phosphatase type 2C n = 2 Tax = Zea mays RepID = B6TW34_MAIZE (1e–20); GO_MF:GO:0003824, catalytic activity# (1e–20); GO_BP:GO: 0004721, phosphoprotein phosphatase activity# (5e–17); GO_CC:GO:0005886, plasma membrane# (1e–11) | 8 | 74.9 | 91968859 | 91969406 |
| 825 | Enzyme inhibitor, putative n = 1 Tax = Ricinus communis RepID = B9RZP7_RICCO (2e–10); PMEI: Plant invertase/pectin methylesterase inhibitor (8.2e–09); GO_MF:GO:0030599, pectinesterase activity# (1e–54); GO_BP:GO:0004857, enzyme inhibitor activity# (1e–54) | 8 | 74.9 | 91992448 | 91993305 |
| 826 | Putative uncharacterized protein n = 1 Tax = Zea mays RepID = B4FA23_MAIZE (8e–24) | 8 | 74.9 | 92048358 | 92048663 |
| 827 | Beta-1,3-galactosyltransferase sqv-2, putative n = 1 Tax = Ricinus communis RepID = B0RRS4_RICCO (2e–87); Galactosyl_T: Galactosyltransferase (1.4e–10); GO_MF:GO:0016757, transferase activity, transferring glycosyl groups# (1e–133); GO_BP:GO:0006486, protein amino acid glycosylation# (1e–133); GO_CC:GO: 0016021, integral to membrane# (1e–133) | 8 | 74.9 | 92078173 | 92082751 |
| 828 | Putative reotransposon protein n = 1 Tax = Zea mays RepID = Q7XBD1_MAIZE (7e–09) | 8 | 74.9 | 92084158 | 92111298 |
| 829 | Lachrymatory factor synthase n = 1 Tax = Zea mays RepID = B6TW34_MAIZE (3e–76); Polyketide_cyc2: Polyketide cyclase/dehydrase and li (3.6e–20); GO_CC: GO:0005773, IDA#vacuole# (3e–19) | 8 | 74.9 | 93032619 | 93033449 |
| 830 | Lustrin A-like n = 2 Tax = Oryza sativa RepID = Q8S237_ORYSJ (1e–127); DUF231: Arabidopsis proteins of unknown function (3.6e–69) | 8 | 75.2 | 94574619 | 94578897 |
| 831 | Probable metal-nicotianamine transporter YSL3 n = 1 Tax = Oryza sativa Japonica Group RepID = YSL3_ORYSJ (0.0); OPT: OPT oligopeptide transporter protein (1.6e–42); GO_BP:GO:0055085, transmembrane transport# (0.0); GO_CC:GO:0016021, integral to membrane# (0.0) | 8 | 75.3 | 94591376 | 94597428 |
| 832 | Probable metal-nicotianamine transporter YSL3 n = 1 Tax = Oryza sativa Japonica Group RepID = YSL3_ORYSJ (0.0); OPT: OPT oligopeptide transporter protein (1.7e–108); GO_BP:GO:0055085, transmembrane transport# (0.0); GO_CC:GO:0016021, integral to membrane# (0.0) | 8 | 75.3 | 94653380 | 94669018 |
| 833 | UPF0497 membrane protein BLE3 n = 1 Tax = Oryza sativa RepID = BLE3_ORYSJ (5e–45); DUF588: Domain of unknown function (DUF588) (1e–41); GO_BP: GO:0035264, IG#multicellular organism growth# (5e–45); GO_CC:GO:0016021, integral to membrane# (5e–45) | 8 | 75.3 | 94697148 | 94698282 |
| 834 | Putative uncharacterized protein Sb09g008160 n = 1 Tax = Sorghum bicolor RepID = C5YV99_SORBI (7e–13); GO_MF:GO:0003779, actin binding# (4e–12); GO_BP:GO:0007010, cytoskeleton organization# (4e–12); GO_CC:GO:0015629, actin cytoskeleton# (4e–12) | 8 | 75.3 | 94755448 | 94758478 |
| 835 | Putative uncharacterized protein Sb09g008150 n = 1 Tax = Sorghum bicolor RepID = C5YV97_SORBI (1e–39); GO_MF:GO:0046872, metal ion binding# (3e–09) | 8 | 75.3 | 94799124 | 94799840 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 836 | Triose phosphate/phosphate translocator n = 2 Tax = Zea mays RepID = B6T5Y2_MAIZE (4e−75); TPT: Triose-phosphate Transporter family (1e−41); DUF6: Integral membrane protein DUF6 (0.013); GO_MF:GO:0005215, transporter activity# (4e−75); GO_BP:GO:0006810, transport# (4e−75); GO_CC:GO:0016021, integral to membrane# (3e−75) | 8 | 75.3 | 94842243 | 94847299 |
| 837 | Triose phosphate/phosphate translocator n = 2 Tax = Zea mays RepID = B6T5Y2_MAIZE (1e−95); GO_MF:GO:0005215, transporter activity# (1e−95); GO_BP:GO:0006810, transport# (1e−95); GO_CC:GO:0016021, integral to membrane# (1e−95) | 8 | 75.3 | 94869786 | 94872368 |
| 838 | Putative retrotransposon protein n = 1 Tax = Phyllostachys edulis RepID = D3IVP0_9POAL (3e−56); GO_MF:GO:0004386, helicase activity## (1e−55) | 8 | 75.3 | 94971334 | 94972115 |
| 839 | Putative retrotransposon protein n = 1 Tax = Phyllostachys edulis RepID = D3IVP0_9POAL (2e−31); GO_MF:GO:0004386, helicase activity## (1e−30) | 8 | 75.3 | 94973500 | 94974300 |
| 840 | OSJNBa0095H06.12 protein n = 1 Tax = Oryza sativa Japonica Group RepID = Q7XS07_ORYSJ (4e−17); DUF889: Eukaryotic protein of unknown function (DUF889) (0.0045); GO_MF:GO:0004386, helicase activity# (2e−16) | 8 | 75.3 | 94974339 | 94989426 |
| 841 | Xylose isomerase n = 7 Tax = Poaceae RepID = Q8H3Q7_ORYSJ (1e−126); Coatomer_E: Coatomer epsilon subunit (2.1e−06); AP_endonuc_2: AP endonuclease family 2 (3.9e−11); GO_MF:GO:0046872, metal ion binding# (1e−126); GO_BP:GO:0042732, D-xylose metabolic process# (1e−126); GO_CC:GO:0005737, cytoplasm# (1e−126) | 8 | 75.3 | 94993912 | 94998988 |
| 842 | Putative uncharacterized protein n = 1 Tax = Zea mays RepID = B6SKI1_MAIZE (2e−33) | 8 | 75.3 | 95009577 | 95012351 |
| 843 | DNA double-strand break repair rad50 ATPase, putative n = 1 Tax = Ricinus communis RepID = B9T5G8_RICCO (2e−70); Tropomyosin: Tropomyosin (0.0042); GO_MF:GO:0008565, protein transporter activity# (1e−142); GO_BP:GO:0008565, protein transporter activity# (1e−142); GO_CC:GO:0005737, cytoplasm# (1e−142) | 8 | 75.3 | 95012946 | 95017551 |
| 844 | DRE-binding protein 1c n = 2 Tax = Zea mays RepID = C3UZ65_MAIZE (1e−142); AP2: AP2 domain (2.8e−20); GO_MF:GO:0003700, transcription factor activity# (1e−135); GO_BP:GO:0045449, regulation of transcription# (1e−135); GO_CC:GO:0005634, nucleus# (1e−135) | 8 | 75.3 | 95020011 | 95023360 |
| 845 | Patellin-5 n = 2 Tax = Zea mays RepID = B6U0S4_MAIZE (0.0; CRAL_TRIO_N: CRAL/TRIO, N-terminus (2.9e−06); CRAL_TRIO: CRAL/TRIO domain (1.7e−19); GO_MF:GO:0008289, lipid binding# (1e−145); GO_BP:GO:0051301, cell division# (1e−145); GO_CC:GO:0016020, membrane# (1e−145) | 8 | 75.3 | 95125931 | 95129886 |
| 846 | OSJNBa0079M09.12 protein n = 9 Tax = Oryza sativa Japonica Group RepID = Q7XVR0_ORYSJ (6e−17); Transposase_28: Putative gypsy type transposon (2.6e−08) | 8 | 75.3 | 95306870 | 95307627 |
| 847 | OSJNBa0079M09.12 protein n = 9 Tax = Oryza sativa Japonica Group RepID = Q7XVR0_ORYSJ (7e−19); Transposase_28: Putative gypsy type transposon (1.4e−09) | 8 | 75.3 | 95328212 | 95328969 |
| 848 | Endo beta n-acetylglucosaminidase, putative n = 1 Tax = Ricinus communis RepID = B9S465_RICCO (1e−33); GO_MF:GO:0033925, mannosyl-glycoprotein endo-beta-N-acetylglucosaminidase activity# (1e−33); GO_BP:GO:0006879, cellular iron ion homeostasis# (2e−12); GO_CC:GO:0005737, cytoplasm# (1e−33) | 8 | 75.3 | 95420532 | 95423294 |
| 849 | Endo beta n-acetylglucosaminidase, putative n = 1 Tax = Ricinus communis RepID = B9S465_RICCO (1e−117); Glyco_hydro_85: Glycosyl hydrolase family 85 (5e−112); GO_MF:GO:0033925, mannosyl-glycoprotein endo-beta-N-acetylglucosaminidase activity# (1e−123); GO_BP:GO:0008152, metabolic process# (9e−75); GO_CC:GO:0005737, cytoplasm# (1e−123) | 8 | 75.3 | 95433379 | 95436049 |
| 850 | Isoform 2 of Probable metal-nicotianamine transporter YSL3 n = 1 Tax = Oryza sativa Japonica Group RepID = Q6AVD0-2 (1e−30); GO_BP:GO:0055085, transmembrane transport# (9e−31); GO_CC:GO:0016021, integral to membrane# (1e−30) | 8 | 75.4 | 94610750 | 94611415 |
| 851 | Putative uncharacterized protein n = 1 Tax = Zea mays RepID = B6U8H0_MAIZE (4e−13) | 8 | 75.4 | 94612455 | 94612974 |
| 852 | ATP-dependent RNA helicase, putative n = 1 Tax = Ricinus communis RepID = B9R8Y0_RICCO (3e−21); GO_MF:GO:0016787, hydrolase activity# (1e−22); GO_BP:GO:0008380, RNA splicing# (2e−20); GO_CC:GO:0005829, IDA#cytosol# (2e−20) | 8 | 75.4 | 94624909 | 94636392 |
| 853 | Putative uncharacterized protein n = 1 Tax = Zea mays RepID = B8A0N1_MAIZE (3e−19) | 8 | 75.4 | 95481303 | 95481716 |
| 854 | Retrotransposon protein, putative, unclassified n = 1 Tax = Oryza sativa Japonica Group RepID = Q2QSH2_ORYSJ (3e−39); GO_MF:GO:0004523, ribonuclease H activity# (3e−39); GO_BP:GO:0006278, RNA-dependent DNA replication# (3e−39) | 8 | 75.4 | 95569042 | 95569679 |
| 855 | Putative uncharacterized protein n = 1 Tax = Zea mays RepID = B6TZX3_MAIZE (7e−30) | 8 | 75.4 | 95573013 | 95573303 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 856 | Aldose reductase n = 3 Tax = Andropogoneae RepID = B6THE1_MAIZE (1e-170); Aldo_ket_red: Aldo/keto reductase family (1.2e-129); GO_MF:GO:0016491, oxidoreductase activity## (1e-170); GO_BP:GO:0055114, oxidation reduction# (1e-170); GO_CC:GO:0005829, IDA#cytosol# (1e-110) | 8 | 75.5 | 95631071 | 95638909 |
| 857 | Putative uncharacterized protein Sb09g022330 n = 3 Tax = Andropogoneae RepID = C5YZ73_SORBI (5e-15) | 8 | 75.6 | 95641896 | 95643652 |
| 858 | Os05g0455600 n = 1 Tax = Oryza sativa Japonica Group RepID = UPI0000E1250C (1e-106); PRA1: PRA1 family protein (3.9e-43); GO_BP:GO:001692, vesicle-mediated transport# (3e-76); GO_CC:GO:0016021, integral to membrane# (3e-76) | 8 | 75.65 | 95646214 | 95650515 |
| 859 | Delta-1-pyrroline-5-carboxylase synthetase 2 n = 2 Tax = Andropogoneae RepID = C8CB72_SORBI (0.0); AA_kinase: Amino acid kinase family (2.4e-55); Aldedh: Aldehyde dehydrogenase family (0.00019); GO_MF:GO:0016740, transferase activity# (0.0); GO_BP:GO:0055114, oxidation reduction# (0.0); GO_CC:GO:0005737, cytoplasm# (0.0) | 8 | 75.9 | 95715355 | 95726173 |
| 860 | Nucleic acid binding protein, putative n = 1 Tax = Ricinus communis RepID = B9RRU4_RICCO (1e-28); KH_1: KH domain (1.5e-10); GO_MF:GO:0003723, RNA binding# (1e-52); GO_BP:GO:0006396, RNA processing# (1e-22) | 8 | 75.9 | 95735166 | 95743294 |
| 861 | Putative transcription factor qSH-1 n = 1 Tax = Oryza rufipogon RepID = A9XWR4_ORYRU (1e-131); POX: Associated with HOX (1.3e-48); Homeobox: Homeobox domain (0.0015); GO_MF:GO:0043565, sequence-specific DNA binding# (0.0); GO_BP:GO:0045449, regulation of transcription# (0.0); GO_CC:GO:0005634, nucleus# (0.0) | 8 | 75.9 | 95774436 | 95779361 |
| 862 | Putative uncharacterized protein Sb03g001220 n = 1 Tax = Sorghum bicolor RepID = C5XKB1_SORBI (1e-10); GO_MF:GO:0005525, GTP binding# (3e-10); GO_CC:GO:0005622, intracellular## (3e-10) | 8 | 76 | 96058925 | 96059534 |
| 863 | Pollen-specific kinase partner protein n = 2 Tax = Zea mays RepID = B6U1X9_MAIZE (0.0); PRONE: PRONE (Plant-specific Rop nucleotide exc (3.8e-223); GO_MF:GO:0016301, kinase activity## (0.0); GO_BP:GO:0016301, kinase activity## (0.0); GO_CC:GO:0016324, IDA#apical plasma membrane# (1e-132) | 8 | 76 | 96075884 | 96079303 |
| 864 | OSJNBa0033G05.13 protein n = 1 Tax = Oryza sativa Japonica Group RepID = Q7XTM9_ORYSJ (1e-176); GO_MF:GO:0008270, zinc ion binding# (1e-176); GO_BP:GO:0015074, DNA integration# (1e-176); GO_CC:GO:0005622, intracellular# (1e-171) | 8 | 76 | 96178451 | 96180104 |
| 865 | Integrase core domain containing protein n = 1 Tax = Oryza sativa Japonica Group RepID = Q75HA9_ORYSJ (1e-38); GO_MF:GO:0008270, zinc ion binding# (1e-38); GO_BP:GO:0015074, DNA integration# (1e-38); GO_CC:GO:0005622, intracellular# (1e-35) | 8 | 76.2 | 96193386 | 96194276 |
| 866 | Probable anion transporter 2, chloroplastic n = 1 Tax = Oryza sativa Japonica Group RepID = PHT42_ORYSJ (0.0); MFS_1: Major Facilitator Superfamily (5.6e-20); Sugar_tr: Sugar (and other) transporter (0.063); GO_MF:GO:0005315, inorganic phosphate transmembrane transporter activity# (1e-131); GO_BP:GO:0055085, transmembrane transport# (0.0); GO_CC:GO:0031969, IDA#chloroplast membrane# (0.0) | 8 | 76.45 | 97844871 | 97849365 |
| 867 | Putative uncharacterized protein Sb09g020830 n = 1 Tax = Sorghum bicolor RepID = C5YY75_SORBI (9e-5) | 8 | 76.55 | 102657595 | 102657840 |
| 868 | Peroxidase 1 n = 3 Tax = Oryza sativa RepID = PER1_ORYSJ (1e-140); peroxidase: Peroxidase (2e-122); GO_MF:GO:0046872, metal ion binding# (1e-140); GO_BP:GO:0055114, oxidation reduction# (1e-140); GO_CC:GO:0005576, extracellular region# (1e-140) | 8 | 76.9 | 96253851 | 96255187 |
| 869 | Pleckstrin homology domain-containing protein 1 n = 2 Tax = Andropogoneae RepID = B6T5A7_MAIZE (1e-92); PH: PH domain (3.5e-24); GO_MF:GO:0008289, lipid binding## (2e-50); GO_BP:GO:0016301, kinase activity# (3e-10); GO_CC:GO:0005737, cytoplasm# (2e-50) | 8 | 76.9 | 96346829 | 96347799 |
| 870 | Putative uncharacterized protein Sb09g022010 n = 1 Tax = Sorghum bicolor RepID = C5YYU9_SORBI (1e-160); TPR_2: Tetratricopeptide repeat (2.6); TPR_2: Tetratricopeptide repeat (1.3); GO_MF:GO:0005488, binding# (1e-145); GO_BP:GO:0006396, RNA processing# (2e-29); GO_CC:GO:0005622, intracellular# (2e-29) | 8 | 76.9 | 96630249 | 96632523 |
| 871 | GHMP kinase-like protein n = 3 Tax = Poaceae RepID = Q6YX79_ORYSJ (8e-62); Scramblase: Scramblase (3.8e-13); GO_MF:GO:0016773, phosphotransferase activity, alcohol group as acceptor# (8e-62); GO_BP:GO:0016310, hyperphosphorylation# (8e-62); GO_CC:GO:0005737, cytoplasm# (8e-62) | 8 | 77 | 96265286 | 96268048 |
| 872 | Emp24/gp25L/p24-like n = 1 Tax = Oryza sativa Japonica Group RepID = Q62GK3_ORYSJ (4e-16); GO_BP:GO:0006810, transport# (4e-18); GO_CC:GO:0016021, integral to membrane# (4e-18) | 8 | 77 | 96636446 | 96637406 |
| 873 | Putative hydroxycinnamoyl transferase n = 2 Tax = Oryza sativa RepID = Q5N7V3_ORYSJ (1e-178); Transferase: Transferase family (9.4e-84); GO_MF:GO:0006747, transferase activity, transferring acyl groups other than amino-acyl groups# (0.0) | 8 | 77 | 96819655 | 96821745 |
| 874 | Coronatine-insensitive protein 1 n = 3 Tax = Andropogoneae RepID = B6TPN4_MAIZE (0.0); LRR_2: Leucine Rich Repeat (10); LRR_1: Leucine Rich Repeat (20); LRR_2: Leucine Rich Repeat (1.5); LRR_1: Leucine Rich Repeat (2.3e+02); LRR_1: Leucine Rich Repeat (13); LRR_1: Leucine Rich Repeat (1.7e+02); LRR_2: Leucine Rich Repeat (2.3); LRR_1: Leucine Rich Repeat (25); GO_MF:GO:0005515, protein binding# (1e-154); GO_BP:GO:0050832, IMP#defense response to fungus# (1e-154); GO_CC:GO:0019005, NAS#SCF ubiquitin ligase complex# (1e-154) | 8 | 77 | 96929607 | 96933269 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 875 | AT_hook: AT hook motif (1); AT_hook: AT hook motif (1); AT_hook: AT hook motif (7); AT_hook: AT hook motif (11) | 8 | 77 | 96935835 | 96950132 |
| 876 | MYB-like transcription factor DIVARICATA n = 2 Tax = Zea mays RepID = B6T0L0_MAIZE (1e-34); GO_MF:GO:0003677, DNA binding# (1e-34); GO_BP:GO:0045449, regulation of transcription# (1e-34); GO_CC:GO:0005634, nucleus# (1e-34) | 8 | 77 | 97042807 | 97043351 |
| 877 | Putative uncharacterized protein n = 1 Tax = Zea mays RepID = B6SUB9_MAIZE (1e-100) | 8 | 77.1 | 97055611 | 97057187 |
| 878 | Putative uncharacterized protein n = 2 Tax = Zea mays RepID = B6TGN0_MAIZE (1e-117) | 8 | 77.1 | 96268745 | 96271064 |
| 879 | Transcription factor, putative n = 1 Tax = Ricinus communis RepID = B9RYX9_RICCO (7e-55); B3: B3 DNA binding domain (1.6e-29); GO_MF:GO:0003677, DNA binding# (2e-61); GO_BP:GO:0045449, regulation of transcription# (2e-61); GO_CC:GO:0005634, nucleus# (2e-61) | 8 | 77.1 | 96690364 | 96690912 |
| 880 | ER glycerol-phosphate acyltransferase n = 1 Tax = Ricinus communis RepID = B9S2F2_RICCO (1e-121); GO_MF:GO:0008415, acyltransferase activity# (0.0); GO_BP:GO:0008152, metabolic process# (0.0); GO_CC:GO:0016021, integral to membrane# (1e-135) | 8 | 77.1 | 96692598 | 96698185 |
| 881 | Ulp1 protease family, C-terminal catalytic domain containing protein n = 2 Tax = Oryza sativa Japonica Group RepID = Q109R5_ORYSJ (4e-33); Peptidase_C48: Ulp1 protease family, C-terminal catalytic domain (7.4e-09); GO_MF:GO:0008234, cysteine-type peptidase activity# (1e-138); GO_BP:GO:0006508, proteolysis# (1e-138) | 8 | 77.1 | 96985721 | 96994606 |
| 882 | Ulp1 protease family, C-terminal catalytic domain containing protein n = 2 Tax = Oryza sativa Japonica Group RepID = Q109R5_ORYSJ (2e-14); GO_MF:GO:0008234, cysteine-type peptidase activity# (2e-14); GO_BP:GO:0006508, proteolysis# (2e-14) | 8 | 77.1 | 96994621 | 96996396 |
| 883 | OSJNBa0036B21.17 protein n = 6 Tax = Oryza sativa RepID = Q7XQ05_ORYSJ (6e-13) | 8 | 77.1 | 96997596 | 96998401 |
| 884 | Putative uncharacterized protein Sb06g030295 n = 1 Tax = Sorghum bicolor RepID = C5Y8Y8_SORBI (2e-30) | 8 | 77.1 | 96998426 | 96998719 |
| 885 | Transposon protein, putative, Pong sub-class n = 1 Tax = Oryza sativa Japonica Group RepID = Q7XDX1_ORYSJ (2e-10); GO_MF:GO:0003677, DNA binding# (4e-10); GO_CC:GO:0005840, ribosome# (4e-10) | 8 | 77.1 | 97031270 | 97031829 |
| 886 | Putative uncharacterized protein Sb09g022000 n = 1 Tax = Sorghum bicolor RepID = C5YYU8_SORBI (5e-97) | 8 | 77.15 | 96350550 | 96361050 |
| 887 | Putative PolI-like DNA polymerase n = 1 Tax = Oryza sativa Japonica Group RepID = Q69S01_ORYSJ (3e-28); GO_MF:GO:0008408, 3'-5' exonuclease activity# (3e-29); GO_BP:GO:0006260, DNA replication (3e-29); GO_CC:GO:0005622, intracellular# (3e-29) | 8 | 77.15 | 96401217 | 96403741 |
| 888 | Galactosyltransferase family n = 3 Tax = Andropogoneae RepID = B6SXL2_MAIZE (1e-12); GO_MF:GO:0016757, transferase activity, transferring glycosyl groups# (1e-12); GO_BP:GO:0006486, protein amino acid glycosylation# (1e-12); GO_CC:GO:0016021, integral to membrane# (1e-12) | 8 | 77.2 | 97117274 | 97117771 |
| 889 | Putative uncharacterized protein n = 1 Tax = Zea mays RepID = C4J8U8_MAIZE (3e-91) | 8 | 77.3 | 97176485 | 97177444 |
| 890 | Putative uncharacterized protein Sb09g022160 n = 2 Tax = Sorghum bicolor RepID = C5YYW5_SORBI (5e-18); PAR1: PAR1 protein (0.0063) | 8 | 77.3 | 97422405 | 97422741 |
| 891 | OSJNBa0067K08.12 protein n = 3 Tax = Oryza sativa RepID = Q7XUK2_ORYSJ (0.0); LETM1: LETM1-like protein (9.2e-157); GO_MF:GO:0005509, calcium ion storage activity# (0.0); GO_BP:GO:0042407, cristae formation# (4e-76); GO_CC:GO:0016021, integral to membrane# (0.0) | 8 | 77.3 | 97466729 | 97477275 |
| 892 | HAT family dimerisation domain containing protein n = 1 Tax = Oryza sativa Japonica Group RepID = Q7XD60_ORYSJ (2e-67); GO_MF:GO:0046983, protein dimerization activity# (2e-67); GO_BP:GO:0006468, protein amino acid phosphorylation# (5e-47) | 8 | 77.3 | 97649960 | 97651201 |
| 893 | Putative uncharacterized protein n = 1 Tax = Zea mays RepID = B4FKU7_MAIZE (1e-118) | 8 | 77.4 | 97552114 | 97555230 |
| 894 | Putative axi 1 n = 2 tax = Oryza sativa RepID = Q5N7B2_ORYSJ (0.0); DUF246: Plant protein family (7.1e-186) | 8 | 77.4 | 97712162 | 97716261 |
| 895 | Putative uncharacterized protein n = 1 Tax = Oryza sativa Indica Group RepID = A2Y596_ORYSI (1e-167); DUF740: Protein of unknown function (DUF740) | 8 | 77.4 | 97939651 | 97941696 |
| 896 | Hexaprenyldihydroxybenzoate methyltransferase, putative n = 1 Tax = Ricinus communis RepID = B9S8D8_RICCO (1e-26); GO_MF:GO:0008425, 2-polyprenyl-6-methoxy-1,4-benzoquinone methyltransferase activity# (1e-36); GO_BP:GO:0008152, metabolic process# (1e-36); GO_CC:GO:0005759, IEP#mitochondrial matrix# (8e-27) | 8 | 77.4 | 97992716 | 97994155 |
| 897 | Putative dihydroxypolyprenylbenzoate methyltransferase n = 1 Tax = Oryza sativa Japonica Group RepID = Q5VMI1_ORYSJ (1e-77); Methyltransf_11: Methyltransferase domain (0.0027); GO_MF:GO:0008425, 2-polyprenyl-6-methoxy-1,4-benzoquinone methyltransferase activity# (9e-78); GO_BP:GO:0008152, metabolic process# (9e-78); GO_CC:GO:0005759, IEP#mitochondrial matrix# (3e-69) | 8 | 77.4 | 98026316 | 98029412 |
| 898 | Dehydrin: Dehydrin (2.4e-36) | 8 | 77.4 | 98030042 | 98031216 |
| 899 | Pentatricopeptide repeat-containing protein, putative n = 1 Tax = Ricinus communis RepID = B9S789_RICCO (1e-153); PPR: PPR repeat (0.72); PPR: PPR repeat (5.6e-09); PPR: PPR repeat (3.2e-09); PPR: PPR repeat (2.8e-13); PPR: PPR repeat (1.3e-12); PPR: PPR repeat (5.5e-09); PPR: PPR repeat (8e-09); PPR: PPR repeat (8.2e-15); PPR: PPR repeat (3.7e-08); PPR: PPR repeat (2.6e-08); PPR: PPR repeat (7.3e-13); PPR: PPR repeat (0.22); PPR: PPR repeat (0.019); PPR: PPR repeat (8.9e-10); PPR: PPR repeat (0.58); PPR: PPR repeat (0.34); GO_MF:GO:0016740, transferase activity# (2e-87); GO_BP:GO:0006278, RNA-dependent DNA replication (2e-76); GO_CC:GO:0005739, mitochondrion# (9e-77) | 8 | 77.4 | 98076480 | 98079155 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 900 | Lipopolysaccharide-modifying protein n = 1 Tax = Zea mays RepID = B6TEG9_MAIZE (1e-12); DUF821: Arabidopsis thaliana protein of unknown function (DUF821) (0.0036) | 8 | 77.4 | 98080366 | 98080632 |
| 901 | Arginyl-tRNA--protein transferase, putative n = 1 Tax = Ricinus communis RepID = B9SLM9_RICCO (4e-09); GO_MF:GO:0004057, arginyltransferase activity# (8e-15); GO_BP:GO:0016598, protein arginylation# (8e-15) | 8 | 77.5 | 98400172 | 98401261 |
| 902 | Arginyl-tRNA--protein transferase, putative n = 1 Tax = Ricinus communis RepID = B9SLM9_RICCO (1e-135); ATE_C: Arginine-tRNA-protein transferase, C terminus (3.1e-70); GO_MF:GO:0030246, carbohydrate binding# (0.0); GO_BP:GO:0016598, protein arginylation# (0.0); GO_CC:GO:0005737, cytoplasm# (1e-48) | 8 | 77.5 | 98423247 | 98426294 |
| 903 | 60S acidic ribosomal protein P2B n = 4 Tax = Andropogoneae RepID = RLA2B_MAIZE (2e-25); GO_MF:GO:0003735, structural constituent of ribosome# (2e-25); GO_BP:GO:0006414, translational elongation# (2e-25); GO_CC:GO:0030529, ribonucleoprotein complex# (2e-25) | 8 | 77.5 | 98594876 | 98599278 |
| 904 | Pentatricopeptide repeat-containing protein, putative n = 1 Tax = Ricinus communis RepID = B9SCR2_RICCO (1e-129); PPR: PPR repeat (2.4e-07); PPR: PPR repeat (0.0094); PPR: PPR repeat (1.4); PPR: PPR repeat (5.4e-10); PPR: PPR repeat (4.2e-07); PPR: PPR repeat (8.5e-07); GO_MF:GO:0005488, binding# (4e-69); GO_CC:GO:0005739, mitochondrion# (1e-58) | 8 | 77.5 | 98655289 | 98656905 |
| 905 | Putative uncharacterized protein n = 2 Tax = Zea mays RepID = Q5GAU8_MAIZE (2e-12) | 8 | 77.5 | 98705541 | 98705880 |
| 906 | Putative uncharacterized protein n = 1 Tax = Zea mays RepID = B4FJ19_MAIZE (1e-30) | 8 | 77.5 | 98706736 | 98707101 |
| 907 | Aluminum-activated malate transporter-like n = 1 Tax = Oryza sativa Japonica Group RepID = Q526M5_ORYSJ (1e-58); GO_MF:GO:0005253, IDA#anion channel activity# (9e-39); GO_BP:GO:0010044, response to aluminum ion# (1e-58); GO_CC:GO:0009705, IDA#plant-type vacuole membrane# (9e-39) | 8 | 77.6 | 98754050 | 98754826 |
| 908 | Zinc finger protein n = 1 Tax = Zea mays RepID = B6TXE6_MAIZE (8e-66); zf-C2H2: Zinc finger, C2H2 type (0.0059); zf-C2H2: Zinc finger, C2H2 type (0.4); zf-C2H2: Zinc finger, C2H2 type (6.9); GO_MF:GO:0008270, zinc ion binding# (2e-93); GO_BP:GO:0045449, regulation of transcription (2e-68); GO_CC:GO:0005622, intracellular# (2e-93) | 8 | 77.6 | 98765962 | 98768759 |
| 909 | Ferredoxin-6 n = 1 Tax = Zea mays RepID = B6STB1_MAIZE (9e-66); Fer2: 2Fe—2S iron-sulfur cluster binding do (1.4e-28); GO_MF:GO:0051537, 2 iron, 2 sulfur cluster binding# (9e-66); GO_BP:GO:0022900, electron transport chain# (9e-66); GO_CC:GO:0009536, plastid# (2e-51) | 8 | 77.6 | 99001628 | 99002374 |
| 910 | Putative uncharacterized protein n = 1 Tax = Zea mays RepID = B4FA60_MAIZE (2e-21) | 8 | 77.6 | 99072549 | 99073184 |
| 911 | Glucan endo-1,3-beta-glucosidase 7 n = 2 Tax = Zea mays RepID = B6SUM3_MAIZE (0.0); Glyco_hydro_17: Glycosyl hydrolases family 17 (8.7e-111); GO_MF:GO:0043169, cation binding# (0.0); GO_BP:GO:0008152, metabolic process# (0.0); GO_CC:GO:0046658, anchored to plasma membrane# (1e-118) | 8 | 77.6 | 99158642 | 99162373 |
| 912 | Protein kinase-like n = 1 Tax = Oryza sativa Japonica Group RepID = Q6KAK1_ORYSJ (1e-111); GO_MF:GO:0016301, kinase activity# (1e-111); GO_BP:GO:0016301, kinase activity# (1e-111) | 8 | 77.6 | 99165877 | 99167516 |
| 913 | Transposase n = 1 Tax = Oryza sativa Japonica Group RepID = A5X2G8_MAIZE (5e-37); hATC: hAT family dimerisation domain (1.5e-24); GO_MF:GO:0046983, protein dimerization activity# (5e-37); GO_BP:GO:0032196, transposition# (5e-14) | 8 | 77.6 | 99194162 | 99194911 |
| 914 | Vesicle coat complex COPII, subunit SEC24/subunit SFB2 (ISS) n = 1 Tax = Ostreococcus tauri RepID = Q013K2_OSTTA (8e-39); zf-Sec23_Sec24; Sec24; Sec23_BS: Sec23/Sec24 beta-sandwich domain (0.012); Sec23_helical: Sec23/Sec24 helical domain (0.00076); GO_MF:GO:0008270, zinc ion binding# (0.0); GO_BP:GO:0006888, ER to Golgi vesicle-mediated transport# (0.0); GO_CC:GO:0030127, COPII vesicle coat# (0.0) | 8 | 77.6 | 99200827 | 99207530 |
| 915 | Putative uncharacterized protein n = 1 Tax = Zea mays RepID = B6TT12_MAIZE (3e-13) | 8 | 77.6 | 99224994 | 99225706 |
| 916 | Tubulin binding cofactor C n = 1 Tax = Medicago truncatula RepID = A2Q4U5_MEDTR (9e-10); GO_MF:GO:0005488, binding# (4e-21) | 8 | 77.6 | 99226248 | 99229285 |
| 917 | NAC transcription factor-like protein n = 2 Tax = Oryza sativa RepID = Q94CW0_ORYSJ (3e-62); NAM: No apical meristem (NAM) protein (8e-39); GO_MF:GO:0003677, DNA binding# (5e-75); GO_BP:GO:0045449, regulation of transcription# (5e-75); GO_CC:GO:0005634, nucleus# (3e-48) | 8 | 77.6 | 99283158 | 99284291 |
| 918 | Retrotransposon protein, putative, unclassified n = 1 Tax = Oryza sativa Japonica Group RepID = Q2QM33_ORYSJ (4e-11); GO_MF:GO:0003676, nucleic acid binding# (4e-11) | 8 | 77.6 | 99417922 | 99422033 |
| 919 | Putative uncharacterized protein OSJNBa0026O12.1 n = 2 Tax = Oryza sativa RepID = Q9AUZ8_ORYSJ (2e-10); GO_MF:GO:0005509, calcium ion storage activity# (2e-10) | 8 | 77.6 | 99513812 | 99514817 |
| 920 | Putative retroelement n = 1 Tax = Zea mays RepID = Q7XBD5_MAIZE (7e-49); GO_MF:GO:0003917, DNA topoisomerase type I activity# (7e-49); GO_BP:GO:0006268, DNA unwinding factor# (7e-49); GO_CC:GO:0005694, chromosome# (7e-49) | 8 | 77.6 | 99519614 | 99523100 |
| 921 | (RAP Annotation release2) Histone deacetylase superfamily protein n = 1 Tax = Oryza sativa Japonica Group RepID = B7ETM3_ORYSJ (3e-85); NC: NC domain (7.8e-06); GO_BP:GO:0006370, mRNA capping# (1e-44) | 8 | 77.6 | 99590456 | 99592590 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 922 | (RAP Annotation release2) Histone deacetylase superfamily protein n = 3 Tax = Oryza sativa RepID = Q60DG7_ORYSJ (0.0); Hist_deacetyl: Histone deacetylase family (4.4e-112); GO_MF:GO:0016787, hydrolase activity# (0.0); GO_BP:GO:0045449, regulation of transcription# (1e-144); GO_CC:GO:0005634, nucleus# (1e-144) | 8 | 77.6 | 99593881 | 99597132 |
| 923 | B1I60F02.10 protein n = 1 Tax = Oryza sativa Japonica Group RepID = Q6MWG6_ORYSJ (6e-44); hATC: hAT family dimerisation domain (7.7e-29); GO_MF:GO:0046983, protein dimerization activity# (1e-66); GO_BP:GO:0055114, oxidation reduction# (4e-21) | 8 | 77.6 | 100258896 | 100259536 |
| 924 | Actin-11 n = 9 Tax = Viridiplantae RepID = ACT11_ARATH (0.0); Actin: Actin (2e-237); GO_MF:GO:0005524, ATP binding# (0.0); GO_BP:GO:0014866, IMP#skeletal myofibril assembly# (0.0); GO_CC:GO:0005886, plasma membrane# (0.0) | 8 | 77.6 | 100394524 | 100398658 |
| 925 | Catalytic, putative n = 1 Tax = Ricinus communis RepID = B9TAI0_RICCO (2e-29); GO_MF:GO:0051536, iron-sulfur cluster binding# (3e-34); GO_BP:GO:0006364, rRNA processing# (3e-34); GO_CC:GO:0005737, cytoplasm# (3e-34) | 8 | 77.6 | 100419432 | 100419995 |
| 926 | Catalytic, putative n = 1 Tax = Ricinus communis RepID = B9TAI0_RICCO (9e-13); GO_MF:GO:0051536, iron-sulfur cluster binding# (7e-29); GO_BP:GO:0006364, rRNA processing# (7e-29); GO_CC:GO:0005737, cytoplasm# (7e-29) | 8 | 77.6 | 100427857 | 100428441 |
| 927 | Putative gag/pol polyprotein n = 1 Tax = Oryza sativa Japonica Group RepID = Q75IA0_ORYSJ (8e-68); RVT_2: Reverse transcriptase (RNA-dependent DNA pol (1.4e-13); GO_MF:GO:0003677, DNA binding# (8e-68); GO_BP:GO:0015074, DNA integration# (8e-68) | 8 | 77.6 | 100469457 | 100470771 |
| 928 | (RAP Annotation release2) Histone deacetylase superfamily protein n = 1 Tax = Oryza sativa Japonica Group RepID = B7ETM3_ORYSJ (6e-85); Hist_deacetyl: Histone deacetylase domain (7.8e-06); GO_BP:GO:0006370, mRNA capping# (7e-45) | 8 | 77.6 | 100472235 | 100472981 |
| 929 | (RAP Annotation release2) Histone deacetylase superfamily protein n = 3 Tax = Oryza sativa RepID = Q60DG7_ORYSJ (1e-131); Hist_deacetyl: Histone deacetylase family (6.6e-68); GO_MF:GO:0016787, hydrolase activity# (1e-155); GO_BP:GO:0045449, regulation of transcription# (1e-103); GO_CC:GO:0005634, nucleus# (1e-103) | 8 | 77.6 | 100473591 | 100478046 |
| 930 | Putative uncharacterized protein Sb09g021760 n = 3 Tax = Andropogoneae RepID = C5YYS1_SORBI (7e-11) | 8 | 77.6 | 100479211 | 100479579 |
| 931 | Putative retroelement n = 1 Tax = Zea mays RepID = Q7XBD5_MAIZE (3e-85); GO_MF:GO:0003917, DNA topoisomerase type I activity# (3e-85); GO_BP:GO:0006268, DNA unwinding factor# (3e-85); GO_CC:GO:0005694, chromosome# (3e-85) | 8 | 77.6 | 100591797 | 100595283 |
| 932 | Retrotransposon protein, putative, unclassified n = 1 Tax = Oryza sativa Japonica Group RepID = Q2QM33_ORYSJ (2e-10); GO_MF:GO:0003676, nucleic acid binding# (2e-10) | 8 | 77.6 | 100598062 | 100599636 |
| 933 | Retrotransposon protein, putative, unclassified n = 1 Tax = Oryza sativa Japonica Group RepID = Q2QQG4_ORYSJ (5e-18); GO_MF:GO:0003964, RNA-directed DNA polymerase, group II intron encoded# (5e-18); GO_BP:GO:0006278, RNA-dependent DNA replication# (5e-18) | 8 | 77.6 | 100618292 | 100618468 |
| 934 | Putative uncharacterized protein n = 1 Tax = Zea mays RepID = B6TBA7_MAIZE (3e-17) | 8 | 77.6 | 100625551 | 100626262 |
| 935 | Putative uncharacterized protein n = 1 Tax = Zea mays RepID = C4J932_MAIZE (4e-18); GO_MF:GO:0048038, quinone binding# (4e-18); GO_BP:GO:0055114, oxidation reduction# (4e-18); GO_CC:GO:0005777, IDA#peroxisome# (7e-11) | 8 | 77.6 | 100626320 | 100630111 |
| 936 | OSJNBa0055H05.12 protein n = 2 Tax = Oryza sativa Japonica Group RepID = Q7XRD0_ORYSJ (1e-23); PHD: PHD-finger (0.00093); GO_MF:GO:0046872, metal ion binding# (1e-23) | 8 | 77.6 | 100630313 | 100630562 |
| 937 | G-box-binding factor 4 n = 1 Tax = Zea mays RepID = B6TGZ0_MAIZE (7e-83); bZIP_1: bZIP transcription factor (7.7e-08); bZIP_2: Basic region leucine zipper (3.1e-07); GO_MF:GO:0046983, protein dimerization activity# (7e-83); GO_BP:GO:0006355, regulation of transcription, DNA-dependent# (7e-83); GO_CC:GO:0005634, nucleus# (7e-83) | 8 | 77.6 | 100710645 | 100714109 |
| 938 | Jacalin-like lectin domain containing protein n = 1 Tax = Oryza sativa Japonica Group RepID = Q2R1E0_ORYSJ (2e-73); Pkinase: Protein kinase domain (7.1e-36); Pkinase_Tyr: Protein tyrosine kinase (8.1e-17); Jacalin: Jacalin-like lectin domain (4.7e-17); GO_MF:GO:0005524, ATP binding# (1e-73); GO_BP:GO:0006468, protein amino acid phosphorylation (1e-73); GO_CC:GO:0016021, integral to membrane# (5e-41) | 8 | 77.6 | 100755519 | 100757762 |
| 939 | Retrotransposon gag protein n = 1 Tax = Asparagus officinalis RepID = Q2AA53_ASPOF (7e-32); 3_5_exonuc: 3'-5' exonuclease (1.3e-06); Retrotrans_gag: Retrotransposon gag protein (5.6e-09); GO_MF:GO:0004523, ribonuclease H activity# (3e-29); GO_BP:GO:0015074, DNA integration# (3e-29); GO_CC:GO:0005634, nucleus# (3e-29) | 8 | 77.7 | 97344781 | 97349148 |
| 940 | Class III peroxidase 124 n = 3 Tax = Oryza sativa RepID = Q5U1G9_ORYSJ (1e-111); peroxidase: Peroxidase (2.4e-106); GO_MF:GO:0046872, metal ion binding# (1e-111); GO_BP:GO:0055114, oxidation reduction# (1e-111); GO_CC:GO:0005886, plasma membrane# (1e-77) | 8 | 77.8 | 102488572 | 102490148 |
| 941 | Putative uncharacterized protein Sb03g010270 n = 3 Tax = Andropogoneae RepID = C5XGH5_SORBI (0.0); GO_MF:GO:0003964, RNA-directed DNA polymerase, group II intron encoded# (3e-63); GO_BP:GO:0006278, RNA-dependent DNA replication# (3e-63) | 8 | 77.95 | 102398429 | 102405402 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 942 | Putative Pol polyprotein from transposon element Bs1 n = 1 Tax = Zea mays RepID = POLB_MAIZE (1e−22); GO_MF:GO:0016887, ATPase activity# (1e−22); GO_BP:GO:0016820, hydrolase activity, acting on acid anhydrides, catalyzing transmembrane movement of substances# (1e−22); GO_CC:GO:0016021, integral to membrane# (1e−22) | 8 | 78 | 100121781 | 100122131 |
| 943 | Protein argonaute 18 n = 2 Tax = Oryza sativa RepID = AGO18_ORYSJ (9e−42); Piwi: Piwi domain (1.5e−08); GO_MF:GO:0003676, nucleic acid binding# (9e−42); GO_BP:GO:0031047, IMP#gene silencing by RNA# (9e−42); GO_CC:GO:0005737, cytoplasm# (1e−34) | 8 | 78 | 102382112 | 102383707 |
| 944 | RNA recognition motif-containing protein n = 2 Tax = Zea mays RepID = B6SM38_MAIZE (6e−11); GO_MF:GO:0003676, nucleic acid binding# (8e−10) | 8 | 78.2 | 102262836 | 102264592 |
| 945 | Fructose-1,6-bisphosphatase 2 n = 3 Tax = Poaceae RepID = A7J2C3_ORYSI (1e−125); FBPase: Fructose 1-6-bisphosphatase (4.1e−92); GO_MF:GO:0042578, phosphoric ester hydrolase activity# (1e−125); GO_BP:GO:0042132, fructose 1,6-bisphosphate 1-phosphatase activity# (1e−125); GO_CC:GO:0005737, cytoplasm# (1e−125) | 8 | 78.3 | 100871386 | 100874570 |
| 946 | Putative polypyrimidine track-binding protein n = 1 Tax = Oryza sativa Japonica Group RepID = Q5TKN2_ORYSJ (0.0); RRM_1: RNA recognition motif. (a.k.a. RRM, RB (0.039); RRM_1: RNA recognition motif, (a.k.a. RRM, RB (1.9e−07); RRM_1: RNA recognition motif, (a.k.a. RRM, RB (3.9e−06); GO_MF:GO:0003723, RNA binding# (0.0); GO_BP:GO:0006397, mRNA processing# (0.0); GO_CC:GO:0005634, nucleus# (0.0) | 8 | 78.3 | 100935130 | 100939953 |
| 947 | COV1-like protein n = 4 Tax = Andropogoneae RepID = B6SMB8_MAIZE (1e−130); DUF502: Protein of unknown function (DUF502) (3.7e−35) | 8 | 78.3 | 100957806 | 100964937 |
| 948 | Serine/arginine rich splicing factor, putative n = 1 Tax = Ricinus communis RepID = B9T013_RICCO (4e−09); GO_MF:GO:0003676, nucleic acid binding# (7e−20) | 8 | 78.4 | 101025715 | 101026655 |
| 949 | Beta-galactosidase n = 1 Tax = Oryza sativa Indica Group RepID = B2Z6M9_ORYSI (0.0); Glyco_hydro_35: Glycosyl hydrolases family 35 (3.7e−155); Glyco_hydro_42: Beta-galactosidase (0.063); Glyco_hydro_2_N: Glycosyl hydrolases family 2, sugar binding domain (0.096); GO_MF:GO:0043169, cation binding# (0.0); GO_BP:GO:0008152, metabolic process# (0.0); GO_CC:GO:0048046, IDA#apoplast# (0.0) | 8 | 78.4 | 102164879 | 102171452 |
| 950 | Retrotransposon protein n = 1 Tax = Zea mays RepID = B6U894_MAIZE (1e−99); GO_MF:GO:0004386, helicase activity# (2e−35) | 8 | 78.5 | 101141978 | 101143455 |
| 951 | Potassium channel protein ZMK2 n = 1 Tax = Zea mays RepID = Q9SM12_MAIZE (0.0); Ion_trans: Ion transport protein (1.7e−21); Ion_trans_2: Ion channel (2.4e−16); cNMP_binding: Cyclic nucleotide-binding domain (5.1e−15); Ank: Ankyrin repeat (2.8e−08); Ank: Ankyrin repeat (1.1); Ank: Ankyrin repeat (0.00058); GO_MF:GO:0005249, voltage-gated potassium channel activity# (0.0); GO_BP:GO:0055085, transmembrane transport# (0.0); GO_CC:GO:0016021, integral to membrane# (0.0) | 8 | 78.5 | 102044140 | 102108633 |
| 952 | Universal stress protein family protein n = 2 Tax = Zea mays RepID = B6TUC5_MAIZE (1e−86); Usp: Universal stress protein family (6.9e−11); GO_BP:GO:0006950, response to stress# (1e−86) | 8 | 78.5 | 102135988 | 102138900 |
| 953 | BRASSINOSTEROID INSENSITIVE 1-associated receptor kinase 1, putative n = 1 Tax = Ricinus communis RepID = B9RDW7_RICCO (1e−141); Pkinase_Tyr: Protein tyrosine kinase (2.3e−28); Pkinase: Protein kinase domain (4.3e−36); GO_MF:GO:0005524, ATP binding# (0.0); GO_BP:GO:0006468, protein amino acid phosphorylation# (0.0); GO_CC:GO:0016021, integral to membrane# (1e−141) | 8 | 78.6 | 101176449 | 101179599 |
| 954 | Potassium channel protein ZMK2 n = 1 Tax = Zea mays RepID = Q9SM12_MAIZE (6e−49); GO_MF:GO:0005249, voltage-gated potassium channel activity# (6e−49); GO_BP:GO:0055085, transmembrane transport# (6e−49); GO_CC:GO:0016021, integral to membrane# (1e−141) | 8 | 78.6 | 102073137 | 102074215 |
| 955 | Cucumisin, putative n = 1 Tax = Ricinus communis RepID = B9R7A2_RICCO (0.0); Inhibitor_I9: Peptidase inhibitor I9 (9.8e−16); Peptidase_S8: Subtilase family (1e−10); PA: PA domain (0.0019); GO_MF:GO:0043086, negative regulation of catalytic activity# (0.0); GO_BP:GO:0043086, negative regulation of catalytic activity# (0.0); GO_CC:GO:0009505, IDA#expansin# (1e−124) | 8 | 78.7 | 101208361 | 101211017 |
| 956 | Putative polyprotein n = 1 Tax = Oryza sativa Japonica Group RepID = Q60DG5_ORYSJ (2e−20); GO_MF:GO:0008270, zinc ion binding# (2e−20); GO_BP:GO:0015074, DNA integration# (2e−20); GO_CC:GO:0005634, nucleus# (2e−17) | 8 | 78.7 | 101230093 | 101231548 |
| 957 | Beta-hydroxyacyl-ACP dehydratase n = 3 Tax = Andropogoneae RepID = B6TG22_MAIZE (1e−120); FabA: FabA-like domain (2.7e−53); GO_MF:GO:0016836, hydro-lyase activity# (1e−120); GO_BP:GO:0009245, lipid A biosynthetic process# (1e−120); GO_CC:GO:0005737, cytoplasm# (1e−120) | 8 | 78.7 | 101237227 | 101240359 |
| 958 | Cyclin-A1-1 n = 3 Tax = Xenopus RepID = CCA11_ORYSI (9e−44); Cyclin_N: Cyclin, N-terminal domain (1.1e−31); GO_BP:GO:0051301, cell division# (9e−44); GO_CC:GO:0005634, nucleus# (9e−44) | 8 | 78.8 | 101261002 | 101265381 |
| 959 | Putative uncharacterized protein Sb09g021460 n = 2 Tax = Andropogoneae RepID = C5YYN8_SORBI (1e−40) | 8 | 78.8 | 101266458 | 101267208 |
| 960 | Putative uncharacterized protein n = 1 Tax = Zea mays RepID = B6UH53_MAIZE (2e−86); DUF1218: Protein of unknown function (DUF1218) (2e−27) | 8 | 78.8 | 101274727 | 101275883 |
| 961 | Putative uncharacterized protein Sb09g021230 n = 3 Tax = Andropogoneae RepID = C5YYC2_SORBI (1e−51) | 8 | 78.9 | 101958089 | 101962101 |
| 962 | Coiled-coil domain-containing protein 47 n = 2 Tax = Xenopus RepID = CCD47_XENLA (1e−30); DUF1682: Protein of unknown function (DUF1682) (2.2e−127); GO_MF:GO:0005515, protein binding# (3e−30); GO_BP:GO:0055074, calcium ion homeostasis# (3e−30); GO_CC:GO:0016021, integral to membrane# (1e−115) | 8 | 79 | 101384099 | 101387219 |
| 963 | Aspartate aminotransferase n = 3 Tax = Andropogoneae RepID = B6TK79_MAIZE (0.0); Aminotran_1_2: Aminotransferase class I and II (2.4e−80); Beta_elim_lyase: Beta-eliminating lyase (0.037); GO_MF:GO:0030170, pyridoxal phosphate binding# (0.0); GO_BP:GO:0016847, 1-aminocyclopropane-1-carboxylate synthase activity# (0.0); GO_CC:GO:0009507, chloroplast# (1e−171) | 8 | 79 | 101389828 | 101413491 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 964 | Acetyltransferase, GNAT family protein n = 2 Tax = Andropogoneae RepID = B6UHR7_MAIZE (7e-74); Acetyltransf_1: Acetyltransferase (GNAT) family (3.6e-05); GO_MF:GO:0016740, transferase activity# (7e-74); GO_BP:GO:0008152, metabolic process# (7e-74) | 8 | 79 | 101417576 | 101419017 |
| 965 | OSJNBa0028I23.15 protein n = 1 Tax = Oryza sativa Japonica Group RepID = Q7XMG7_ORYSJ (1e-40); GO_MF:GO:0003964, RNA-directed DNA polymerase, group II intron encoded# (1e-40); GO_BP:GO:0006278, RNA-dependent DNA replication# (1e-40); GO_CC:GO:0016020, membrane# (1e-10) | 8 | 79 | 101424956 | 101425932 |
| 966 | Cytosolic factor-like protein n = 2 Tax = Oryza sativa RepID = Q8RYZ1_ORYSJ (3e-67); GO_MF:GO:0005215, transporter activity# (9e-47); GO_BP:GO:0006810, transport#(9e-47); GO_CC:GO:0005622, intracellular# (9e-47) | 8 | 79 | 101899837 | 101900533 |
| 967 | Peptide transporter PTR2-B n = 2 Tax = Zea mays RepID = B6SWT0_MAIZE (0.0); MFS_1: Major Facilitator Superfamily (4.6e-05); Sugar_tr: Sugar (and other) transporter (0.066); PTR2: POT family (8.1e-93); GO_MF:GO:0005215, transporter activity# (0.0); GO_BP:GO:0006857, oligopeptide transport# (0.0); GO_CC:GO:0016021, integral to membrane# (0.0) | 8 | 79.05 | 101425993 | 101431760 |
| 968 | Asparagine synthetase [glutamine-hydrolyzing] n = 1 Tax = Zea mays RepID = ASNS_MAIZE (2e-16); GO_MF:GO:0016874, ligase activity# (2e-16); GO_BP:GO:0008652, cellular amino acid biosynthetic process# (2e-16) | 8 | 79.1 | 101433486 | 101436392 |
| 969 | Amidophosphoribosyltransferase n = 2 Tax = Andropogoneae RepID = B6SRU6_MAIZE (0.0); GATase_2: Glutamine amidotransferases class-II (3.3e-34); Pribosyltran: Phosphoribosyl transferase domain (8.2e-17); GO_MF:GO:0016757, transferase activity, transferring glycosyl groups# (0.0); GO_BP:GO:0009116, nucleoside metabolic process# (0.0); GO_CC:GO:0005618, IDA#cell wall# (1e-174) | 8 | 79.1 | 101438279 | 101440231 |
| 970 | Retrotransposon protein, putative, unclassified n = 1 Tax = Oryza sativa Japonica Group RepID = Q2QQR5_ORYSJ (5e-30); zf-CCHC: Zinc knuckle (0.0083); GO_MF:GO:0008270, zinc ion binding# (2e-35); GO_BP:GO:0006278, RNA-dependent DNA replication# (5e-30) | 8 | 79.1 | 101476251 | 101478825 |
| 971 | Hydrolase, putative n = 1 Tax = Ricinus communis RepID = B9S718_RICCO (1e-67); DLH: Dienelactone hydrolase family (8e-10); Peptidase_S9: Prolyl oligopeptidase family (0.053); Abhydrolase_4: TAP-like protein (0.062); GO_MF:GO:0016787, hydrolase activity# (1e-67) | 8 | 79.1 | 101872864 | 101874328 |
| 972 | Gibberellin-regulated protein 2 n = 3 Tax = Andropogoneae RepID = B6SKV6_MAIZE (6e-32); GASA: Gibberellin regulated protein (4.5e-37); GO_MF:GO:0005515, protein binding# (1e-16); GO_BP:GO:0009826, IMP#unidimensional cell growth# (1e-16); GO_CC:GO:0009505, IDA#expansin# (1e-16) | 8 | 79.2 | 101507754 | 101508326 |
| 973 | Myb-like DNA-binding domain containing protein n = 2 Tax = Andropogoneae RepID = B4G152_MAIZE (6e-32); GO_MF:GO:0003677, DNA binding# (1e-34); GO_BP:GO:0045449, regulation of transcription# (1e-34); GO_CC:GO:0005634, nucleus# (1e-34) | 8 | 79.2 | 101817191 | 101818525 |
| 974 | Putative polyprotein n = 1 Tax = Oryza sativa Japonica Group RepID = Q75LZ2_ORYSJ (4e-40); GO_MF:GO:0003964, RNA-directed DNA polymerase, group II intron encoded# (4e-40); GO_BP:GO:0015074, DNA integration# (4e-40); GO_CC:GO:0005634, nucleus# (3e-39) | 8 | 79.2 | 101819090 | 101819454 |
| 975 | Retrotransposon protein, putative, unclassified n = 1 Tax = Oryza sativa Japonica Group RepID = Q2QTY9_ORYSJ (3e-77); GO_MF:GO:0004190, penicillopepsin activity# (8e-84); GO_BP:GO:0015074, DNA integration# (8e-84); GO_CC:GO:0005634, nucleus# (8e-84) | 8 | 79.2 | 101819470 | 101820719 |
| 976 | ATP binding protein n = 1 Tax = Zea mays RepID = B6U6Y9_MAIZE (0.0); dNK: Deoxynucleoside kinase (1.4e-25); GO_MF:GO:0016773, phosphotransferase activity, alcohol group as acceptor# (0.0); GO_BP:GO:0006139, nucleobase, nucleoside, nucleotide and nucleic acid metabolic process# (0.0); GO_CC:GO:0005634, nucleus# (1e-172) | 8 | 79.2 | 101822359 | 101828755 |
| 977 | Transposon protein, putative, CACTA, En/Spm sub-class n = 1 Tax = Oryza sativa Japonica Group RepID = Q2R337_ORYSJ (3e-18); GO_MF:GO:0004803, transposase activity# (2e-17); GO_BP:GO:0006313, transposition, DNA-mediated# (2e-17) | 8 | 79.3 | 101749333 | 101749489 |
| 978 | Transposon protein, putative, CACTA, En/Spm sub-class n = 1 Tax = Oryza sativa Japonica Group RepID = Q2QWY8_ORYSJ (2e-46); GO_MF:GO:0004803, transposase activity# (2e-29); GO_BP:GO:0006313, transposition, DNA-mediated# (2e-29) | 8 | 79.3 | 101749553 | 101750213 |
| 979 | Putative uncharacterized protein Sb01g018120 n = 1 Tax = Sorghum bicolor RepID = C5WX97_SORBI (1e-17) | 8 | 79.3 | 101751450 | 101752438 |
| 980 | Phosphoribosylanthranilate transferase n = 2 Tax = Andropogoneae RepID = B6UEE3_MAIZE (0.0); C2: C2 domain (2.1e-15); C2: C2 domain (2e-24); PRT_C: Plant phosphoribosyltransferase C-ter (1.2e-121); GO_MF:GO:0016740, transferase activity# (0.0); GO_CC:GO:0009507, chloroplast# (0.0) | 8 | 79.3 | 101754270 | 101757247 |
| 981 | Myb transcription factor n = 3 Tax = Oryza sativa RepID = Q5TKI8_ORYSJ (3e-60); Myb_DNA-binding domain (2.3e-05); GO_MF:GO:0003677, DNA binding# (2e-95); Myb_DNA-binding: Myb-like DNA-binding domain (5e-11); GO_BP:GO:0045449, regulation of transcription# (2e-95); GO_CC:GO:0005634, nucleus# (2e-95) | 8 | 79.3 | 101774593 | 101775500 |
| 982 | Clathrin assembly protein, putative n = 1 Tax = Ricinus communis RepID = B9SCP6_RICCO (1e-134); ANTH: ANTH domain (1.3e-92); ENTH: ENTH domain (0.019); GO_MF:GO:0030276, clathrin binding# (0.0); GO_BP:GO:0048268, IDA#clathrin coat assembly# (0.0); GO_CC:GO:0030118, clathrin coat# (0.0) | 8 | 79.35 | 102531812 | 102534027 |
| 983 | OSJNBa0088K19.7 protein n = 3 Tax = Oryza sativa RepID = Q7XU24_ORYSJ (1e-105); DUF668: Protein of unknown function (DUF668) (1.5e-47); GO_MF:GO:0016301, kinase activity# (1e-105); GO_BP:GO:0016301, kinase activity# (1e-105); GO_CC:GO:0005886, plasma membrane# (1e-169) | 8 | 79.5 | 101670238 | 101675867 |

TABLE 13-continued

Annotated coding sequences within the FSR-3.01 and FSR-8.01 regions.

| Gene ID | Annotation | Chr | MON Map cM† | Physical Map Position bp†† Start | End |
|---|---|---|---|---|---|
| 984 | Hexaprenyldihydroxybenzoate methyltransferase, putative n = 1 Tax = Ricinus communis RepID = B9S8D8_RICCO (2e–22); GO_BP:GO:0008152, metabolic process# (8e–27); GO_CC:GO:0005759, IEP#mitochondrial matrix# (5e–22) | 8 | 80.8 | 97281684 | 97282429 |
| 985 | Pentatricopeptide (PPR) repeat-containing protein-like n = 9 Tax = Oryza RepID = Q69XF8_ORYSJ (4e–82); PPR: PPR repeat (0.011); PPR: PPR repeat (9.4e–11); PPR: PPR repeat (5.1); GO_MF:GO:0005488, binding# (6e–43); GO_BP:GO:0055085, transmembrane transport# (6e–41); GO_CC:GO:0016020, membrane# (6e–41) | 8 | 80.9 | 102573183 | 102573785 |
| 986 | 60S ribosomal protein L36 n = 3 Tax = Zea mays RepID = B6TRR4_MAIZE (1e–23); Ribosomal_L36e: Ribosomal protein L36e (3.7e–14); GO_MF:GO:0003735, structural constituent of ribosome# (1e–23); GO_BP:GO:0006412, translation# (1e–23); GO_CC:GO:0030529, ribonucleoprotein complex# (1e–23) | 8 | 81 | 116533029 | 116534824 |
| 987 | Nodulin-like protein n = 1 Tax = Zea mays RepID = B6U1N6_MAIZE (0.0); Caa3_CtaG: Cytochrome c oxidase caa3 assembly fa (0.069); DUF6: Integral membrane protein DUF6 (2.6e–09); TPT: Triose-phosphate Transporter family (0.024); DUF6: Integral membrane protein DUF6 (0.0099); GO_CC:GO:0016020, membrane# (0.0) | 8 | 81.05 | 97286995 | 97289328 |
| 988 | 26S proteasome non-ATPase regulatory subunit 8 n = 4 Tax = Andropogoneae RepID = B4FCY9_MAIZE (4e–44); GO_MF:GO:0005488, binding# (1e–15); GO_BP:GO:0006508, proteolysis# (4e–44); GO_CC:GO:0005838, IDA#proteasome regulatory particle# (4e–44) | 8 | 81.1 | 115892831 | 115894124 |
| 989 | Putative uncharacterized protein n = 2 Tax = Zea mays RepID = B4FK11_MAIZE (1e–144); zf-C3HC4: Zinc finger, C3HC4 type (RING finger) (0.00067); GO_MF:GO:0046872, metal ion binding# (1e–144) | 8 | 81.1 | 115904453 | 115906293 |
| 990 | Putative uncharacterized protein Sb09g022420 n = 3 Tax = Andropogoneae RepID = C5YZ83_SORBI (0.0); TPR_2: Tetratricopeptide repeat (2.5); TPR_2: Tetratricopeptide repeat (8); TPR_2: Tetratricopeptide repeat (0.28); GO_MF:GO:0005488, binding# (1e–69) | 8 | 81.1 | 116022174 | 116026953 |
| 991 | Heat shock cognate 70 kDa protein n = 7 Tax = Magnoliophyta RepID = HSP7C_PETHY (0.0); HSP70: Hsp70 protein (0); MreB_Mbl: MreB/Mbl protein (0.0035); Hydantoinase_A: Hydantoinase/oxoprolinase (0.1); GO_MF:GO:0005524, ATP binding# (0.0); GO_BP:GO:0006950, response to stress# (0.0); GO_CC:GO:0048046, IDA#apoplast# (0.0) | 8 | 81.1 | 116617617 | 116621838 |
| 992 | Cysteinyl-tRNA synthetase n = 2 Tax = Zea mays RepID = B6SH65_MAIZE (0.0); tRNA-synt_1e: tRNA synthetases class I (C) (3e–164); tRNA-synt_1g: tRNA synthetases class I (M) (6.5e–05); GO_MF:GO:0005524, ATP binding# (0.0); GO_BP:GO:0006423, cysteinyl-tRNA aminoacylation# (0.0); GO_CC:GO:0005737, cytoplasm# (0.0) | 8 | 81.1 | 116620898 | 116625760 |
| 993 | Glycerol-3-phosphate acyltransferase 8 n = 3 Tax = Andropogoneae RepID = B6SWK2_MAIZE (1e–174); Acyltransferase: Acyltransferase (2.4e–06); GO_MF:GO:0008415, acyltransferase activity# (0.0); GO_BP:GO:0008152, metabolic process# (0.0); GO_CC:GO:0016021, integral to membrane# (1e–118) | 8 | 81.15 | 116118395 | 116120825 |
| 994 | Vrga1 n = 1 Tax = Aegilops ventricosa RepID = Q9SED7_AEGVE (2e–92); NB-ARC: NB-ARC domain (6e–56); NACHT: NACHT domain (0.042); GO_MF:GO:0005524, ATP binding# (0.0); GO_BP:GO:0006952, defense response# (0.0) | 8 | 81.2 | 104379532 | 104382266 |
| 995 | Putative uncharacterized protein n = 1 Tax = Zea mays RepID = B4FBY9_MAIZE (4e–12) | 8 | 81.2 | 115828221 | 115831895 |
| 996 | Putative uncharacterized protein Sb07g019100 n = 1 Tax = Sorghum bicolor RepID = C5YKI4_SORBI (1e–125); hATC: hAT family dimerisation domain (0.00027); GO_MF:GO:0046983, protein dimerization activity# (7e–53); GO_BP:GO:0015074, DNA integration# (5e–46); GO_CC:GO:0005622, intracellular# (3e–47) | 8 | 81.25 | 116199837 | 116201263 |
| 997 | Putative growth regulator n = 4 Tax = Malvoideae RepID = B2ZAU8_GOSAR (9e–88); DUF246: Plant protein family (3.9e–198); GO_CC:GO:0005794, IDA#Golgi apparatus# (7e–87) | 8 | 81.35 | 116425630 | 116442282 |
| 998 | Putative uncharacterized protein Sb01g035540 n = 1 Tax = Sorghum bicolor RepID = C5X0M0_SORBI (5e–12) | 8 | 81.4 | 115779956 | 115780594 |
| 999 | Importin beta 1 n = 3 Tax = Oryza sativa RepID = Q9ZWR5_ORYSJ (0.0); IBN_N: Importin-beta N-terminal domain (1e–23); HEAT: HEAT repeat (5.5); HEAT: HEAT repeat (0.013); HEAT: HEAT repeat (0.62); HEAT: HEAT repeat (0.025); HEAT: HEAT repeat (31); GO_MF:GO:0008565, protein transporter activity# (0.0); GO_CC:GO:0009507, chloroplast# (0.0) | 8 | 81.4 | 115785480 | 115791621 |
| 1000 | Flavonoid 3-monooxygenase n = 2 Tax = Zea mays RepID = B6TML3_MAIZE (0.0); p450: Cytochrome P450 (2.9e–93); GO_MF:GO:0046872, metal ion binding# (0.0); GO_BP:GO:0055114, oxidation reduction# (0.0); GO_CC:GO:0016021, integral to membrane# (1e–143) | 8 | 81.4 | 116203880 | 116209001 |
| 1001 | Osmotic avoidance abnormal protein, putative n = 1 Tax = Ricinus communis RepID = B9T259_RICCO (1e–159); Kinesin: Kinesin motor domain (1.2e–122); HHH: Helix-hairpin-helix motif (0.024); GO_MF:GO:0005524, ATP binding# (0.0); GO_BP:GO:0007018, microtubule-based movement# (0.0); GO_CC:GO:0005874, microtubule# (0.0) | 8 | 81.45 | 116420366 | 116424771 |

TABLE 13-continued

Annotated coding sequences within the FSR-3.01 and FSR-8.01 regions.

| Gene | | | MON Map | Physical Map Position bp†† | |
|---|---|---|---|---|---|
| ID | Annotation | Chr | cM† | Start | End |
| 1002 | Putative MURAZC n = 1 Tax = Zea mays RepID = Q8H6I1_MAIZE (7e−41); GO_MF:GO:0008270, zinc ion binding# (2e−43); GO_BP:GO:0006313, transposition, DNA-mediated# (2e−43) | 8 | 81.6 | 116399389 | 116399814 |

†cM = centiMorgans;
††bp = base pair of Arizona Genomics Institute B73 RefGen_v2 sequence.

What is claimed is:

1. A method of obtaining a corn plant with enhanced *Fusarium* stalk rot resistance, said method comprising:
   a) providing a population of corn plants;
   b) obtaining a DNA sample from at least one corn plant within said population;
   c) detecting in said DNA sample the presence of a *Fusarium* stalk rot resistance allele at a polymorphic locus within 5 cM of SEQ ID NO:93, wherein said locus comprises a nucleotide at position 151 of SEQ ID NO:93 that is associated with *Fusarium* stalk rot resistance, and wherein said nucleotide is an "A";
   d) selecting a corn plant from said population of corn plants based on the presence of the *Fusarium* stalk rot resistance allele;
   e) crossing the plant comprising the *Fusarium* stalk rot resistance allele with a second, different corn plant to produce progeny plants wherein at least one progeny plant comprises the *Fusarium* stalk rot resistance allele and exhibits enhanced *Fusarium* stalk rot resistance when compared to a plant lacking said allele.

2. The method of claim 1, wherein said segment is flanked by:
marker loci SEQ ID NO: 1 and SEQ ID NO: 100; or
marker loci SEQ ID NO: 90 and SEQ ID NO: 2.

3. The method of claim 1, wherein said polymorphic locus comprises a nucleic acid sequence selected from the group consisting of SEQ ID NO: 1, SEQ ID NO: 2, SEQ ID NO: 3, SEQ ID NO: 87, SEQ ID NO: 88, SEQ ID NO: 89, SEQ ID NO: 90, SEQ ID NO: 91, SEQ ID NO: 92, SEQ ID NO: 94, SEQ ID NO: 95, SEQ ID NO: 96, SEQ ID NO: 97, SEQ ID NO: 98, SEQ ID NO: 99, and SEQ ID NO: 100.

4. The method of claim 1, further defined as comprising selecting from said population at least two plants, thereby forming a population of corn plants comprising said allele and enhanced *Fusarium* stalk rot resistance compared to a plant lacking said allele.

5. The method of claim 1, wherein said *Fusarium* stalk rot resistance allele was introgressed into said population of corn plants from a starting plant or population of corn plants containing said allele.

6. The method of claim 1, wherein producing the progeny plant comprises marker-assisted selection for *Fusarium* stalk rot resistance.

7. The method of claim 1, wherein the progeny plant is an F2-F6 progeny plant.

8. The method of claim 1, wherein producing the progeny plant comprises backcrossing.

\* \* \* \* \*

SEQUENCE LISTING

<160> NUMBER OF SEQ ID NOS: 165

<210> SEQ ID NO 1
<211> LENGTH: 686
<212> TYPE: DNA
<213> ORGANISM: Zea mays
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t
<220> FEATURE:
<221> NAME/KEY: misc_feature
<222> LOCATION: (650)..(651)
<223> OTHER INFORMATION: n is a, c, g, or t
<220> FEATURE:
<221> NAME/KEY: misc_feature
<222> LOCATION: (657)..(663)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (673)..(683)
<223> OTHER INFORMATION: n is a, c, g, or t

<400> SEQUENCE: 1

```
ttcccattcc catcaagcaa gcacattctc acttttccag catcaaggca tggagtatgg      60
caacggatga caccttgctg nataatttcc acacataacct taacatcacc aaacagcact    120
tgccatgaac tgtgaggggg attgcaaagg aagtctccta caatgataac ctgcattaca    180
ttttcataag tccccaacca ttgtagttct cggcacaggt ttgtccaaac tgataagttc    240
ttttttgttt cnttgggttc tctggactca ggcttcaagc tttcagatca aaatacttaa    300
gtattactcc tcaattctga tttctaaaag taacttgatt ttagattttg ccactcgtat    360
atatatgcag gtcattatag gattctagna acccgtcccc cattttttct tcttatgccc    420
atgctaaaca atctactaat cacagttaaa ggtcatttga atcatttcaa cacttcatta    480
atttntatgc acaagcctaa aacaacttac atttggcatc agagtatgta agtaccacat    540
gaagatatgt tttgttcaat attatgccan tagaaaagaa gaagaagaa tgcatgttgc     600
agtaatttaa tcaagcctag taactcgtac tcatatcata cctnngtacn ntcatannnn    660
nnngctgntn ctnnnnnnnn nnnatg                                          686
```

```
<210> SEQ ID NO 2
<211> LENGTH: 254
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t

<400> SEQUENCE: 2
agggtagtat atgtgcattc atcgtttttc attagccttg attagnccaa agtgatagtt     60
tatgcttggt catcgagagt ttggtgatca gacgatgaag attgtgagtg cacaactta    120 agaggtaaac agttgtgtga ttcaacatag tagagtgaca aatgatcgac tcatagagag   180
ccctcgtatg agacgtgagc gacactcctt cataggtgtt ctaataagga ttagttagaa   240
gtgtcaactc ttga                                                      254

<210> SEQ ID NO 3
<211> LENGTH: 391
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (277)..(279)
<223> OTHER INFORMATION: n is a, c, g, or t
<220> FEATURE:
<221> NAME/KEY: misc_feature
<222> LOCATION: (298)..(300)
<223> OTHER INFORMATION: n is a, c, g, or t
<220> FEATURE:
<221> NAME/KEY: misc_feature
<222> LOCATION: (329)..(332)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t

<400> SEQUENCE: 3
gcttgccaat tcaactgtag agatcatgac acagttcgat gaatttgang tgcctgcagc     60
tctttataca gcttaaaatg caattgttgc aatagcagaa ggtgctcgcg tgagcaccta   120
gaaccaggca catttatcct gggatattca atcatttgta catgtacact tgaaagagaa   180
ctgacatctt ttcaacctga aaatttataa gctttatgta accgtgaagg tcggatattg   240
cacatgtaaa attgggcttt tcccctagac ccanggnnna gaaaaattaa gaaactcnnn   300
gtgattcata tggacccagc tgcactaann nnctgctgtg ccactcagct nattaccta    360 aaattattac ctgtgttgtt gtcctttgct c                                   391

<210> SEQ ID NO 4
<211> LENGTH: 788
<212> TYPE: DNA
<213> ORGANISM: Zea mays
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (721)..(721)
```

<223> OTHER INFORMATION: n is a, c, g, or t
<220> FEATURE:
<221> NAME/KEY: misc_feature
<222> LOCATION: (736)..(741)
<223> OTHER INFORMATION: n is a, c, g, or t
<220> FEATURE:
<221> NAME/KEY: misc_feature
<222> LOCATION: (746)..(757)
<223> OTHER INFORMATION: n is a, c, g, or t
<220> FEATURE:
<221> NAME/KEY: misc_feature
<222> LOCATION: (768)..(773)
<223> OTHER INFORMATION: n is a, c, g, or t

<400> SEQUENCE: 4

```
gtttgcttcg cagctgtttg taggacatgg agagaaatgt gtaaagagat tgtgttgagc    60
ccggagtttt gtggcaagct caccttccct gtgtctctaa aacaggtaag ggaaagaaca   120
atcaacctcc ttcagttcga gcaatcttga accggatgtt gagaattgcc tccaaacctt   180
gagcagcgga tatctatatc tccctctggt ccttgatata ttgcttgttt cttttgacag   240
cctggtcctc gagatggaaa tacaatggtc cagtgtttta taaagaggaa taagtcaaaa   300
tccacttacc atctctacnt gtgccttagc aatggtacgt cacatgattt gcacattttc   360
aagattcaat agcaatgttc ataagtttat actgttttat tggagcatat gggattattg   420
ttagccagat atgtttctcc tttttgagtg tttgattttg tgattatatc tcgtatcttg   480
taatcctcat aaattctgaa attgtgtggc cttttaatct catattcatg agagtattta   540
cagttaaatg atcaatggtc tgtttatctt gtttcacttt atcaaatttg ttgactcatt   600
ttcttctgtg cacagttgtt acttcagaaa gtgggaaatt cctcttatca gctaaacgac   660
accgcaaaac cacatgcacc gagtacacta tatcaatgga ttctggcaac atctcaagat   720
ngaaaagaac ctacannnnn naaatnnnnn nnnnnnnatg ttttgannn nntgttctt   780
gtttcccc                                                             788
```

<210> SEQ ID NO 5
<211> LENGTH: 679
<212> TYPE: DNA
<213> ORGANISM: Zea mays
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (634)..(635)
<223> OTHER INFORMATION: n is a, c, g, or t
<220> FEATURE:
<221> NAME/KEY: misc_feature
<222> LOCATION: (638)..(644)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (648)..(649)
<223> OTHER INFORMATION: n is a, c, g, or t
<220> FEATURE:
<221> NAME/KEY: misc_feature
<222> LOCATION: (653)..(654)
<223> OTHER INFORMATION: n is a, c, g, or t
<220> FEATURE:
<221> NAME/KEY: misc_feature
<222> LOCATION: (660)..(669)
<223> OTHER INFORMATION: n is a, c, g, or t
<220> FEATURE:
<221> NAME/KEY: misc_feature
<222> LOCATION: (671)..(676)
<223> OTHER INFORMATION: n is a, c, g, or t

<400> SEQUENCE: 5

```
ggaacacgaa caaacacata tatgaaaagg tgagatgtcg catcagngtt gttccttgtc    60
ttgctatgct gcacatgagc acattggcgc ttccantatc ttgaatgaca gggcattctc   120
ggatcatgca gttgcatcta ttctagtgct gttcttctgt cttttcccag ttatattcta   180
gtntggacaa ttgctgaaag ttcccagntg ctgcttaagc ttaatctaat gaattcttgt   240
ttttatcaaa gtttggagtt tagatagtgt agcatttatt ttcatactga tggtgtattg   300
tccttatcat ttcttttnaa tcttcagcca aacctaangc aacaagaaat ctgatattat   360
taagaataag cagcctctat cctgaaagag nggggnaaa aggaagggtg acantatcat    420
ctgtgatcgt gtttgttgca aatcttcttc atatgcacct ttataatcta aatatactgc   480
gctcctagcg actttgttca ttgcaaggct ttgtgtgaaa tcattgctcc aatcatgaat   540
ctaggaaata tactttaagc tctaaaataa gtgcatttat agaatgtttt ggagacatca   600
atgctactat anaattacat atatacactc ctanngtnnn nnnntntnnt aanngcactn   660
nnnnnnnna nnnnnncaa                                                 679
```

<210> SEQ ID NO 6
<211> LENGTH: 558
<212> TYPE: DNA
<213> ORGANISM: Zea mays
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:

```
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t

<400> SEQUENCE: 6
ggttgtacca gagttgggta tgaaaatcga ggtgcctgaa attattggat ctggggaggt    60
tattgatgcc gcagaagcng agacntgtgg gaagaagatt gacaagaagg gggatgctgg   120
tgcccgtgga agagaggtat ttgccaatgt gagtgccaag aggaagagga ataagaaggn   180
gcaggttgag gatgatgttg cgatgcagga agaagtccag gtggagatan agaaaaagaa   240
gaggaaaagc attgtgattt ctgctaatga cagccagatg gctggcaaga agggtgaaaa   300
gaagggcaaa cgtggtttgg aaaataaggt gaacgaagcc agtttggaca acaagaaggt   360
taagatgggg aagactgagc agaggaagaa gaagagcatg aacggtgatg gtgaagtcgg   420
tactgaggaa atgcagggag ataagaagat caaggtggag aaatcagatg tcaagatcaa   480
gaagttgagg accaggataa gagtataagg ttgcagttga tatcactgtt ggaggtgcct   540
cttaaaatat tcagntct                                                 558

<210> SEQ ID NO 7
<211> LENGTH: 472
<212> TYPE: DNA
<213> ORGANISM: Zea mays
<220> FEATURE:
<221> NAME/KEY: misc_feature
<222> LOCATION: (263)..(263)
<223> OTHER INFORMATION: n is a, c, g, or t

<400> SEQUENCE: 7
ggttgcatca acatcggctg gcgagtagta gttggtacag cttccaaaag aatgcgctga    60
ttgcctactt gttgtataca tacagcagag tgttttgaac caacaaagag atcaaaaaat   120
cggatttctg tatatgcagc ctctggcaat tgaatctctc agttcccgt atatgttcga   180 atcctaccaa gcaaagggaa atccaggcca gagctggaaa catcctatca agcaaacact   240
ttacaagaaa ccttctacta tcnagattgc ttggtgtatg ttcatccctg cagatgcaat   300
aggctgtgct tggttacatg agttacagag agattactgc aaacactgta agtttcgggt   360
gtttacctat acaacaggaa tcttcagaag aataagtgag cagagataca ggcacactga   420
gatggcgatc ccagcaacga aattttggta cagacggcta ttatccctac tg           472

<210> SEQ ID NO 8
<211> LENGTH: 364
<212> TYPE: DNA
<213> ORGANISM: Zea mays
<220> FEATURE:
<221> NAME/KEY: misc_feature
<222> LOCATION: (132)..(132)
<223> OTHER INFORMATION: n is a, c, g, or t

<400> SEQUENCE: 8
ataattgaaa ctaaacttta gcacttcaat tcatatagct aaagtttagt aggaagctaa    60
agtttatccc gtgacattga aacgggggcct aagatatatt tttccgcggt cagaggggag  120
agcaactgat antcgaaagt gggattcagt ctgggcatat gtgcaatgat attacagact  180
```

```
ttggacaagt catcagtcat gggtgattgc ctttgtgttg cttccatttt cgaccatctc    240
atcctacgat ctttccaagt tatctttaat gaggtgtgtc gtgtggtcta tgtttcctgc    300
ctctggatct tttatgtaag agaaacggac ttgtaaaaca gttccaaatt atcatatacc    360
aggc                                                                 364
```

<210> SEQ ID NO 9
<211> LENGTH: 679
<212> TYPE: DNA
<213> ORGANISM: Zea mays
<220> FEATURE:
<221> NAME/KEY: misc_feature
<222> LOCATION: (538)..(538)
<223> OTHER INFORMATION: n is a, c, g, or t

<400> SEQUENCE: 9

```
ttttgtaccc agcagaccag aagagtccaa acgggaaact acggtataac aaaggcaaca     60
atcttttttt tacttactat tattactatt cccggaactg tagtttagct tcctgtcctc    120
acattggttg gttctatgtg gaattgcagc gttctgtatg aagtcttccc gatgtcattc    180
ctgatggaac aagctggagg ccaggctttc acaggcaaac aacgggtgtg tttcagtttc    240
cctttctcag accccaatcc ccaactgaaa atcttgatg ctagagctat cacatttgcc    300
tgagatatca gggggatttt tcaacacttt tacaggttga aattattgag aaagggcac    360 tattttaaca tgccatgttt ttttttacca gtggttggca ttgcatataa ctgaaaatgc    420
tcctgctaaa tttataatgc aggcccttga acttgctccc gctaaacttc acgacagatc    480
cccagtgttc ctcgggagct acgatgacgt tgaggagatc aaagcactgt acgcttcnat    540
gtcaaacagc ggttgacctt tctgcctgag gaaacgagcg agatcaaaag caccgtacgc    600
ttcagagtca actgcttgat ctttatagat tgtaataaaa taataaaaga gtttgtaaaa    660
aaaacaacaa cactgcttg                                                 679
```

<210> SEQ ID NO 10
<211> LENGTH: 397
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t

<400> SEQUENCE: 10

```
cctagaggtg gtccgcttac cagtttacta tccttctgag caagaaaang atgatcctaa     60
gctctatgca aacaatgtac ggaaactgat ggcagtggag gtatcttaaa cacttgaaaa    120
tgattaatta cattgaatgg tattgctgta caagtgtttg gtattattgt aaccatgtgg    180
taatcttgat ttcttttcag ggaaacttga ttctttcaga ccttgggctg gcggagaagc    240
gagtgtacca tgccgcactg aatggtaata gtctagctcg tgctttacat cagaaagatg    300
attgaaatgc catgctatcg tgcttccata atactggctt gcttgtaact gtgtgcttgc    360
ttgtgcatcg tcatggttga gaggaatgtc gtgaata                             397
```

<210> SEQ ID NO 11
<211> LENGTH: 381
<212> TYPE: DNA
<213> ORGANISM: Zea mays
<220> FEATURE:
<221> NAME/KEY: misc_feature
<222> LOCATION: (139)..(139)

<223> OTHER INFORMATION: n is a, c, g, or t

<400> SEQUENCE: 11

```
agactctggc tgggtacctt cccaaccgcg gaggatgcag ctagggccta tgatgaggca    60
gccagagcga tgtatggaga cttggcacgg actaacttcc ccggacagga tgcaacaacc   120
tctgcccaag ctgctctanc atcgacctct gcccaggctg ctccaacagc tgttgaagct   180
cttcagactg gcacgtcatg cgagtcgaca acgacatcaa atcactcgga catcgcatcc   240
acctcacaca agcctgagcc tgaagcctct gacatctcga gctccctaaa ggaaaaatgt   300
ccagctggat catgtggtat ccaagagggt acacccagtg tagctgacaa ggaggtcttt   360
gggccgttgg agcctatcac a                                             381
```

<210> SEQ ID NO 12
<211> LENGTH: 201
<212> TYPE: DNA
<213> ORGANISM: Zea mays
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 12

```
taccccttaga aagatcctgg cttcgccact ggctagttct attaaaaaan ctttaggcca    60
tacaagtgaa ttaaaatgga ctaaagcccct gtttggcaca ncttattttc agcttcttca   120
caaatttaag cagaagttct gccaaacagg tagcttctgc agcagcttat cagttcagct   180
gcttctcaga atacactaaa a                                              201
```

<210> SEQ ID NO 13
<211> LENGTH: 695
<212> TYPE: DNA
<213> ORGANISM: Zea mays
<220> FEATURE:
<221> NAME/KEY: misc_feature
<222> LOCATION: (551)..(551)
<223> OTHER INFORMATION: n is a, c, g, or t

<400> SEQUENCE: 13

```
tacgggggca tattttttgta cccagcagac cagaagagtc caaacgggaa actacggtat    60
aacaaaggca acaatctttt ttttactaac tattattact actcccggaa ctgtagttta   120
gcttcctgtc ctcacattgg ttggttctat gtggaattgc agcgttctgt atgaagtctt   180
cccgatgtca ttcctgatgg aacaagctgg aggccaggct ttcacaggca acaacgggt    240
gtgtttcagt ttccctttct cagaccccaa tccccaactg aaaaatcttg atgctagagc   300
tatcacatct gcctgagata tcaggggat ttttcaacac ttttacaggt tgaaattatt    360
gagaaaaggg cactatttta acatgccatg ttttttttta ccagtggttg gcattgcata   420
taactgaaaa tgctcctgct aaatttataa tgcaggccct tgaacttgct cccgctaaac   480
ttcacgacag atccccagtg ttcctcggga gctacgatga cgttgaggag atcaaagcac   540
tgtacgcttc natgtcaaac agcggttgac ctttctgcct gaggaaacga gcgagatcaa   600
aagcaccgta cgcttcagag tcaactgctt gatctttata gattgtaata aaataataaa   660
agagtttgta aaaaaaacaa caacactgct tgatc                               695
```

<210> SEQ ID NO 14
<211> LENGTH: 201
<212> TYPE: DNA
<213> ORGANISM: Zea mays
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 14

```
cgagggcctc ggtagcctcc tcttcgctct ngaacaaaat gagagcctgc ctcttgccat      60
tcacctcgaa tagcttcgtg ttgagaacag tgccgtgctc ngacacatgg ttcaggattg     120
cttcctcaga gatatcttga gggagggcag aaatgtggat catcttcgtt ggagagcagc     180
aatgtcggta gttcttgacc a                                               201
```

<210> SEQ ID NO 15
<211> LENGTH: 1443
<212> TYPE: DNA
<213> ORGANISM: Zea mays
<220> FEATURE:
<221> NAME/KEY: misc_feature
<222> LOCATION: (615)..(695)
<223> OTHER INFORMATION: n is a, c, g, or t
<220> FEATURE:
<221> NAME/KEY: misc_feature
<222> LOCATION: (968)..(968)
<223> OTHER INFORMATION: n is a, c, g, or t

<400> SEQUENCE: 15

```
aagaggagca tacagatctg tagttgtaaa agaaaaaaca gttagttacc actgtatcgc      60
ttttgatacg agattcagat tcaataagcc aaaaagattt cacatgtacc catcaagaaa     120
agctattaat cttttttatt tttctgaaga acgagaatat aaaaaaacag ctaggttctg     180
tggccttgca aacaatcta gaaacaaaat gttaagtatt tggaaaaaat acgtgccagc      240
agtcagcaca tcacaagtaa ttagtagcag gtccaatttc aaaaacatgg aaatggtgga     300
ccatctcttg atccataaat atgaagacaa agttttgatg tcctgacaat aactgccaac     360
agaacaatct ccaggtactc gaagcaaatc accgaatcac ttttccattc aaccaactt      420
gctgccgaaa attgacctac tttagcaggg attgttgaat tggtacccaa tacaatgcag     480
tagcataaag tgccaactct ttgttggatt tatagatgca tatgtatttt ctctctacct     540
ggagggtttc ttcgtaaatg taaacttgta tatttgtccc ttttgggcct tggaaaagaa     600
ctgatcttat tttannnnnn nnnnnnnnnn nnnnnnnnnn nnnnnnnnnn nnnnnnnnnn     660
nnnnnnnnnn nnnnnnnnnn nnnnnnnnnn nnnnccttc cacctgaaac ctagtaccta     720
ttttacattt aaccccttcc atatgaatct ttgaatctaa attggatgcc tggatggttt     780
aattgcacac ttgcactaag tgggtgattg cacaggatat gtcccctaa ttctataagg      840
ctactaatgt ggaagtgggc aatttgtgac accagtgacc aaggtcttat gctatgggag     900
aacctggtaa agcatgtttg cataatgttg tcgtcaaatc aaaaattgca tatatcacat     960
agcaaacntt catctttcca gtagagaagg gctaaatcat gattcattaa actaagaagc    1020
atttacctga agtaagggtt ggatcatgtt ctcttgtaga atgcagtaca acagtaccag    1080
taagcacagt aagaaaccca caaatctcag aggcaatact gcttatactc tgcccagacc    1140
agtcctagtt gtaaatttgt aatcacaaaa ccttagttca gcttcagcaa gaaacaaaaa    1200
```

```
tagttggagt ttatggaagt tttccaaaat tagaataoct tgaacattat ggcacttgcc    1260
aaaattgtga gggatgtaaa catcgcatag tagatgggag aaacaactgc agtattgaaa    1320
gtatccaatg cctgaaagtt taacatgatg tggaaatgca tatcaacatc gtaaatattg    1380
ctacctaaat tttaaagtta atgctggctg taccttgttc aggtaaatta actgaataat    1440
tat                                                                 1443

<210> SEQ ID NO 16
<211> LENGTH: 440
<212> TYPE: DNA
<213> ORGANISM: Zea mays
<220> FEATURE:
<221> NAME/KEY: misc_feature
<222> LOCATION: (58)..(58)
<223> OTHER INFORMATION: n is a, c, g, or t

<400> SEQUENCE: 16
acatcagtgg gatatggaat gtgcatatta gaattgttat agtttgttag ttgcgtantt     60
aatacatgta tgtttcagt tatatatatt agacctttat aagaaacaca actctgtata    120
tttgcaagta tggaacgtgg ccgacaatat tatttacac caggaggtgc cttagcagca    180
caggtggcgc cttagtctgg ttcctgttct agtaaggctg catacaatgc attcttcttt    240
gtgtccatca gtttgtgcc ttggaggaga atttggagat cctcggcaac cctggggtgt    300 aaatttttt tgtgtcttgc tgtcaaaaag tggtctggat ggctaatcaa aattgtacaa    360
acaatattgt acaaacatag tttaacgcat cctgctgcta gcttattgtg tgatcaagct    420
gaagagacca tcctgcatat                                               440

<210> SEQ ID NO 17
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 17
tgaaagagca ctccgagagt gccacaactc ccgccgccgt gatcgtcgcc acgcccagga     60
gcgcgagcgg gaacaagtcg agcaggacgt taggctccaa ngtgagaatc cacttcttgc    120
tcagaaccta ttccattact ttgctcgagc actgaatatg ccaagcgagg ttggaggggt    180
cctggctcag atcgccaatg g                                             201

<210> SEQ ID NO 18
<211> LENGTH: 21
<212> TYPE: DNA
<213> ORGANISM: Zea mays

<400> SEQUENCE: 18
tggagtatgg caacggatga c                                              21

<210> SEQ ID NO 19
<211> LENGTH: 29
<212> TYPE: DNA
<213> ORGANISM: Zea mays

<400> SEQUENCE: 19
ggtagtatat gtgcattcat cgttttca                                       29
```

```
<210> SEQ ID NO 20
<211> LENGTH: 27
<212> TYPE: DNA
<213> ORGANISM: Zea mays

<400> SEQUENCE: 20
gccaattcaa ctgtagagat catgaca                                    27

<210> SEQ ID NO 21
<211> LENGTH: 31
<212> TYPE: DNA
<213> ORGANISM: Zea mays

<400> SEQUENCE: 21
ggtccagtgt tttataaaga ggaataagtc a                               31

<210> SEQ ID NO 22
<211> LENGTH: 22
<212> TYPE: DNA
<213> ORGANISM: Zea mays

<400> SEQUENCE: 22
tgtcttgcta tgctgcacat ga                                         22

<210> SEQ ID NO 23
<211> LENGTH: 23
<212> TYPE: DNA
<213> ORGANISM: Zea mays

<400> SEQUENCE: 23
aatgtgagtg ccaagaggaa gag                                        23

<210> SEQ ID NO 24
<211> LENGTH: 25
<212> TYPE: DNA
<213> ORGANISM: Zea mays

<400> SEQUENCE: 24
ccagagctgg aaacatccta tcaag                                      25

<210> SEQ ID NO 25
<211> LENGTH: 25
<212> TYPE: DNA
<213> ORGANISM: Zea mays

<400> SEQUENCE: 25
agatatattt ttccgcggtc agagg                                      25

<210> SEQ ID NO 26
<211> LENGTH: 23
<212> TYPE: DNA
<213> ORGANISM: Zea mays

<400> SEQUENCE: 26
ctacgatgac gttgaggaga tca                                        23

<210> SEQ ID NO 27
<211> LENGTH: 25
<212> TYPE: DNA
<213> ORGANISM: Zea mays

<400> SEQUENCE: 27
gtccgcttac cagtttacta tcctt                                      25
```

<210> SEQ ID NO 28
<211> LENGTH: 20
<212> TYPE: DNA
<213> ORGANISM: Zea mays

<400> SEQUENCE: 28
cggacaggat gcaacaacct                                           20

<210> SEQ ID NO 29
<211> LENGTH: 27
<212> TYPE: DNA
<213> ORGANISM: Zea mays

<400> SEQUENCE: 29
tcgccactgg ctagttctat taaaaaa                                   27

<210> SEQ ID NO 30
<211> LENGTH: 23
<212> TYPE: DNA
<213> ORGANISM: Zea mays

<400> SEQUENCE: 30
ctacgatgac gttgaggaga tca                                       23

<210> SEQ ID NO 31
<211> LENGTH: 25
<212> TYPE: DNA
<213> ORGANISM: Zea mays

<400> SEQUENCE: 31
cgaatagctt cgtgttgaga acagt                                     25

<210> SEQ ID NO 32
<211> LENGTH: 26
<212> TYPE: DNA
<213> ORGANISM: Zea mays

<400> SEQUENCE: 32
gcatgtttgc ataatgttgt cgtcaa                                    26

<210> SEQ ID NO 33
<211> LENGTH: 25
<212> TYPE: DNA
<213> ORGANISM: Zea mays

<400> SEQUENCE: 33
catcagtggg atatggaatg tgcat                                     25

<210> SEQ ID NO 34
<211> LENGTH: 21
<212> TYPE: DNA
<213> ORGANISM: Zea mays

<400> SEQUENCE: 34
caagtcgagc aggacgttag g                                         21

<210> SEQ ID NO 35
<211> LENGTH: 25
<212> TYPE: DNA
<213> ORGANISM: Zea mays

<400> SEQUENCE: 35
tgctgtttgg tgatgttaag gtatg                                     25

```
<210> SEQ ID NO 36
<211> LENGTH: 25
<212> TYPE: DNA
<213> ORGANISM: Zea mays

<400> SEQUENCE: 36
ccaaactctc gatgaccaag cataa                                       25

<210> SEQ ID NO 37
<211> LENGTH: 18
<212> TYPE: DNA
<213> ORGANISM: Zea mays

<400> SEQUENCE: 37
tcacgcgagc accttctg                                               18

<210> SEQ ID NO 38
<211> LENGTH: 24
<212> TYPE: DNA
<213> ORGANISM: Zea mays

<400> SEQUENCE: 38
tgcaaatcat gtgacgtacc attg                                        24

<210> SEQ ID NO 39
<211> LENGTH: 20
<212> TYPE: DNA
<213> ORGANISM: Zea mays

<400> SEQUENCE: 39
gatccgagaa tgccctgtca                                             20

<210> SEQ ID NO 40
<211> LENGTH: 20
<212> TYPE: DNA
<213> ORGANISM: Zea mays

<400> SEQUENCE: 40
ctgcatcgca acatcatcct                                             20

<210> SEQ ID NO 41
<211> LENGTH: 23
<212> TYPE: DNA
<213> ORGANISM: Zea mays

<400> SEQUENCE: 41
ctgcagggat gaacatacac caa                                         23

<210> SEQ ID NO 42
<211> LENGTH: 24
<212> TYPE: DNA
<213> ORGANISM: Zea mays

<400> SEQUENCE: 42
ccatgactga tgacttgtcc aaag                                        24

<210> SEQ ID NO 43
<211> LENGTH: 22
<212> TYPE: DNA
<213> ORGANISM: Zea mays

<400> SEQUENCE: 43
```
cagaaaggtc aaccgctgtt tg                                              22

<210> SEQ ID NO 44
<211> LENGTH: 25
<212> TYPE: DNA
<213> ORGANISM: Zea mays

<400> SEQUENCE: 44
catcagtttc cgtacattgt ttgca                                           25

<210> SEQ ID NO 45
<211> LENGTH: 20
<212> TYPE: DNA
<213> ORGANISM: Zea mays

<400> SEQUENCE: 45
cgtgccagtc tgaagagctt                                                 20

<210> SEQ ID NO 46
<211> LENGTH: 22
<212> TYPE: DNA
<213> ORGANISM: Zea mays

<400> SEQUENCE: 46
ctgtttggca gaacttctgc tt                                              22

<210> SEQ ID NO 47
<211> LENGTH: 22
<212> TYPE: DNA
<213> ORGANISM: Zea mays

<400> SEQUENCE: 47
cagaaaggtc aaccgctgtt tg                                              22

<210> SEQ ID NO 48
<211> LENGTH: 23
<212> TYPE: DNA
<213> ORGANISM: Zea mays

<400> SEQUENCE: 48
gccctccctc aagatatctc tga                                             23

<210> SEQ ID NO 49
<211> LENGTH: 27
<212> TYPE: DNA
<213> ORGANISM: Zea mays

<400> SEQUENCE: 49
catgatttag cccttctcta ctggaaa                                         27

<210> SEQ ID NO 50
<211> LENGTH: 40
<212> TYPE: DNA
<213> ORGANISM: Zea mays

<400> SEQUENCE: 50
gcaaatatac agagttgtgt ttcttataaa ggtctaatat                           40

<210> SEQ ID NO 51
<211> LENGTH: 25
<212> TYPE: DNA
<213> ORGANISM: Zea mays

<400> SEQUENCE: 51

```
gctcgagcaa agtaatggaa taggt                                            25

<210> SEQ ID NO 52
<211> LENGTH: 15
<212> TYPE: DNA
<213> ORGANISM: Zea mays

<400> SEQUENCE: 52
accttgctgg ataat                                                       15

<210> SEQ ID NO 53
<211> LENGTH: 18
<212> TYPE: DNA
<213> ORGANISM: Zea mays

<400> SEQUENCE: 53
cttgattaga ccaaagtg                                                    18

<210> SEQ ID NO 54
<211> LENGTH: 15
<212> TYPE: DNA
<213> ORGANISM: Zea mays

<400> SEQUENCE: 54
caggcacctc aaatt                                                       15

<210> SEQ ID NO 55
<211> LENGTH: 17
<212> TYPE: DNA
<213> ORGANISM: Zea mays

<400> SEQUENCE: 55
ctaaggcaca ggtagag                                                     17

<210> SEQ ID NO 56
<211> LENGTH: 16
<212> TYPE: DNA
<213> ORGANISM: Zea mays

<400> SEQUENCE: 56
aagatattgg aagcgc                                                      16

<210> SEQ ID NO 57
<211> LENGTH: 15
<212> TYPE: DNA
<213> ORGANISM: Zea mays

<400> SEQUENCE: 57
cctgctcctt cttat                                                       15

<210> SEQ ID NO 58
<211> LENGTH: 19
<212> TYPE: DNA
<213> ORGANISM: Zea mays

<400> SEQUENCE: 58
cttctactat caagattgc                                                   19

<210> SEQ ID NO 59
<211> LENGTH: 17
<212> TYPE: DNA
<213> ORGANISM: Zea mays
```

```
<400> SEQUENCE: 59
ccactttcga gtatcag                                                    17

<210> SEQ ID NO 60
<211> LENGTH: 18
<212> TYPE: DNA
<213> ORGANISM: Zea mays

<400> SEQUENCE: 60
cactgtacgc ttcaatgt                                                   18

<210> SEQ ID NO 61
<211> LENGTH: 19
<212> TYPE: DNA
<213> ORGANISM: Zea mays

<400> SEQUENCE: 61
cttaggatca tcttttct                                                   19

<210> SEQ ID NO 62
<211> LENGTH: 16
<212> TYPE: DNA
<213> ORGANISM: Zea mays

<400> SEQUENCE: 62
ctgctctagc atcgac                                                     16

<210> SEQ ID NO 63
<211> LENGTH: 16
<212> TYPE: DNA
<213> ORGANISM: Zea mays

<400> SEQUENCE: 63
ttggcacagc ttattt                                                     16

<210> SEQ ID NO 64
<211> LENGTH: 18
<212> TYPE: DNA
<213> ORGANISM: Zea mays

<400> SEQUENCE: 64
cactgtacgc ttcaatgt                                                   18

<210> SEQ ID NO 65
<211> LENGTH: 17
<212> TYPE: DNA
<213> ORGANISM: Zea mays

<400> SEQUENCE: 65
ccatgtgtct gagcacg                                                    17

<210> SEQ ID NO 66
<211> LENGTH: 17
<212> TYPE: DNA
<213> ORGANISM: Zea mays

<400> SEQUENCE: 66
catagcaaac gttcatc                                                    17

<210> SEQ ID NO 67
<211> LENGTH: 20
<212> TYPE: DNA
<213> ORGANISM: Zea mays
```

```
<400> SEQUENCE: 67
tgttagttgc gtagttaata                                              20

<210> SEQ ID NO 68
<211> LENGTH: 18
<212> TYPE: DNA
<213> ORGANISM: Zea mays

<400> SEQUENCE: 68
tggattctca cattggag                                                18

<210> SEQ ID NO 69
<211> LENGTH: 15
<212> TYPE: DNA
<213> ORGANISM: Zea mays

<400> SEQUENCE: 69
ttgctgtata atttc                                                   15

<210> SEQ ID NO 70
<211> LENGTH: 16
<212> TYPE: DNA
<213> ORGANISM: Zea mays

<400> SEQUENCE: 70
tgattaggcc aaagtg                                                  16

<210> SEQ ID NO 71
<211> LENGTH: 15
<212> TYPE: DNA
<213> ORGANISM: Zea mays

<400> SEQUENCE: 71
caggcacatc aaatt                                                   15

<210> SEQ ID NO 72
<211> LENGTH: 17
<212> TYPE: DNA
<213> ORGANISM: Zea mays

<400> SEQUENCE: 72
ctaaggcaca agtagag                                                 17

<210> SEQ ID NO 73
<211> LENGTH: 16
<212> TYPE: DNA
<213> ORGANISM: Zea mays

<400> SEQUENCE: 73
aagataatgg aagcgc                                                  16

<210> SEQ ID NO 74
<211> LENGTH: 13
<212> TYPE: DNA
<213> ORGANISM: Zea mays

<400> SEQUENCE: 74
acctgcccct tct                                                     13

<210> SEQ ID NO 75
<211> LENGTH: 16
<212> TYPE: DNA
```

```
<213> ORGANISM: Zea mays

<400> SEQUENCE: 75
ctactatcga gattgc                                          16

<210> SEQ ID NO 76
<211> LENGTH: 16
<212> TYPE: DNA
<213> ORGANISM: Zea mays

<400> SEQUENCE: 76
cactttcgaa tatcag                                          16

<210> SEQ ID NO 77
<211> LENGTH: 18
<212> TYPE: DNA
<213> ORGANISM: Zea mays

<400> SEQUENCE: 77
cactgtacgc ttcgatgt                                        18

<210> SEQ ID NO 78
<211> LENGTH: 19
<212> TYPE: DNA
<213> ORGANISM: Zea mays

<400> SEQUENCE: 78
cttaggatca tcctttct                                        19

<210> SEQ ID NO 79
<211> LENGTH: 16
<212> TYPE: DNA
<213> ORGANISM: Zea mays

<400> SEQUENCE: 79
ctgctctatc atcgac                                          16

<210> SEQ ID NO 80
<211> LENGTH: 17
<212> TYPE: DNA
<213> ORGANISM: Zea mays

<400> SEQUENCE: 80
tttggcacat cttattt                                         17

<210> SEQ ID NO 81
<211> LENGTH: 18
<212> TYPE: DNA
<213> ORGANISM: Zea mays

<400> SEQUENCE: 81
cactgtacgc ttcgatgt                                        18

<210> SEQ ID NO 82
<211> LENGTH: 16
<212> TYPE: DNA
<213> ORGANISM: Zea mays

<400> SEQUENCE: 82
catgtgtccg agcacg                                          16

<210> SEQ ID NO 83
<211> LENGTH: 17
```

<212> TYPE: DNA
<213> ORGANISM: Zea mays

<400> SEQUENCE: 83
catagcaaac attcatc                                                17

<210> SEQ ID NO 84
<211> LENGTH: 18
<212> TYPE: DNA
<213> ORGANISM: Zea mays

<400> SEQUENCE: 84
ttagttgcgt aattaata                                               18

<210> SEQ ID NO 85
<211> LENGTH: 18
<212> TYPE: DNA
<213> ORGANISM: Zea mays

<400> SEQUENCE: 85
tggattctca cgttggag                                               18

<210> SEQ ID NO 86
<211> LENGTH: 393
<212> TYPE: DNA
<213> ORGANISM: Zea mays
<220> FEATURE:
<221> NAME/KEY: misc_feature
<222> LOCATION: (216)..(216)
<223> OTHER INFORMATION: n is a, c, g, or t

<400> SEQUENCE: 86
gcggcggcgg tggaggtggc tgaccatagc gccttcgttg gagcagttgt tgggaaggag      60
gtggaggtgc aggtgcaggt gcaggtgaaa gaagaggagg agcaggagga ggaggaggag     120
gaaggaaacg aggaggagct gcacacgaga gtggaggact tcattgcgag ggtcaagagg     180
caaaggaagc tggagctcaa gagcttcttc gatgtngatc gatgatgact atatgatatg     240
tttggcaggt gcaaaattac agtaaggttg cgggcgccct aaaaaggatc tgtaatggtt     300
tgtgctgcta gctatccttt tgattaattc tgtcacttgt agttgtagta ggttaaaatg     360
tcgaaggtaa aacgataagg agacgaaccc atc                                  393

<210> SEQ ID NO 87
<211> LENGTH: 301
<212> TYPE: DNA
<213> ORGANISM: Zea mays
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t

<400> SEQUENCE: 87
cgaacaggaa gcncagttgg gaaaactttc gactttttag tagggaactg aactcatccg      60
agatgccttt tgcacccatt gcatcagact caataagctt gatgatatca gttgaagata     120
cgggtgctgg aatcccgttc gatgctcaat nccgtgtctt caccccttc atgcaagtag      180

```
gtccatccat cgctcgcata cacgggggca ctggcattgg attaagcatc agcaaatgct    240
tggttggcct catgaaggga gagatcggat ttncaagtaa accccaagtt ggttctactt    300
t                                                                   301
```

```
<210> SEQ ID NO 88
<211> LENGTH: 301
<212> TYPE: DNA
<213> ORGANISM: Zea mays
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (206)..(207)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t

<400> SEQUENCE: 88
```

```
taaatggagt agttactgac cacatccagg tttttctcat caccttcttt tagtgtgatt    60
ggaagtccat ttggtggaat ttttgggcac tctggcttta cccttcctct gtttttttg    120 tcgtacattg tttaccaggg ggtacggcct nctgctgagg cagagagacc aggatcttct   180
ggtaatgcat tttactgcaa atgcanntgt aacagtttat atttaaacat tagagaatta   240
ctatttataa gagaattnca tcgttgagtt ttgtttngtt tttgttgtga tccctgtgca   300
t                                                                   301
```

```
<210> SEQ ID NO 89
<211> LENGTH: 417
<212> TYPE: DNA
<213> ORGANISM: Zea mays
<220> FEATURE:
<221> NAME/KEY: misc_feature
<222> LOCATION: (194)..(194)
<223> OTHER INFORMATION: n is a, c, g, or t

<400> SEQUENCE: 89
```

```
tgatgtttga cgggcaggac gacaagctgt tcgagcactt ctccatggtc gcgcagaggc    60
ttggcgttta caccgccagg gactacgccg acatcctcga gttcctcgtc gacaggtgga   120
aggtggcgaa cctgactggt ctgtcgggtg aagggaacaa ggcgcaggac tacctttgca   180
cccttgcttc aagnatcagg aggctggagg agagggccca gagcagagcc aagaaagcag   240
gcacgctgcc tttcagctgg gtatacggta gggacgtcca actgtgagat cggaaacctg   300
ctgcggactg cttagacaag acctgctgtg ctgtgtctgc gttacatagt tctccaggtt   360
ttgatcagat ggtcccgtgt cgtcttatag agcgatagga gaacgtgttg gtctgtg      417
```

```
<210> SEQ ID NO 90
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
```

<222> LOCATION: (144)..(144)
<223> OTHER INFORMATION: n is a, c, g, or t

<400> SEQUENCE: 90
caatccaaca gccggaccgg acggacgacg gctgtggcgg gcgcaggtca gtcgtcattt    60
cagcagagat ctgggcgcac ttgctgggat cctgacaggt ngtattcccg accgacagga   120
agcccagggc gcgggcagga cagntgtggt tcgggaccat gacgagctcg ctggtccatc   180
gtcggaccca gagcgggctc t                                             201

<210> SEQ ID NO 91
<211> LENGTH: 301
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t

<400> SEQUENCE: 91
ccgtctctct cctcccttttg tcgtcgtgnc tctctgcatg aagcctccn ccggctcgtc    60 gccaccgcac tcccaagaga acccgccgga gcacggtggc gacatgggag gggccccgc   120 ggaggagatc ggaggggagg cggcggatga nttcatgttc gctgaagaca cgttcccctc   180
cctcccggac ttcccttgcc tttcgtcgcc gtccagctcc accttctcgt ccaactcctc   240
gtcaaactcc tccagcgcct acaccaacac ggcaggaaga gccggcggcg agccctccga   300
g                                                                   301

<210> SEQ ID NO 92
<211> LENGTH: 301
<212> TYPE: DNA
<213> ORGANISM: Zea mays
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (266)..(267)
<223> OTHER INFORMATION: n is a, c, g, or t

<400> SEQUENCE: 92
cgaaaagctc cacggcagcg gatctgtgcg cgtcggagac tgggcgaacg gcggaggaga    60
tgggggcgaa tgccgcggcg aggagaagga ggatggccnc cggtgccggg cgcctcccgg   120
ccatggcgat ggcaattacc gtggccgaga nagatgtgta gggtttagga gactggggca   180
tgtgggagtg gccagatctg gaggttagaa ggggacgact ataaatattt cgccagatca   240
tactgccgtc tcgacgtctg cgctcnngag gagagttgga tgctttgaga tgggtgtttg   300
t                                                                   301

<210> SEQ ID NO 93

```
<211> LENGTH: 301
<212> TYPE: DNA
<213> ORGANISM: Zea mays
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t

<400> SEQUENCE: 93
gctgtctgaa gcaatcgaga tctcttggcc aaatgcaggt gtagagggag gngacaatgt      60
cccagatgct gtggagtatg gttctnaaaa ggtatgctgc ttctctccac ccctctaatt     120
catcnaagaa ttccaaaggt agacagagac ntgtacgctt ctccatgcct ttctattatg     180
ccatgcttag aatcattgat gacacttcat ctttgttatt gttaattggt accagntcca     240
agnaaagcaa gattacaaag atattttaca agaagtccaa gatagccacc atgatgtata     300
t                                                                     301

<210> SEQ ID NO 94
<211> LENGTH: 201
<212> TYPE: DNA
<213> ORGANISM: Zea mays
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 94
ttatccagca gatgacaaag caaatcaaca ttgccaatgt ttgtnacagc taatttgagt      60
aatacatgtc aataaaaggg aaactgaaat aacagaattt nttacctgct ccaagcacct     120
ctttgagttc ttatgctcac catccatgta atatgcattt gcaagattaa cccaaactga     180
tgcagctcta ggatcagcct t                                                201

<210> SEQ ID NO 95
<211> LENGTH: 301
<212> TYPE: DNA
<213> ORGANISM: Zea mays
<220> FEATURE:
<221> NAME/KEY: misc_feature
<222> LOCATION: (151)..(151)
<223> OTHER INFORMATION: n is a, c, g, or t

<400> SEQUENCE: 95
gctgtaacat ggctatttgc ggcggcggag gcaccggcat ggctggatat gggtgggggc      60
```

```
agtatagctg ttgcggaagc ggctgtagag gatagggggc acagaccgta gggtggaact    120
cctgagctgc ggcatcgaga aggttacccg nggcttccgg gaacccaccc attccactcc    180
ctcccccacc ctccatggct agagctcaga acaaaagaaa ccgaggagtc caaggaagac    240
tgccgtctaa agatctagaa ctttctggtg attcttgatc atgccttcga tcaagaacca    300
g                                                                    301
```

<210> SEQ ID NO 96
<211> LENGTH: 562
<212> TYPE: DNA
<213> ORGANISM: Zea mays
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t

<400> SEQUENCE: 96

```
nnnnnnnagc tcgtanggca ggagttccaa aacgggcacg caaagagaag caactcagta     60
cttgtagtcc ttgacgtgga ggctctcggt gtcggcggca gcatcaccct tgtaggtgcc    120
gagggtagcc tcagagttgg ccttgcacct ggcgaggaag gcagctctag ccttctccan    180
gttctccacc ttgccagccc aggccttgag ggtgctcgcc tggagggcac ggccgaagga    240
gaaagacagg gaccacggct tcttggtgct gagcttgttc atggcattga ggttgcgggt    300
ggcctcctcc tcgctctgtc caccagagag gaagacaaca gcaggcacag cagcagggac    360
ggtcctctgg agggtacgga cggtgtactc agcaatcacc tcagggtca ccttcttgga    420 gtcggagcct ggagtcacca tgttgggctt caggagggta ccctccagga ggacatggtg    480
ctcgttgagc gccttgtagc aggcagcaag gacggtctca gtgacgtaag cgcagcgatc    540
aatgtcatga gggccancaa ca                                             562
```

<210> SEQ ID NO 97
<211> LENGTH: 301
<212> TYPE: DNA
<213> ORGANISM: Zea mays
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t

<400> SEQUENCE: 97

```
ttcttcatga acagatgttg atcaacattg tcaaggggct tctgctccac gtgaggaaaa     60
agttagcaac ctnaaagctg tgagttcttg gttttgatgc catttgaaat aatnaatctt    120
```
tcatgcaata gataagtggc agtgtgacac ngtattataa tacatttaat gccgtatgaa    180
ccctgatgtt gttttacctt cttaatttgt ggtactggta cggttaacaa aaatgattga    240
gggcctaacc ttacttcttg caggctttgg ttcatgtggc ccgaaaaatg cctaagaatg    300
c                                                                    301

<210> SEQ ID NO 98
<211> LENGTH: 201
<212> TYPE: DNA
<213> ORGANISM: Zea mays
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t

<400> SEQUENCE: 98
taccctgtca aaggatgacc anaaacatgt accatacgga caacttcgag ccgcttctgt     60
tcgattgcct atctcttgga aatacaagga aaggtaaggc ngacaataat gagctgtaca    120
aggatgctcc tngaggacac acaacatgat catgtaacta atctatatac tatatttagc    180
ctggcgtttt tttgttgtgc t                                              201

<210> SEQ ID NO 99
<211> LENGTH: 201
<212> TYPE: DNA
<213> ORGANISM: Zea mays
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 99
gcagtcttga agggtggggc atgcttgttt tttacaatct tcacagcaan ctgactacct     60
attgtctgca aatggaagga atcatcattc aaaagctaca nagagtgcat actgtttcag    120
acaacacatg tagatgccta ttacatgtgt ctagtagtgg ctcagttaaa taggtctcat    180
aaagacatgt atatctctgt t                                              201

<210> SEQ ID NO 100
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 100
aaccgactgt tttttttttc tataggaaaa ggacatcata tatatatatt aatagagcat     60
gccttggaag atgataaaat gactttgaat aatttgcatt ngtgaagctg atcggaaaaa    120

```
aaggtccatg tgcacttaca tttgatgttt tcccttcgaa catccaacat atgtgcatgc    180
agaggacnca aaacggttag a                                              201
```

<210> SEQ ID NO 101
<211> LENGTH: 748
<212> TYPE: DNA
<213> ORGANISM: Zea mays
<220> FEATURE:
<221> NAME/KEY: misc_feature
<222> LOCATION: (42)..(45)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (635)..(642)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (649)..(651)
<223> OTHER INFORMATION: n is a, c, g, or t
<220> FEATURE:
<221> NAME/KEY: misc_feature
<222> LOCATION: (654)..(656)
<223> OTHER INFORMATION: n is a, c, g, or t
<220> FEATURE:
<221> NAME/KEY: misc_feature
<222> LOCATION: (666)..(667)
<223> OTHER INFORMATION: n is a, c, g, or t
<220> FEATURE:

<221> NAME/KEY: misc_feature
<222> LOCATION: (673)..(679)
<223> OTHER INFORMATION: n is a, c, g, or t
<220> FEATURE:
<221> NAME/KEY: misc_feature
<222> LOCATION: (685)..(693)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (715)..(723)
<223> OTHER INFORMATION: n is a, c, g, or t
<220> FEATURE:
<221> NAME/KEY: misc_feature
<222> LOCATION: (726)..(730)
<223> OTHER INFORMATION: n is a, c, g, or t
<220> FEATURE:
<221> NAME/KEY: misc_feature
<222> LOCATION: (732)..(742)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t

<400> SEQUENCE: 101

```
cataatgcaa caaacgttaa aaaactacag agatggaaaa annnncagtc accataaaag    60
atgncttgta caacaagttc atgcaaaaaa nttattatta ctattaatga gctaactana   120
aacaaacacc cnaaatataa catcatgaca tcaaaaggaa gacatgtacc ttgagggcac   180
caaagacacg gttcccagtn gtagtcctaa taaggccaac atccaagaga gcacggaaag   240
gcctcctctc atcagctggc tcaacagaga antcctcacc agtggcctga tgaangaaaa   300
gaaacaatat aaatgcccaa ccaatgtgac atcagcaaaa aataagatcn aaatttagcc   360
aaatttttacc tcaacattgc cctcatattc cttatctaaa ccacgggtct tgagcacacg   420
gcgagccaac agaaggccag tgcagtaggc tacaagatga gtgtaagcag ttgaactagt   480
gaatatataa attcattaag gtacaatatg caatttacac antatttcca gaaggnaaat   540
taccagctgc atagttggtc agaccaactt caagaccata tcgtggcaac tcatgcgagt   600
aagcagaagc aagnnccata tcacctgcta tactnnnnnn nntgatntnn nctnnnatgt   660
ccttgnnggt ctnnnnnnnt ctagnnnnnn nnnacaatat tatgcnactg nagcnnnnnn   720
nnnatnnnnn tnnnnnnnnn nnanatga                                     748
```

<210> SEQ ID NO 102
<211> LENGTH: 22
<212> TYPE: DNA
<213> ORGANISM: Zea mays

<400> SEQUENCE: 102

```
aaaggaagct ggagctcaag ag                                            22
```

<210> SEQ ID NO 103
<211> LENGTH: 20
<212> TYPE: DNA
<213> ORGANISM: Zea mays

<400> SEQUENCE: 103

```
gtgctggaat cccgttcgat                                               20
```

```
<210> SEQ ID NO 104
<211> LENGTH: 26
<212> TYPE: DNA
<213> ORGANISM: Zea mays

<400> SEQUENCE: 104
ccttcctctg ttttttttgt cgtaca                                        26

<210> SEQ ID NO 105
<211> LENGTH: 19
<212> TYPE: DNA
<213> ORGANISM: Zea mays

<400> SEQUENCE: 105
gcgcaggact acctttgca                                                19

<210> SEQ ID NO 106
<211> LENGTH: 18
<212> TYPE: DNA
<213> ORGANISM: Zea mays

<400> SEQUENCE: 106
cgcacttgct gggatcct                                                 18

<210> SEQ ID NO 107
<211> LENGTH: 16
<212> TYPE: DNA
<213> ORGANISM: Zea mays

<400> SEQUENCE: 107
ccccgcggag gagatc                                                   16

<210> SEQ ID NO 108
<211> LENGTH: 20
<212> TYPE: DNA
<213> ORGANISM: Zea mays

<400> SEQUENCE: 108
ccatggcgat ggcaattacc                                               20

<210> SEQ ID NO 109
<211> LENGTH: 25
<212> TYPE: DNA
<213> ORGANISM: Zea mays

<400> SEQUENCE: 109
cttctctcca cccctctaat tcatc                                         25

<210> SEQ ID NO 110
<211> LENGTH: 33
<212> TYPE: DNA
<213> ORGANISM: Zea mays

<400> SEQUENCE: 110
tgagtaatac atgtcaataa aagggaaact gaa                                33

<210> SEQ ID NO 111
<211> LENGTH: 18
<212> TYPE: DNA
<213> ORGANISM: Zea mays

<400> SEQUENCE: 111
```

```
ctgcggcatc gagaaggt                                                    18

<210> SEQ ID NO 112
<211> LENGTH: 19
<212> TYPE: DNA
<213> ORGANISM: Zea mays

<400> SEQUENCE: 112
ggcgaggaag gcagctcta                                                   19

<210> SEQ ID NO 113
<211> LENGTH: 25
<212> TYPE: DNA
<213> ORGANISM: Zea mays

<400> SEQUENCE: 113
gtgagttctt ggttttgatg ccatt                                            25

<210> SEQ ID NO 114
<211> LENGTH: 25
<212> TYPE: DNA
<213> ORGANISM: Zea mays

<400> SEQUENCE: 114
ctgttcgatt gcctatctct tggaa                                            25

<210> SEQ ID NO 115
<211> LENGTH: 26
<212> TYPE: DNA
<213> ORGANISM: Zea mays

<400> SEQUENCE: 115
tgtctgcaaa tggaaggaat catcat                                           26

<210> SEQ ID NO 116
<211> LENGTH: 26
<212> TYPE: DNA
<213> ORGANISM: Zea mays

<400> SEQUENCE: 116
agagcatgcc ttggaagatg ataaaa                                           26

<210> SEQ ID NO 117
<211> LENGTH: 20
<212> TYPE: DNA
<213> ORGANISM: Zea mays

<400> SEQUENCE: 117
ccttgagggc accaaagaca                                                  20

<210> SEQ ID NO 118
<211> LENGTH: 23
<212> TYPE: DNA
<213> ORGANISM: Zea mays

<400> SEQUENCE: 118
gcccgcaacc ttactgtaat ttt                                              23

<210> SEQ ID NO 119
<211> LENGTH: 24
<212> TYPE: DNA
<213> ORGANISM: Zea mays

<400> SEQUENCE: 119
```

```
ggatggacct acttgcatga aagg                                         24

<210> SEQ ID NO 120
<211> LENGTH: 28
<212> TYPE: DNA
<213> ORGANISM: Zea mays

<400> SEQUENCE: 120
gcagtaaaat gcattaccag aagatcct                                     28

<210> SEQ ID NO 121
<211> LENGTH: 17
<212> TYPE: DNA
<213> ORGANISM: Zea mays

<400> SEQUENCE: 121
gccctctcct ccagcct                                                 17

<210> SEQ ID NO 122
<211> LENGTH: 15
<212> TYPE: DNA
<213> ORGANISM: Zea mays

<400> SEQUENCE: 122
cgccctgggc ttcct                                                   15

<210> SEQ ID NO 123
<211> LENGTH: 20
<212> TYPE: DNA
<213> ORGANISM: Zea mays

<400> SEQUENCE: 123
cgacgaaagg caagggaagt                                              20

<210> SEQ ID NO 124
<211> LENGTH: 22
<212> TYPE: DNA
<213> ORGANISM: Zea mays

<400> SEQUENCE: 124
ccccagtctc ctaaacccta ca                                           22

<210> SEQ ID NO 125
<211> LENGTH: 25
<212> TYPE: DNA
<213> ORGANISM: Zea mays

<400> SEQUENCE: 125
gcatggcata atagaaaggc atgga                                        25

<210> SEQ ID NO 126
<211> LENGTH: 25
<212> TYPE: DNA
<213> ORGANISM: Zea mays

<400> SEQUENCE: 126
acatggatgg tgagcataag aactc                                        25

<210> SEQ ID NO 127
<211> LENGTH: 22
<212> TYPE: DNA
<213> ORGANISM: Zea mays
```

```
<400> SEQUENCE: 127
tgttctgagc tctagccatg ga                                          22

<210> SEQ ID NO 128
<211> LENGTH: 18
<212> TYPE: DNA
<213> ORGANISM: Zea mays

<400> SEQUENCE: 128
caggcgagca ccctcaag                                               18

<210> SEQ ID NO 129
<211> LENGTH: 25
<212> TYPE: DNA
<213> ORGANISM: Zea mays

<400> SEQUENCE: 129
tcagggttca tacggcatta aatgt                                       25

<210> SEQ ID NO 130
<211> LENGTH: 23
<212> TYPE: DNA
<213> ORGANISM: Zea mays

<400> SEQUENCE: 130
ggagcatcct tgtacagctc att                                         23

<210> SEQ ID NO 131
<211> LENGTH: 28
<212> TYPE: DNA
<213> ORGANISM: Zea mays

<400> SEQUENCE: 131
gtaataggca tctacatgtg ttgtctga                                    28

<210> SEQ ID NO 132
<211> LENGTH: 25
<212> TYPE: DNA
<213> ORGANISM: Zea mays

<400> SEQUENCE: 132
tcaaatgtaa gtgcacatgg acctt                                       25

<210> SEQ ID NO 133
<211> LENGTH: 23
<212> TYPE: DNA
<213> ORGANISM: Zea mays

<400> SEQUENCE: 133
gctctcttgg atgttggcct tat                                         23

<210> SEQ ID NO 134
<211> LENGTH: 17
<212> TYPE: DNA
<213> ORGANISM: Zea mays

<400> SEQUENCE: 134
atcatcgatc gacatcg                                                17

<210> SEQ ID NO 135
<211> LENGTH: 14
<212> TYPE: DNA
<213> ORGANISM: Zea mays
```

```
<400> SEQUENCE: 135
acacgggatt gagc                                                    14

<210> SEQ ID NO 136
<211> LENGTH: 15
<212> TYPE: DNA
<213> ORGANISM: Zea mays

<400> SEQUENCE: 136
acggcctgct gctga                                                   15

<210> SEQ ID NO 137
<211> LENGTH: 15
<212> TYPE: DNA
<213> ORGANISM: Zea mays

<400> SEQUENCE: 137
tgcttcaaga atcag                                                   15

<210> SEQ ID NO 138
<211> LENGTH: 17
<212> TYPE: DNA
<213> ORGANISM: Zea mays

<400> SEQUENCE: 138
cgggaatacg acctgtc                                                 17

<210> SEQ ID NO 139
<211> LENGTH: 17
<212> TYPE: DNA
<213> ORGANISM: Zea mays

<400> SEQUENCE: 139
cgaacatgaa atcatcc                                                 17

<210> SEQ ID NO 140
<211> LENGTH: 15
<212> TYPE: DNA
<213> ORGANISM: Zea mays

<400> SEQUENCE: 140
tggccgagag agatg                                                   15

<210> SEQ ID NO 141
<211> LENGTH: 16
<212> TYPE: DNA
<213> ORGANISM: Zea mays

<400> SEQUENCE: 141
agcgtacagg tctctg                                                  16

<210> SEQ ID NO 142
<211> LENGTH: 16
<212> TYPE: DNA
<213> ORGANISM: Zea mays

<400> SEQUENCE: 142
agcaggtaag aaattc                                                  16

<210> SEQ ID NO 143
<211> LENGTH: 16
<212> TYPE: DNA
```

```
<213> ORGANISM: Zea mays

<400> SEQUENCE: 143
ccggaagcca cgggta                                                  16

<210> SEQ ID NO 144
<211> LENGTH: 14
<212> TYPE: DNA
<213> ORGANISM: Zea mays

<400> SEQUENCE: 144
tctccaagtt ctcc                                                    14

<210> SEQ ID NO 145
<211> LENGTH: 19
<212> TYPE: DNA
<213> ORGANISM: Zea mays

<400> SEQUENCE: 145
cagtgtgaca ctgtattat                                               19

<210> SEQ ID NO 146
<211> LENGTH: 17
<212> TYPE: DNA
<213> ORGANISM: Zea mays

<400> SEQUENCE: 146
aaggtaaggc ggacaat                                                 17

<210> SEQ ID NO 147
<211> LENGTH: 20
<212> TYPE: DNA
<213> ORGANISM: Zea mays

<400> SEQUENCE: 147
cagtatgcac tctgtgtagc                                              20

<210> SEQ ID NO 148
<211> LENGTH: 17
<212> TYPE: DNA
<213> ORGANISM: Zea mays

<400> SEQUENCE: 148
tttgcattgg tgaagct                                                 17

<210> SEQ ID NO 149
<211> LENGTH: 14
<212> TYPE: DNA
<213> ORGANISM: Zea mays

<400> SEQUENCE: 149
cccagtcgta gtcc                                                    14

<210> SEQ ID NO 150
<211> LENGTH: 15
<212> TYPE: DNA
<213> ORGANISM: Zea mays

<400> SEQUENCE: 150
catcgatcaa catcg                                                   15

<210> SEQ ID NO 151
<211> LENGTH: 14
```

```
<212> TYPE: DNA
<213> ORGANISM: Zea mays

<400> SEQUENCE: 151
acacggaatt gagc                                              14

<210> SEQ ID NO 152
<211> LENGTH: 15
<212> TYPE: DNA
<213> ORGANISM: Zea mays

<400> SEQUENCE: 152
acggcctact gctga                                             15

<210> SEQ ID NO 153
<211> LENGTH: 16
<212> TYPE: DNA
<213> ORGANISM: Zea mays

<400> SEQUENCE: 153
ttgcttcaag gatcag                                            16

<210> SEQ ID NO 154
<211> LENGTH: 18
<212> TYPE: DNA
<213> ORGANISM: Zea mays

<400> SEQUENCE: 154
tcgggaatac aacctgtc                                          18

<210> SEQ ID NO 155
<211> LENGTH: 17
<212> TYPE: DNA
<213> ORGANISM: Zea mays

<400> SEQUENCE: 155
cgaacatgaa gtcatcc                                           17

<210> SEQ ID NO 156
<211> LENGTH: 15
<212> TYPE: DNA
<213> ORGANISM: Zea mays

<400> SEQUENCE: 156
tggccgagat agatg                                             15

<210> SEQ ID NO 157
<211> LENGTH: 17
<212> TYPE: DNA
<213> ORGANISM: Zea mays

<400> SEQUENCE: 157
aagcgtacat gtctctg                                           17

<210> SEQ ID NO 158
<211> LENGTH: 16
<212> TYPE: DNA
<213> ORGANISM: Zea mays

<400> SEQUENCE: 158
agcaggtaat aaattc                                            16

<210> SEQ ID NO 159
```

```
<211> LENGTH: 15
<212> TYPE: DNA
<213> ORGANISM: Zea mays

<400> SEQUENCE: 159
cggaagccgc gggta                                                    15

<210> SEQ ID NO 160
<211> LENGTH: 15
<212> TYPE: DNA
<213> ORGANISM: Zea mays

<400> SEQUENCE: 160
ctccaggttc tccac                                                    15

<210> SEQ ID NO 161
<211> LENGTH: 18
<212> TYPE: DNA
<213> ORGANISM: Zea mays

<400> SEQUENCE: 161
agtgtgacac agtattat                                                 18

<210> SEQ ID NO 162
<211> LENGTH: 16
<212> TYPE: DNA
<213> ORGANISM: Zea mays

<400> SEQUENCE: 162
aggtaaggca gacaat                                                   16

<210> SEQ ID NO 163
<211> LENGTH: 20
<212> TYPE: DNA
<213> ORGANISM: Zea mays

<400> SEQUENCE: 163
cagtatgcac tctttgtagc                                               20

<210> SEQ ID NO 164
<211> LENGTH: 16
<212> TYPE: DNA
<213> ORGANISM: Zea mays

<400> SEQUENCE: 164
ttgcattcgt gaagct                                                   16

<210> SEQ ID NO 165
<211> LENGTH: 16
<212> TYPE: DNA
<213> ORGANISM: Zea mays

<400> SEQUENCE: 165
cccagttgta gtccta                                                   16
```